US012454564B2

(12) United States Patent
Wang et al.

(10) Patent No.: US 12,454,564 B2
(45) Date of Patent: Oct. 28, 2025

(54) COMPOSITIONS AND METHODS FOR T CELL ENGINEERING

(71) Applicants: Gracell Biotechnologies (Shanghai) Co., Ltd., Shanghai (CN); Suzhou Gracell Biotechnologies Co., Ltd., Jiangsu (CN)

(72) Inventors: Xinxin Wang, Shanghai (CN); Tao Jin, Shanghai (CN); Chunhui Yang, Shanghai (CN); Zhongdong Shi, Shanghai (CN); Liping Liu, Shanghai (CN); Jing Sun, Shanghai (CN); Shuyi Qiu, Shanghai (CN); Wei Cao, Shanghai (CN)

(73) Assignees: Gracell Biotechnologies (Shanghai) Co., Ltd., Shanghai (CN); Suzhou Gracell Biotechnologies Co., Ltd., Jiangsu (CN)

( * ) Notice: Subject to any disclaimer, the term of this patent is extended or adjusted under 35 U.S.C. 154(b) by 0 days.

(21) Appl. No.: 17/821,664

(22) Filed: Aug. 23, 2022

(65) Prior Publication Data

US 2023/0068085 A1 Mar. 2, 2023

Related U.S. Application Data

(60) Division of application No. 17/246,394, filed on Apr. 30, 2021, now abandoned, which is a continuation of application No. PCT/CN2019/114939, filed on Nov. 1, 2019.

(30) Foreign Application Priority Data

| | | |
|---|---|---|
| Nov. 1, 2018 | (CN) | 201811297174.3 |
| Dec. 14, 2018 | (CN) | 201811535338.1 |
| Dec. 18, 2018 | (CN) | 201811549651.0 |
| Jun. 6, 2019 | (CN) | 201910492882.0 |
| Aug. 20, 2019 | (WO) | PCT/CN2019/101651 |

(51) Int. Cl.

| | |
|---|---|
| ***C07K 14/725*** | (2006.01) |
| ***A61K 40/11*** | (2025.01) |
| ***A61K 40/31*** | (2025.01) |
| ***A61K 40/42*** | (2025.01) |
| ***A61K 40/50*** | (2025.01) |
| ***A61P 35/00*** | (2006.01) |
| ***C07K 14/705*** | (2006.01) |
| ***C07K 14/71*** | (2006.01) |
| ***C07K 16/28*** | (2006.01) |
| ***C12N 5/0783*** | (2010.01) |
| ***C12N 15/113*** | (2010.01) |
| ***C12N 15/90*** | (2006.01) |
| *A61K 35/38* | (2015.01) |
| *A61K 35/545* | (2015.01) |
| *A61K 38/00* | (2006.01) |

(52) U.S. Cl.

CPC .......... *C07K 14/7051* (2013.01); *A61K 40/11* (2025.01); *A61K 40/31* (2025.01); *A61K 40/4202* (2025.01); *A61K 40/4204* (2025.01); *A61K 40/421* (2025.01); *A61K 40/4211* (2025.01); *A61K 40/4215* (2025.01); *A61P 35/00* (2018.01); *C07K 14/70507* (2013.01); *C07K 14/70596* (2013.01); *C12N 5/0636* (2013.01); *A61K 38/00* (2013.01); *A61K 40/50* (2025.01); *A61K 2239/23* (2023.05); *A61K 2239/29* (2023.05); *A61K 2239/31* (2023.05); *A61K 2239/38* (2023.05); *A61K 2239/48* (2023.05)

(58) Field of Classification Search

CPC ..... A61K 35/17; A61K 40/31; A61K 40/4211

See application file for complete search history.

(56) References Cited

U.S. PATENT DOCUMENTS

| | | | |
|---|---|---|---|
| 2,779,780 | A | 1/1957 | Middleton |
| 5,641,870 | A | 6/1997 | Rinderknecht et al. |
| 6,534,055 | B1 | 3/2003 | June et al. |
| 6,780,996 | B2 | 8/2004 | Boschelli et al. |
| 6,905,874 | B2 | 6/2005 | Berenson et al. |
| 7,572,631 | B2 | 8/2009 | Berenson et al. |
| 7,612,181 | B2 | 11/2009 | Wu et al. |

(Continued)

FOREIGN PATENT DOCUMENTS

| | | | | |
|---|---|---|---|---|
| CA | 3109630 | A1 * | 2/2020 | A61K 35/17 |
| CN | 106191062 | A | 12/2016 | |

(Continued)

OTHER PUBLICATIONS

Zah et al. (Cancer Immunol. Res. Jun. 2016; 4 (6): 498-508).*

(Continued)

*Primary Examiner* — Juliet C Switzer
*Assistant Examiner* — Katherine Ann Holtzman
(74) *Attorney, Agent, or Firm* — Sterne, Kessler, Goldstein &Fox P.L.L.C.

(57) ABSTRACT

The present disclosure relates to an engineered immune cell and use thereof. The present disclosure provides an engineered immune cell comprising a CAR or engineered TCR, which CAR or engineered TCR can comprise a first antigen binding domain and a second antigen binding domain. The engineered immune cells of the present disclosure, when administered into a subject, can inhibit the host immune cells such as T cells and/or NK cells and enhance the survival and persistence of the engineered immune cells in vivo, thereby exhibiting more effective tumor killing activity.

11 Claims, 73 Drawing Sheets

Specification includes a Sequence Listing.

(56) References Cited

U.S. PATENT DOCUMENTS

| | | | |
|---|---|---|---|
| 7,741,465 B1 | 6/2010 | Eshhar et al. | |
| 7,838,637 B2 | 11/2010 | Kontermann et al. | |
| 9,089,615 B2 | 7/2015 | Stull et al. | |
| 9,128,080 B2 | 9/2015 | Robbins et al. | |
| 9,447,194 B2 | 9/2016 | Jensen | |
| 9,464,140 B2 | 10/2016 | June et al. | |
| 9,605,049 B2 | 3/2017 | Campana et al. | |
| 9,944,702 B2 | 4/2018 | Galetto | |
| 10,137,155 B2 | 11/2018 | Mukherjee et al. | |
| 10,266,608 B2 | 4/2019 | Wu | |
| 10,273,280 B2 | 4/2019 | Ma et al. | |
| 10,273,300 B2 | 4/2019 | Bedoya et al. | |
| 10,287,350 B2 | 5/2019 | Kochenderfer | |
| 10,457,730 B2 | 10/2019 | Pule et al. | |
| 10,513,686 B2 | 12/2019 | Ostertag et al. | |
| 10,550,183 B2 | 2/2020 | Png et al. | |
| 10,570,186 B2 | 2/2020 | Cooper et al. | |
| 10,696,749 B2 | 6/2020 | June et al. | |
| 11,078,291 B2 | 8/2021 | Sussman et al. | |
| 11,186,824 B2 | 11/2021 | Duchateau et al. | |
| 11,319,380 B2 * | 5/2022 | Sabzevari | C07K 14/70578 |
| 2002/0004587 A1 | 1/2002 | Miller et al. | |
| 2003/0087817 A1 | 5/2003 | Cox, III et al. | |
| 2007/0036773 A1 | 2/2007 | Cooper et al. | |
| 2007/0219133 A1 | 9/2007 | Lazar et al. | |
| 2009/0155275 A1 | 6/2009 | Wu et al. | |
| 2010/0260668 A1 | 10/2010 | Ghayur et al. | |
| 2013/0101562 A1 | 4/2013 | Har-Noy | |
| 2013/0116167 A1 | 5/2013 | Morgan et al. | |
| 2016/0289341 A1 | 10/2016 | Wu | |
| 2016/0361360 A1 | 12/2016 | Chang et al. | |
| 2017/0081405 A1 | 3/2017 | Adusumilli et al. | |
| 2017/0137783 A1 | 5/2017 | Bedoya et al. | |
| 2017/0260261 A1 | 9/2017 | Short | |
| 2017/0267721 A1 | 9/2017 | Chung et al. | |
| 2017/0267742 A1 | 9/2017 | Jensen et al. | |
| 2017/0274014 A1 | 9/2017 | Brogdon et al. | |
| 2017/0368098 A1 | 12/2017 | Chen et al. | |
| 2018/0021378 A1 | 1/2018 | Kang et al. | |
| 2018/0133296 A1 | 5/2018 | Barrett et al. | |
| 2018/0148506 A1 * | 5/2018 | Png | A61K 35/17 |
| 2018/0162939 A1 | 6/2018 | Ma et al. | |
| 2018/0179280 A1 | 6/2018 | Png et al. | |
| 2018/0291343 A1 * | 10/2018 | Duchateau | C12N 15/11 |
| 2019/0055314 A1 | 2/2019 | Luo et al. | |
| 2019/0119635 A1 | 4/2019 | Robbins et al. | |
| 2019/0119638 A1 | 4/2019 | Sadelain et al. | |
| 2019/0136186 A1 | 5/2019 | Germeroth et al. | |
| 2019/0151365 A1 | 5/2019 | Anak et al. | |
| 2019/0161553 A1 | 5/2019 | Sather et al. | |
| 2019/0309307 A1 | 10/2019 | Garcia et al. | |
| 2019/0314411 A1 * | 10/2019 | Xiao | C12N 15/86 |
| 2019/0336504 A1 | 11/2019 | Gill et al. | |
| 2019/0350978 A1 | 11/2019 | Beauchesne et al. | |
| 2019/0365809 A1 | 12/2019 | Terrett et al. | |
| 2020/0040056 A1 | 2/2020 | DiPersio et al. | |
| 2020/0055948 A1 | 2/2020 | Daley et al. | |
| 2020/0330515 A1 * | 10/2020 | Maus | C12N 5/0637 |
| 2021/0369779 A1 | 12/2021 | He et al. | |

FOREIGN PATENT DOCUMENTS

| | | | | |
|---|---|---|---|---|
| CN | 106544321 A | 3/2017 | | |
| CN | 106591363 A | 4/2017 | | |
| CN | 107249602 A | 10/2017 | | |
| CN | 108017717 A | 5/2018 | | |
| CN | 108018312 A | 5/2018 | | |
| EP | 2443154 B1 | 12/2013 | | |
| EP | 3331920 A1 | 6/2018 | | |
| EP | 3517125 A1 | 7/2019 | | |
| EP | 3988648 A1 | 4/2022 | | |
| WO | WO-02066470 A1 | 8/2002 | | |
| WO | WO-03064383 A2 | 8/2003 | | |
| WO | WO-2006127585 A2 | 11/2006 | | |
| WO | WO-2012079000 A1 | 6/2012 | | |
| WO | WO-2014055442 A2 | 4/2014 | | |
| WO | WO-2014100385 A1 | 6/2014 | | |
| WO | WO-2014138348 A1 | 9/2014 | | |
| WO | WO-2015120096 A2 | 8/2015 | | |
| WO | WO-2015134877 A1 * | 9/2015 | | A61K 31/4545 |
| WO | WO-2016029855 A1 | 3/2016 | | |
| WO | WO-2016073602 A2 | 5/2016 | | |
| WO | WO-2016126213 A1 | 8/2016 | | |
| WO | WO-2016138491 A1 | 9/2016 | | |
| WO | WO-2017068421 A1 | 4/2017 | | |
| WO | WO-2017070042 A1 | 4/2017 | | |
| WO | WO-2017112877 A1 | 6/2017 | | |
| WO | WO-2017149515 A1 | 9/2017 | | |
| WO | WO-2017213979 A1 | 12/2017 | | |
| WO | WO-2017214333 A1 * | 12/2017 | | A61K 39/001104 |
| WO | WO-2017222593 A1 | 12/2017 | | |
| WO | WO-2018027036 A1 | 2/2018 | | |
| WO | WO-2018027038 A1 | 2/2018 | | |
| WO | WO-2018038945 A1 | 3/2018 | | |
| WO | WO-2018106732 A1 | 6/2018 | | |
| WO | WO-2018111340 A1 | 6/2018 | | |
| WO | WO-2018115906 A1 | 6/2018 | | |
| WO | WO-2018231759 A1 | 12/2018 | | |
| WO | WO-2019032929 A1 | 2/2019 | | |
| WO | WO-2019057122 A1 | 3/2019 | | |
| WO | WO-2019079034 A1 | 4/2019 | | |
| WO | WO-2019102234 A1 | 5/2019 | | |
| WO | WO-2019108900 A1 | 6/2019 | | |
| WO | WO-2019133969 A2 | 7/2019 | | |
| WO | WO-2019210153 A1 | 10/2019 | | |
| WO | WO-2019222547 A1 | 11/2019 | | |
| WO | WO-2019223226 A1 | 11/2019 | | |
| WO | WO-2019232444 A1 | 12/2019 | | |
| WO | WO-2020033927 | 2/2020 | | |
| WO | WO-2020047452 | 3/2020 | | |
| WO | WO-2020055862 A1 | 3/2020 | | |
| WO | WO-2020088631 A1 * | 5/2020 | | A61K 35/17 |
| WO | WO-2020114491 A9 | 6/2020 | | |
| WO | WO-2020210398 A1 | 10/2020 | | |
| WO | WO-2020248486 A1 | 12/2020 | | |

OTHER PUBLICATIONS

Ruella et al. (J. Clin. Invest. Oct. 3, 2016; 126 (10): 3814-3826).*
Rizzo et al. (Cytometry B. Clin. Cytom. Mar. 2009; 76 (2): 142-9).*
Kochenderfer et al. (J. Immunother. Sep. 2009; 32 (7): 689-702).*
Rasaiyaah et al. (JCI Insight. Jul. 12, 2018; 3 (13): e99442; pp. 1-14).*
Torikai et al. (Blood. Jun. 14, 2012; 119 (24): 5697-705).*
Shum et al. (Cancer Discov. 2017; 7 (11): 1238-47).*
Kita et al. (Blood. May 1, 1993; 81 (9): 2399-405).*
Inaba et al. (Br. J. Haematol. Jun. 2000; 109 (3): 592-9).*
Grada et al. (Mol. Ther. Nucleic Acids. Jul. 9, 2013; 2 (7): e105; pp. 1-11).*
Ye et al. (J. Immunol. Res. 2017; 2017: 5210459; pp. 1-13).*
Bridgeman et al. (J. Immunol. Jun. 15, 2010; 184 (12): 6938-49).*
Hudecek et al. (Clin. Cancer Res. Jun. 15, 2013; 19 (12): 3153-64).*
Kaleem et al. (Am. J. Clin. Pathol. Mar. 2001; 115 (3): 396-403).*
Nicholson et al. (Mol. Immunol. Nov.-Dec. 1997; 34 (16-17): 1157-65).*
Sotillo et al. (Cancer Discov. Dec. 2015; 5 (12): 1282-95).*
Betts et al. (Case Rep. Hematol. 2016; 2016: 5415974; pp. 1-4).*
Vassallo et al. (J. Clin. Pathol. May 2007; 60 (5): 573-5).*
Dwivedi et al. (Front. Immunol. Jan. 18, 2019; 9: 3180; pp. 1-9).*
Alabanza et al. (Mol. Ther. Nov. 1, 2017; 25 (11): 2452-65).*
Noyan et al. (Am. J. Transplant. Apr. 2017; 17 (4): 917-930).*
Valton et al. (Mol. Ther. Sep. 2015; 23 (9): 1507-18).*
Mamonkin et al. (Blood. Aug. 20, 2015; 126 (8): 983-92).*
Gomes-Silva et al. (Blood. Jul. 20, 2017; 130 (3): 285-96).*
Ren et al. (Clin. Cancer Res. May 1, 2017; 23 (9): 2255-66).*
Poirot et al. (Cancer Res. Sep. 15, 2015; 75 (18): 3853-64).*
Hedge et al. (J. Clin. Invest. Aug. 1, 2016; 126 (8): 3036-52).*
Pira et al. (Blood Rev. Jul. 2016; 30 (4): 297-307).*
Martyniszyn et al. (Hum. Gene Ther. Dec. 2017; 28 (12): 1147-57).*
Chmielewski et al. (Immunol. Rev. Jan. 2014; 257 (1): 83-90).*
Ridell et al. (Nat. Med. Feb. 1996; 2 (2): 216-23).*

(56) References Cited

OTHER PUBLICATIONS

Kochenderfer et al. (Blood. Mar. 22, 2012; 119 (12): 2709-20).*
Png et al. (Blood Adv. Nov. 28, 2017; 1 (25): 2348-60).*
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Winkler et al. (J. Immunol. Oct. 15, 2000; 165 (8): 4505-4514).*
Gerby et al. (Leukemia. Aug. 2011; 25 (8): 1249-58).*
Baum et al. (Br. J. Haematol. Nov. 1996; 95 (2): 327-38).*
Khurram et al. (Med. J. Islamic World Acad. Sci. 2010; 18 (2): 55-60).*
Manuri et al. (Hum. Gene Ther. Apr. 2010; 21 (4): 427-37).*
Cichocki et al. (Blood. Dec. 8, 2022; 140 (23): 2451-2462).*
Arslan et al. (Sci. Rep. Mar. 31, 2022; 12 (1): 5449; pp. 1-8).*
Bitra et al. (J. Biol. Chem. Feb. 8, 2019; 294 (6): 1831-45).*
Dai et al. (Signal Transduct. Target. Ther. Mar. 25, 2022; 7 (1): 85; pp. 1-12).*
Hu et al. (Cell Res. Nov. 2022; 32 (11): 995-1007).*
Ge et al. (Blood. 2021; 138: 1722-23).*
Arslan et al. (Sci. Rep. Mar. 31, 2022; 12 (1): 5449; pp. 1-8) (Year: 2022).*
Bitra et al. (J. Biol. Chem. Feb. 8, 2019; 294 (6): 1831-45) (Year: 2019).*
Dai et al. (Signal Transduct. Target. Ther. Mar. 25, 2022; 7 (1): 85; pp. 1-12) (Year: 2022).*
Hu et al. (Cell Res. Nov. 2022; 32 (11): 995-1007) (Year: 2022).*
Ge et al. (Blood. 2021; 138: 1722-23) (Year: 2021).*
"Adachi K, Kano Y, Nagai T, Okuyama N, Sakoda Y, Tamada K. IL-7 and CCL19 expression in CAR-T cells improves immune cell infiltration and CAR-T cell survival in the tumor. Nat Biotechnol. Apr. 2018;36(4):346-351. doi: 10.1038/nbt.4086. Epub Mar. 5, 2018. PMID: 29505028".
Alabanza, Leah et al. "Function of Novel Anti-CD19 Chimeric Antigen Receptors with Human Variable Regions Is Affected by Hinge and Transmembrane Domains." Molecular therapy : the journal of the American Society of Gene Therapy vol. 25,11 (2017): 2452-2465. doi:10.1016/j.ymthe.2017.07.013.
Bierer et al., Cyclosporin A and FK506: molecular mechanisms of immunosuppression and probes for transplantation biology, Curr. Opin. Immun 5:763-773, (1993).
"BioDrugs. Dec. 2017; 31(6): 473-481. doi: 10.1007/s40259-017-0247-0".
"Bonifant, et al., "Toxicity and management in CAR T-cell therapy" Molecular Therapy—Oncolytics (2016) 3, 16011".
Campbell et al.: Differential effects of CD4 and CD8 engagement on the development of cytokine profiles of murine CD4+ and CD8+ T lymphocytes. Immunology. 2000 99(3):394-401 doi:10.1046/j.1365-2567.2000.00971.x (2000).
Chmielewski et al.: Of CARs and TRUCKs: chimeric antigen receptor (CAR) T cells engineered with an inducible cytokine to modulate the tumor stroma. Immunol Rev. 257(1):83-90 doi:10.1111/imr.12125 (2014).
Clark et al.: Activation of rat T lymphocytes by anti-CD2 monoclonal antibodies. J Exp Med. 167(6):1861-1872 doi:10.1084/jem.167.6.1861 (1988).
Clement et al.: Anti-CD8 antibodies can trigger CD8+ T cell effector function in the absence of TCR engagement and improve peptide-MHCI tetramer staining. J Immunol. 187(2):654-663 doi:10.4049/jimmunol.1003941 (2011).
Cooper et al.: An Off-the-Shelf™ Fratricide-Resistant CAR-T for the Treatment of T Cell Hematologic Malignancies. Blood 130(Suppl. 1):844, pp1-3 (Abstract Only) doi:10.1182/blood.V130.Suppl_1.844.844 (2017).
Cooper et al.: An "off-the-shelf" fratricide-resistant CAR-T for the treatment of T cell hematologic malignancies. Leukemia 32(9):1970-1983 doi:10.1038/s41375-018-0065-5 (2018).
Diskin et al.: PD-L1 engagement on T cells promotes self-tolerance and suppression of neighboring macrophages and effector T cells in cancer. Nat Immunol. 21(4):442-454 doi:10.1038/s41590-020-0620-x (2020).
Feucht J, et al. Calibration of CAR activation potential directs alternative T cell fates and therapeutic potency. Nat Med. Jan. 2019;25(1):82-88. doi: 10.1038/s41591-018-0290-5. Epub Dec. 17, 2018. Erratum in: Nat Med. Mar. 2019;25(3):530. PMID: 30559421; PMCID: PMC6532069.
Fuchs et al.: A second combinatorial immune receptor in monocytes/macrophages is based on the TCRγσ [TCRgamma delta]. Immunobiology 218(7):960-968 doi:10.1016/j.imbio.2012.11.005 (2013).
Garcia et al.: Analysis of proliferative grade using anti-PCNA/cyclin monoclonal antibodies in fixed, embedded tissues. Comparison with flow cytometric analysis. Am J Pathol. 134(4):733-739 (1989).
Gracell Biotechnologies Inc. Press Release, pp. 1-2, dated Nov. 4, 2021.
"Graham, et al., "Allogeneic CAR-T Cells: More than Ease ofAccess?" (2018) Cells, 7, 155".
Hedge et al.: Tandem CAR T cells targeting HER2 and IL13Ra2 mitigate tumor antigen escape. J Clin Invest. 126(8):3036-3052 doi:10.1172/JCI83416 (2016).
Henderson et al., Comparison of the effects of FK-506, cyclosporin A and rapamycin on IL-2 production, Immun 73:316-321, (1991).
"Hoffman, et al., "Blinatumomab, a bi-spoecific anti-CD19/CD3 BiTE antibody for the treatment of accute lymphoblastic leukemia: perspectives and currect pediatric applications", (2014) Frontiers in Oncology, vol. 4, Article 63, p. 1-5".
"International Search Report and Written Opinion for corresponding PCT Application No. PCT/CN2019/123684 issued Mar. 10, 2020".
Jiang et al.: A novel peptide isolated from a phage display peptide library with trastuzumab can mimic antigen epitope of HER-2 *. J Biol Chem. 280(6):4656-4662 doi:10.1074/jbc.M411047200 (2005).
Kagoya et al.: A novel chimeric antigen receptor containing a JAK-STAT signaling domain mediates superior antitumor effects. Nat Med. 24(3):352-359 doi:10.1038/nm.4478 (2018).
Kaminski et al.: On the horizon: flexible immune recognition outside lymphocytes. Immunobiology 218(3):418-426 doi:10.1016/j.imbio.2012.05.024 (2013).
Kochenderfer et al: B-cell depletion and remissions of malignancy along with cytokine-associated toxicity in a clinical trial of anti-CD19 chimeric-antigen-receptor-transduced T cells. Blood 119(12):2709-2720 doi:10.1182/blood-2011-10-384388 (2012). Published online Dec. 8, 2011.
Kochenderfer et al., Donor-derived CD19-targeted T cells cause regression of malignancy persisting after allogeneic hematopoietic stem cell transplantation, Blood. 2013;122(25):4129-4139.
Li et al.: Design and synthesis of paclitaxel conjugated with an ErbB2-recognizing peptide, EC-1. Biopolymers87(4):225-230 doi:10.1002/bip.20828 (2007).
Liu et al. Calcineurin is a common target of cyclophilin-cyclosporin A and FKBP-FK506 complexes. Cell66:807-815 (1991).
Mahotka et al.: Alternative splicing of T cell receptor (TCR) alpha chain transcripts containing V alpha 1 or V alpha 14 elements. Leukemia 9(10):1700-1703 [Abstract only] (1995).
Martyniszyn et al.: CD20-CD19 Bispecific CAR T Cells for the Treatment of B-Cell Malignancies. Hum Gene Ther.28(12):1147-1157 doi:10.1089/hum.2017.126 (2017).
Nicholson et al., Construction and characterisation of a functional CD19 specific single chain Fv fragment for immunotherapy of B lineage leukaemia and lymphoma. Mol Immunol. Nov.-Dec. 1997;34(16-17):1157-65. doi: 10.1016/s0161-5890(97)00144-2. PMID: 9566763.
PCT/CN2019/114939 International Search Report and Written Opinion dated Jan. 23, 2020.
"PNAS Mar. 2, 2010 107 (9) 4275-4280; https://doi.org/10.1073/pnas.0915174107".
Png, et al., "Blockade of CD7 expression in T cells for effective chimeric antigen receptor targeting of T-cell malignancies", Blood Advances, vol. 1, No. 25, Nov. 28, 2017, pp. 2348-2360.
Poirot et al. Multiplex Genome-Edited T-cell Manufacturing Platform for Off-the-ShelfAdoptive T-cell Immunotherapies. Cancer Research 75(18):3853-3864 (2015).
Ren et al.: A versatile system for rapid multiplex genome-edited CAR T cell generation. Oncotarget 8(10):17002-17011 (2017).

(56) References Cited

OTHER PUBLICATIONS

Ren et al. Multiplex Genome Editing to Generate Universal Car T Cells Resistant to PD1 Inhibition. Clin Cancer Res. May 1, 2017;23(9):2255-2266. doi: 10.1158/1078-0432.CCR-16-1300. Epub Nov. 4, 2016.
Riddell et al.: T-cell mediated rejection of gene-modified HIV-specific cytotoxic T lymphocytes in HIV-infected patients. Nat Med. 2(2):216-223 doi: 10.1038/nm0296-216 (1996).
Riemer et al.: Matching of trastuzumab (Herceptin®) epitope mimics onto the surface of Her-2/neu—a new method of epitope definition. Mol. Immunol. 42:1121-1124 (2005).
Ruella et al.: Dual CD19 and CD123 targeting prevents antigen-loss relapses after CD19-directed immunotherapies. J Clin Invest. 126(10):3814-3826 doi:10.1172/JCI87366 (2016).
Shi et al.: Genome Editing and Directed Differentiation of hPSCs for Interrogating Lineage Determinants in Human Pancreatic Development. J Vis Exp. 121(55267)1-14 doi:10.3791/55267 (2017).
Shum et al.: Constitutive Signaling from an Engineered IL7 Receptor Promotes Durable Tumor Elimination by Tumor-Redirected T Cells. Cancer Discov. 7(11):1238-1247 doi:10.1158/2159-8290.CD-17-0538 (2017).
Stephens et al.: Engagement of glucocorticoid-induced TNFR family-related receptor on effector T cells by its ligand mediates resistance to suppression by CD4+CD25+ T cells. J Immunol. 173(8):5008-5020 doi:10.4049/jimmunol.173.8.5008 (2004).
Stillwell et al.: T cell signal transduction and the role of CD7 in costimulation. Immunol Res. 24(1):31-52 doi:10.1385/ir:24:1:31 (2001).
Tomonari et al.: Epitope-specific binding of CD8 regulates activation of T cells and induction of cytotoxicity. Int Immunol. 2(12):1189-1194 doi:10.1093/intimm/2.12.1189 (1990).
Torikai et al.: A foundation for universal T-cell based immunotherapy: T cells engineered to express a CD19-specific chimeric-antigen-receptor and eliminate expression of endogenous TCR. Blood 119(24):5697-5705 doi:10.1182/blood-2012-01-405365 (2012).
Torikai et al.: Toward eliminating HLA class I expression to generate universal cells from allogeneic donors. Blood 122(8):1341-1349 doi:10.1182/blood-2013-03-478255 (2013).
Ward et al.: Antibody ligation of CD7 leads to association with phosphoinositide 3-kinase and phosphatidylinositol 3,4,5-trisphosphate formation in T lymphocytes. Eur J Immunol. 25(2):502-507 doi:10.1002/eji.1830250229 (1995).
Woodbridge et al.: Anti-CD8 antibodies can inhibit or enhance peptide-MHC class I (pMHCI) multimer binding: this is paralleled by their effects on CTL activation and occurs in the absence of an interaction between pMHCI and CD8 on the cell surface. J Immunol. 171(12):6650-6660 doi:10.4049/jimmunol.171.12.6650 (2003).
"Yang, et al., "Clinical-scale lentiviral vector transduction of PBL for TCR gene therapy and potential for expression in less differentiated cells" (2008) J Immunother 31(9): 830-839".
Yang et al.: In vitro generated anti-tumor T lymphocytes exhibit distinct subsets mimicking in vivo antigen-experienced cells. Cancer Immunol Immunother. 60(5):739-749 doi:10.1007/s00262-011-0977-7 (2011).
"Yeku, O.O., Purdon, T.J., Koneru, M. et al. Armored CAR T cells enhance antitumor efficacy and overcome the tumor microenvironment. Sci Rep 7, 10541 (2017). https://doi.org/10.1038/s41598-017-10940-8".
Ying Z, et al. A safe and potent anti-CD19 CAR T cell therapy. Nat Med. Jun. 2019;25(6):947-953. doi: 10.1038/s41591-019-0421-7. Epub Apr. 22, 2019. PMID: 31011207; PMCID: PMC7518381.
Yong et al.: CAR T-cell therapy of solid tumors. Immunol Cell Biol. 95(4):356-363 doi:10.1038/icb.2016.128 (2017).
Zhang et al.: Recombination of a dual-CAR-modified T lymphocyte to accurately eliminate pancreatic malignancy. J Hematol Oncol. 11(1):102:1-14 doi:10.1186/s13045-018-0646-9 (2018).
Zheng et al.: Current situation and development trend of CAR-T in anti-tumor research. Journal of Shandong University(Health Sciences) 54(11):1-7 [English Abstract Only] doi:10.6040/j.issn.1671-7554.0.2016.835 (2016).
Zola et al., Preparation and characterization of a chimeric CD19 monoclonal antibody. Immunol Cell Biol. Dec. 1991;69 ( Pt 6):411-22. doi: 10.1038/icb.1991.58. PMID: 1725979.
Blaeschke et al.: Induction of a central memory and stem cell memory phenotype in functionally active CD4+ and CD8+ CAR T cells produced in an automated good manufacturing practice system for the treatment of CD19+ acute lymphoblastic leukemia. Cancer Immunol Immunother. 67(7):1053-1066. doi:10.1007/s00262-018-2155-7 (2018).
Campos-González et al.: Deterministic Lateral Displacement: The Next-Generation CAR T-Cell Processing? SLAS Technol. Aug. 2018;23(4):338-351. Epub Jan. 23, 2018.
Ghassemi et al.: Reducing Ex Vivo Culture Improves the Antileukemic Activity of Chimeric Antigen Receptor (CAR) T Cells. Cancer Immunol Res. 6(9):1100-1109. doi:10.1158/2326-6066.CIR-17-0405 (2018).
Sharma et al.: Automated Generation and Phenotypic Characterization of Clinical Grade CD19 CAR-T Cells. Blood. 132(Supplement_1):1675:1-3. doi:10.1182/blood-2018-99-120098 (2018).
Sun et al.: Early transduction produces highly functional chimeric antigen receptor-modified virus-specific T-cells with central memory markers: a Production Assistant for Cell Therapy (PACT) translational application. J Immunother Cancer. 3:5:1-17. doi:10.1186/s40425-015-0049-1 (2015).
Yang et al.: A Feasibility and Safety Study of a New CD19-Directed Fast CAR-T Therapy for Refractory and Relapsed B Cell Acute Lymphoblastic Leukemia. Blood. 134 (Supplement_1):825:1-4. doi:10.1182/blood-2019-121751 (2019).
Yang et al.: Successful 24-Hours Manufacture of Anti-CD19/CD22 Dual Chimeric Antigen Receptor (CAR) T Cell Therapy for B-Cell Acute Lymphoblastic Leukemia (B-ALL). vol. 136:(Supplement_1):2-3. doi:10.1182/blood-2020-136866 (2020).
Zhu et al.: Closed-system manufacturing of CD19 and dual-targeted CD20/19 chimeric antigen receptor T cells using the CliniMACS Prodigy device at an academic medical center. Cytotherapy. 20(3):394-406. doi:10.1016/j.jcyt.2017.09.005 (2018).
Wang; Xiuli et al.: Phenotypic and Functional Attributes of Lentivirus Modified CD19-specific Human CD8+ Central Memory T Cells Manufactured at Clinical Scale. J Immunother. 35(9):689-701 (2012). doi: 10.1097/CJI.0b013e318270dec7.
Georgiadis, C., et al., "Long Terminal Repeat CRISPR-CAR-Coupled 'Universal' T Cells Mediate Potent Anti-leukemic Effects," Mol Ther 26(5):1215-1227, Cell Press, United States (May 2018).

* cited by examiner

*FIG. 13*
0
250
500
750
800
Kidney.1
Tonsil.1
Lymphnode.1
Thymus.1
Bonemarrow.1
Adrenalgland.1
AdrenalCortex.1
OlfactoryBulb.1
Trachea.1
Salivarygland.1
Pituitary.1
Fetalliver.1
Fetallung.1
FetalThyroid.1
Uterus.1
Adipocyte.1
Pancreaticlslet.1
Pancreas.1
TestisSeminiferousTubule.1
TestisLeydigCell.1
TestisIntersitial.1
TestisGermCell.1
Testis.1
Colorectaladenocarcinoma.1
BronchialEpithelialCells.1
SmoothMuscle.1
CardiacMyocytes.1
Leukemialymphoblastic(MOLT-4).1
Leukemia_chronicMyelogenousK-562.1
Lymphoma_burkitts(Daudi).1
Leukemia_promyelocytic-HL-60.1
Lymphoma_burkitts(Raji).1
Thyroid.1
Prostate.1
Lung.1
Placenta.1
CD71+_EarlyErythroid.1
Small_intestine.1
Colon.1
Liver.1
Heart.1
UterusCorpus.1
Appendix.1
Ovary.1
DorsalRootGanglion.1
CiliaryGanglion.1
AtrioventricularNode.1
Skin.1
TrigeminalGanglion.1
SuperiorCervicalGanglion.1
Tongue.1
SkeletalMuscle.1
Retina.1
Pineal_night.1
Pineal_day.1
WholeBrain.1
Amygdala.1
PrefrontalCortex.1
Spinalcord.1
Hypothalamus.1
Fetalbrain.1
Thalamus.1
Caudatenucleus.1
ParietalLobe.1
MedullaOblongata.1
CingulateCortex.1
OccipitalLobe.1
TemporalLobe.1
SubthalamicNucleus.1
Pons.1
GlobusPallidus.1
Cerebellum.1
CerebellumPeduncles.1
CD34+.1
CD105+_Endothelial.1
721_B_lymphoblasts.1
CD19+_BCells(neg._sel.).1
BDCA4+_DentriticCells.1
CD8+_Tcells.1
CD4+_Tcells.1
CD56+_NKCells.1
CD33+_Myeloid.1
CD14+_Monocytes.1
WholeBlood.1
Median(6.3)
3xM
10xM
30xM

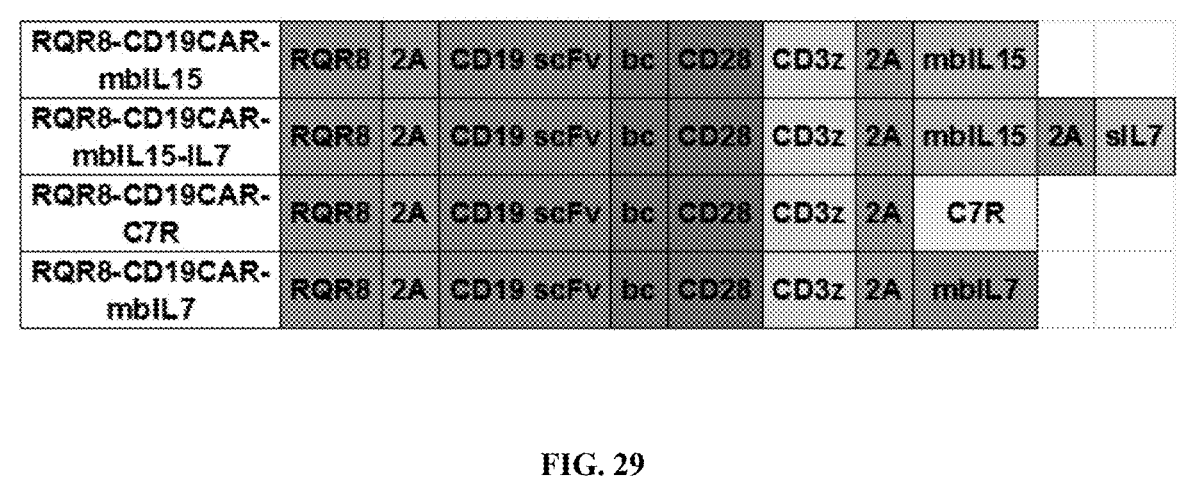

| | | | | | | | | | | |
|---|---|---|---|---|---|---|---|---|---|---|
| RQR8-CD19CAR-mbIL15 | RQR8 | 2A | CD19 scFv | bc | CD28 | CD3z | 2A | mbIL15 | | |
| RQR8-CD19CAR-mbIL15-IL7 | RQR8 | 2A | CD19 scFv | bc | CD28 | CD3z | 2A | mbIL15 | 2A | sIL7 |
| RQR8-CD19CAR-C7R | RQR8 | 2A | CD19 scFv | bc | CD28 | CD3z | 2A | C7R | | |
| RQR8-CD19CAR-mbIL7 | RQR8 | 2A | CD19 scFv | bc | CD28 | CD3z | 2A | mbIL7 | | |

FIG. 29

| gRNA | CD2-1 | CD2-2 | CD2-3 | CD2-4 |
|---|---|---|---|---|
| Knockout % | 0 | 68 | 3 | 1 |

COMPOSITIONS AND METHODS FOR T CELL ENGINEERING

CROSS-REFERENCE

This application is a divisional of U.S. patent application Ser. No. 17/246,394, filed Apr. 30, 2021 (abandoned after filing of the instant divisional application), which is a continuation application which claims priority to International Application No. PCT/CN2019/114939, filed Nov. 1, 2019, which claims priority to Chinese Patent Application No. 201811297174.3, filed Nov. 1, 2018; Chinese Patent Application No. 201811535338.1, filed Dec. 14, 2018; Chinese Patent Application No. 201811549651.0, filed Dec. 18, 2018; Chinese Patent Application No. 201910492882.0, filed Jun. 6, 2019; and International Application No. PCT/CN2019/101651, filed Aug. 20, 2019, each of which is entirely incorporated herein by reference.

SEQUENCE LISTING

The instant application contains a Sequence Listing which has been submitted electronically in XML file format and is hereby incorporated by reference in its entirety. Said XML copy, created on Aug. 23, 2022, is named 56758-702.401-SL.xml and is 160,038 bytes in size.

BACKGROUND

The generation of tumor-specific T lymphocytes by genetic modification to express chimeric antigen receptors (CARs) is gaining traction as a form of synthetic biology generating powerful antitumor effects. Because the specificity is conferred by antibody fragments, the CAR-T cells are not MHC restricted and are therefore more practical than approaches based on T-cell receptors that require MHC matching.

Although early CAR-T cell clinical data obtained in the treatment of cancer have shown promising results, the risk to patients is higher, and some patients' T cells are effective even after TCR or CAR redirection. Treatment is also not sufficiently effective, which promotes the modification of allogeneic donor T cells. However, endogenous αβ T cell receptors on infused allogeneic T cells can recognize primary and secondary histocompatibility antigens in the recipient, which results in graft versus host disease (GVHD). As a result, most current clinical trials using autologous CAR-T cell infusion rely on immune tolerance to prevent TCR-mediated deleterious recognition of normal tissues following adoptive cell transfer. This approach has achieved early clinical success, but is limited by the time and expense of manufacturing patient-specific T cell products.

SUMMARY

Recognized herein is a need for compositions and methods for genetically modifying immune cells (e.g., T cells) for allogeneic cell therapy. Also recognized herein is a need for methods of modifying immune cells (e.g., T cells) while circumventing the time and expense of making patient-specific T cell products.

In an aspect, the present disclosure provides an engineered immune cell, comprising: a chimeric polypeptide comprising (i) an enhancer moiety capable of enhancing one or more activities of the engineered immune cell, and (ii) an inducible cell death moiety capable of effecting death of the engineered immune cell upon contacting the chimeric polypeptide with a cell death activator, wherein the enhancer moiety is linked to the inducible cell death moiety, and one or more chimeric polypeptide receptors (CPRs) comprising a binding moiety, wherein the binding moiety comprises (i) a first antigen binding domain, which first antigen binding domain suppresses or reduces a subject's immune response toward the engineered immune cell when administered into the subject and (ii) a second antigen binding domain capable of binding to a disease-associated antigen, wherein an individual CPR of the one or more CPRs comprises (i) the first antigen binding domain, (ii) the second antigen binding domain, or (iii) both the first antigen binding domain and the second antigen binding domain, wherein each CPR of the one or more CPRs further comprises a transmembrane domain and an intracellular signaling domain.

In some embodiments, the one or more CPRs are one or more chimeric antigen receptor (CARs) or engineered T cell receptors (TCRs). In some embodiments, the first antigen binding domain binds to an immune cell antigen. In some embodiments, a gene encoding an endogenous surface marker of the engineered immune cell is inactivated (e.g., silenced or knocked out), wherein the endogenous surface marker is capable of binding to the first antigen binding domain when expressed. In some embodiments, an endogenous T cell receptor (TCR) of the engineered immune cell is inactivated. In some embodiments, a function of the endogenous TCR of the engineered immune cell is inhibited by an inhibitor. In some embodiments, a gene encoding a subunit of the endogenous TCR is inactivated such that the endogenous TCR is inactivated. In some embodiments, the gene encoding the subunit is TCRα, TCRβ, CD3ε, CD3δ, CD3γ, or CD3ζ. In some embodiments, the chimeric polypeptide does not comprise any self-cleaving peptide flanked by the enhancer moiety and the inducible cell death moiety. In some embodiments, the enhancer moiety is configured to constitutively enhance the one or more activities of the engineered immune cell. In some embodiments, the enhancer moiety is configured to constitutively upregulate one or more intracellular signaling pathways of the engineered immune cell. In some embodiments, the one or more intracellular signaling pathways are one or more cytokine signaling pathways. In some embodiments, the enhancer moiety is self-activating through self-oligomerizing. In some embodiments, the enhancer moiety is self-activating through self-dimerizing. In some embodiments, the chimeric polypeptide is a secreted protein. In some embodiments, the chimeric polypeptide is an intracellular protein. In some embodiments, the chimeric polypeptide is a transmembrane protein. In some embodiments, the enhancer moiety or the inducible cell death moiety is contained in an ectodomain of the transmembrane protein. In some embodiments, the enhancer moiety or the inducible cell death moiety is contained in an endodomain of the transmembrane protein. In some embodiments, (i) the enhancer moiety is contained in an endodomain of the transmembrane protein and (ii) the inducible cell death moiety are contained in an ectodomain of the transmembrane protein. In some embodiments, (i) the enhancer moiety is contained in an ectodomain of the transmembrane protein, and (ii) the inducible cell death moiety is contained in an endodomain of the transmembrane protein. In some embodiments, the enhancer moiety is a cytokine or a cytokine receptor. In some embodiments, the enhancer moiety is selected from the group consisting of IL-2, IL-3, IL-4, IL-6, IL-7, IL-8, IL-10, IL-11, IL-12, IL-15, IL-17, IL-18, IL-21, IL-23, PD-1, PD-L1, CD122, CSF1R, CTAL-4, TIM-3, CCL21, CCL19, TGFR beta, receptors for the same, functional fragments thereof, functional variants thereof, and combinations thereof. In some embodiments, the enhancer moiety functions as a trans-activating factor or a cis-activating factor. In some embodiments, the inducible cell death moiety is selected from the group consisting of rapaCasp9, iCasp9, HSV-TK, ΔCD20, mTMPK, ΔCD19, RQR8, Her2t, CD30, BCMA and EGFRt. In some embodiments, the inducible cell death moiety is EGFRt, and the cell death activator is an antibody or an antigen binding fragment thereof that binds EGFRt. In some embodiments, the inducible cell death moiety is HSV-TK, and the cell death activator is GCV. In some embodiments, the inducible cell death moiety is iCasp9, and the cell death activator is AP1903. In some embodiments, the cell death activator comprises a nucleic acid, a polynucleotide, an amino acid, a polypeptide, lipid, a carbohydrate, a small molecule, an enzyme, a ribosome, a proteasome, a variant thereof, or any combination thereof. In some embodiments, the individual CPR of the one or more CPRs comprises both the first antigen binding domain and the second antigen binding domain. In some embodiments, the first antigen binding domain and the second antigen binding domain is linked via a linker. In some embodiments, the linker does not comprise a self-cleaving peptide. In some embodiments, the first antigen binding domain or the second antigen binding is a scFv. In some embodiments, the first antigen binding domain and the second antigen binding domain is arranged, from amino terminus to carboxyl terminus, as: (i) VL2-VH1-VL1-VH2; (ii) VH2-VL1-VH1-VL2; (iii) VL1-VH2-VL2-VH1; (iv) VH1-VL2-VH2-VL1; (v) VL2-VL1-VH1-VH2; (vi) VH2-VH1-VL1-VL2; (vii) VL1-VL2-VH2-VH1; or (viii) VH1-VH2-VL2-VL1; wherein VH1 is heavy chain variable domain of the first antigen binding domain, VL1 is light chain variable light domain of the first antigen binding domain, VH2 is heavy chain variable domain of the second antigen binding domain, and VL2 is light chain variable domain of the second antigen binding domain. In some embodiments, the first antigen binding domain and the second antigen binding domain is arranged, from amino terminus to carboxyl terminus, as: (i) VL2-VH2-VL1-VH1; (ii) VL2-VH2-VH1-VL1; (iii) VL1-VH1-VL2-VH2; (iv) VL1-VH1-VH2-VL2; (v) VH2-VL2-VL1-VH1; (vi) VH2-VL2-VH1-VL1; (vii) VH1-VL1-VL2-VH2; or (viii) VH1-VL1-VH2-VL2, wherein VH1 is heavy chain variable domain of the first antigen binding domain, VL1 is light chain variable light domain of the first antigen binding domain, VH2 is heavy chain variable domain of the second antigen binding domain, and VL2 is light chain variable domain of the second antigen binding domain. In some embodiments, the first antigen binding domain and the second antigen binding domain bind to the immune cell antigen and the disease-associated antigen. In some embodiments, the individual CPR of the one or more CPRs comprises only the first antigen binding domain and an additional individual CPR of the one or more CPRs comprises only the second antigen binding domain. In some embodiments, the immune cell antigen is a surface protein or a secreted protein of an immune cell. In some embodiments, the immune cell is an NK cell, a T cell, a monocyte, an innate lymphocyte, a macrophage or a granulocyte. In some embodiments, the immune cell is obtained from peripheral blood, cord blood, or is derived from a stem cell. In some embodiments, the immune cell antigen is selected from the group consisting of CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ and SLAMF7. In some embodiments, the disease-associated antigen is a tumor-associated antigen. In some embodiments, the tumor-associated antigen is CD19, CD2, CD3, CD4, CD5, CD7, CD8, CD19, CD20, CD22, CD25, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, RORl, TNFRSF4, TWEAK-R, LTPR, LIFRP, LRP5, MUC1, MUC16, TCRα, TCRb, TLR7, TLR9, PTCH1, WT-1, Robol, Frizzled, OX40, Notch-1-4, APRIL, CS1, MAGE3, Claudin 18.2, Folate receptor α, Folate receptor β, GPC2, CD70, BAFF-R or TROP-2. In some embodiments, the first antigen binding domain binds to an immune cell antigen selected from the group consisting of CD2, CD3, CD5, CD7 and CD137, and the second antigen binding domain binds to CD19. In some embodiments, the first antigen binding domain binds to CD3, and the second antigen binding domain binds to CD19. In some embodiments, the first antigen binding domain binds to CD7, and the second antigen binding domain binds to CD19. In some embodiments, the first antigen binding domain binds to CD137, and the second antigen binding domain binds to CD19. In some embodiments, expression of one or more endogenous human leukocyte antigen (HLA) genes of the engineered immune cell remains intact. In some embodiments, expression of endogenous HLA-I and/or HLA-II genes of the engineered immune cell remains intact. In some embodiments, expression of endogenous HLA-E and/or HLA-G and/or HLA-C genes of the engineered immune cell remains intact. In some embodiments, expression of one or more endogenous HLA genes of the engineered immune cell is upregulated. In some embodiments, expression of endogenous HLA-E and/or HLA-G and/or HLA-C genes of the engineered immune cell is upregulated. In some embodiments, expression of an endogenous HLA-I, an endogenous HLA-II, or both of the engineered immune cell is inhibited. In some embodiments, a gene encoding endogenous HLA-I, endogenous HLA-II, or both is inactivated. In some embodiments, HLA-E or HLA-G of the engineered immune cell is overexpressed. In some embodiments, CD24, CD47, FASL and/or PD-1 of the engineered immune cell is overexpressed. In some embodiments, the engineered immune cell is a T cell, an NKT cell or an NK cell. In some embodiments, the engineered immune cell is derived from a stem cell. In some embodiments, the stem cell is a hematopoietic stem cell (HSC) or an induced pluripotent stem cell (iPSC). In some embodiments, the engineered immune cell is an autologous cell or an allogeneic cell. In some embodiments, the engineered immune cell is obtained from a subject having a condition. In some embodiments, the engineered immune cell is obtained from a healthy donor.

In another aspect, the present disclosure provides an engineered immune cell, comprising: (a) one or more chimeric antigen receptors (CARs) comprising a binding moiety, wherein the binding moiety comprises a first antigen binding domain capable of binding to an immune cell antigen and a second antigen binding domain capable of binding to a disease-associated antigen, and wherein each CAR of the one or more CARs further comprises a transmembrane domain and an intracellular signaling domain; and (b) an enhancer moiety capable of enhancing one or more activities of the engineered immune cell, wherein an endogenous T cell receptor (TCR) of the engineered immune cell is inactivated, and wherein the engineered immune cell exhibits (i) enhanced degree of persistence by remaining viable in vitro for at least about 20 days while in presence of cells that are heterologous to the engineered immune cell, (ii) enhanced degree of expansion by at least about 10-fold within 15 days, or (iii) enhanced cytotoxicity against a target cell comprising the immune cell antigen or the disease-associated antigen, compared to an additional engineered immune cell comprising the one or more CARs in (a) but not the enhancer moiety in (b).

In some embodiments, the engineered immune cell is characterized by exhibiting two or more of (i), (ii), and (iii). In some embodiments, (i), (ii), and/or (iii) is measured in absence of any exogenous enhancer moiety. In some embodiments, the immune cell antigen is selected from the group consisting of CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD160, CD161 CD178, CD218, CD226, CD244, CD159a (NKG2A), CD159c (NKG2C), NKG2E, CD314 (NKG2D), CD305, CD335 (NKP46), CD337, CST, TCRα, TCRβ, and SLAMF7. In some embodiments, the immune cell antigen is CD7. In some embodiments, the enhancer moiety is configured to constitutively enhance the one or more activities of the engineered immune cell. In some embodiments, the enhancer moiety is configured to constitutively upregulate one or more intracellular signaling pathways of the engineered immune cell. In some embodiments, the one or more intracellular signaling pathways are one or more cytokine signaling pathways. In some embodiments, the enhancer moiety is self-activating through self-oligomerizing. In some embodiments, the enhancer moiety is self-activating through self-dimerizing. In some embodiments, the enhancer moiety is a cytokine or a cytokine receptor. In some embodiments, the enhancer moiety is selected from the group consisting of IL-2, IL-3, IL-4, IL-6, IL-7, IL-8, IL-10, IL-11, IL-12, IL-15, IL-17, IL-18, IL-21, IL-23, PD-1, PD-L1, CD122, CSF1R, CTAL-4, TIM-3, CCL21, CCL19, TGFR beta, receptors for the same, functional fragments thereof, functional variants thereof, and combinations thereof. In some embodiments, a gene encoding a subunit of the endogenous TCR is inactivated such that the endogenous TCR is inactivated. In some embodiments, the gene encoding the subunit is TCRα, TCRβ, CD3ε, CD3δ, CD3γ, or CD3ζ. In some embodiments, the engineered immune cell further comprises an inducible cell death moiety, which inducible cell death moiety effects suicide of the engineered immune cell upon contact with a cell death activator. In some embodiments, the inducible cell death moiety is selected from the group consisting of rapaCasp9, iCasp9, HSV-TK, ΔCD20, mTMPK, ΔCD19, RQR8, Her2t, CD30, BCMA, and EGFRt. In some embodiments, the inducible cell death moiety is EGFRt, and the cell death activator is an antibody or an antigen binding fragment thereof that binds EGFRt. In some embodiments, the inducible cell death moiety is HSV-TK, and the cell death activator is GCV. In some embodiments, the inducible cell death moiety is iCasp9, and the cell death activator is AP1903. In some embodiments, the cell death activator comprises a nucleic acid, a polynucleotide, an amino acid, a polypeptide, lipid, a carbohydrate, a small molecule, an enzyme, a ribosome, a proteasome, a variant thereof, or any combination thereof. In some embodiments, expression of one or more endogenous human leukocyte antigen (HLA) genes of the engineered immune cell remains intact. In some embodiments, expression of endogenous HLA-I and/or HLA-II genes of the engineered immune cell remains intact. In some embodiments, expression of endogenous HLA-E and/or HLA-G and/or HLA-C genes of the engineered immune cell remains intact. In some embodiments, expression of one or more endogenous HLA genes of the engineered immune cell is upregulated. In some embodiments, expression of endogenous HLA-E and/or HLA-G and/or HLA-C genes of the engineered immune cell is upregulated. In some embodiments, expression of an endogenous HLA-I, an endogenous HLA-II, or both of the engineered immune cell is inhibited. In some embodiments, a gene encoding endogenous HLA-I, endogenous HLA-II, or both is inactivated. In some embodiments, HLA-E or HLA-G of the engineered immune cell is overexpressed. In some embodiments, CD24, CD47, FASL and/or PD-1 of the engineered immune cell is overexpressed. In some embodiments, the disease-associated antigen is a tumor-associated antigen. In some embodiments, the first antigen binding domain or the second antigen binding domain is a scFv. In some embodiments, a gene encoding an endogenous surface marker of the engineered immune cell is inactivated, wherein the endogenous surface marker is capable of binding to the first antigen binding domain when expressed. In some embodiments, the endogenous surface marker is CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ or SLAMF7. In some embodiments, the engineered immune cell is a T cell, an NKT cell or an NK cell. In some embodiments, the engineered immune cell is derived from a stem cell. In some embodiments, the stem cell is a hematopoietic stem cell (HSC) or an induced pluripotent stem cell (iPSC). In some embodiments, the engineered immune cell is an autologous cell or an allogeneic cell. In some embodiments, the engineered immune cell is obtained from a subject having a condition. In some embodiments, the engineered immune cell is obtained from a healthy donor.

In another aspect, the present disclosure provides a pharmaceutical composition for treating a disease, comprising the engineered immune cell described herein, and a pharmaceutically acceptable carrier. In another aspect, the present disclosure provides a method of treating or diagnosing a disease in a subject, comprising administering the pharmaceutical composition to the subject. In some embodiments, the engineered immune cell in the pharmaceutical composition is derived from an allogeneic immune cell. In some embodiments, the engineered immune cell derived from the allogeneic immune cell does not induce graft versus host disease (GvHD) in the subject. In some embodiments, the engineered immune cell in the pharmaceutical composition is derived from an autologous immune cell. In some embodiments, an endogenous TCR of the engineered immune cell in the pharmaceutical composition is functionally inactive. In some embodiments, the engineered immune cell reduces GvHD in the subject compared to an additional immune cell having a functionally active TCR. In some embodiments, the disease is a cancer. In some embodiments, the cancer is lymphoma or leukemia.

In another aspect, the present disclosure provides a cell, comprising: a functionally inactive T cell receptor (TCR), and one or more chimeric antigen receptors (CARs), wherein each individual CAR of the one or more CARs comprises a binding moiety, which binding moiety comprises (i) a first antigen binding domain, which first antigen binding domain suppresses or reduces a subject's immune response toward the engineered immune cell when administered into the subject and (ii) a second antigen binding domain that binds to a disease-associated antigen, and wherein each CAR of the one or more CARs further comprises a transmembrane domain and an intracellular signaling domain.

In some embodiments, the first antigen binding domain and the second antigen binding domain is linked by a linker. In some embodiments, the linker does not comprise a self-cleaving peptide. In some embodiments, the first antigen binding domain and the second antigen binding domain is arranged, from amino terminus to carboxyl terminus, as: (i) VL2-VH1-VL1-VH2; (ii) VH2-VL1-VH1-VL2; (iii) VL1-VH2-VL2-VH1; (iv) VH1-VL2-VH2-VL1; (v) VL2-VL1-VH1-VH2; (vi) VH2-VH1-VL1-VL2; (vii) VL1-VL2-VH2-VH1; or (viii) VH1-VH2-VL2-VL1, wherein VH1 is heavy chain variable domain of the first antigen binding domain, VL1 is light chain variable light domain of the first antigen binding domain, VH2 is heavy chain variable domain of the second antigen binding domain, and VL2 is light chain variable domain of the second antigen binding domain. In some embodiments, the first antigen binding domain and the second antigen binding domain is arranged, from amino terminus to carboxyl terminus, as: (i) VL2-VH2-VL1-VH1; (ii) VL2-VH2-VH1-VL1; (iii) VL1-VH1-VL2-VH2; (iv) VL1-VH1-VH2-VL2; (v) VH2-VL2-VL1-VH1; (vi) VH2-VL2-VH1-VL1; (vii) VH1-VL1-VL2-VH2; or (viii) VH1-VL1-VH2-VL2, wherein VH1 is heavy chain variable domain of the first antigen binding domain, VL1 is light chain variable light domain of the first antigen binding domain, VH2 is heavy chain variable domain of the second antigen binding domain, and VL2 is light chain variable domain of the second antigen binding domain. In some embodiments, a gene encoding a subunit of an endogenous TCR of the cell is inactivated, thereby generating the functionally inactive TCR. In some embodiments, the gene encoding the subunit is TCRα, TCRβ, CD3ε, CD3δ, CD3γ, or CD3ζ. In some embodiments, the first antigen binding domain binds to an immune cell antigen. In some embodiments, the immune cell antigen is a surface protein or a secreted protein of an immune cell. In some embodiments, the immune cell is an NK cell, a T cell, a monocyte, a macrophage, or a granulocyte. In some embodiments, the immune cell antigen is CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ or SLAMF7. In some embodiments, the disease-associated antigen is a tumor-associated antigen. In some embodiments, the tumor-associated antigen is CD19, CD2, CD3, CD4, CD5, CD7, CD8, CD19, CD20, CD22, CD25, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, RORl, TNFRSF4, TWEAK-R, LTPR, LIFRP, LRP5, MUC1, MUC16, TCRα, TCRb, TLR7, TLR9, PTCH1, WT-1, Robol, Frizzled, OX40, Notch-1-4, APRIL, CS1, MAGE3, Claudin 18.2, Folate receptor α, Folate receptor β, GPC2, CD70, BAFF-R or TROP-2. In some embodiments, the first antigen binding domain binds to an immune cell antigen selected from the group consisting of CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ and SLAMF7, and the second antigen binding domain binds to CD19. In some embodiments, the first antigen binding domain binds to CD3, and the second antigen binding domain binds to CD19. In some embodiments, the first antigen binding domain binds to CD7, and the second antigen binding domain binds to CD19. In some embodiments, the first antigen binding domain binds to CD137, and the second antigen binding domain binds to CD19. In some embodiments, the cell further comprises an enhancer moiety, which enhancer moiety enhances one or more activities of the engineered immune cell. In some embodiments, the enhancer moiety is configured to constitutively enhance the one or more activities of the engineered immune cell. In some embodiments, the enhancer moiety is configured to constitutively upregulate one or more intracellular signaling pathways of the engineered immune cell. In some embodiments, the one or more intracellular signaling pathways are one or more cytokine signaling pathways. In some embodiments, the enhancer moiety is a cytokine or a cytokine receptor. In some embodiments, the enhancer moiety is selected from the group consisting of IL-2, IL-3, IL-4, IL-6, IL-7, IL-8, IL-10, IL-11, IL-12, IL-15, IL-17, IL-18, IL-21, IL-23, PD-1, PD-L1, CD122, CSF1R, CTAL-4, TIM-3, CCL21, CCL19, TGFR beta, receptors for the same, functional fragments thereof, functional variants thereof, and combinations thereof. In some embodiments, the cell further comprises an inducible cell death moiety capable of effecting death of the cell upon contacting the inducible cell death moiety with a cell death activator. In some embodiments, the inducible cell death moiety is selected from the group consisting of rapaCasp9, iCasp9, HSV-TK, ΔCD20, mTMPK, ΔCD19, RQR8, Her2t, CD30, BCMA, and EGFRt. In some embodiments, the inducible cell death moiety is EGFRt, and the cell death activator is an antibody or an antigen binding fragment thereof that binds EGFRt. In some embodiments, the inducible cell death moiety is HSV-TK, and the cell death activator is GCV. In some embodiments, the inducible cell death moiety is iCasp9, and the cell death activator is AP1903.

In another aspect, the present disclosure provides a nucleic acid molecule comprising a first sequence encoding a chimeric antigen receptor (CAR), wherein the CAR comprises a binding moiety, which binding moiety comprises (i) a first antigen binding domain, which first antigen binding domain suppresses or reduces a subject's immune response toward the engineered immune cell when administered into the subject linked to (ii) a second antigen binding domain capable of binding to a disease-associated antigen, and wherein each CAR of the one or more CARs further comprises a transmembrane domain and an intracellular signaling domain.

In some embodiments, the first antigen binding domain binds to an antigen selected from the group consisting of CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ and SLAMF7. In some embodiments, the second antigen binding domain binds to CD19, CD2, CD3, CD4, CD5, CD7, CD8, CD19, CD20, CD22, CD25, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, RORl, TNFRSF4, TWEAK-R, LTPR, LIFRP, LRP5, MUC1, MUC16, TCRα, TCRb, TLR7, TLR9, PTCH1, WT-1, Robol, Frizzled, OX40, Notch-1-4, APRIL, CS1, MAGE3, Claudin 18.2, Folate receptor α, Folate receptor β, GPC2, CD70, BAFF-R or TROP-2. In some embodiments, the nucleic acid molecule further comprises a second sequence encoding an enhancer moiety, which enhancer moiety enhances one or more activities of the CAR when expressed in a cell. In some embodiments, the enhancer moiety is selected from the group consisting of IL-2, IL-3, IL-4, IL-6, IL-7, IL-8, IL-10, IL-11, IL-12, IL-15, IL-17, IL-18, IL-21, IL-23, PD-1, PD-L1, CD122, CSF1R, CTAL-4, TIM-3, CCL21, CCL19, TGFR beta, receptors for the same, functional fragments thereof, functional variants thereof, and combinations thereof. In some embodiments, the nucleic acid molecule further comprises a second sequence encoding an inducible cell death moiety, which inducible cell death moiety, when expressed in a cell, effects death of the cell upon contacting the inducible cell death moiety with a cell death activator. In some embodiments, the inducible cell death moiety is selected from the group consisting of rapaCasp9, iCasp9, HSV-TK, ΔCD20, mTMPK, ΔCD19, RQR8, Her2t, CD30, BCMA, and EGFRt. In some embodiments, the nucleic acid molecule further comprises a third sequence flanked by the first sequence and the second sequence, wherein the third sequence encodes a cleavable linker. In some embodiments, the cleavable linker is a self-cleaving peptide. In some embodiments, the nucleic acid molecule further comprises a regulatory sequence regulating expression of the first sequence and/or the second sequence.

In another aspect, the present disclosure provides a kit comprising a nucleic acid molecule described herein.

In another aspect, the present disclosure provides a method of generating an engineered cell, comprising (a) delivering the nucleic acid molecule described herein into a cell; and (b) expressing the nucleic acid molecule in the cell, thereby generating the engineered cell.

In another aspect, the present disclosure provides an engineered immune cell, comprising: an enhancer moiety capable of enhancing one or more activities of the engineered immune cell; a chimeric antigen receptor (CAR) comprising an antigen binding domain that specifically binds CD7, wherein the CAR further comprises a transmembrane domain and an intracellular signaling domain; wherein an endogenous CD7 in the engineered immune cell is inactivated. In some embodiments, the enhancer moiety is selected from the group consisting of IL-2, IL-7, IL-12, IL-15, IL-18, IL-21, PD-1, PD-L1, CSF1R, CTAL-4, TIM-3, CCL21, CCL19, and TGFR beta, receptors for the same, and a combination thereof. In some embodiments, an endogenous T cell receptor (TCR) of the engineered immune cell is inactivated. In some embodiments, the engineered immune cell further comprises a polypeptide that comprises an inducible cell death moiety capable of effecting death of the engineered immune cell upon contacting the polypeptide with a cell death activator. In some embodiments, the enhancer moiety is part of the polypeptide. In some embodiments, the enhancer moiety is not a part of the CAR. In some embodiments, the enhancer moiety is a part of the CAR. In some embodiments, the engineered immune cell is a T cell, an NKT cell or an NK cell. In some embodiments, the engineered immune cell is derived from a stem cell. In some embodiments, the stem cell is a hematopoietic stem cell (HSC) or an induced pluripotent stem cell (iPSC). In some embodiments, the engineered immune cell is an autologous cell or an allogeneic cell. In some embodiments, the engineered immune cell is obtained from a subject having a condition. In some embodiments, the engineered immune cell is obtained from a healthy donor.

In another aspect, the present disclosure provides a method of generating the engineered immune cell described herein, comprising (a) delivering one or more nucleic acid molecules encoding (i) the enhancer moiety and (ii) the CAR in to an immune cell; and (b) expressing the one or more nucleic acid molecules in the immune cell, thereby generating the engineered immune cell. In some embodiments, a single nucleic acid molecule encodes (i) the enhancer moiety and (ii) the CAR. In some embodiments, the single nucleic acid molecule comprises a self-cleaving peptide flanked by (i) the enhancer moiety and (ii) the CAR. In some embodiments, the single nucleic acid molecule does not comprise any self-cleaving peptide flanked by (i) the enhancer moiety and (ii) the CAR. In some embodiments, (i) a first nucleic acid molecule encodes the enhancer moiety and (ii) a second nucleic acid molecule encodes the CAR.

In another aspect, the present disclosure provides a method of treating or diagnosing a condition in a subject, comprising administering the engineered immune cell described herein to the subject. In some embodiments, the engineered immune cell is derived from an autologous immune cell of the subject. In some embodiments, the engineered immune cell is derived from an allogeneic immune cell. In some embodiments, the condition is cancer (e.g., T cell and/or NK cell malignancies).

In another aspect, the present disclosure provides an engineered immune cell, comprising: a single chimeric antigen receptor (CAR) comprising (i) a first antigen binding domain that specifically binds CD7 and (ii) a second antigen binding domain capable of binding to a disease-associated antigen, the CAR further comprises a transmembrane domain and an intracellular signaling domain, wherein a gene encoding endogenous CD7 is inactivated in the engineered immune cell. In some embodiments, the engineered immune further comprises an enhancer moiety capable of enhancing one or more activities of the engineered immune cell. In some embodiments, the enhancer moiety is selected from the group consisting of IL-2, IL-7, IL-12, IL-15, IL-18, IL-21, PD-1, PD-L1, CSF1R, CTAL-4, TIM-3, CCL21, CCL19, and TGFR beta, receptors for the same, and a combination thereof. In some embodiments, an endogenous T cell receptor (TCR) of the engineered immune cell is inactivated. In some embodiments, the engineered immune cell further comprises a polypeptide that comprises an inducible cell death moiety capable of effecting death of the engineered immune cell upon contacting the polypeptide with a cell death activator. In some embodiments, the enhancer moiety is part of the polypeptide. In some embodiments, the engineered immune cell is a T cell, an NKT cell or an NK cell. In some embodiments, the engineered immune cell is derived from a stem cell. In some embodiments, the stem cell is a hematopoietic stem cell (HSC) or an induced pluripotent stem cell (iPSC). In some embodiments, the engineered immune cell is an autologous cell or an allogeneic cell. In some embodiments, the engineered immune cell is obtained from a subject having a condition. In some embodiments, the engineered immune cell is obtained from a healthy donor.

In another aspect, the present disclosure provides a method of generating the engineered immune cell, comprising (a) delivering one or more nucleic acid molecules encoding the single CAR into an immune cell; and (b) expressing the one or more nucleic acid molecules in the immune cell, thereby generating the engineered immune cell. In some embodiments, a single nucleic acid molecule encodes the single CAR.

In another aspect, the present disclosure provides a method of treating or diagnosing a condition in a subject, comprising administering the engineered immune cell to the subject. In some embodiments, the engineered immune cell is derived from an autologous immune cell of the subject. In some embodiments, the engineered immune cell is derived from an allogeneic immune cell. In some embodiments, the condition is cancer (e.g., T cell and/or NK cell malignancies).

In another aspect, the present disclosure provides a method of delivering an allogeneic cell therapy comprising: administering to a subject in need thereof a population of engineered immune cells, an individual engineered immune cell of the population comprises: (a) one or more chimeric antigen receptors (CARs) comprising a binding moiety, wherein the binding moiety comprises a first antigen binding domain capable of binding to an immune cell antigen and a second antigen binding domain capable of binding to a disease-associated antigen, which first antigen binding domain suppresses or reduces a subject's immune response toward the engineered immune cell when administered into the subject; (b) an enhancer moiety capable of enhancing one or more activities of the engineered immune cell, wherein an endogenous T cell receptor (TCR) of the engineered immune cell is inactivated, and wherein the engineered immune cell exhibits (i) enhanced degree of persistence by remaining viable in vitro for at least about 20 days while in presence of cells that are heterologous to the engineered immune cell, (ii) enhanced degree of expansion by at least about 10-fold within 15 days, or (iii) enhanced cytotoxicity against a target cell comprising the immune cell antigen or the disease-associated antigen.

In some embodiments, the administering of the population of the engineered immune cells alone without the use of an additional proliferation agent yields (i) enhanced degree of persistence by remaining viable in vitro for at least about 20 days while in presence of immune cells that are heterologous to the engineered immune cell, (ii) enhanced degree of expansion by at least about 10-fold within 15 days, or (iii) enhanced cytotoxicity against a target cell comprising the immune cell antigen or the disease-associated antigen. In some embodiments, each CAR of the one or more CARs further comprises a transmembrane domain and an intracellular signaling domain, wherein the first antigen binding domain suppresses or reduces a subject's immune response toward the engineered immune cell when administered into the subject. In some embodiments, an endogenous CD7 of the individual engineered immune cell is inactivated. In some embodiments, the immune cell antigen is CD7.

In some embodiments, the enhancer moiety is configured to constitutively enhance the one or more activities of the individual engineered immune cell. In some embodiments, the enhancer moiety is configured to constitutively upregulate one or more intracellular signaling pathways of the engineered immune cell. In some embodiments, the one or more intracellular signaling pathways are one or more cytokine signaling pathways. In some embodiments, the enhancer moiety is self-activating through self-oligomerizing. In some embodiments, the enhancer moiety is self-activating through self-dimerizing. In some embodiments, the enhancer moiety is a cytokine or a cytokine receptor. In some embodiments, the enhancer moiety is selected from the group consisting of IL-2, IL-3, IL-4, IL-6, IL-7, IL-8, IL-10, IL-11, IL-12, IL-15, IL-17, IL-18, IL-21, IL-23, PD-1, PD-L1, CD122, CSF1R, CTAL-4, TIM-3, CCL21, CCL19, TGFR beta, receptors for the same, functional fragments thereof, functional variants thereof, and combinations thereof. In some embodiments, a gene encoding a subunit of the endogenous TCR is inactivated such that the endogenous TCR is inactivated. In some embodiments, the gene encoding the subunit is TCRα, TCRβ, CD3ε, CD3δ, CD3γ, or CD3ζ. In some embodiments, the individual engineered immune cell further comprises an inducible cell death moiety, which inducible cell death moiety effects suicide of the engineered immune cell upon contact with a cell death activator. In some embodiments, the inducible cell death moiety is selected from the group consisting of rapaCasp9, iCasp9, HSV-TK, ΔCD20, mTMPK, ΔCD19, RQR8, Her2t, CD30, BCMA, and EGFRt. In some embodiments, the inducible cell death moiety is EGFRt, and the cell death activator is an antibody or an antigen binding fragment thereof that binds EGFRt. In some embodiments, the inducible cell death moiety is HSV-TK, and the cell death activator is GCV. In some embodiments, the inducible cell death moiety is iCasp9, and the cell death activator is AP1903. In some embodiments, the cell death activator comprises a nucleic acid, a polynucleotide, an amino acid, a polypeptide, lipid, a carbohydrate, a small molecule, an enzyme, a ribosome, a proteasome, a variant thereof, or any combination thereof. In some embodiments, expression of one or more endogenous human leukocyte antigen (HLA) genes of the individual engineered immune cell remains intact. In some embodiments, expression of endogenous HLA-I and/or HLA-II genes of the individual engineered immune cell remains intact. In some embodiments, expression of endogenous HLA-E and/or HLA-G and/or HLA-C genes of the individual engineered immune cell remains intact. In some embodiments, expression of one or more endogenous HLA genes of the individual engineered immune cell is upregulated. In some embodiments, expression of endogenous HLA-E and/or HLA-G and/or HLA-C genes of the individual engineered immune cell is upregulated. In some embodiments, expression of an endogenous HLA-I, an endogenous HLA-II, or both of the individual engineered immune cell is inhibited. In some embodiments, a gene encoding endogenous HLA-I, endogenous HLA-II, or both is inactivated. In some embodiments, HLA-E or HLA-G of the engineered immune cell is overexpressed. In some embodiments, CD24, CD47, FASL and/or PD-1 of the engineered immune cell is overexpressed.

In some embodiments, the disease-associated antigen is a tumor-associated antigen. In some embodiments, the first antigen binding domain or the second antigen binding domain is a scFv. In some embodiments, the individual engineered immune cell is a T cell, an NKT cell or an NK cell. In some embodiments, the individual engineered immune cell is derived from a stem cell. In some embodiments, the stem cell is a hematopoietic stem cell (HSC) or an induced pluripotent stem cell (iPSC). In some embodiments, the individual engineered immune cell is an allogeneic cell. In some embodiments, the individual engineered immune cell is obtained from a healthy donor.

In an aspect, the present disclosure provides a cell comprising: (a) one or more chimeric antigen receptors (CARs) comprising a binding moiety, wherein the binding moiety comprises an antigen binding domain capable of binding to an immune cell antigen, and wherein each CAR of the one or more CARs further comprises a transmembrane domain and an intracellular signaling domain; and (b) an enhancer moiety capable of enhancing one or more activities of the cell, wherein an endogenous T cell receptor (TCR) of the cell is inactivated.

In some embodiments, the enhancer moiety enhances one or more activities of the cell. In some embodiments, the enhancer moiety is configured to constitutively enhance the one or more activities of the cell. In some embodiments, the enhancer moiety is configured to constitutively upregulate one or more intracellular signaling pathways of the cell. In some embodiments, the one or more intracellular signaling pathways are one or more cytokine signaling pathways. In some embodiments, the enhancer moiety is a cytokine or a cytokine receptor. In some embodiments, the enhancer moiety is selected from the group consisting of IL-2, IL-3, IL-4, IL-6, IL-7, IL-8, IL-10, IL-11, IL-12, IL-15, IL-17, IL-18, IL-21, IL-23, PD-1, PD-L1, CD122, CSF1R, CTAL-4, TIM-3, CCL21, CCL19, TGFR beta, receptors for the same, functional fragments thereof, functional variants thereof, and combinations thereof. In some embodiments, the method further comprises an inducible cell death moiety capable of effecting death of the cell upon contacting the inducible cell death moiety with a cell death activator. In some embodiments, the inducible cell death moiety is selected from the group consisting of rapaCasp9, iCasp9, HSV-TK, ΔCD20, mTMPK, ΔCD19, RQR8, Her2t, CD30, BCMA, and EGFRt. In some embodiments, the inducible cell death moiety is EGFRt, and the cell death activator is an antibody or an antigen binding fragment thereof that binds EGFRt. In some embodiments, the inducible cell death moiety is HSV-TK, and the cell death activator is GCV. In some embodiments, the inducible cell death moiety is iCasp9, and the cell death activator is AP1903. In some embodiments, a gene encoding an endogenous surface marker of the cell is inactivated, wherein the endogenous surface marker is capable of binding to the first antigen binding domain when expressed. In some embodiments, the endogenous surface marker is CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ or SLAMF7.

In an aspect, the present disclosure provides a method for treating a lymphoid malignancy, comprising administering to a patient in need thereof a population of engineered immune cells, wherein an individual engineered immune cell of the population comprises: (a) one or more chimeric antigen receptors (CARs) comprising a binding moiety, wherein the binding moiety comprises an antigen binding domain capable of binding to an immune cell antigen, and wherein each CAR of the one or more CARs further comprises a transmembrane domain and an intracellular signaling domain; and (b) an enhancer moiety capable of enhancing one or more activities of the engineered immune cell, wherein an endogenous T cell receptor (TCR) of the engineered immune cell is inactivated, wherein (i) the number of affected cells in peripheral blood or the number of affected cells in bone marrow is reduced by at least 50% within 3 weeks after a last dosing of the engineered immune cells, and (ii) the number of any one or more of autologous T cell, granulocyte, and NK cell in peripheral blood starts to increase within 3 weeks after a last dosing of the engineered immune cells.

In some embodiments, the enhancer moiety enhances one or more activities of the engineered immune cell. In some embodiments, the enhancer moiety is configured to constitutively enhance the one or more activities of the engineered immune cell. In some embodiments, the enhancer moiety is configured to constitutively upregulate one or more intracellular signaling pathways of the engineered immune cell. In some embodiments, the one or more intracellular signaling pathways are one or more cytokine signaling pathways. In some embodiments, the enhancer moiety is a cytokine or a cytokine receptor. In some embodiments, the enhancer moiety is selected from the group consisting of IL-2, IL-3, IL-4, IL-6, IL-7, IL-8, IL-10, IL-11, IL-12, IL-15, IL-17, IL-18, IL-21, IL-23, PD-1, PD-L1, CD122, CSF1R, CTAL-4, TIM-3, CCL21, CCL19, TGFR beta, receptors for the same, functional fragments thereof, functional variants thereof, and combinations thereof. In some embodiments, the engineered immune cell further comprises an inducible cell death moiety capable of effecting death of the cell upon contacting the inducible cell death moiety with a cell death activator.

In some embodiments, the inducible cell death moiety is selected from the group consisting of rapaCasp9, iCasp9, HSV-TK, ΔCD20, mTMPK, ΔCD19, RQR8, Her2t, CD30, BCMA, and EGFRt. In some embodiments, the inducible cell death moiety is EGFRt, and the cell death activator is an antibody or an antigen binding fragment thereof that binds EGFRt. In some embodiments, the inducible cell death moiety is HSV-TK, and the cell death activator is GCV. In some embodiments, the inducible cell death moiety is iCasp9, and the cell death activator is AP1903. In some embodiments, a gene encoding an endogenous surface marker of the cell is inactivated, wherein the endogenous surface marker is capable of binding to the first antigen binding domain when expressed. In some embodiments, the endogenous surface marker is CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ or SLAMF7. In some embodiments, the number of any one or more of autologous T cell, granulocyte, and NK cell in peripheral blood starts to increase before the number of affected cells in peripheral blood or the number of affected cells in bone marrow is reduced by at least 50%. In some embodiments, the number of any one or more of autologous T cell, granulocyte, and NK cell in peripheral blood starts to increase after the number of affected cells in peripheral blood or the number of affected cells in bone marrow is reduced by at least 50%.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 29 illustrates an example structure of RQR8-CD19CAR-MBIL15, RQR8-CDT9CAR-MBIL15-IL7, RQR8-CD19CAR-C7R and RQR8-CD19CAR-MBIL7.

FIG. 42A shows the experimental data of the clearance efficiencies of in vitro expanded peripheral blood NK by different CARs. FIG. 42B illustrates experimental data of the in vitro expanded NK comprises ~80% CD7+ cells; after killing by L719-LHLH and T197-LHLH, the remaining NK cells are CD7-cells.

FIG. 45A shows experimental data using L719: L719-LHLH as a standard control for screening, and CAR7, CAR19 and Mock T as other controls. FIG. 45B shows experimental data of the clearance of the remaining CD7+ cells by different CARs after CD7 knockout.

FIG. 50A illustrates experimental data of the expressions of L719 and L719-C7R dual CARs. FIG. 50B illustrates experimental data of the killing effects of dual CARs on HeLa-CD7+ cells. FIG. 50C illustrates experimental data of the killing effects of dual CARs on HeLa-CD19+ cells. FIG. 50D illustrates experimental data of the expressions of enhancer and CD7 in L718 dual CAR-T cells. FIG. 50E illustrates experimental data of cytotoxicity of L719 dual CAR-T cells. FIG. 50F illustrates experimental data of cytotoxicity of L719 dual CAR-T cells. FIG. 50G illustrates experimental data of the expressions of phosphorylated STAT5 and the enhancer in L719 dual CAR-T cells. FIG. 50H illustrates experimental data of L719 dual CAR-T cell proliferation. FIG. 50I illustrates experimental data of the killing effects of dual CARs on HeLa-CD19+ cells. FIG. 50J illustrates experimental data of the killing effects of dual CARs on HeLa-CD7+ cells.

FIG. 54A illustrates FACS data showing fraction of TCR+ cells pre- and post-infusion. FIG. 54B illustrates bar-graph of the FACS data in FIG. 54A. FIG. 54C illustrates comparison of expansion differences of CAR-T cells with or without TCRs.

FIG. 55A illustrates TCR KO CD7 CAR-T expansion data with or without enhancer C7R. FIG. 55B illustrates proliferation data of TCR KO CD7 CAR-T cells with or without enhancer.

FIG. 56A illustrates experimental data of fraction of CAR-T cells expressing enhancer. FIG. 56B illustrates cytotoxicity of TCR KO CD7 CAR-T cells. FIG. 56C illustrates proliferation data of CAR-T cells in the absence of IL2. FIG. 56D illustrates experimental data of fractions of CAR-T cells expressing enhancer and having phosphorylated STAT5. FIG. 56E illustrates a bar graph of mean fluorescent index (MFI) of phosphorylated STAT5 of FIG. 56D.

FIG. 57A illustrates proliferation data of UCAR-T GC197 cells expressing enhancer C7R from two different donors in the presence of cancer antigen stimulation. FIG. 57B illustrates proliferation data of UCAR-T GC197 cells expressing enhancer C7R in the absence of IL2 or antigen stimulation.

FIG. 58A illustrates experimental data showing fractions of CAR-T cells expressing CD7 and the enhancer C7R or E3 (EGFRt+IL7R$\alpha$). FIG. 58B illustrates proliferation data of UCAR-T GC197 cells expressing enhancer C7R or E3 (EGFRt+IL7R$\alpha$). FIG. 58C illustrates proliferation data of UCAR-T GC197 cells expressing enhancer C7R or E3 (EGFRt+IL7R$\alpha$) in the presence of cancer antigen stimulation.

FIG. 59A illustrates experimental data of fractions of K562 cells expressing CAR (e.g., CAR19 or CAR targeting CD19) and enhancer CD47 or E4 (CD47+IL7R$\alpha$). FIG. 59B illustrates experimental data of cytotoxicity of NK cells toward K562-CAR19 expressing the enhancer CD47 or E4 (CD47+IL7Rα).

FIG. 60A illustrates experimental data of fractions of TCR KO CAR19 cells having phosphorylated STAT5 and CAR19. FIG. 60B illustrates proliferation data of TCR KO CD19 CAR expressing enhancer C7R, CD47 or E4 (CD47+IL7Rα).

FIG. 61A illustrates experimental data of CDC effects on TCR/CD7 double knockout L719-E3 cells. FIG. 61B illustrates experimental data of CDC effects on L719-E2 cells.

FIG. 62A illustrates of experimental data of CDC effects on E3 expressing CAR7-E3 cells. FIG. 62B illustrates experimental data of CDC effects on E3 expressing CAR7-E3 cells in the presence of Cetuximab or Herceptin®.

FIG. 63A illustrates experimental data showing supernatant IL12 measurements. FIG. 63B illustrates experimental data showing supernatant IFN γ measurements.

FIG. 66A illustrates body weight (g) post CD19 CART-T infusion. FIG. 66B illustrates body weight (g) post TCR KO CD19 CAR-T infusion. FIG. 66C illustrates $CD45^{+}CD8^{+}$ cell counts in peripheral blood post CD19 CAR-T or TCR KO CD19 CAR-T infusion.

FIG. 67A shows the kinetics of T-ALL elimination in the peripheral blood. FIG. 67B shows the CAR7-C7R cell concentration in the peripheral blood. FIG. 67C shows CAR7-C7R DNA copy/ug DNA of peripheral blood cells. FIG. 67D shows the granulocyte and lymphocyte (T and NK cells) recovery in the bone marrow. FIG. 67E shows the granulocyte and lymphocyte (T and NK cells) recovery in peripheral blood.

DETAILED DESCRIPTION

Figure 1:
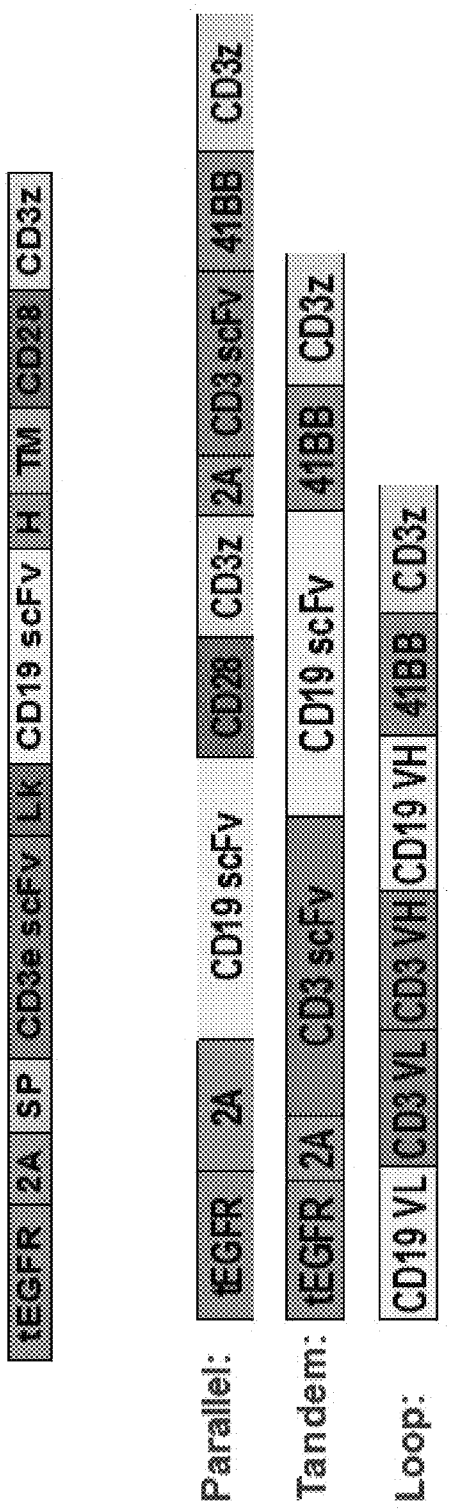
FIG. 1 illustrates an example structure of EGFRt-CD3-CD19 CAR.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "about," as used herein, refers to a value or composition within a range of acceptable tolerances for a particular value or composition as determined, which will depend in part on how the value or composition is measured or measured, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The term "administering," as used herein, refers to physically introducing a product of the present disclosure into a subject using any of a variety of methods and delivery systems, including intravenous, intramuscular, subcutaneous, intraperitoneal, spinal or other routes of parenteral administration, for example by injection or infusion.

The term "antigen," as used herein, refers to a molecule or a fragment thereof capable of being bound by a selective binding agent. As an example, an antigen can be a ligand that can be bound by a selective binding agent such as a receptor. As another example, an antigen can be an antigenic molecule that can be bound by a selective binding agent such as an immunological protein (e.g., an antibody). An antigen can also refer to a molecule or fragment thereof capable of being used in an animal to produce antibodies capable of binding to that antigen. In some cases, an antigen may be bound to a substrate (e.g., a cell membrane). Alternatively, an antigen may not be bound to a substrate (e.g., a secreted molecule, such as a secreted polypeptide).

The term "antibody (Ab)," as used herein, include, but is not limited to, an immunoglobulin that specifically binds to an antigen and comprises at least two heavy (H) chains and two light (L) chains interconnected by disulfide bonds, or an antigen thereof. Each H chain comprises a heavy chain variable region (abbreviated herein as VH) and a heavy chain constant region. The heavy chain constant region comprises three constant domains CH1, CH2 and CH3. Each light chain comprises a light chain variable region (abbreviated herein as VL) and a light chain constant region. The light chain constant region comprises a constant domain CL. The VH and VL regions can be further subdivided into hypervariable regions called complementarity determining regions (CDRs) interspersed with more conserved regions called framework regions (FR). Each VH and VL contains three CDRs and four FRs, arranged from the amino terminus to the carboxy terminus in the following order: FR1, CDR1, FR2, CDR2, FR3, CDR3, FR4. The variable regions of the heavy and light chains contain a binding domain that interacts with the antigen.

The term "nucleotide," as used herein, generally refers to a base-sugar-phosphate combination. A nucleotide can comprise a synthetic nucleotide. A nucleotide can comprise a synthetic nucleotide analog. Nucleotides can be monomeric units of a nucleic acid sequence (e.g. deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide can be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides can include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif; FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g. biotin-11-dUTP, biotin-16-dUTP, biotin-20-dUTP).

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. A polynucleotide can be exogenous or endogenous to a cell. A polynucleotide can exist in a cell-free environment. A polynucleotide can be a gene or fragment thereof. A polynucleotide can be DNA. A polynucleotide can be RNA. A polynucleotide can have any three dimensional structure, and can perform any function, known or unknown. A polynucleotide can comprise one or more analogs (e.g. altered backbone, sugar, or nucleobase). If present, modifications to the nucleotide structure can be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides can be interrupted by non-nucleotide components.

The term "gene," as used herein, refers to a nucleic acid (e.g., DNA such as genomic DNA and cDNA) and its corresponding nucleotide sequence that is involved in encoding an RNA transcript. The term as used herein with reference to genomic DNA includes intervening, non-coding regions as well as regulatory regions and can include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes non-transcribed regions including upstream and downstream regulatory regions, enhancers and promoters. A gene can refer to an "endogenous gene" or a native gene in its natural location in the genome of an organism. A gene can refer to an "exogenous gene" or a non-native gene. A non-native gene can refer to a gene not normally found in the host organism but which is introduced into the host organism by gene transfer. A non-native gene can also refer to a gene not in its natural location in the genome of an organism. A non-native gene can also refer to a naturally occurring nucleic acid or polypeptide sequence that comprises mutations, insertions and/or deletions (e.g., non-native sequence).

The term "endogenous," as used herein, refers to a nucleic acid molecule or polypeptide normally expressed in a cell or tissue.

The term "exogenous," as used herein, refers to the nucleic acid molecule or polypeptide is not endogenously present in the cell or is present at a level sufficient to achieve the functional effects obtained upon overexpression. Thus, the term "exogenous" includes any recombinant nucleic acid molecule or polypeptide expressed in a cell, e.g., a foreign, heterologous, and overexpressed nucleic acid molecule and polypeptide.

The term "T cell and NK cell consensus marker," as used herein, refers to a marker co-existing on T cells and NK cells, including but not limited to: CD2, CD7, CD38, CD45, CD48, CD50, CD52, CD56, CD69, CD100, CD122, CD132, CD161, CD159a, CD159c, CD314.

The term "marker of T cells and/or NK cells," as used herein, refers to markers present in T cells or NK cells, respectively, or both T cells and NK cells, including but not limited to: CD2, CD3, CD4, CD5, CD7, CD8, CD16a, CD16b, CD25, CD27, CD28, CD38, CD45, CD48, CD50, CD52, CD56, CD57, CD62L, CD69, CD94, CD100, CD102, CD122, CD127, CD132, CD160, CD161 CD178, CD218, CD226, CD244, CD159a (NKG2A), CD159c (NKG2C), NKG2E, CD314 (NKG2D), CD305, CD335 (NKP46), CD337, SLAMF7.

The term "functionally inactivate" or "functional inactivation" as used herein refers to that a functional gene or the product of the gene such as mRNA or protein is prevented or inhibited. The inactivation may be achieved by deletion, addition or substitution of the gene or the promoter thereof, so that expression does not occur, or mutation of the coding sequence of the gene so that the gene product such as mRNA or protein is inactive. The functional inactivation may be complete or partial. Inactivation of a gene can encompass all degrees of inactivation, including gene silencing, knockout, inhibition and disruption. In some embodiments, the functional inactivation is introduced by CRISPR-Cas9 system.

The terms "subject," "individual," and "patient" are used interchangeably herein to refer to a vertebrate, preferably a mammal such as a human. Mammals include, but are not limited to, murines, simians, humans, farm animals, sport animals, and pets. Tissues, cells and their progeny of a biological entity obtained in vivo or cultured in vitro are also encompassed.

The terms "treatment" and "treating," as used herein, refer to an approach for obtaining beneficial or desired results including but not limited to a therapeutic benefit and/or a prophylactic benefit. For example, a treatment can comprise administering a system or cell population disclosed herein. By therapeutic benefit is meant any therapeutically relevant improvement in or effect on one or more conditions (e.g., diseases or symptoms) under treatment. For prophylactic benefit, a composition can be administered to a subject at risk of developing a particular condition, or to a subject reporting one or more of the physiological symptoms of a disease, even though the condition may not have yet been manifested.

Overview

CARs can comprise an extracellular antigen recognition region, for example, a scFv (single-chain variable fragment), a transmembrane region, and an intracellular costimulatory signal region. The extracellular domain of CARs can recognize a specific antigen and then transduce the signal through the intracellular domain, causing T cell activation and proliferation, cytolysis toxicity, and secretion of cytokines, thereby eliminating target cells. The patient's autologous T cells (or heterologous donors) can be first isolated, activated and genetically engineered to produce CAR-T cells, which can be then injected into the same patient. In this way, the probability of graft-versus-host disease may be reduced, and the antigen can be recognized by T cells in a non-MHC-restricted manner. In addition, a CAR-T can treat all cancers that express the antigen.

The present disclosure provides compositions and methods to engineer a cell, e.g., an immune cell, such that it can target both disease-associated antigen (e.g., tumor-associated antigen or tumor cell marker) and immune cell antigen (e.g., CD3, CD7 or CD137) through bispecific or multivalent CAR(s). For example, the present disclosure provides an engineered immune cell that can target a tumor cell marker and an immune cell antigen such as CD3. The endogenous TCR can be inactivated (e.g., disrupted, inhibited, knocked out or silenced). The CAR-T of the present disclosure which targets the tumor cell marker and the immune cell antigen can eliminate positive tumor cells and clear host immune cell antigen positive T and NK cells, thereby avoiding host rejection (HVG). In the present disclosure, the endogenous TCR of the engineered immune cell can be knocked out, and graft-versus-host disease (GVHD) can be prevented, thereby preparing a general-purpose or universal CAR-T (UCAR-T) cell. The engineered immune cell can be derived from an autologous T cell or an allogeneic T cell.

Moreover, the engineered immune cell can comprise a cell suicide element (e.g., inducible cell death moiety), and the CAR-T can be inactivated/cleared at any time to reduce side effects. In some cases, the engineered immune cell can further comprise an enhancer moiety. The enhancer moiety can regulate one or more activities of the engineered immune cell when the engineered immune cell is administered to a subject. For example, the enhancer moiety can be a cytokine (e.g., IL-5 or IL-7) or a cytokine receptor (e.g., IL-5R or IL-7R). The enhancer moiety can enhance a signaling pathway within the engineered immune cell, for example, STAT5 signaling pathway. In some embodiments, the engineered immune cell comprises a bispecific CAR targeting both CD19 and CD3. The engineered immune cell show in this example can further comprise an inducible cell death moiety such as a truncated epidermal growth factor receptor (EGFRt or tEGFR, which can be used interchangeably herein; see U.S. Pat. No. 9,447,194B2 and PCT Publication No. WO2018038945).

The inducible cell death moiety or the enhancer moiety can be introduced in the immune cell via a separate expression vector. In some cases, the inducible cell death moiety and the enhancer moiety may be introduced into the immune cell via an expression vector comprising sequences encoding both moieties. In some cases, the inducible cell death moiety and the enhancer moiety are linked and are expressed as a chimeric polypeptide.

The application of the engineered immune cells provided herein in cell therapy can treat the disease (e.g., cancer) of a patient, be prepared in large-scale in advance to avoid GVHD and HvG, reduce treatment costs, inactivate CAR-T at any time if necessary, reduce side effects of immunotherapy, and ensure product safety. The engineered cells provided herein can be referred to as universal CAR T cells (UCAR-T cells).

Chimeric Antigen Receptor (CAR)

The cell (e.g., immune cell or engineered immune cell) provided herein can comprise one or more CARs. The CAR can include an extracellular domain, a transmembrane domain, and an intracellular signaling domain. The extracellular domain can include a target-specific binding element (also known as an antigen binding domain). The intracellular domain can include a costimulatory signaling region and a zeta (ζ) chain portion. A costimulatory signaling region refers to a portion of the CAR comprising the intracellular domain of a costimulatory molecule. Costimulatory molecules are cell surface molecules other than antigens receptors or their ligands that may be needed for an efficient response of lymphocytes to antigen. Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in the present disclosure may be derived from (e.g., comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or from an immunoglobulin such as IgG4. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

The cytoplasmic domain or otherwise the intracellular signaling domain of the CAR of the present disclosure can be responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the present disclosure include the cytoplasmic sequences of the TCR and co-receptors that act in concert to initiate signal transduction following antigen receptor engagement, as well as any derivative or variant of these sequences and any synthetic sequence that has the same functional capability.

Signals generated through the TCR alone may be insufficient for full activation of the T cell and that a secondary or co-stimulatory signal may be included. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences can regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences that are of particular use in the present disclosure include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the present disclosure comprises a cytoplasmic signaling sequence derived from CD3-zeta.

In some embodiments, the cytoplasmic domain of the CAR can be designed to comprise the CD3-zeta signaling domain by itself or combined with any other desired cytoplasmic domain(s) useful in the context of the CAR of the present disclosure. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or its ligands that may be needed for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the present disclosure is, in some cases, exemplified with 4-1BB as the co-stimulatory signaling element, other costimulatory elements are within the scope of the present disclosure.

The cytoplasmic signaling sequences within the cytoplasmic signaling portion of the CAR of the present disclosure may be linked to each other in a random or specified order. Optionally, a short oligo- or polypeptide linker, preferably between 2 and 10 amino acids in length may form the linkage. A glycine-serine doublet provides a particularly suitable linker.

In some embodiments, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB. In yet another embodiment, the cytoplasmic domain is designed to comprise the signaling domain of CD3-zeta and the signaling domain of CD28 and 4-1BB.

A CAR provided herein can comprise one or more antigen binding domains. In some cases, a CAR provided herein comprises an antigen binding domain that can target both an immune cell antigen (e.g., to inhibit killing activity of a T cell or NK cell) and a disease-associated antigen (e.g., a tumor-associated antigen). For example, an antigen binding domain targeting both immune cell antigens and cancer antigens include, but not limited to, CD2, CD3, CD4, CD5, CD7, CD8, CD30, CD38, CD45, CD48, CD50, CD52, CD56, CD69, CD100, CD122, CD132, CD137, CD161, CD159a, CD159c, CD279, CD314, CD319 (CS1) and TCR.

In some cases, a CAR provided herein comprises two antigen binding domains such that one individual CAR is a bispecific CAR, targeting two different antigens. For bispecific CAR, one antigen binding domain can target immune cell antigen, and the other antigen binding domain can target disease-associated antigen. The two antigen binding domains of a bispecific CAR can have a tandem structure, a parallel structure or a loop structure.

For example, a CAR can target a tumor cell marker and CD3. The CAR can have a structure as formula I. L-scFv1-I-scFv2-H-TM-C-CD3ζ (I), wherein each "-" is independently a linker peptide or a peptide bond; L is optionally a signaling peptide sequence; I is a flexible linker; H is optionally a hinge region; TM is a transmembrane domain; C is a costimulatory domain; CD3ζ is a cytoplasmic signaling sequence derived from CD3ζ; one of scFv1 and scFv2 is an antigen binding domain targeting a tumor cell marker, and the other one is an antigen binding domain targeting CD3. The CAR can have a structure as formula II or II': L-VL-scFv-VH-H-TM-C-CD3ζ (II), L-VH-scFv-VL-H-TM-C-CD3ζ (II'), wherein each "-" is independently a linker peptide or a peptide bond; the elements L, H, TM, C and CD3ζ as described above; scFv is an antigen binding domain targeting a tumor cell marker, VH is an anti-CD3 antibody heavy chain variable region, and VL is an anti-CD3 antibody light chain variable region; or scFv is an antigen binding domain targeting CD-3, VH is an anti-tumor cell marker antibody heavy chain variable region, and VL is an anti-tumor cell marker antibody light chain variable region.

In some cases, a CAR can comprise the structure of EGFRt-CD3 scFv-CD19 scFv-Hinge-TM-CD28/41BB-CD3ζ, wherein EGFRt is a truncated EGFR, as a safety switch (e.g., inducible cell death moiety), CD3 scFv is the svFCv fragment of the heavy and light chain variable regions of the monoclonal antibody OKT3 or UCHT1 linked by a GS linker, and the CD19 scFv fragment is the heavy and light chain variable region of the monoclonal FMC63 antibody linked by a GS linker. The structure of the CAR can further comprise a hinge, transmembrane regions, costimulatory signaling region of CD28 or 41BB, and/or CD3 (intracellular domain. In the present disclosure, the nucleic acid construct of EGFRt-CD3 scFv-CD19 scFv-Hinge-TM-CD28/41BB-CD3ζ can be inserted into a vector (e.g., a lentiviral vector). The vector can be packaged in 293T cells. T cells can be sorted from PBMC, and after activation, TCR and PD-1 genes can be knocked out by CRISPR/CAS technology. T cells can then be infected with the vectors to express the CARs. The prepared CAR-T cells can be used to detect the infection efficiency and gene editing efficiency of CAR by flowcytometry.

The immune cell marker, e.g., CD3, of the above examples can be replaced with other immune cell markers such as CD7 and CD137.

In some cases, a CAR comprising two antigen binding domains arranged in a tandem form. In some embodiments, the first antigen binding domain and the second antigen binding domain is arranged, from amino terminus to carboxyl terminus, as: (i) VL2-VH2-VL1-VH1; (ii) VL2-VH2-VH1-VL1; (iii) VL1-VH1-VL2-VH2; (iv) VL1-VH1-VH2-VL2; (v) VH2-VL2-VL1-VH1; (vi) VH2-VL2-VH1-VL1; (vii) VH1-VL1-VL2-VH2; or (viii) VH1-VL1-VH2-VL2, wherein VH1 is heavy chain variable domain of the first antigen binding domain, VL1 is light chain variable light domain of the first antigen binding domain, VH2 is heavy chain variable domain of the second antigen binding domain, and VL2 is light chain variable domain of the second antigen binding domain. For example, the CAR can have a structure represented by the following formula IV or IV': L3-scFv1-R-scFv2-H3-TM3-C3-CD3ζ (IV); L3-scFv2-R-scFv1-H3-TM3-C3-CD3ζ (IV'), wherein each "-" is independently a linker peptide or peptide bond; L3 is an optional signal peptide sequence; scFv1 is an antigen binding domain that targets tumor cell markers; R is a rigid or flexible joint; scFv2 is an antigen binding domain (e.g., an antibody single-chain variable region sequence) that targets T cell and NK cell consensus markers; H3 is an optional hinge region; TM3 is a transmembrane domain; C3 is a costimulatory domain; CD3ζ is a cytoplasmic signaling sequence derived from CD3ζ.

In some cases, a CAR comprising two antigen binding domains arranged in a loop form. In some cases, the first antigen binding domain and the second antigen binding domain is arranged, from amino terminus to carboxyl terminus, as: (i) VL2-VH1-VL1-VH2; (ii) VH2-VL1-VH1-VL2; (iii) VL1-VH2-VL2-VH1; (iv) VH1-VL2-VH2-VL1; (v) VL2-VL1-VH1-VH2; (vi) VH2-VH1-VL1-VL2; (vii) VL1-VL2-VH2-VH1; or (viii) VH1-VH2-VL2-VL1, wherein VH1 is heavy chain variable domain of the first antigen binding domain, VL1 is light chain variable light domain of the first antigen binding domain, VH2 is heavy chain variable domain of the second antigen binding domain, and VL2 is light chain variable domain of the second antigen binding domain. For example, the CAR can have the following formula VI, VI', VI" or VI'" structure:

L8-VL1-VH2-I-VL2-VH1-H8-TM8-C8-CD3ζ (VI);

L8-VH1-VL2-I-VH2-VL1-H8-TM8-C8-CD3ζ (VI');

L8-VL2-VHT-I-VL1-VH2-H8-TM8-C8-CD3ζ (VI");

L8-VH2-VL1-I-VH1-VL2-H8-TM8-C8-CD3ζ (VI'"), wherein each "-" is independently a linker peptide or peptide bond; L8 is an optional signal peptide sequence; VHT is an anti-tumor cell marker antibody heavy chain variable region, and VL1 is an anti-tumor cell marker antibody light chain variable region; VH2 is an anti-T cell and NK cell consensus marker (such as CD7 or CD2) antibody heavy chain variable region; and VL2 is an anti-T cell and NK cell consensus marker (such as CD7 or CD2) antibody light chain variable region; I is a flexible joint; H8 is an optional hinge region; TM8 is a transmembrane domain; C8 is a costimulatory domain; CD3ζ is a cytoplasmic signaling sequence derived from CD3ζ.

In some cases, a CAR comprising two antigen binding domains are arranged in a parallel form. The parallel form can comprise a full construct of a first CAR having a first antigen binding domain linked to a full construct of a second CAR having a second antigen binding domain. An example of parallel form can be tEGFR-CD19 scFv-CD28-CD3ζ-CD3 scFv-41BB-CD3ζ. The tEGFR shown here can function as a safety switch, which can be replaced by other safety switches as described in the present disclosure. As described herein, CD19 scFv and CD3 scFv are two examples of antigen binding domains, which may be replaced with various antigen binding domains as described in the present disclosure. CD28 can be an example of transmembrane domain and can be replaced with other transmembrane domains described herein. 41BB can be an example of co-stimulatory domain and can be replaced with other co-stimulatory domains described herein. In some cases, a linker is used to link the first CAR and the second CAR. The linker can be a cleavable linker. The cleavable linker can be self-cleaving peptide such as 2A self-cleaving peptide.

Also contemplated in the present disclosure is a nucleic acid molecule encoding a CAR or a bispecific CAR. The nucleic acid can comprise a first sequence encoding a chimeric antigen receptor (CAR), wherein the CAR can comprise a binding moiety, which binding moiety comprises (i) a first antigen binding domain, which first antigen binding domain suppresses or reduces a subject's immune response toward the engineered immune cell when administered into the subject linked to (ii) a second antigen binding domain capable of binding to a disease-associated antigen, and wherein each CAR of the one or more CARs can further comprise a transmembrane domain and an intracellular signaling domain. The first antigen binding domain can target an immune cell antigen selected from the group consisting of CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ and SLAMF7. The second antigen binding domain can target a disease-associated antigen such as CD19. Other non-limiting examples of disease-associated antigen includes BCMA, VEGFR2, CD19, CD20, CD30, CD22, CD25, CD28, CD30, CD33, CD52, CD56, CD80, CD86, CD81, CD123, cd171, CD276, B7H4, CD133, EGFR, GPC3; PMSA, CD 3, CEACAM6, c-Met, EGFRvIII, ErbB2, ErbB3 HER-2, HER3, ErbB4/HER-4, EphA2, IGF1R, GD2, O-acetyl GD2, O-acetyl GD3, GHRHR, GHR, Flt1, KDR, Flt4, CD44V6, CEA, CA125, CD151, CTLA-4, GITR, BTLA, TGFBR2, TGFBR1, IL6R, gp130, Lewis, TNFR1, TNFR2, PD1, PD-L1, PD-L2, HVEM, MAGE-A, Mesothelin, NY-ESO-1, PSMA, RANK, ROR1, TNFRSF4, CD40, CD137, TWEAK-R, LTPR, LIFRP, LRP5, MUC1, TCRa, TCRp, TLR7, TLR9, PTCH1, WT-1, Robl, Frizzled, OX40, CD79b, Claudin 18.2, Folate receptor α, Folate receptor β, GPC2, CD70, BAFF-R and Notch-1-4.

The nucleic acid molecule can further comprise a second sequence encoding an enhancer moiety, which enhancer moiety can enhance one or more activities of the CAR when expressed in a cell. The enhancer moiety can be selected from the group consisting of IL-2, IL-3, IL-4, IL-6, IL-7, IL-8, IL-10, IL-11, IL-12, IL-15, IL-17, IL-18, IL-21, IL-23, PD-1, PD-L1, CD122, CSF1R, CTAL-4, TIM-3, CCL21, CCL19, TGFR beta, receptors for the same, functional fragments thereof, functional variants thereof, and combinations thereof. The nucleic acid molecule can further comprise a second sequence encoding an inducible cell death moiety, which inducible cell death moiety, when expressed in a cell, can effect death of the cell upon contacting the inducible cell death moiety with a cell death activator. The inducible cell death moiety can be selected from the group consisting of rapaCasp9, iCasp9, HSV-TK, ΔCD20, mTMPK, ΔCD19, RQR8, and EGFRt.

The nuclei acid molecule can further comprise a third sequence flanked by the first sequence and the second sequence, wherein the third sequence can encode a cleavable linker. The cleavable linker can be a self-cleaving peptide.

The nucleic acid molecule can further comprise a regulatory sequence regulating expression of the first sequence and/or the second sequence.

Also contemplated in the present disclosure is a kit comprising the nucleic acid molecule described herein.

In some cases, the nucleic acid encoding the CAR described herein can be delivered into an immune cell for expression of the CAR to generate an engineered cell.

Source Cell

The present disclosure provides an engineered cell, such as an engineered immune cell. The engineered immune cell can be prepared from a cell (e.g., an immune cell) isolated from a sample obtained from a subject. The engineered immune cell can be prepared from a cell line cell. The immune cell used to prepare the engineered immune cell can be a T cell, a B cell, a natural killer (NK) cell or a macrophage. The immune cell used to prepare the engineered immune cell can be an innate lymphocyte (ILC).

The immune cell used to prepare the engineered immune cell can be a stem cell. The stem cell can be a hematopoietic stem cell (HSC) or an induced pluripotent stem cell (iPSC).

The immune cell may comprise a T-cell receptor (TCR). The TCR can be endogenous TCR of the immune cell. In some cases, the endogenous TCR can be inactivated. For example, a gene encoding a subunit of the TCR can be inactivated. For example, the immune cell can be an alpha beta T cells with impaired TCRs such that the immune cells can avoid GVHD. For another example, the function of the endogenous TCR can be inhibited by an inhibitor such as TCR-derived peptides, peptides derived from amino acid sequences of fusion and other protein regions of various viruses, antibodies and small molecule inhibitors. The viruses from which the TCR inhibiting peptides can be derived from include, but are not limited to, severe acute respiratory syndrome coronavirus (SARS-CoV), herpesvirus saimiri (HVS), human herpesvirus 6 (HHV-6), Lassa virus (LASV), lymphocytic choriomeningitis virus (LCMV), Mopeia virus (MOPV), Tacaribe virus (TACV), Friend murine leukemia virus (MLV); human T lymphotropic virus type 1 (HTLV-1,); herpesvirus ateles (HVA); Marburg virus (MARV); Sudan Ebola virus (SEBOV); and Zaire Ebola virus (ZEBOV).

In some cases, the immune cells can be T cells containing TCRs that may not cause GVHD responses. For example, the immune cell can be an alpha beta T cell with TCRs that can recognize specific antigens such as viral specific antigen, tumor-associated antigens (TAAs) or tumor-specific antigens (TSAs). For another example, the immune cell can be a gamma delta T cell or a natural killer T (NKT) cell. For another example, the immune cell can be induced pluripotent stem cells produced from antigen-specific T cells (e.g., antigen-specific cytotoxic T cells). The immune cell can be cord-blood T cells.

The immune cell may comprise a cell surface marker. The cell surface marker can be an immune cell antigen. The gene encoding the immune cell antigen of the immune cell used for preparing the engineered immune cell can be inactivated. Examples of immune cell antigens include, but are not limited to, CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ and SLAMF7. For example, in some cases, the gene encoding CD7 of the immune cell is inactivated. In some cases, the gene encoding CD3 of the immune cell is inactivated. In some cases, the gene encoding CD137 of the immune cell is inactivated.

The immune cells can be isolated from a sample from a subject. The subject can be a healthy donor. The subject can have a condition (e.g., a disease such as cancer). The sample can be a bodily fluid or a tissue, including but not limited to, peripheral blood mononuclear cells, bone marrow, lymph node tissue, cord blood, thymus tissue, tissue from a site of infection, ascites, pleural effusion, spleen tissue, and tumors. In some cases, a sample comprises NK cells, NKT cells, T-cells or T-cell progenitor cells. For example, in some cases, the sample is an umbilical cord blood sample, a peripheral blood sample (e.g., a mononuclear cell fraction) or a sample from the subject comprising pluripotent cells. In some aspects, a sample from the subject can be cultured to generate induced pluripotent stem (iPS) cells and these cells used to produce NK cells, NKT cells or T-cells. Cell samples may be cultured directly from the subject or may be cryopreserved prior to use. In some aspects, obtaining a cell sample comprises collecting a cell sample. In other aspects, the sample is obtained by a third party. In still further aspects, a sample from a subject can be treated to purify or enrich the T-cells or T-cell progenitors in the sample. For example, the sample can be subjected to gradient purification, cell culture selection and/or cell sorting (e.g., via fluorescence-activated cell sorting (FACS)).

The immune cell can be an NK cell. The NK cells can be obtained from peripheral blood, cord-blood, or other sources described herein. The NK cells can be derived from induced pluripotent stem cells.

In some embodiments, a cell that can be utilized in a method provided herein can be positive or negative for a given factor. In some embodiments, a cell utilized in a method provided herein can be a CD3+ cell, CD3− cell, a CD5+ cell, CD5− cell, a CD7+ cell, CD7− cell, a CD14+ cell, CD14− cell, CD8+ cell, a CD8− cell, a CD103+ cell, CD103− cell, CD11 b+ cell, CD11b− cell, a BDCA1+ cell, a BDCA1− cell, an L-selectin+ cell, an L-selectin− cell, a CD25+, a CD25− cell, a CD27+, a CD27− cell, a CD28+ cell, CD28− cell, a CD44+ cell, a CD44− cell, a CD56+ cell, a CD56− cell, a CD57+ cell, a CD57− cell, a CD62L+ cell, a CD62L− cell, a CD69+ cell, a CD69− cell, a CD45RO+ cell, a CD45RO− cell, a CD127+ cell, a CD127− cell, a CD132+ cell, a CD132− cell, an IL-7+ cell, an IL-7− cell, an IL-15+ cell, an IL-15− cell, a lectin-like receptor G1 positive cell, a lectin-like receptor G1 negative cell, or an differentiated or de-differentiated cell thereof. The examples of factors expressed by cells is not intended to be limiting, and a person having skill in the art will appreciate that a cell may be positive or negative for any factor known in the art. In some embodiments, a cell may be positive for two or more factors. For example, a cell may be CD4+ and CD8+. In some embodiments, a cell may be negative for two or more factors. For example, a cell may be CD25−, CD44−, and CD69−. In some embodiments, a cell may be positive for one or more factors, and negative for one or more factors. For example, a cell may be CD4+ and CD8−. In some aspects, a cellular marker provided herein can be utilized to select, enrich, or deplete a population of cells. In some aspects, enriching comprises selecting a monocyte fraction. In some aspects, enriching comprises sorting a population of immune cells from a monocyte fraction. In some embodiments, the cells may be selected for having or not having one or more given factors (e.g., cells may be separated based on the presence or absence of one or more factors). In some embodiments, the selected cells can also be transduced and/or expanded in vitro. The selected cells can be expanded in vitro prior to infusion. In some embodiments, selected cells can be transduced with a vector provided herein. It should be understood that cells used in any of the methods disclosed herein may be a mixture (e.g., two or more different cells) of any of the cells disclosed herein. For example, a method of the present disclosure may comprise cells, and the cells are a mixture of CD4+ cells and CD8+ cells. In another example, a method of the present disclosure may comprise cells, and the cells are a mixture of CD4+ cells and naïve cells. In some cases, a cell can be a stem memory TSCM cell comprised of CD45RO (−), CCR7(+), CD45RA (+), CD62L+ (L-selectin), CD27+, CD28+ and IL-7Rα+, stem memory cells can also express CD95, IL-2Rβ, CXCR3, and LFA-1, and show numerous functional attributes distinctive of stem memory cells. Cells provided herein can also be central memory TCM cells comprising L-selectin and CCR7, where the central memory cells can secrete, for example, IL-2, but not IFNγ or IL-4. Cells can also be effector memory TEM cells comprising L-selectin or CCR7 and produce, for example, effector cytokines such as IFNγ and IL-4. In some cases, a population of cells can be introduced to a subject. For example, a population of cells can be a combination of T cells and NK cells. In other cases, a population can be a combination of naïve cells and effector cells. A population of cells can be TILs.

The source immune cells can be T cells. The T cells can be alpha beta T cells or gamma delta T cells. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present disclosure, various T cell lines may be used. In certain embodiments of the present disclosure, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments of the present disclosure, the cells are washed with phosphate buffered saline (PBS). In an alternative embodiment, the wash solution lacks calcium and may lack magnesium or may lack many if not all divalent cations. Initial activation steps in the absence of calcium may lead to magnified activation. A washing step may be accomplished by methods such as by using a semi-automated "flow-through" centrifuge (for example, the Cobe® 2991 cell processor, the Baxter CytoMate®, or the Haemonetics Cell Saver® 5) according to the manufacturer's instructions. After washing, the cells may be resuspended in a variety of biocompatible buffers, such as, for example, Ca2+-free, Mg2+-free PBS, PlasmaLyte® A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. In some cases, multiple rounds of selection can also be used. In certain embodiments, it may be useful to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. An example method can be cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, lower concentrations of cells may be used. By significantly diluting the mixture of T cells and surface (e.g., particles such as beads), interactions between the particles and cells is minimized. This method can select for cells that express high amounts of desired antigens to be bound to the particles. For example, CD4+ T cells express higher levels of CD28 and are more efficiently captured than CD8+ T cells in dilute concentrations. In some embodiments, the concentration of cells used is $5\times10^6$/ml. In other embodiments, the concentration used can be from about $1\times10^5$/ml to $1\times10^6$/ml, and any integer value in between. In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte®-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan® and PlasmaLyte® A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In some embodiments, cryopreserved cells are thawed and washed as described herein and allowed to rest for one hour at room temperature prior to activation using the methods of the present disclosure.

In some embodiments, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, CYTOXAN®, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan®.

Engineered Immune Cell

The engineered immune cell provided herein can exhibit enhanced activity toward tumor cells, but with reduced side effects such as GVHD. The engineered immune cell can target a disease-associated antigen (e.g., tumor-associated antigen, or tumor cell marker) and at the same time suppress host immune cells. One or more endogenous genes (e.g., a gene encoding a subunit of a TCR, or a gene encoding a cell surface marker) of the engineered immune cell can be inactivated. In some cases, the engineered immune cell comprises a first CAR and a second CAR, each targeting a different antigen. In some cases, the engineered immune cell comprises a CAR having a first antigen binding domain and a second antigen binding domain.

The engineered immune cell can comprise one or more chimeric antigen receptors (CARs) comprising a binding moiety. The binding moiety can comprise a first antigen binding domain capable of binding to an immune cell antigen and a second antigen binding domain capable of binding to a disease-associated antigen. Each CAR of the one or more CARs may further comprise a transmembrane domain and an intracellular signaling domain. The engineered immune cell can also comprise an enhancer moiety capable of enhancing one or more activities of the engineered immune cell. The endogenous T cell receptor (TCR) of the engineered immune cell can be inactivated. In some cases, the engineered immune cell can exhibit (i) enhanced degree of persistence by remaining viable in vitro for at least about 20 days while in presence of cells that are heterologous to the engineered immune cell, (ii) enhanced degree of expansion by at least about 10-fold within 15 days, or (iii) enhanced cytotoxicity against a target cell comprising the immune cell antigen or the disease-associated antigen, compared to an additional engineered immune cell comprising the one or more CARs but not the enhancer moiety. In some cases, the engineered immune cell can be characterized by exhibiting two or more of (i) enhanced degree of persistence, (ii) enhanced degree of expansion, and (iii) enhanced cytotoxicity. The (i), (ii), and/or (iii) characteristics can be measured in absence of any exogenous enhancer moiety such as exogenous cytokines.

The engineered immune cell can comprise a multi-specific CAR. In some cases, the engineered immune cell comprises a bispecific CAR targeting an immune cell antigen and a disease-associated antigen. The two antigen binding domains of the bispecific CAR can be arranged in any form as described in the present disclosure, for example, parallel form, loop form, and tandem form. For example, an engineered immune cell described herein can comprise comprising a single chimeric antigen receptor (CAR) comprising (i) a first antigen binding domain that specifically binds CD7 and (ii) a second antigen binding domain capable of binding to a disease-associated antigen. The CAR can further comprise a transmembrane domain and an intracellular signaling domain. In various cases, a gene encoding endogenous CD7 can be inactivated (e.g., silenced or knocked out) in the engineered immune cell.

The immune cell antigen can be selected from the group consisting of CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ and SLAMF7. In some cases, the immune cell antigen is CD2, CD3, CD4, CD5, CD7, CD8, CD30, CD38, CD45, CD48, CD50, CD52, CD56, CD69, CD100, CD122, CD132, CD137, CD161, CD159a, CD159c, CD279, CD314, CD319 (CS1), TCRα or TCRβ. In some cases, the immune cell antigen is CD2, CD3, CD5, CD7, or CD137. In some cases, the immune cell antigen is CD7. The enhancer moiety can be configured to constitutively enhance the one or more activities of the engineered immune cell. The enhancer moiety can be configured to constitutively upregulate one or more intracellular signaling pathways of the engineered immune cell. The one or more intracellular signaling pathways can be one or more cytokine signaling pathways. The enhancer moiety can be self-activating through self-oligomerizing. The enhancer moiety can be self-activating through self-dimerizing.

The enhancer moiety can be a cytokine or a cytokine receptor. The enhancer moiety can be selected from the group consisting of IL-2, IL-3, IL-4, IL-6, IL-7, IL-8, IL-10, IL-11, IL-12, IL-15, IL-17, IL-18, IL-21, IL-23, PD-1, PD-L1, CD122, CSF1R, CTAL-4, TIM-3, CCL21, CCL19, TGFR beta, receptors for the same, functional fragments thereof, functional variants thereof, and combinations thereof.

In some cases, a gene encoding a subunit of the endogenous TCR of the engineered immune cell can be inactivated such that the endogenous TCR is inactivated. The gene encoding the subunit can be TCRα, TCRβ, CD3ε, CD3δ, CD3γ, or CD3ζ.

The engineered immune cell can further comprise an inducible cell death moiety, which inducible cell death moiety can effect suicide of the engineered immune cell upon contact with a cell death activator. The inducible cell death moiety can be selected from the group consisting of rapaCasp9, iCasp9, HSV-TK, ΔCD20, mTMPK, ΔCD19, RQR8, and EGFRt. In some cases, the inducible cell death moiety is EGFRt, and the cell death activator is an antibody or an antigen binding fragment thereof that binds EGFRt. In some cases, the inducible cell death moiety is HSV-TK, and the cell death activator is GCV. In some cases, the inducible cell death moiety is iCasp9, and the cell death activator is AP1903. The cell death activator can comprise a nucleic acid, a polynucleotide, an amino acid, a polypeptide, lipid, a carbohydrate, a small molecule, an enzyme, a ribosome, a proteasome, a variant thereof, or any combination thereof.

The expression of one or more endogenous human leukocyte antigen (HLA) genes of the engineered immune cell may remain intact. In some cases, the expression of endogenous HLA-I and/or HLA-II genes of the engineered immune cell may remain intact. The expression of endogenous HLA-E and/or HLA-G and/or HLA-C genes of the engineered immune cell may remain intact.

The expression of one or more endogenous HLA genes of the engineered immune cell can be upregulated. In some cases, the expressions of endogenous HLA-E and/or HLA-G and/or HLA-C genes of the engineered immune cell are upregulated.

The expression of one or more endogenous HLA genes of the engineered immune cell may be knocked out or partially knocked out. For example, HLA-I, HLA-II or both can be knocked out. In some cases, HLA-I, HLA-2, or both can be partially knocked out. In some cases, HLA-I/II can be partially knockout. In some cases, an endogenous HLA can be knocked out to reduce T cell killing activity but keep anti-NK killer function. For example, HLA-A/B can be knocked out while keeping HLA-C/E in the engineered immune cell. In some cases, HLA-A, HLA-B, or both is knocked out. In some cases, HLA-C, HLA-E, or both remains intact. In some cases, a killer/phagocyte inhibitor of the engineered immune cell can be overexpressed. In some other cases, an endogenous HLA can be knocked out with co-expression of killer/phagocyte inhibitor(s). For example, HLA-I, HLA-II, or both can be knocked out with co-expression of killer/phagocyte inhibitors. The killer/phagocyte inhibitor may suppress immune response toward the engineered immune cell. The killer/phagocyte inhibitors include, but are not limited to, CD47, CD24, FASL, PDL1, or functional domains thereof.

The disease-associated antigen described herein can be a tumor-associated antigen or a tumor-specific antigen. The first antigen binding domain or the second antigen binding domain can be an antibody or fragment thereof, for example, a scFv or a single domain antibody.

A gene encoding an endogenous surface marker of the engineered immune cell can be inactivated, wherein the endogenous surface marker is capable of binding to the first antigen binding domain when expressed. The endogenous surface marker can be the antigen that CAR targets. In various embodiments, when a CAR of the engineered immune cell targets an antigen that is endogenously expressed by the engineered immune cell, the endogenous antigen or the gene encoding such antigen may be inactivated (e.g., disrupted, inhibited, silenced or knocked out). Various gene editing methods described herein can be used. The endogenous surface marker can be, for example, CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ and SLAMF7.

The engineered immune cell provided herein can comprise a chimeric polypeptide comprising (i) an enhancer moiety capable of enhancing one or more activities of the engineered immune cell, and (ii) an inducible cell death moiety capable of effecting death of the engineered immune cell upon contacting the chimeric polypeptide with a cell death activator, wherein the enhancer moiety is linked to the inducible cell death moiety. In some cases, the enhancer moiety and the inducible moiety may be linked by a linker. The linker can be a cleavable linker, for example, a self-cleaving peptide. The engineered immune cell can further comprise one or more chimeric polypeptide receptors (CPRs) comprising a binding moiety, wherein the binding moiety comprises (i) a first antigen binding domain, which first antigen binding domain suppresses or reduces a subject's immune response toward the engineered immune cell when administered into the subject and (ii) a second antigen binding domain capable of binding to a disease-associated antigen. An individual CPR of the one or more CPRs can comprise (i) the first antigen binding domain, (ii) the second antigen binding domain, or (iii) both the first antigen binding domain and the second antigen binding domain. A CPR of the one or more CPRs can further comprise a transmembrane domain and an intracellular signaling domain. In some cases, the one or more CPRs in the engineered immune cell are one or more chimeric antigen receptors (CARs) or engineered T cell receptors (TCRs). In some cases, the engineered immune cells comprise both CARs and engineered TCRs. The engineered TCR can be a TCR fusion protein. For example, the TCR fusion protein can comprise a heterologous antigen binding domain fused to one or more subunits of a TCR complex. In some cases, the TCR fusion protein can comprise a TCR subunit comprising at least a portion of a TCR extracellular domain and a TCR intracellular domain; and an antibody domain comprising an antigen binding domain, where the TCR subunit and the antibody domain are linked. The TCR fusion protein can incorporate into a TCR complex when expressed in a T cell. In some cases, the TCR fusion protein can further comprise a TCR transmembrane domain. The TCR extracellular domain, the TCR intracellular domain, or the TCR transmembrane domain can be derived from TCR alpha chain, TCR beta chain, TCR gamma chain, TCR delta chain, CD3 epsilon, CD3 gamma, CD3 delta or CD3 zeta. In some cases, an endogenous TCR of the engineered immune cell comprising an engineered TCR is inactivated. In some cases, the engineered immune cell comprising inactivated endogenous TCR may not cause GVHD. For example, a gene encoding an endogenous TCR subunit can be inactivated. For another example, a gene encoding an endogenous TCR subunit may be mutated such that an endogenous TCR may not be formed.

The engineered immune cell provided herein can comprise a chimeric polypeptide comprising (i) an enhancer moiety capable of enhancing one or more activities of the engineered immune cell, and (ii) an inducible cell death moiety capable of effecting death of the engineered immune cell upon contacting the chimeric polypeptide with a cell death activator. In some cases, the enhancer moiety is linked to the inducible cell death moiety. The one or more chimeric antigen receptors (CARs) can comprise a binding moiety. The binding moiety can comprise (i) a first antigen binding domain, which first antigen binding domain suppresses or reduces a subject's immune response toward the engineered immune cell when administered into the subject and (ii) a second antigen binding domain capable of binding to a disease-associated antigen. In some cases, an individual CAR of the one or more CARs comprises (i) the first antigen binding domain or (ii) the second antigen binding domain. In some cases, an individual CAR of the one or more CARs comprises both the first antigen binding domain and the second antigen binding domain. In some cases, each CAR of the one or more CARs further comprises a transmembrane domain and an intracellular signaling domain.

The first antigen binding domain of the engineered immune cell can bind to an immune cell antigen. In some cases, endogenous T cell receptors (TCRs) of the engineered immune cell is inactivated. Various methods can be used to inactivate endogenous TCRs. For example, a gene encoding a subunit of the endogenous TCR can be inactivated such that the endogenous TCR is inactivated. The gene encoding the subunit can be TCRα, TCRβ, CD3ε, CD3δ, CD3γ, or CD3ζ.

The chimeric polypeptide may or may not comprise any self-cleaving peptide flanked by the enhancer moiety and the inducible cell death moiety. The enhancer moiety can be configured to constitutively enhance the one or more activities of the engineered immune cell. The enhancer moiety can be configured to constitutively upregulate one or more intracellular signaling pathways of the engineered immune cell. The one or more intracellular signaling pathways can be one or more cytokine signaling pathways. The enhancer moiety can be self-activating through self-oligomerizing. The enhancer moiety can be self-activating through self-dimerizing.

The chimeric polypeptide described herein can be a secreted protein. The chimeric polypeptide can be an intracellular protein. The chimeric polypeptide can be a transmembrane protein. The enhancer moiety or the inducible cell death moiety can be contained in an ectodomain of the transmembrane protein. The enhancer moiety or the inducible cell death moiety is contained in an endodomain of the transmembrane protein. The enhancer moiety can be contained in an endodomain of the transmembrane protein and the inducible cell death moiety can be contained in an ectodomain of the transmembrane protein. The enhancer moiety can be contained in an ectodomain of the transmembrane protein, and the inducible cell death moiety can be contained in an endodomain of the transmembrane protein. The enhancer moiety can be a cytokine or a cytokine receptor. For example, the enhancer moiety can be selected from the group consisting of IL-2, IL-3, IL-4, IL-6, IL-7, IL-8, IL-10, IL-11, IL-12, IL-15, IL-17, IL-18, IL-21, IL-23, PD-1, PD-L1, CD122, CSF1R, CTAL-4, TIM-3, CCL21, CCL19, TGFR beta, receptors for the same, functional fragments thereof, functional variants thereof, and combinations thereof. The inducible cell death moiety can be selected from the group consisting of rapaCasp9, iCasp9, HSV-TK, ΔCD20, mTMPK, ΔCD19, RQR8, and EGFRt. In some cases, the inducible cell death moiety is EGFRt, and the cell death activator is an antibody or an antigen binding fragment thereof that binds EGFRt. In some cases, the inducible cell death moiety is HSV-TK, and the cell death activator is GCV. In some cases, the inducible cell death moiety is iCasp9, and the cell death activator is AP1903. The cell death activator may comprise a nucleic acid, a polynucleotide, an amino acid, a polypeptide, lipid, a carbohydrate, a small molecule, an enzyme, a ribosome, a proteasome, a variant thereof, or any combination thereof.

The engineered immune cell can be a CAR-T cell. The CAR-T cell can express a CAR targeting a tumor cell marker and CD3. The expression of endogenous CD3 gene can be silenced in the CAR-T cell. The CAR can be a single CAR targeting both a tumor cell marker and CD3. The CAR can comprise a first CAR targeting a tumor cell marker and a second CAR targeting CD3. The CAR-T cell can have one or more of the following characteristics: (a) expression of PD-1 gene is silenced in the CAR-T cell; (b) expression of TCR gene is silenced in the CAR-T cell; (c) the CAR-T cell expresses an exogenous cellular suicide element (e.g., inducible cell death moiety).

The engineered immune cell can express a CAR and/or an exogenous TCR, and the CAR and/or exogenous TCR target a tumor cell marker. The engineered immune cell can comprise a cytokine-related signaling pathway that is enhanced. The cytokine-related signaling pathway can comprise a related signaling pathway of a cytokine selected from a group consisting of IL-2, IL-3, IL-4, IL-6, IL-7, IL-8, IL-10, IL-11, IL-12, IL-15, IL-17, IL-18, IL-21, or a combination thereof. Enhancing the cytokine-related signaling pathway can comprise introducing a gene encoding a cytokine and/or a receptor thereof; up-regulating a gene encoding a cytokine and/or a receptor thereof; or exogenously adding a cytokine, a receptor of cytokine that is introduced, or a combination thereof. The engineered immune cell can be a CAR-T cell having one or more characteristics selected from a group consisting of (a) gene expression an endogenous TCR being silenced; (b) expressing an element for cellular suicide; (c) normal expression of endogenous HLA-I and HLA-II genes; (d) normal expression or overexpression of endogenous HLA-E and/or HLA-G.

The engineered immune cell can comprise a CAR or an exogenous TCR targeting a tumor cell marker. The engineered immune cell can comprise a substance targeting a T cell or NK cell. For example, the engineered immune cell can comprise a CAR targeting a T cell and/or NK cell. The engineered immune cell can comprise a bispecific CAR targeting both (i) a tumor cell marker and (ii) a T cell and/or NK cell marker. In some cases, the substance is an antibody. The antibody target both T cell and NK cell can be H-69, 3A1e, 3A1f, T3-3A1, RFT2, SDZ214-380 (SDZCHH380), CD7-6B7, 124-1D1, 4H9, RPA-2.10, TS1/8, OKT11, AB75, 3E11, BH1, or Lo-CD2a.

The CAR-T cell provided herein can be a universal CAR-T cell. The CAR-T cell can express a chimeric antigen receptor CAR that targets a tumor cell marker and the binding of the T cell receptor to PD-1 is inhibited. The CAR-T cell can target a tumor cell marker and an immune cell marker such as CD2 or CD7. The endogenous TCR expression in the CAR-T cells provided herein can be knocked out by gene editing technology. Upon knocking out the endogenous TCRs of the CAR-T cells, the normal cells may not be recognized and killed by the CAR-T cells during the allogeneic infusion. The GVHD reaction may be inhibited. Moreover, targeting tumor cells through CD19 while eliminating host T cells and/or NK cells through CD2 or CD7 can avoid host versus graft (HVG) and/or NK killing and improve the survival and anti-tumor effect of the allogeneic CAR-T cells in the recipient. The CAR-T can further comprise a suicide gene switch (e.g., an inducible cell death moiety). The CAR-T cells can be inactivated or removed by turning on the suicide gene switch (e.g., binding of an activator to the inducible cell death moiety) to reduce the side effects of the CAR-T cell therapy. For example, a CAR provided herein can have a structure of CD19 scFv-CD7 scFv-Hinge-TM-CD28/41BB-CD3ζ, wherein the CD7 scFv fragment is a monoclonal 3Ale antibody, the heavy and light chain variable regions are joined by a GS linker, and the CD19 scFV fragment is the heavy and light chain variable region of the monoclonal FMC63 antibody linked by a GS linker. The CAR can also include a hinge region and a transmembrane region in tandem, human CD28 and/or 41BB intracellular co-stimulatory elements, as well as human CD3 intracellular domain. In some cases of the present disclosure, a gene fragment of a CAR construct CD19 scFv-CD7 scFv-Hinge-TM-CD28/41BB-CD3ζ can be inserted into a lentiviral vector, and the recombinant vector can be packaged into viral particles in 293T cells. To prepare universal CAR-T cells, T cells can be isolated from peripheral blood mononuclear cells, and after activation, some endogenous genes (e.g., CD7, TCR and PD-1 genes) can be knocked out by gene editing technologies such as CRISPR/CAS technology. Next, T cells can be infected by the viral particles containing the CAR construct describe herein to express the CAR. The prepared CAR-T cells can be used to detect the infection efficiency and gene editing efficiency of CAR by flowcytometry.

The engineered immune cell may have one or more characteristics described herein: (a) the expression of the endogenous CD7 or CD2 gene of the engineered immune cell is silenced; (b) the PD-1 gene expression of the engineered immune cell is silenced; (c) the TCR gene expression of the engineered immune cell is silenced; (d) the engineered immune cell expresses a cytokine or cytokine receptor complex and the pSTAT5 signaling level is up-regulated; (e) the engineered immune cell expresses an exogenous inducible cell death moiety; (f) the first CAR, and/or the second CAR in the engineered immune cell is co-expressed with the inducible cell death moiety.

The engineered immune cell may comprise two different CARs, each having a different antigen binding domain target a different antigen. The engineered immune cell may comprise a single CAR, which further comprises two antigen binding domains targeting two different antigens. In some cases, a first CAR, and/or a second CAR is linked to an inducible cell death moiety and/or an enhancer moiety by a self-cleaving element. In some cases, the enhancer moiety is a cytokine or cytokine complex. Examples of cytokines or cytokine complexes include IL2, IL7, IL15, membrane-bound IL15 (mbIL15 or mb15), and a constitutive activating cytokine receptor such as an IL7 receptor (C7R). As used herein, "mbIL" and "mb" are used interchangeably to refer to a membrane-bound interleukin factor, for example, mbIL7 or mb7, and mbIL17 or mb17.

The engineered immune cell described herein may have the following characteristics: (a) the engineered immune cell expresses a CAR and/or an exogenous TCR, and the CAR and/or exogenous TCR targets tumor cell markers; and (b) the cytokine-associated signaling pathway is enhanced. The engineered immune cell may be (i) chimeric antigen receptor T cells (CAR-T cells); (ii) chimeric antigen receptor NK cells (CAR-NK cells); or (iii) Exogenous T cell receptor (TCR) T cells (TCR-T cells). The engineered immune cell can be a CAR-T cell, preferably a universal CAR-T cell (UCAR-T cell). The "cytokine-related signaling pathway," as used herein, refers to a signaling pathway initiated by the cytokine binding to the corresponding receptor, converting the extracellular signal into an intracellular signal, which is then amplified, dispersed, and regulated by a signal cascade. A series of cellular responses can be produced. In some cases, the cytokine-related signaling pathway comprises a related signaling pathway of a cytokine selected from the group consisting of IL-2, IL-3, IL-4, IL-6, IL-7, IL-8, IL-10, IL-11, IL-12, IL-15, IL-17, IL-18, IL-21, 25 or a combination thereof.

The engineered immune cell can comprise a bispecific CAR (or a dual CAR). For example, the bispecific CAR can comprise both a first antigen binding domain and a second antigen binding domain. The first antigen binding domain and the second antigen binding domain can be linked via a linker. The linker may not comprise a self-cleaving peptide. The first antigen binding domain or the second antigen binding can be a scFv.

The first antigen binding domain and the second antigen binding domain can be arranged, from amino terminus to carboxyl terminus, as: (i) VL2-VH1-VL1-VH2; (ii) VH2-VL1-VH1-VL2; (iii) VL1-VH2-VL2-VH1; or (iv) VH1-VL2-VH2-VL1, wherein VH1 is heavy chain variable domain of the first antigen binding domain, VL1 is light chain variable light domain of the first antigen binding domain, VH2 is heavy chain variable domain of the second antigen binding domain, and VL2 is light chain variable domain of the second antigen binding domain.

The first antigen binding domain and the second antigen binding domain can be arranged, from amino terminus to carboxyl terminus, as: (i) VL2-VH2-VL1-VH1; (ii) VL2-VH2-VH1-VL1; (iii) VL1-VH1-VL2-VH2; or (iv) VL1-VH1-VH2-VL1, wherein VH1 is heavy chain variable domain of the first antigen binding domain, VL1 is light chain variable light domain of the first antigen binding domain, VH2 is heavy chain variable domain of the second antigen binding domain, and VL2 is light chain variable domain of the second antigen binding domain. The first antigen binding domain and the second antigen binding domain can bind to the immune cell antigen and the disease-associated antigen.

In some cases, the engineered immune cell may not comprise a bispecific CAR. For example, an individual CAR of the engineered immune cell can comprise only the first antigen binding domain and an additional individual CAR of the engineered immune cell can comprise only the second antigen binding domain.

The immune cell antigen can be a surface protein or a secreted protein of an immune cell. The immune cell can be an NK cell, a T cell, a monocyte, a macrophage or a granulocyte. The immune cell antigen can be selected from the group consisting of CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ and SLAMF7.

The disease-associated antigen can be a tumor-associated antigen. The tumor-associated antigen can be CD19 or other antigens described herein. In some cases, the first antigen binding domain can bind to an immune cell antigen selected from the group consisting of CD2, CD3, CD5, CD7 and CD137, and the second antigen binding domain can bind to CD19. In some cases, the first antigen binding domain can bind to CD3, and the second antigen binding domain can bind to CD19. In some cases, the first antigen binding domain can bind to CD7, and the second antigen binding domain can bind to CD19. In some cases, the first antigen binding domain can bind to CD137, and the second antigen binding domain can bind to CD19. The expression of one or more endogenous human leukocyte antigen (HLA) genes of the engineered immune cell can remain intact. The expression of endogenous HLA-I and/or HLA-II genes of the engineered immune cell can remain intact. The expression of endogenous HLA-E and/or HLA-G and/or HLA-C genes of the engineered immune cell can remain intact. The expression of one or more endogenous HLA genes of the engineered immune cell can be upregulated. The expression of endogenous HLA-E and/or HLA-G and/or HLA-C genes of the engineered immune cell can be upregulated.

In various embodiments, the engineered immune cell is a T cell, an NKT cell or an NK cell. In some cases, the engineered immune cell is derived from a stem cell. The stem cell can be a hematopoietic stem cell (HSC) or an induced pluripotent stem cell (iPSC).

A cell (e.g., an engineered immune cell) provided herein can comprise one or more chimeric antigen receptors (CARs) comprising a binding moiety, where the binding moiety can comprise an antigen binding domain capable of binding to an immune cell antigen. Each CAR of the one or more CARs can further comprise a transmembrane domain and an intracellular signaling domain. The cell can further comprise an enhancer moiety capable of enhancing one or more activities of the cell, where an endogenous T cell receptor (TCR) of the cell may be inactivated.

The enhancer moiety can enhance one or more activities of the cell. The enhancer moiety can be configured to constitutively enhance the one or more activities of the cell. The enhancer moiety can be configured to constitutively upregulate one or more intracellular signaling pathways of the cell. For example, the one or more intracellular signaling pathways can be one or more cytokine signaling pathways. The enhancer moiety can be a cytokine or a cytokine receptor. The enhancer moiety can be selected from the group consisting of IL-2, IL-3, IL-4, IL-6, IL-7, IL-8, IL-10, IL-11, IL-12, IL-15, IL-17, IL-18, IL-21, IL-23, PD-1, PD-L1, CD122, CSF1R, CTAL-4, TIM-3, CCL21, CCL19, TGFR beta, receptors for the same, functional fragments thereof, functional variants thereof, and combinations thereof.

The cell can further comprise an inducible cell death moiety capable of effecting death of the cell upon contacting the inducible cell death moiety with a cell death activator. The inducible cell death moiety can be selected from the group consisting of rapaCasp9, iCasp9, HSV-TK, ΔCD20, mTMPK, ΔCD19, RQR8, Her2t, CD30, BCMA, and EGFRt. For example, the inducible cell death moiety can be EGFRt, and the cell death activator can be an antibody or an antigen binding fragment thereof that binds EGFRt. For another example, the inducible cell death moiety can be HSV-TK, and the cell death activator can be GCV. For another example, the inducible cell death moiety can be iCasp9, and the cell death activator can be AP1903.

A gene encoding an endogenous surface marker of the cell can be inactivated, where the endogenous surface marker may be capable of binding to the first antigen binding domain when expressed. The endogenous surface marker can be CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ or SLAMF7.

Antigen Binding Domain

The engineered immune cell can comprise a first antigen binding domain and a second antigen binding domain. In some cases, a single or individual CAR of the engineered immune cell comprises both the first antigen binding domain and the second antigen binding domain. In some cases, two CARs of the engineered immune cell comprise the first antigen binding domain and the second antigen binding domain with each CAR contains only one antigen binding domain. In some cases, two engineered immune cells comprise the first antigen binding domain and the second antigen binding domain with each engineered immune cell comprises only one type of antigen binding domain. In some cases, the first antigen binding domain can target an immune cell antigen and the second antigen binding domain can target a disease-associated antigen. The antigen binding domain can be a Fab, $F(ab')_2$, single domain antibody, single chain Fv (scFv), centyrin, darpin, or other polypeptides with antigen binding specificities.

The antigen binding domain can target an immune cell antigen. Examples of immune cell antigen include, but are not limited to, CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ and SLAMF7. In some cases, the immune cell antigen is a cell marker expressed on both T cells and NK cells, including, but not limited to, CD2, CD7, CD38, CD45, CD48, CD50, CD52, CD56, CD69, CD100, CD122, CD132, CD134 (OX40), CD137 (4-1BB), CD178 (ICOS), CD161, CD159a, CD159c and CD314.

CD3 is a marker present on the surface of T lymphocytes. There are three subtypes, CD 3δ, CD 3ε and CD 3γ. CD 3δ and CD 3ε have a molecular weight of 20 kDa, and CD3γ has a molecular weight of 26 kDa, which is expressed on the surface of T lymphocytes, thymocytes and NK cell membranes. CD3 can be expressed in 61% to 85% of normal peripheral blood lymphocytes and 60% to 85% in thymocytes. It belongs to the immunoglobulin superfamily. CD3 is a component of the T-lymphocyte receptor (TCR) complex and forms a complex with the α-β and γ/δ T-lymphocyte receptors (TCRs), which can be the main membrane protein for conducting TCR signals upon TCR binding to peptide/MHC. TCR can be essential for cell surface expression, antigen recognition, and signaling. CD3 is a surface-specific molecule of T lymphocytes through which T lymphocytes with killing effects can be recruited. Monoclonal antibodies to CD3 can induce or prevent T lymphocyte activation. Anti-CD3 antibodies induce apoptosis of T lymphocytes in the presence of anti-CD28 antibodies or IL-2. CD3 is one of the markers of mature T lymphocytes in peripheral blood. Determination of CD3+ T lymphocytes for evaluation of immunodeficiency (T lymphocyte deficiency), leukemia, lymphoma (T lymphocyte type) classification diagnosis. Anti-CD3 monoclonal antibodies can be used for immunosuppressive therapy in organ transplantation or bone marrow transplantation, and can also be used for immunomodulatory treatment of severe autoimmune diseases to remove T lymphocytes.

Figure 13:
FIG. 13 illustrates an example tissue distribution of CD7 mRNA.

In some cases, the antigen binding domain can target CD7. CD7 is a transmembrane protein and is a member of the immunoglobulin superfamily. CD7 proteins are expressed on the surface of mature T cells and NK cells as well as their precursor cells. CD7 can bind to its ligand K12/SECTM1 and function as a co-stimulatory effecter on T cell activation. In mice, CD7 knockout T cell precursors can develop into normal T cells with only a slight effect on T cell effector function. More than 90% of T-cell acute lymphoblastic leukemia (T-ALL) can express CD7, and therefore CD7 can be a marker for T-ALL. Moreover, CD7 can also be expressed in NK lymphoma, T-cell lymphoma/leukemia, chronic myelogenous leukemia, acute myeloid leukemia, and lymphocyte-rich thymoma. An example tissue distribution of CD7 expression is shown in FIG. 13.

Figure 14:
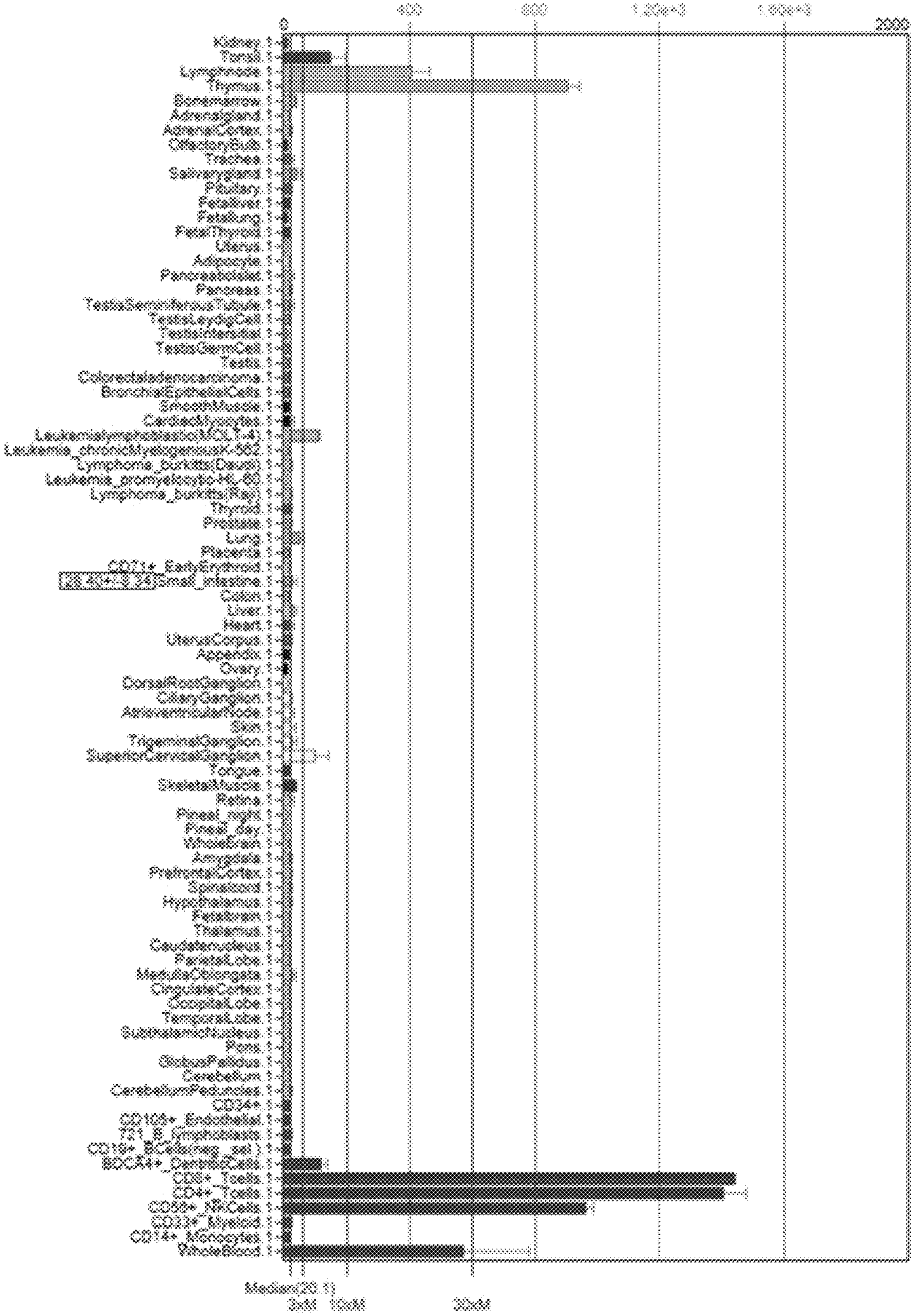
FIG. 14 illustrates an example tissue distribution of CD2 mRNA.

In some cases, the antigen binding domain can target CD2. Similar to CD7, CD2 adhesion molecules may expressed on all peripheral blood T cells and natural killer cells, but not on B lymphocytes. The CD2 extracellular domain contains an immunoglobulin-like domain that mediates homodimerization. Binding of CD2 to CD58 (LFA-3) or CD48 can help T cells adhere to antigen presenting cells, triggering signal transduction of T cell receptors for antigen binding. The function of CD2 may be similar to other T cell costimulatory receptors (such as CD28). CD2 knockout mice can have normal immune function. CD2 expression in cells of T-ALL, T-cell lymphoma/leukemia, acute promyelocytic leukemia (microparticle variant), systemic mastocytosis, mast cell disease, thymoma, and acute myeloid lymphoma and NK cell leukemia. An example tissue distribution of CD2 expression is shown in FIG. 14.

Figure 51:
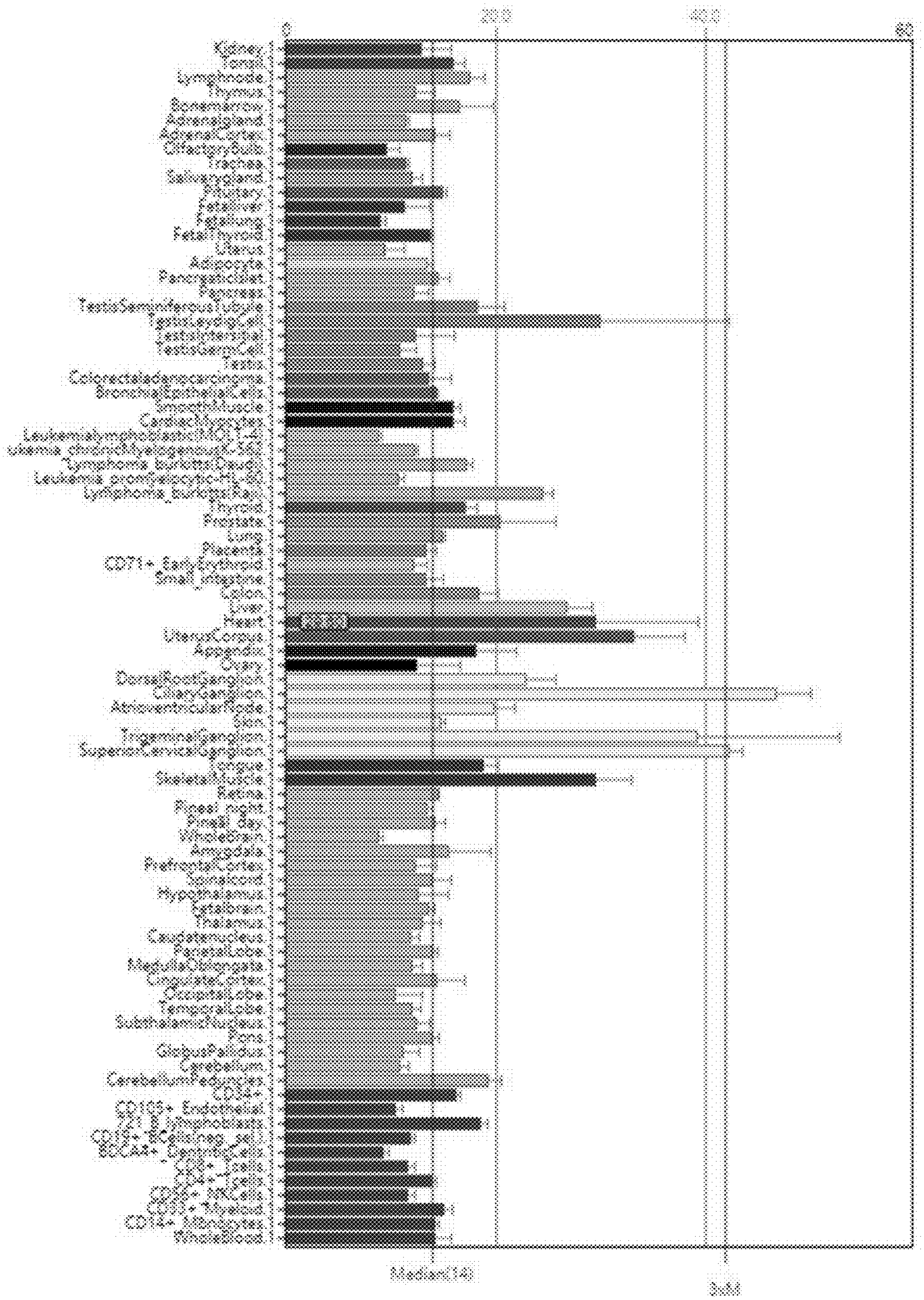
FIG. 51 illustrates an example tissue distribution of CD137 mRNA.

The antigen binding domain can target CD137. CD137, also known as 4-1BB, is a member of the TNF receptor superfamily. CD137 protein can be an activation-induced co-stimulatory receptor, which can be widely expressed in activated T cells, NK cells, dendritic cells, granulocytes and other immune cell types and certain tumor cells. CD137 expression was found on activated T and NK cells with little expression in naïve T cells and inactivated T and NK cells. In T cells, CD137 can initiate NF-κB pathway through TRAF2 and participate in T cell proliferation, cytokine secretion and anti-apoptosis. In clinical applications, CD137 can be used as a marker for reactive T cells. Activation of CD137 signaling pathway by CD137 natural ligand or agonistic antibody can increase cytokine secretion and anti-tumor activity of cytotoxic lymphocytes. Inhibition of reactive T cells with specific inhibitory CD137 antibodies can reduce autologous rejection in transplant rejection or reduce GVHD response caused by autoreactive T cells of an allogeneic origin. CD137 expression can be regulated by TCR signaling and downstream signaling of cytokine IL-2/IL-15. Knockout of CD137 molecule may have no effect on the function of mature T cells in a non-activated state. The endogenous CD137 of the engineered immune cell can be knocked out to avoid fratricide. The endogenous TCRs of the engineered immune cell can be inactivated to prevent GVHD. An example tissue distribution of CD137 expression is shown in FIG. 51.

The antigen binding domain can target a disease-associated antigen, for example, tumor-associated antigen. Examples of the tumor-associated antigens include, but are not limited to, BCMA, VEGFR2, CD19, CD20, CD30, CD22, CD25, CD28, CD30, CD33, CD52, CD56, CD80, CD86, CD81, CD123, cd171, CD276, B7H4, CD133, EGFR, GPC3; PMSA, CD 3, CEACAM6, c-Met, EGFRvIII, ErbB2, ErbB3 HER-2, HER3, ErbB4/HER-4, EphA2, IGF1R, GD2, O-acetyl GD2, O-acetyl GD3, GHRHR, GHR, Flt1, KDR, Flt4, CD44V6, CEA, CA125, CD151, CTLA-4, GITR, BTLA, TGFBR2, TGFBR1, IL6R, gp130, Lewis, TNFR1, TNFR2, PD1, PD-L1, PD-L2, HVEM, MAGE-A, Mesothelin, NY-ESO-1, PSMA, RANK, ROR1, TNFRSF4, CD40, CD137, TWEAK-R, LTPR, LIFRP, LRP5, MUC1, TCRa, TCRp, TLR7, TLR9, PTCH1, WT-1, Robl, Frizzled, OX40, CD79b, Claudin 18.2, Folate receptor α, Folate receptor β. GPC2, CD70, BAFF-R and Notch-1-4. In some cases, the tumor-associated antigens comprise CD19, CD2, CD3, CD4, CD5, CD7, CD8, CD19, CD20, CD22, CD25, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, RORl, TNFRSF4, TWEAK-R, LTPR, LIFRP, LRP5, MUC1, MUC16, TCRa, TCRb, TLR7, TLR9, PTCH1, WT-1, Robol, Frizzled, OX40, Notch-1-4, APRIL, CS1, MAGE3, Claudin 18.2, Folate receptor α, Folate receptor β, GPC2, CD70, BAFF-R or TROP-2.

In some cases, the tumor-associated antigen is CD19. CD19 is a 95 kDa glycoprotein on the surface of B cells that begins to express from the early development of B cells until it differentiates into plasma cells. CD19 is a member of the immunoglobulin (Ig) superfamily and is involved in the regulation of the signal transduction process of B cell receptors as one of the constituent elements of the B cell surface signal transduction complex. In a CD19-deficient mouse model, the number of B cells in peripheral lymphoid tissue can be significantly reduced, and the response to vaccines and mitogens is also reduced, accompanied by a decrease in serum Ig levels. It can be generally believed that the expression of CD19 is restricted to the B-cell lineage and not to the surface of pluripotent hematopoietic stem cells. CD19 can also be expressed on the surface of most B cell lymphomas, mantle cell lymphomas, ALLs, CLLs, hairy cell leukemias, and some acute myeloid leukemia cells. CD19 can be a target for immunotherapy in the treatment of leukemia/lymphoma. CD19 may not be expressed on most normal cell surfaces other than B cells, including pluripotent hematopoietic stem cells. This feature can make CD19 a safe therapeutic target for autoimmune diseases because the risk of irreversible bone marrow toxicity damage can be minimized.

The antigen binding domain provided herein can have a structure shown as $V_H$-$V_L$ or $V_L$-$V_H$, wherein $V_H$ is a heavy chain variable region of an antibody; $V_L$ is a light chain variable region of an antibody; "-" is a linker peptide (or flexible linker) or a peptide bond. In some embodiments, the antigen binding domain targets a tumor-associated antigen. In some embodiments, the tumor-associated antigen comprises CD19. In some embodiments, the antigen binding domain that targets CD19 comprises the heavy chain variable region and the light chain variable region of the monoclonal FMC63 antibody. In some embodiments, the sequence of the linker peptide or flexible linker comprises 2-6, preferably 3-4 consecutive (GGGGS) amino acid sequences (SEQ ID NO: 93). In some embodiments, the amino acid sequence of $V_L$1 is as shown in SEQ ID NO.: 87, and the amino acid sequence of $V_H$1 is shown in SEQ ID NO.: 88. An example amino acid sequence of CAR targeting CD19 is shown in SEQ ID NO.: 89. In some embodiments, the antigen binding domain targets an immune cell antigen. In some embodiments, the immune cell antigen targets CD7. In some other embodiments, the immune cell antigen targets CD2. In some embodiments, the monoclonal antibody of CD7 is selected from the group consisting of TH-69, 3Ale, 3Alf, T3-3A1, RFT2, CD7-6B7, 124-1D1, 4H9, SDZ214-380, or a combination thereof. In some other embodiments, the monoclonal antibody to CD2 is selected from the group consisting of RPA-2.10, TS1/8, OKT11, AB75, 3E11, BH1, or a combination thereof. In some embodiments, the amino acid sequence of $V_L$ is as shown in SEQ ID NO.: 90, and the amino acid sequence of $V_H$ is shown in SEQ ID NO.: 91.

Enhancer Moiety

The engineered immune cell provided herein can comprise an enhancer moiety. The enhancer moiety can regulate one or more activities of the engineered immune cell, for example, enhance or upregulate one or more signaling pathways to enhance or upregulate effector functions of the engineered immune cell. The signaling pathways can be a cytokine-related signaling pathway. The enhancer moiety can be a cytokine. The enhancer moiety can be a cytokine receptor.

The cytokine-related signaling pathway can comprise a related signaling pathway of a cytokine. Examples of cytokines include, but are not limited to, IL-2, IL-3, IL-4, IL-6, IL-7, IL-8, IL-10, IL-11, IL-12, IL-15, IL-17, IL-18, IL-21 and IL25. In some cases, the cytokine-related signaling pathway comprises a related signaling pathway of two or more cytokines, wherein the cytokines include: IL-2 and IL-7, IL-2 and IL-15. IL-7 and IL-15, IL15 and IL21. The cellular response can include regulation of downstream gene expression, changes in intracellular enzyme activity, changes in cellular bone architecture, changes in DNA synthesis, promotion of gene transcription, regulation of immune cell differentiation, proliferation, and resistance to cell death. In some cases, the cytokine-related signaling pathway is enhanced comprising: introducing or up-regulating a gene encoding a cytokine and/or a receptor thereof, exogenously adding a cytokine, being introduced into a cytokine receptor, or a combination thereof. In some cases, up-regulating the gene encoding the cytokine and/or its receptor comprises up-regulating the level of transcription and/or translation of the encoding gene. In some cases, the enhanced cytokine-related signaling pathway can be achieved by one or more of the following methods: expressing a gene encoding the cytokine and/or its receptor in the immune cell, increasing the copy number of the gene encoding the cytokine and/or its receptor in the immune cell, engineering a regulatory sequence (e.g., a promoter) of the encoding gene to enhance transcription speed (e.g., transcriptional initiation rate), modifying a translational regulatory region of a messenger RNA carrying the encoded gene to enhance translational strength, modifying the coding gene itself to enhance mRNA stability, protein stability and to release protein feedback inhibition.

The cytokine-related signaling pathway can be enhanced by membrane expression of a cytokine and its receptor, secretion of a cytokine, enhancement of transcriptional regulation of a cytokine and/or its receptor, or a combination thereof. The membrane-expressed cytokine and its receptors can include: IL-15 and its receptor (e.g., mbIL15 fusion protein), IL-7 and its receptor (e.g., mbIL7 fusion protein), IL-17 and its receptor (e.g., mbIL17 fusion protein), IL-2 and its receptor (e.g., mbIL2 fusion protein), IL-21 and its receptor (e.g., mbIL21 fusion protein), constitute the activated IL-7 receptor (C7R), or a combination thereof. In some cases, the enhancer moiety comprised in the engineered immune cell is a secretive cytokine. The secretive cytokine can function with various mechanisms, for example, the secretive cytokine can be a trans-activating factor or a cis-activating factor. The secretive cytokines can include IL-2, IL-3, IL-4, IL-6, IL-7, IL-8, IL-10, IL-11, IL-12, IL-15, IL-17, IL-18, IL-21, or a combination thereof. In some cases, the enhancer is a membrane bound protein such as mbIL15, mbIL7, mbIL21 and mbIL2. In some cases, the enhancer moiety is constitutively active cytokine receptor downstream signaling protein such as STAT5 and STAT3. In some cases, the enhancer moiety is a constitutively active cytokine receptor such as constitutively active IL-7 receptor (C7R) or derivatives thereof. For example, the constitutively active cytokine receptor can be an engineered protein (e.g., referred to as "E3" in the present disclosure) where the ecto domain of C7R is replaced by a safety switch, such as EGFRt or truncated form of human epidermal growth factor receptor 2 (Her2t; see U.S. Patent Application Publication No. 20170267742A1) or other peptides described in the present disclosure. For another example, the constitutively active cytokine receptor can be an engineered protein (e.g., referred to as "E4" in the present disclosure) where the ectodomain of C7R is replaced by an immune cell inhibitor, such as CD47, CD24 or other peptides that inhibit killer or phagocytic immune cell function and protect therapeutic cells (e.g., the engineered immune cells described herein). In some cases, the cytokine can be a chemokine such as CCL21 and CCL19. Other non-limiting examples of chemokines that may be used include CCL27, CCL28, CCL20, CXCL9, CXCLIO, CXCL11, CXCL16, CXCL13, CXCL5, CXCL6, CXCL8, CXCL12, CCL2, CCL8, CCL13, CCL25, CCL3, CCL4, CCL5, CCL7, CCL14, CCL15, CCL16, CCL23, CX3CL1, XCL1, XCL2, CCL1, CCL17, CCL22, CCL11, CCL24, CCL26, CXCL1, CXCL2, CXCL3 and CXCL7. In some cases, the enhancer moiety is a ligand of CCR7, which can function to enhance infiltration of T cells, NK cells or dendritic cells. CCR7 ligand includes, but not limited to, CCL21 and CCL19. In some cases, the enhancer moiety comprises co-expression of chemokines CCL21 and CCL19 for therapeutic use to treat lymphomas or other solid tumors.

In some situations, the engineered immune cell is used as a therapeutic agent to treat liquid tumors, and in such situations, the enhancer moiety can comprise any cytokine in any form as described herein. In some situations, the engineered immune cell is used as a therapeutic agent to treat solid tumors, and in such situations, the enhancer moiety can comprise any cytokine in any form and further comprise one or more chemokines.

In some cases, two cytokines may be used to enhance the cytokine-related signaling pathway in the engineered immune cell, including IL-2 and IL-7, IL-2 and IL-15, IL-7 and IL-15, and IL15 and IL21. The cytokine-related signaling pathway enhancement can comprise the expression of a polypeptide selected from the group consisting of a mbIL fusion protein, a constitutively active IL-7 receptor (C7R), an interleukin, or a combination thereof.

The enhancer moiety described herein can be interleukin 15 (IL-15) or IL-15 receptor. IL-15 is a 14-15kDs glycoprotein composed of 114 amino acids and belongs to the family of four helix bundle cytokines. IL-15 is structurally homologous to interleukin 2 (IL-2). IL-15 receptor comprises a high affinity IL-15 receptor alpha chain, an IL2/15 receptor beta chain, and a common gamma chain. Therefore, IL-15 may have some functions similar to IL-2, such as stimulating T cell activation and proliferation, enhancing NK cell killing activity and promoting B cell production of immunoglobulin. Recent studies have found that IL-15 may play a role in the differentiation, proliferation and activation of NK cells, NKT cells and intestinal epithelial cells. IL-15 and IL-17 may play a role in the regulation of CD8+ memory T cells. Studies have also shown that IL-15 can regulate the proliferation of CD8+ memory T cells and the survival cycle of NK cells through a mechanism, in which a cell expressing IL-15a chain receptor can present IL-15 to a cell expressing an IL-150 chain and a common gamma chain. IL-15 may also play a role in the non-immune system, such as regulation of skeletal muscle anabolism. The enhancer moiety described herein can be interleukin 7 (IL-7). IL-7 can promote the growth of pre-B cells, pro-B cells, B cells, and T cells. It can also promote growth and anti-apoptosis of B cells and T cells. IL-7 can play a role in the early differentiation and proliferation of thymus and the development and differentiation of dendritic cells. However, IL-7 may not have an enhanced effect on the killing activity of antigen-specific cytotoxic T lymphocytes. It can first transfer from the thymus to the peripheral blood, then induce thymocytes or peripheral blood lymphocytes to produce lymphokines, activate and enhance lymphokine-activated killer cell activity of LAK cells. CD8+ subpopulation can be the main effector cell of IL-7, and IL-7 Can also support memory CD8+ T cell expansion and survival. IL-7 can promote bone marrow tissue production. IL-7 not only can stimulate myeloid precursor cells and megakaryocytes to produce colony forming units and platelets, but also can restore the body from the immunosuppression of cyclophosphamide. At higher concentrations, it can also induce cytotoxicity that enhances macrophages, function as a synergistic factor for the production of CTL cells, NK cells, and activated monocytes, induce monocyte-macrophages to secrete various cytokines and promote the expression of inflammatory factors such as macrophage inflammatory protein alpha (MIP-alpha), MIP-β, IL-8 and monocyte chemoattractant protein-1 (MCP-1) and the like. By activating a large number of inflammatory factors produced by inflammatory cells, IL-7 not only can regulate the interaction between the components of the inflammatory process, but also enhance the inflammatory cytokine receptors (CCR) such as CCR1, CCR2 and CCR5. In addition, IL-7 can play a role in inducing immune responses. IL-7 can induce type I immune responses and increase the production of IFN-γ and IL2. IL-7 can synergize with IL12 to induce IFN-γ and T cell proliferation. IL-7 and transforming growth factor beta (TGFβ) can play a regulatory role and can be part of the immune regulatory mechanism. IL-7 not only can promote immune reconstitution of T cells, but also can induce up-regulation of T cell cycle and BCL-2 expression, which broadens the diversity and persistence of circulating T cell receptor pools and increases the number of CD4+ and CD8+ T cells. Moreover, for HIV antigens, expanded T cells can also secrete IL2 and IFN-γ, and have good antiviral function. Therefore, IL-7 can reverse the defects of HIV-specific T lymphocytes in proliferation, cytokine secretion and cell function.

The enhance moiety can regulate (e.g., activate) signal transducer and activator of transcription 5 (STAT5)-mediated signaling pathway. STAT5 can be widely present in the cytoplasm. When cytokines (e.g., IL2, IL7, IL15 and IL21) bind to the cytokine receptors, the receptor-coupled JAK is activated, thereby phosphorylating the Tyr residue at the C-terminus of the STAT5 protein. The phosphorylated STAT5 can form homologous or heterologous dimers through its SH2 region. The homologous or heterodimer can be transferred to the nucleus and bind to the target gene, thereby regulating the expression of the target gene including the cell regulatory factor and the anti-apoptotic gene. Activation of STAT5 can play a role in maintaining normal cell function and regulating cell proliferation and differentiation. Therefore, regulating the activity of STAT5 signaling pathway may regulate the survival and persistence of CAR-T cells described herein.

The enhancer moiety can be introduced into a cell (e.g., an immune cell or an engineered immune cell) by delivering a nucleic acid molecule encoding the enhancer moiety into the cell. The nucleic acid molecule can be a vector. The enhancer moiety can be a part of a fusion construct. A fusion protein or corresponding nucleic acid construct can have a structure as presented by a formula selected from: S-2A-L1-scFv-H-TM-C-CD3ζ-2A-L2-IL15-IL15Ra (A); S-2A-L1-scFv-H-TM-C-CD3ζ-2A-L2-IL15-IL15Ra-2A-L3-IL7 (B); S-2A-L1-scFv-H-TM-C-CD3ζ-2A-L2-C7R (C); S-2A-L1-scFv-H-TM-C-CD3ζ-2A-L2-IL7-IL7Ra (D); wherein: each "-" is independently a linker peptide or a peptide bond; S is a safety switch; 2A is an optional self-cleaving peptide; each of L1, L2 and L3 is independently null or a signal peptide sequence; C7R is as described above; scFv is an antigen binding domain; H is null or a hinge region; TM is a transmembrane domain; C is a costimulatory signaling molecule; CD3ζ is a cytoplasmic signaling sequence derived from CD3ζ; IL15 is interleukin 15, IL15Ra is IL-15 receptor a; IL7 is interleukin 7, IL7Ra is IL-7 receptor a; C7R is a constitutively activated IL-7 receptor.

The enhancer moiety can be part of a chimeric polypeptide. For example, the enhancer moiety can be linked to an inducible cell death moiety. The enhancer moiety can be linked to the inducible cell death moiety by a linker. The linker may not be cleaved. The linker may not comprise a self-cleaving peptide. In some other cases, the enhancer moiety and the inducible cell death moiety can be expressed in a cell from a same nucleic acid molecule and can be cleaved to form two polypeptides.

Inducible Cell Death Moiety

The engineered immune cell described herein may comprise an inducible cell death moiety, also referred to as "suicide gene switch." "suicide switch," "safety switch," or "cell suicide element." The inducible cell death moiety can be used to effectively remove of the engineered immune cells (e.g., CAR-T cells) in vivo under the action of exogenous factors (e.g., drugs). The inducible cell death moiety described herein may be rapaCasp9, iCasp9, CD20 (and its mimotope), RQR8, Her2t, CD30, BCMA, EGFRt, HSV-TK, mTMPK and the like. iCasp9, CD20 (and its mimotope), RQR8, and HSV-TK may have the same ability to clear T cells, but rapaCasp9, iCasp9, RQR8, and CD20 (and their mimotope) may be faster in comparison with HSV-TK.

In some cases, an inducible cell death moiety is capable of effecting death of said cell upon contacting said inducible cell death moiety with a cell death activator. The inducible cell death moiety can be, for example, rapaCasp9, iCasp9, HSV-TK, ΔCD20, mTMPK, ΔCD19, RQR8, or EGFRt. In some cases, the inducible cell death moiety is EGFRt, and said cell death activator is an antibody or an antigen binding fragment thereof that binds EGFRt. In some cases, the inducible cell death moiety is HSV-TK, and said cell death activator is GCV. In some cases, the inducible cell death moiety is iCasp9, and said cell death activator is AP1903.

The inducible cell death moiety can be linked to an enhancer moiety and can be co-expressed in a cell as a chimeric polypeptide as described above.

Graft Versus Host Disease (GVHD)

To prepare "off-the-shelf" allogeneic T cells for the treatment of malignant and infectious diseases, cell therapy by infusion of T cells can be designed to re-establish immunity against pathogens and malignancies. The amount of time required to produce the T cells with tumor-targeting properties with a sufficient number of T cells in vitro can be generally incompatible with the patient's therapeutic window. Furthermore, autologous T cells from patients with advanced disease may have impaired function and are tolerant to the desired antigen.

To address these issues, patients can be administered with allogeneic T cells but need to be prevented from immune-mediated rejection by host T cells by recognizing different major or minor histocompatibility antigens on the infused cells. Infusion of T cells without the expression of TCR alpha and beta chains and HLA-A molecules may not cause GVHD and HVG. Thus the T cells edited with CRISPR/CAS9 to delete TCR alpha chain and HLA-A molecular can serve as a source of universal effector donor cells.

Although knockdown of Beta-2-Microglobulin (B2M) may prevent donor CAR-T cells from being attacked by the host T cells. The donor CAR-T cells may be attacked by host NK cells and affect the survival of CAR-T cells. Therefore, the present disclosure provides engineered immune cells which target tumor cells and host T cells and/or NK cells. The engineered immune cells described herein can scavenge host T cells and/or NK cells, and enhance the survival, persistence and expansion ability of CAR-T cells, thereby being more effective against tumor cells.

Gene Editing

Various gene editing methods can be used in the present disclosure to make the engineered immune cells, including CRISPR, RNA interference technology, TALENs (transcription activator-like (TAL) effector nucleases) and Zinc finger nucleases (ZFNs).

In some cases, CRISPR/Cas9 system is used to edit the genes of the immune cells. For example, CRISPR/Cas9 system can be used to knockout endogenous TCRs or cell surface markers (e.g., CD7) of the immune cells to generate the engineered immune cells for T cell therapy. The CRISPR/Cas9 (clustered regular interspaced short palindromic repeats)/Cas (CRISPR-associated) system is a natural immune system unique to prokaryotes that is resistant to viruses or exogenous plasmids. The Type II CRISPR/Cas system has been applied in many eukaryotic and prokaryotic organisms as a direct genome-directed genome editing tool. The development of the CRISPR/Cas9 system has revolutionized the ability of people to edit DNA sequences and regulate the expression levels of target genes, providing a powerful tool for accurate genome editing of organisms. The simplified CRISPR/Cas9 system can comprise Cas9 protein and gRNA. The principle of action is that gRNA forms a Cas9-gRNA complex with Cas9 protein through its own Cas9 handle, and the base complementary pairing sequence of gRNA in the Cas9-gRNA complex is paired with the target sequence of the target gene by the principle of base complementary pairing. Cas9 uses its own endonuclease activity to cleave the target DNA sequence. Compared to traditional genome editing techniques, the CRISPR/Cas9 system has several distinct advantages: ease of use, simplicity, low cost, programmability, and the ability to edit multiple genes simultaneously.

Pharmaceutical Composition

The present disclosure also provides a pharmaceutical composition comprising an engineered immune cell described herein and a pharmaceutically acceptable carrier, diluent or excipient. In some embodiments, the pharmaceutical composition is a liquid composition. The pharmaceutical composition can be administered into a subject, for example, by injection. The concentration of the engineered immune cells in the preparation can be at least about $10^2$, $10^3$, $10^4$, $10^5$, $10^6$, $10^7$, $10^8$, $10^9$, or more cells/ml. In some case, the concentration of the engineered immune cells in the preparation can be $1\times10^3$–$1\times10^8$ cells/ml, or $1\times10^4$–$1\times10^7$ cells/ml.

The pharmaceutical compositions of the present disclosure may comprise engineered immune cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for intravenous administration.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an antitumor effective amount", "an tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can generally be stated that a pharmaceutical composition comprising the engineered immune cells (e.g., CAR-T cells) described herein may be administered at a dosage of $10^4$ to $10^9$ cells/kg body weight, or in some cases, $10^5$ to $10^6$ cells/kg body weight, including all integer values within those ranges. T cell compositions may also be administered multiple times at these dosages. The cells can be administered by using infusion techniques. The optimal dosage and treatment regime for a particular patient can readily be determined by monitoring the patient for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In some embodiments, the T cell compositions of the present disclosure are administered to a patient by intradermal or subcutaneous injection. In some other embodiments, the T cell compositions of the present disclosure are preferably administered by i.v. injection. The compositions of T cells may be injected directly into a tumor, lymph node, or site of infection.

Therapeutics

The present disclosure provides therapeutic applications with engineered immune cells (e.g., T cells or NK cells) transduced with a lentiviral vector (LV) encoding an expression cassette described herein. Transduced T cells or NK cells can target tumor cell markers (such as CD19) and activated T cell and/or NK cell consensus markers (such as CD3, CD7, CD137, etc.). The engineered immune cells can be used for allogeneic tumor treatment and can be prepared on a large scale.

Accordingly, the present disclosure also provides a method of stimulating a T cell mediated immune response to a target cell population or tissue of a subject (e.g., a mammal) comprising the step of administering to the subject an engineered immune cell (e.g., CAR-T cell) of the disclosure.

In some embodiments, the present disclosure provides a type of cell therapy comprising directly administering engineered universal CAR-T cells of the present disclosure to a patient in need thereof. The CAR-T cells of the present disclosure may have the endogenous TCR expression knocked out or silenced in the cells by gene editing technology. Inactivation of the endogenous TCRs can prevent killing of normal cells by the TCRs during the allogeneic infusion. The GVHD reaction may be prevented. The CAR-T cells targeting a tumor cell marker (such as CD19) and a marker for activated T cells and/or NK cells (such as CD137) can remove activated T cells and/or NK cells while scavenging tumor cells. In addition, host versus graft response (HVG) can also be prevented. The cell therapy provided herein can also improve the survival and antitumor effect of allogeneic CAR-T cells in the subject.

In some embodiments, provided herein is a method of treating or diagnosing a disease in a subject, comprising administering the pharmaceutical composition described herein to said subject.

The engineered immune cell in said pharmaceutical composition can be derived from an allogeneic immune cell. The engineered immune cell derived from said allogeneic immune cell may not induce graft versus host disease (GvHD) in said subject. The engineered immune cell in said pharmaceutical composition can be derived from an autologous immune cell.

The endogenous TCR of said engineered immune cell in said pharmaceutical composition may be functionally inactive. The engineered immune cell can reduce GVHD in said subject compared to an additional immune cell having a functionally active TCR. The disease can be a cancer. The cancer can be, for example, lymphoma or leukemia.

The CAR-T cells of the present disclosure can undergo robust in vivo cell expansion and can be extended. The CAR-mediated immune response can be part of a step of adoptive immunotherapy in which CAR-modified T cells can induce an immune response specific for the antigen-binding domain in the CAR. For example, anti-CD19 CAR-T cells elicit a specific immune response against cells expressing CD19.

The engineered immune cells provided herein can be used to treat cancers. Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the present disclosure include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In some embodiments, the antigen bind moiety portion of the CAR of the present disclosure is designed to treat a particular cancer. For example, the CAR designed to target CD19 can be used to treat cancers and disorders including but are not limited to pre-B ALL (pediatric indication), adult ALL, mantle cell lymphoma, diffuse large B-cell lymphoma, salvage post allogeneic bone marrow transplantation, and the like. In some embodiments, the CAR can be designed to target CD22 to treat diffuse large B-cell lymphoma. In some embodiments, cancers and disorders include but are not limited to pre-B ALL (pediatric indication), adult ALL, mantle cell lymphoma, diffuse large B-cell lymphoma, salvage post allogeneic bone marrow transplantation, and the like can be treated using a combination of CARs that target CD19, CD20, CD22, and ROR1. In some embodiments, the CAR can be designed to target mesothelin to treat mesothelioma, pancreatic cancer, ovarian cancer, and the like. In some embodiments, the CAR can be designed to target CD33/IL3Ra to treat acute myelogenous leukemia and the like. In some embodiments, the CAR can be designed to target c-Met to treat triple negative breast cancer, non-small cell lung cancer, and the like. In some embodiments, the CAR can be designed to target PSMA to treat prostate cancer and the like. In some embodiments, the CAR can be designed to target Glycolipid F77 to treat prostate cancer and the like. In some embodiments, the CAR can be designed to target EGFRvIII to treat gliobastoma and the like. In some embodiments, the CAR can be designed to target GD-2 to treat neuroblastoma, melanoma, and the like. In some embodiments, the CAR can be designed to target NY-ESO-1 TCR to treat myeloma, sarcoma, melanoma, and the like. In some embodiments, the CAR can be designed to target MAGE A3 TCR to treat myeloma, sarcoma, melanoma, and the like.

The present disclosure should not be construed to be limited to solely to the antigen targets and diseases disclosed herein. Rather, the present disclosure should be construed to include any antigenic target that is associated with a disease where a CAR can be used to treat the disease.

The cell therapy disclosed herein can be co-formulated with, and/or co-administered with, one or more additional therapeutic agents, e.g., one or more anti-cancer agents, cytotoxic or cytostatic agents, hormone treatment, vaccines, and/or other immunotherapies. In some embodiments, the engineered immune cells are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

In certain embodiments, the methods and compositions described herein are administered in combination with one or more antibody molecules, chemotherapy, other anti-cancer therapy (e.g., targeted anti-cancer therapies, or oncolytic drugs), cytotoxic agents, immune-based therapies (e.g., cytokines), surgical and/or radiation procedures. Exemplary cytotoxic agents that can be administered in combination with include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteasome inhibitors, and radiation (e.g., local or whole body irradiation).

In certain embodiments, the combination therapy, is used in combination with a standard of cancer care chemotherapeutic agent including, but not limited to, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cy-tosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeox-ycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), MYLOTARG®, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injec-tion (Hycamptin®), vinblastine (Velban®), vincristine (Oncovin®), and vinorelbine (Navelbine®).

Examples of alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pi-pobroman (Amedel®, Vercyte®), triethylenemelamine (Hemel®, Hexalen®, Hexastat®), triethy-lenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Car-boplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, ThioplexR); Cyclophosphamide (Endoxan®, Cytoxan®, Neosar®, Procytox®, Revimmune®); and Bendamustine HCl (Treanda®).

Examples of anthracyclines include, e.g., doxorubicin (Adriamycin® and Rubex®); bleomycin (Lenoxane®); daunorubicin (dauorubicin hydrochloride, daunomycin, and rubidomycin hydro-chloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetyl-ravidomycin.

Examples of vinca alkaloids that can be used in combination with the cell therapy described herein, include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Examples of proteasome inhibitors that can be used in combination with the cell therapy described herein, include, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); 0-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912); danoprevir (RG7227, CAS 850876-88-9); ixazomib (MLN2238, CAS 1072833-77-2); and (S)—N-[(phenylmethoxy)carbonyl]-L-leucyl-N-(1-formyl-3-methylbutyl)-L-Leucinamide (MG-132, CAS 133407-82-6).

In some embodiments, the cell therapy may be used in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor and a RET inhibitor. In some embodiments, the anti-cancer agent used in combination with the hedgehog inhibitor is selected from the group consisting of: axitinib (AG013736), bosutinib (SKI-606), cediranib (RE-CENTIN®, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENTR, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAM-PATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (ZACTIMA®), WZ3146, WZ4002, WZ8040, ABT-869 (linifanib), AEE788, AP24534 (ponatinib), AV-951 (tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, Sorafenib Tosylate (Bay 43-9006), SU 5402, TSU-68 (SU6668), vatalanib, XL880 (GSK1363089, EXEL-2880). Further examples of hedgehog inhibitors include, but are not limited to, vismodegib (2-chloro-N-[4-chloro-3-(2-pyridinyl)phenyl]-4-(methylsulfonyl)-benzamide, GDC-0449); 1-(4-Chloro-3-(trifluoromethyl)phenyl)-3-((3-(4-fluorophenyl)-3,4-dihydro-4-oxo-2-quinazolinyl)methyl)-urea (CAS 330796-24-2); N-[(2S,3R,3'R,3aS,4'aR,6S,6'aR,6'bS,7aR,12'aS,12'bS)-2',3',3a,4,4',4'a,5,5',6,6',6'a,6'b,7,7',7a,8',10',12',12'a,12'b-Eicosahydro-3,6,11',12'b-tetramethylspiro[furo[3,2-b]pyridine-2(3H),9'(1'H)-naphth[2,1-a]azulen]-3'-yl]-methanesulfonamide (IPI926, CAS 1037210-93-7); and 4-Fluoro-N-methyl-N-[1-[4-(1-methyl-1H-pyrazol-5-yl)-1-phthalazinyl]-4-piperidinyl]-2-(trifluoromethyl)-benzamide (LY2940680, CAS 1258861-20-9); and Erismodegib (LDE225). Selected tyrosine kinase inhibitors are chosen from sunitinib, erlotinib, gefitinib, or sorafenib erlotinib hydrochloride (Tarceva®); linifanib (N-[4-(3-amino-1H-indazol-4-yl)phenyl]-N'-(2-fluoro-5-methylphenyl)urea, also known as ABT 869, available from Genentech); sunitinib malate (Sutent®); bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, described in U.S. Pat. No. 6,780,996); dasatinib (Sprycel®); pazopanib (Votrient®); sorafenib (Nexavar®); ZACTIMA® (ZD6474); and imatinib or imatinib mesylate (Gil-vec® and Gleevec®).

In certain embodiments, the cell therapy can be used in combination with a Vascular Endothelial Growth Factor (VEGF) receptor inhibitors, including but not limited to, Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)$_2$-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TK1258, CAS 852433-84-2); Linfan-ib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

In some embodiments, the cell therapy described herein can be used in combination with a PI3K inhibitor. The PI3K inhibitor can be an inhibitor of delta and gamma isoforms of PI3K. Examples of PI3K inhibitors include, but are not limited to, 4-[2-(1H-Indazol-4-yl)-6-[[4-(methylsulfonyl)piperazin-1-yl]methyl]thieno[3,2-d]pyrimidin-4-yl]morpholine; 2-Methyl-2-[4-[3-methyl-2-oxo-8-(quinolin-3-yl)-2,3-dihydroimidazo[4,5-c]quinolin-1-yl]phenyl] propionitrile; 4-(trifluoromethyl)-5-(2,6-dimorpholinopyrimidin-4-yl)pyridin-2-amine; Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); 8-Phenyl-2-(morpholin-4-yl)-chromen-4-one (LY294002, CAS 154447-3δ-6); 2-Amino-8-ethyl-4-methyl-6-(1H-pyrazol-5-yl)pyrido[2,3-d]pyrimidin-7(8H)-one (SAR 245409 or XL 765); 1,3-Dihydro-8-(6-methoxy-3-pyridinyl)-3-methyl-1-[4-(1-piperazinyl)-3-(trifluoromethyl)phenyl]-2H-imidazo[4,5-c]quinolin-2-one, (2Z)-2-butenedioate (1:1) (BGT 226); 5-Fluoro-3-phenyl-2-[(1S)-1-(9H-purin-6-ylamino)ethyl]-4(3H)-quinazolinone (CAL101); 2-Amino-N-[3-[N-[3-[(2-chloro-5-methoxyphenyl)amino]quinoxalin-2-yl]sulfamoyl]phenyl]-2-methylpropanamide (SAR 245408 or XL 147); and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (BYL719).

In some embodiments, the cell therapy described herein can be used in combination with a mTOR inhibitor, e.g., one or more mTOR inhibitors chosen from one or more of rapamycin, temsirolimus (TORISEL®), AZD8055, BEZ235, BGT226, XL765, PF-4691502, GDC0980, SF1126, OSI-027, GSK1059615, KU-0063794, WYE-354, Palomid 529 (P529), PF-04691502, or PKI-587. ridaforolimus (formally known as deferolimus, (1R,2R,4S)-4-[(2R)-2[(1R,9S,12S,15R,16E,18R,19R,21R, 23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.04,9]hexatriaconta-16,24,26,28-tetraen-12-yl]propyl]-2-methoxycyclohexyl di-methylphosphinate, also known as AP23573 and MK8669, and described in PCT Publication No. WO 03/064383); everolimus (Afinitor® or RAD001); rapamycin (AY22989, Sirolimus®); simapi-mod (CAS 164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-3δ-4); and N2-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 94), inner salt (SF1126, CAS 936487-67-1), (1r,4r)-4-(4-amino-5-(7-methoxy-1H-indol-2-yl)imidazo[1,5-f][1,2,4]triazin-7-yl)cyclohexanecarboxylic acid (OSI-027); and XL765.

In some embodiments, the cell therapy can be used in combination with a BRAF inhibitor, e.g., GSK2118436, RG7204, PLX4032, GDC-0879, PLX4720, and sorafenib tosylate (Bay 43-9006). In further embodiments, a BRAF inhibitor includes, but is not limited to, regorafenib (BAY73-4506, CAS 755037-03-7); tuvizanib (AV951, CAS 475108-18-0); vemurafenib (Zel-boraf®, PLX-4032, CAS 918504-65-1); encorafenib (also known as LGX818); 1-Methyl-5-[[2-[5-(trifluoromethyl)-1H-imidazol-2-yl]-4-pyridinyl]oxy]-N-[4-(trifluoromethyl)phenyl-1H-benzimidazol-2-amine (RAF265, CAS 927880-90-8); 5-[1-(2-Hydroxyethyl)-3-(pyridin-4-yl)-1H-pyrazol-4-yl]-2,3-dihydroinden-1-one oxime (GDC-0879, CAS 905281-76-7); 5-[2-[4-[2-(Dimethylamino)ethoxy]phenyl]-5-(4-pyridinyl)-1H-imidazol-4-yl]-2,3-dihydro-1H-Inden-1-one ox-ime (GSK2118436 or SB590885); (+/−)-Methyl (5-(2-(5-chloro-2-methylphenyl)-1-hydroxy-3-oxo-2,3-dihydro-1H-isoindol-1-yl)-1H-benzimidazol-2-yl)carbamate (also known as XL-281 and BMS908662) and N-(3-(5-chloro-1H-pyrrolo[2,3-b]pyridine-3-carbonyl)-2,4-difluorophenyl)propane-1-sulfonamide (also known as PLX4720).

In some embodiments, the cell therapy described herein can be used in combination with a MEK inhibitor. Any MEK inhibitor can be used in combination including, but not limited to, selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886); ARRY-142886 trametinib dimethyl sulfoxide (GSK-1120212, CAS 1204531-25-80); G02442104 (also known as GSK1120212), RDEA436; N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766); RDEA119/BAY 869766, AS703026; G00039805 (also known as AZD-6244 or selumetinib), BIX 02188; BIX 02189; 2-[(2-Chloro-4-iodophenyl)amino]-N-(cyclopropylmethoxy)-3,4-difluoro-benzamide (also known as CI-1040 or PD184352); CI-1040 (PD-184352), N-[(2R)-2,3-Dihydroxypropoxy]-3,4-difluoro-2-[(2-fluoro-4-iodophenyl)amino]-benzamide (also known as PD0325901); PD03259012'-amino-3'-methoxyflavone (also known as PD98059 available from Biaffin GmbH & Co., KG, Germany); PD98059, 2,3-bis[amino[(2-aminophenyl)thio]methylene]-butanedinitrile (also known as U0126); U0126, XL-518 (also known as GDC-0973, Cas No. 1029872-29-4, available from ACC Corp.); GDC-0973 (Methanone, [3,4-difluoro-2-[(2-fluoro-4-iodophenyl)amino]phenyl][3-hydroxy-3-(25)-2-piperidinyl-1-azetidinyl]-), G-38963; and G02443714 (also known as AS703206), or a pharmaceutically acceptable salt or solvate thereof. Further examples of MEK inhibitors include, but are not limited to, benimetinib (6-(4-bromo-2-fluorophenylamino)-7-fluoro-3-methyl-3H-benzoimidazole-5-carboxylic acid (2-hydroxyethyoxy)-amide, also known as MEK162, CAS 1073666-70-2); 2,3-Bis[amino[(2-aminophenyl)thio]methylene]-butanedinitrile (also known as U0126 and described in U.S. Pat. No. 2,779,780); (3S,4R,5Z,8S,9S,11E)-14-(Ethylamino)-8,9,16-trihydroxy-3,4-dimethyl-3,4,9,19-tetrahydro-1H-2-benzoxacyclotetradecine-1,7(8H)-dione](also known as E6201); vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); pimasertib (AS-703026, CAS 1204531-26-9); 2-(2-Fluoro-4-iodophenylamino)-N-(2-hydroxyethoxy)-1,5-dimethyl-6-oxo-1,6-dihydropyridine-3-carboxamide (AZD 8330); and 3,4-Difluoro-2-[(2-fluoro-4-iodophenyl)amino]-N-(2-hydroxyethoxy)-5-[(3-oxo-[1,2]oxazinan-2-yl)methyl]benzamide (CH 4987655 or Ro 4987655).

In some embodiments, the cell therapy described herein can be used in combination with a JAK2 inhibitor, e.g., CEP-701, INCB18424, CP-690550 (tasocitinib). Example JAK inhibitors include, but are not limited to, ruxolitinib (Jakafi®); tofacitinib (CP690550); axitinib (AG013736, CAS 319460-85-0); 5-Chloro-N2-[(1S)-1-(5-fluoro-2-pyrimidinyl)ethyl]-N4-(5-methyl-1H-pyrazol-3-y)-12,4-pyrimidinediamine (AZD1480, CAS 935666-88-9); (9E)-15-[2-(1-Pyrrolidinyl)ethoxy]-7,12,26-trioxa-19,21,24-triazatetracyclo[18.3.1.12,5.114,18]-hexacosa-1(24),2,4,9,14,16,18(25),20,22-nonaene (SB-1578, CAS 937273-04-6); momelotinib (CYT 387); baricitinib (INCB-028050 or LY-3009104); pacritinib (SB1518); (16E)-14-Methyl-20-oxa-5,7,14,27-tetraazatetracyclo[19.3.1.12,6.18,12]heptacosa-1(25),2,4,6(27),8,10,12(26),16,21,23-decaene (SB 1317); gandotinib (LY 2784544); and N,N-cicyclopropyl-4-[(1,5-dimethyl-1H-pyrazol-3-yl)amino]-6-ethyl-1,6-dihydro-1-methyl-imidazo[4,5-d]pyrrolo[2,3-b]pyridine-7-carboxamide (BMS 911543).

In some embodiments, the combination therapies disclosed herein include paclitaxel or a paclitaxel agent, e.g., TAXOL®, protein-bound paclitaxel (e.g., ABRAXANE®). Exemplary paclitaxel agents include, but are not limited to, nanoparticle albumin-bound paclitaxel (ABRAX-ANE®, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX®, marketed by Cell Therapeutic), the tumor-activated prodrug (TAP), ANG105 (Angiopep-2 bound to three molecules of paclitaxel, marketed by Im-munoGen®), paclitaxel-EC-1 (paclitaxel bound to the erbB2-recognizing peptide EC-1; see Li et al., Biopolymers (2007) 87:225-230), and glucose-conjugated paclitaxel (e.g., 2'-paclitaxel me-thyl 2-glucopyranosyl succinate).

Methods

The present disclosure provides methods for generating an engineered cell. In some aspects, the method can comprise (a) delivering a nucleic acid molecule expressing a chimeric polypeptide into a cell; and (b) expressing the nucleic acid molecule in the cell, thereby generating the engineered cell. The chimeric polypeptide can be a chimeric antigen receptor as described herein.

The present disclosure also provides methods for administering an engineered cell as described herein. The engineered cell can be an engineered immune cell. The engineered immune cell can be a T cell. The engineered immune cell can be derived from an autologous T cell. The engineered immune cell can be derived from an allogeneic T cell.

In some aspects, provided herein is a method for administering an engineered immune cell comprising a chimeric polypeptide comprising (i) an enhancer moiety capable of enhancing one or more activities of the engineered immune cell, and (ii) an inducible cell death moiety capable of effecting death of the engineered immune cell upon contacting the chimeric polypeptide with a cell death activator. The enhancer moiety can be linked to the inducible cell death moiety. The engineered immune cell can further comprise one or more chimeric antigen receptors (CARs) comprising a binding moiety. The binding moiety can comprise a first antigen binding domain, which first antigen binding domain suppresses or reduces a subject's immune response toward the engineered immune cell when administered into the subject. The binding moiety can further comprise a second antigen binding domain capable of binding to a disease-associated antigen. An individual CAR of the one or more CARs can comprise (i) the first antigen binding domain, (ii) the second antigen binding domain, or (iii) both the first antigen binding domain and the second antigen binding domain. Each CAR of the one or more CARs can further comprise a transmembrane domain and an intracellular signaling domain.

In some aspects, provided herein is a method of administering an engineered immune cell comprising one or more chimeric antigen receptors (CARs) comprising a binding moiety. The binding moiety can comprise a first antigen binding domain capable of binding to an immune cell antigen and a second antigen binding domain capable of binding to a disease-associated antigen. Each CAR of the one or more CARs can further comprise a transmembrane domain and an intracellular signaling domain. The engineered immune cell can further comprise an enhancer moiety capable of enhancing one or more activities of the engineered immune cell. In some cases, an endogenous T cell receptor (TCR) of the engineered immune cell can be inactivated. The engineered immune cell can exhibit (i) enhanced degree of persistence by remaining viable in vitro for at least about 5, 10, 15, 20, 25, 30, 35, 40, 45, 50, 55, 60, 65, 70, 75, 80, 85, 90, 95, 100, 150, 200, 250, 300, 350, 400, 450, 500, or more days while in presence of cells (e.g., cancer cells, immune cells, or both) that are heterologous to the engineered immune cell, (ii) enhanced degree of expansion by at least about 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 110-fold, 120-fold, 130-fold, 140-fold, 150-fold, 200-fold, 250-fold, 300-fold, or more within 15 days, or (iii) enhanced cytotoxicity against a target cell comprising the immune cell antigen or the disease-associated antigen, compared to an additional engineered immune cell comprising the one or more CARs but not the enhancer moiety. In some cases, the engineered immune cell can exhibit enhanced degree of expansion by at least about 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 350-fold, 400-fold, 450-fold, 500-fold, or more within 30 days. In some cases, the engineered immune cell can exhibit enhanced degree of expansion by at least about 100-fold, 200-fold, 300-fold, 400-fold, 500-fold, 600-fold, 700-fold, 800-fold, 900-fold, 1,000-fold, 2,000-fold, 3,000-fold, 4,000-fold, 5,000-fold, 6,000-fold, 7,000-fold, 8,000-fold, 9,000-fold, 10,000-fold, 20,000-fold, 30,000-fold, 40,000-fold, 50,000-fold, 60,000-fold, 70,000-fold, 80,000-fold, 90,000-fold, 100,000-fold, 200,000-fold, 300,000-fold, 400,000-fold, 500,000-fold, 600,000-fold, 700,000-fold, 800,000-fold, 900,000-fold, 1,000,000-fold, or more within 60 days. The viability or expansion can be measured in the presence of stimulation, for example, stimulation by a cancer antigen or a cancer cell. The viability or expansion can be measured in the presence of multiple rounds or repeated stimulations.

In some aspects, provided herein is a method of administering a cell (e.g., an engineered immune cell), comprising a functionally inactive T cell receptor (TCR). The cell can further comprise one or more chimeric antigen receptors (CARs). Each individual CAR of the one or more CARs can comprise a binding moiety. The binding moiety can comprise (i) a first antigen binding domain, which first antigen binding domain suppresses or reduces a subject's immune response toward the engineered immune cell when administered into the subject and (ii) a second antigen binding domain that binds to a disease-associated antigen. Each CAR of the one or more CARs can further comprise a transmembrane domain and an intracellular signaling domain.

In some aspects, provided herein is a method of administering an engineered immune cell comprising an enhancer moiety capable of enhancing one or more activities of the engineered immune cell. The engineered cell can further comprise a chimeric antigen receptor (CAR) comprising an antigen binding domain that specifically binds CD7. The CAR can further comprise a transmembrane domain and an intracellular signaling domain. The endogenous CD7 in the engineered immune cell can be inactivated. In some embodiments, the engineered cell can comprise a CAR comprising an antigen binding domain that specifically binds an immune cell antigen. The immune cell antigen can be any immune cell antigen described herein such as CD2, CD3, CD4, CD5, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ and SLAMF7. The endogenous immune cell antigen of the engineered cell, which the antigen binding domain binds, can be inactivated in the engineered cell.

In some aspects, provided herein is a method of administering an engineered immune cell comprising a single chimeric antigen receptor (CAR) comprising (i) a first antigen binding domain that specifically binds CD7 and (ii) a second antigen binding domain capable of binding to a disease-associated antigen. The CAR can further comprise a transmembrane domain and an intracellular signaling domain. A gene encoding endogenous CD7 can be inactivated in the engineered immune cell.

The present disclosure also provides methods of treating or diagnosing a disease in a subject. In some cases, the method comprises administering a pharmaceutical composition comprising an engineered immune cell into a subject. The engineered immune cell in the pharmaceutical composition can be derived from an allogeneic immune cell. The engineered immune cell derived from the allogeneic immune cell may not induce graft versus host disease (GVHD) in the subject. The engineered immune cell in the pharmaceutical composition can be derived from an autologous immune cell. In some cases, an endogenous TCR of the engineered immune cell in the pharmaceutical composition is functionally inactive. The engineered immune cell can reduce GVHD in the subject compared to an immune cell having a functionally active TCR. The disease can be a cancer. For example, the cancer can be lymphoma or leukemia.

The present disclosure also provides a method of delivering an allogeneic cell therapy comprising administering to a subject in need thereof a population of engineered immune cells. An individual engineered immune cell of the population can comprise one or more chimeric antigen receptors (CARs) comprising a binding moiety. The binding moiety can comprise a first antigen binding domain capable of binding to an immune cell antigen. The binding moiety can further comprise a second antigen binding domain capable of binding to a disease-associated antigen. The first antigen binding domain can suppress or reduce a subject's immune response toward the engineered immune cell when administered into the subject. The engineered immune cell can further comprise an enhancer moiety capable of enhancing one or more activities of the engineered immune cell. The endogenous T cell receptor (TCR) of the engineered immune cell can be inactivated. For example, a gene encoding a subunit of TCR can be inactivated. Various gene editing methods described herein can be used to inactivate endogenous TCRs of a T cell.

In some embodiments, a method provided herein can include activation of a population of cells. In some cases, the cell used to prepare the engineered immune cell can be activated before preparing the engineered immune cell. In some cases, the engineered immune cell can be activated. Activation as used herein can refer to a process whereby a cell transitions from a resting state to an active state. This process can comprise a response to an antigen, migration, and/or a phenotypic or genetic change to a functionally active state. In some aspects, activation can refer to the stepwise process of T cell activation. In some cases, a T cell can require one or more signals to become activated. For example, a T cell can require at least two signals to become fully activated. The first signal can occur after engagement of a TCR by the antigen-MHC complex, and the second signal can occur by engagement of co-stimulatory molecules. Anti-CD3 antibody (or a functional variant thereof) can mimic the first signal and anti-CD28 antibody (or a functional variant thereof) can mimic the second signal in vitro.

In some aspects, a method provided herein can comprise activation of a population of cells. Activation can be performed by contacting a population of cells with a surface having attached thereto an agent that can stimulate a CD3 TCR complex associated signal and a ligand that can stimulate a co-stimulatory molecule on the surface of the cells. In particular, T cell populations can be stimulated in vitro such as by contact with an anti-CD3 antibody or antigen-binding fragment thereof, or an anti-CD2 antibody immobilized on a surface, or by contact with a protein kinase C activator (e.g., bryostatin) sometimes in conjunction with a calcium ionophore. For co-stimulation of an accessory molecule on the surface of the T cells, a ligand that binds the accessory molecule can be used. For example, a population of cells can be contacted with an anti-CD3 antibody and an anti-CD28 antibody, under conditions that can stimulate proliferation of the T cells. In some cases, 4-1BB can be used to stimulate cells. For example, cells can be stimulated with 4-1BB and IL-21 or another cytokine. For activation of either CD4 T cells or CD8 T cells, an anti-CD3 antibody and an anti-CD28 antibody can be used. For example, the agents providing a signal may be in solution or conjugated to a solid phase surface. The ratio of particles to cells may depend on particle size relative to the target cell. In further embodiments, the cells, such as T cells, can be combined with agent-coated beads, where the beads and the cells can be subsequently separated, and optionally cultured. Each bead can be coated with either anti-CD3 antibody or an anti-CD28 antibody, or in some cases, a combination of the two. In an alternative embodiment, prior to culture, the agent-coated beads and cells are not separated but are cultured together. Cell surface proteins may be conjugated by allowing paramagnetic beads to which anti-CD3 antibody and anti-CD28 antibody can be attached (3×28 beads) to contact the T cells. In one embodiment the cells and beads (for example, DYNABEADS® M-450 CD3/CD28 T paramagnetic beads at a ratio of 1:1) are combined in a buffer, for example, phosphate buffered saline (PBS) (e.g., without divalent cations such as, calcium and magnesium). Any cell concentration may be used. The mixture may be cultured for or for about several hours (e.g., about 3 hours) to or to about 14 days or any hourly integer value in between. In another embodiment, the mixture may be cultured for or for about 21 days or for up to or for up to about 21 days. Conditions appropriate for T cell culture can include an appropriate media (e.g., Minimal Essential Media or RPMI Media 1640 or, X-vivo™ 5, (Lonza)) that may contain factors necessary for proliferation and viability, including serum (e.g., fetal bovine or human serum), interleukin-2 (IL-2), insulin, IFN-g, IL-4, IL-7, GM-CSF, IL-10, IL-21, IL-15, TGF beta, and TNF alpha or any other additives for the growth of cells. Other additives for the growth of cells include, but are not limited to, surfactant, plasmanate, and reducing agents such as N-acetyl-cysteine and 2-mercaptoethanol. Media can include RPMI 1640, A1 M-V, DMEM, MEM, α-MEM, F-12, X-Vivo™ 1, and X-Vivo™ 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, can be included only in experimental cultures, possibly not in cultures of cells that are to be infused into a subject. The target cells can be maintained under conditions necessary to support growth; for example, an appropriate temperature (e.g., 37° C.) and atmosphere (e.g., air plus 5% $CO_2$). In some instances, T cells that have been exposed to varied stimulation times may exhibit different characteristics. In some cases, a soluble monospecific tetrameric antibody against human CD3, CD28, CD2, or any combination thereof may be used. In some embodiments, activation can utilize an activation moiety, a costimulatory agent, and any combination thereof. In some aspects, an activation moiety binds: a CD3/T cell receptor complex and/or provides costimulation. In some aspects, an activation moiety is any one of anti-CD3 antibody and/or anti-CD28 antibody. In some aspects, a solid phase is at least one of a bead, plate, and/or matrix. In some aspects, a solid phase is a bead. Alternatively or in addition to, the activation moiety may be not be conjugated a substrate, e.g., the activation moiety may be free-floating in a medium.

In some cases, a population of cells can be activated or expanded by co-culturing with tissue or cells. A cell can be an antigen presenting cell. An artificial antigen presenting cells (aAPCs) can express ligands for T cell receptor and costimulatory molecules and can activate and expand T cells for transfer, while improving their potency and function in some cases. An aAPC can be engineered to express any gene for T cell activation. An aAPC can be engineered to express any gene for T cell expansion. An aAPC can be a bead, a cell, a protein, an antibody, a cytokine, or any combination. An aAPC can deliver signals to a cell population that may undergo genomic transplant. For example, an aAPC can deliver a signal 1, signal, 2, signal 3 or any combination. A signal 1 can be an antigen recognition signal. For example, signal 1 can be ligation of a TCR by a peptide-MHC complex or binding of agonistic antibodies directed towards CD3 that can lead to activation of the CD3 signal-transduction complex. Signal 2 can be a co-stimulatory signal. For example, a co-stimulatory signal can be anti-CD28, inducible co-stimulator (ICOS), CD27, and 4-1BB (CD137), which bind to ICOS-L, CD70, and 4-1BBL, respectively. Signal 3 can be a cytokine signal. A cytokine can be any cytokine. A cytokine can be IL-2, IL-7, IL-12, IL-15, IL-21, or any combination thereof. In some cases an artificial antigen presenting cell (aAPC) may be used to activate and/or expand a cell population. In some cases, an artificial may not induce allospecificity. An aAPC may not express HLA in some cases. An aAPC may be genetically modified to stably express genes that can be used to activation and/or stimulation. In some cases, a K562 cell may be used for activation. A K562 cell may also be used for expansion. A K562 cell can be a human erythroleukemic cell line. A K562 cell may be engineered to express genes of interest. K562 cells may not endogenously express HLA class I, II, or CD1d molecules but may express ICAM-1 (CD54) and LFA-3 (CD58). K562 may be engineered to deliver a signal 1 to T cells. For example, K562 cells may be engineered to express HLA class I. In some cases, K562 cells may be engineered to express additional molecules such as B7, CD80, CD83, CD86, CD32, CD64, 4-1BBL, anti-CD3, anti-CD3 mAb, anti-CD28, anti-CD28mAb, CD1d, anti-CD2, membrane-bound IL-15, membrane-bound IL-17, membrane-bound IL-21, membrane-bound IL-2, truncated CD19, or any combination. In some cases, an engineered K562 cell can expresses a membranous form of anti-CD3 mAb, clone OKT3, in addition to CD80 and CD83. In some cases, an engineered K562 cell can expresses a membranous form of anti-CD3 mAb, clone OKT3, membranous form of anti-CD28 mAb in addition to CD80 and CD83.

An aAPC can be a bead. A spherical polystyrene bead can be coated with antibodies against CD3 and CD28 and be used for T cell activation. A bead can be of any size. In some cases, a bead can be or can be about 3 and 6 micrometers.

A bead can be or can be about 4.5 micrometers in size. A bead can be utilized at any cell to bead ratio. For example, a 3 to 1 bead to cell ratio at 1 million cells per milliliter can be used. An aAPC can also be a rigid spherical particle, a polystyrene latex microbeads, a magnetic nano- or micro-particles, a nanosized quantum dot, a 4, poly(lactic-co-glycolic acid) (PLGA) microsphere, a nonspherical particle, a 5, carbon nanotube bundle, a 6, ellipsoid PLGA microparticle, a 7, nanoworms, a fluidic lipid bilayer-containing system, an 8, 2D-supported lipid bilayer (2D-SLBs), a 9, liposome, a 10, RAFTsomes/microdomain liposome, an 11, SLB particle, or any combination thereof. In some cases, an aAPC can expand CD4 T cells. For example, an aAPC can be engineered to mimic an antigen processing and presentation pathway of HLA class II-restricted CD4 T cells. A K562 can be engineered to express HLA-D, DP α, DP β chains, Ii, DM α, DM β, CD80, CD83, or any combination thereof. For example, engineered K562 cells can be pulsed with an HLA-restricted peptide in order to expand HLA-restricted antigen-specific CD4 T cells. In some cases, the use of aAPCs can be combined with exogenously introduced cytokines for T cell activation, expansion, or any combination. Cells can also be expanded in vivo, for example in the subject's blood after administration of genomically transplanted cells into a subject.

In some embodiments, a method provided herein can comprise transduction of a population of cells. In some embodiments, a method comprises introducing a polynucleotide encoding for a cellular receptor such as a chimeric antigen receptor and/or a T cell receptor. In some cases, a transfection of a cell can be performed.

In some embodiments, a viral supernatant comprising a polynucleotide encoding for a cellular receptor such as a CAR and/or TCR is generated. In some embodiments, a viral vector can be a retroviral vector, a lentiviral vector and/or an adeno-associated viral vector. Packaging cells can be used to form virus particles capable of infecting a host cell. Such cells can include 293 cells, (e.g., for packaging adenovirus), and Psi2 cells or PA317 cells (e.g., for packaging retrovirus). Viral vectors can be generated by producing a cell line that packages a nucleic acid vector into a viral particle. The vectors can contain the minimal viral sequences required for packaging and subsequent integration into a host. The vectors can contain other viral sequences being replaced by an expression cassette for the polynucleotide(s) to be expressed. The missing viral functions can be supplied in trans by the packaging cell line. For example, AAV vectors can comprise ITR sequences from the AAV genome which are required for packaging and integration into the host genome. Viral DNA can be packaged in a cell line, which can contain a helper plasmid encoding the other AAV genes, namely rep and cap, while lacking ITR sequences. The cell line can also be infected with adenovirus as a helper. The helper virus can promote replication of the AAV vector and expression of AAV genes from the helper plasmid. Contamination with adenovirus can be reduced by, e.g., heat treatment to which adenovirus is more sensitive than AAV. Additional methods for the delivery of nucleic acids to cells can be used, for example, as described in US20030087817, incorporated herein by reference.

In some embodiments, a host cell can be transiently or non-transiently transfected with one or more vectors described herein. A cell can be transfected as it naturally occurs in a subject. A cell can be taken or derived from a subject and transfected. A cell can be derived from cells taken from a subject, such as a cell line. In some embodiments, a cell transfected with one or more vectors described herein is used to establish a new cell line comprising one or more vector-derived sequences. Non-limiting examples of vectors for eukaryotic host cells include but are not limited to: pBs, pQE-9 (Qiagen), phagescript, PsiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWL-neo, pSv2cat, pOG44, pXT1, pSG (Stratagene) pSVK3, pBPv, pMSG, pSVL (Pharmiacia). Also, any other plasmids and vectors can be used as long as they are replicable and viable in a selected host. Any vector and those commercially available (and variants or derivatives thereof) can be engineered to include one or more recombination sites for use in the methods. Such vectors can be obtained from, for example, Vector Laboratories Inc., Invitrogen, Promega, Novagen, NEB, Clontech, Boehringer Mannheim, Pharmacia, EpiCenter, OnGenes Technologies Inc., Stratagene, PerkinElmer, Pharmingen, and Research Genetics. Other vectors of interest include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMClneo, and pOG44 (Stratagene, Inc.), and pYES2, pAC360, pBlueBacHis A, B, and C, pVL1392, pBlueBac111, pCDM8, pcDNA1, pZeoSV, pcDNA3 pREP4, pCEP4, and pEBVHis (Invitrogen, Corp.), and variants or derivatives thereof. Other vectors include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSYSPORT1 (Invitrogen) and variants or derivatives thereof. Additional vectors of interest can also include pTrxFus, pThioHis, pLEX, pTrcHis, pTrcHis2, pRSET, pBlueBacHis2, pcDNA3.1/His, pcDNA3.1(−)/Myc-His, pSecTag, pEBVHis, pPIC9K, pPIC3.5K, pA081S, pPICZ, pPICZA, pPICZB, pPICZC, pGAPZA, pGAPZB, pGAPZC, pBlueBac4.5, pBlueBacHis2, pMelBac, pSinRep5, pSinHis, pIND, pIND(SP1), pVgRXR, pcDNA2.1, pYES2, pZEr01.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; X ExCell, X gt11, pTrc99A, pKK223-3, pGEX-1X T, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-lb(+), pT7Blue(R), pT7Blue-2, pCITE-4-abc(+), pOCUS-2, pTAg, pET-32L1C, pET-30LIC, pBAC-2 cp LIC, pBACgus-2 cp LIC, pT7Blue-2 LIC, pT7Blue-2, X SCREEN-1, X BlueSTAR, pET-3abcd, pET-7abc, pET9abcd, pET11 abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd (+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3 cp, pBACgus-2 cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFPN, pEGFP-C, pEBFP, pGFPuv, pGFP, p6xHis-GFP, pSEAP2-Basic, pSEAP2-Contral, pSEAP2-Promoter, pSEAP2-Enhancer, p I3 gal-Basic, pl3 gal-Control, p I3 gal-Promoter, p I3 gal-Enhancer, pCMV, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, 2Xgt10, Xgt11, pWE15, and X TriplEx from Clontech; Lambda ZAP II, pBK-CMV, pBK-RSV, pBluescript II KS+/−, pBluescript II SK+/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS+/−, pBC KS+/−, pBC SK+/−, Phag-escript, pCAL-n-EK, pCAL-n, pCAL-c, pCAL-kc, pET-3abcd, pET-llabcd, pSPUTK, pESP-1, pCMVLacI, pOPRSVI/MCS, pOPI3 CAT, pXT1, pSG5, pPbac, pMbac, pMClneo, pMClneo Poly A, pOG44, p0G45, pFRTI3GAL, pNE0I3GAL, pRS403, pRS404, pRS405, pRS406, pRS413, pRS414, pRS415, and pRS416 from Stratagene, pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp, and variants or derivatives thereof. In some embodiments, a vector can be a minicircle vector. A vector provided herein can be used to deliver a polypeptide coding for a CAR and/or TCR.

Transduction and/or transfection can be performed by any one of: non-viral transfection, biolistics, chemical transfection, electroporation, nucleofection, heat-shock transfection, lipofection, microinjection, or viral transfection. In some embodiments a provided method comprises viral transduction, and the viral transduction comprises a lentivirus. Viral particles can be used to deliver a viral vector comprising a polypeptide sequence coding for a cellular receptor into a cell ex vivo or in vivo. In some cases, a viral vector as disclosed herein may be measured as pfu (plaque forming units). In some cases, the pfu of recombinant virus or viral vector of the compositions and methods of the disclosure may be about $10^8$ to about $5\times10^{10}$ pfu. In some cases, recombinant viruses of this disclosure are at least about $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, and $5\times10^{10}$ pfu. In some cases, recombinant viruses of this disclosure are at most about $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, and $5\times10^{10}$ pfu. In some aspects, the viral vector of the disclosure may be measured as vector genomes. In some cases, recombinant viruses of this disclosure are $1\times10^{10}$ to $3\times10^{12}$ vector genomes, or $1\times10^9$ to $3\times10^{13}$ vector genomes, or $1\times10^8$ to $3\times10^{14}$ vector genomes, or at least about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ vector genomes, or are $1\times10^8$ to $3\times10^{14}$ vector genomes, or are at most about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ vector genomes. In some cases, a viral vector provided herein can be measured using multiplicity of infection (MOI). In some cases, MOI may refer to the ratio, or multiple of vector or viral genomes to the cells to which the nucleic may be delivered. In some cases, the MOI may be $1\times10^6$. In some cases, the MOI may be $1\times10^5$ to $1\times10^7$. In some cases, the MOI may be $1\times10^4$ to $1\times10^8$. In some cases, recombinant viruses of the disclosure are at least about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10_{13}$, $1\times10^{14}$, $1\times10^{15}$, $1\times10^{16}$, $1\times10^{17}$, and $1\times10^{18}$ MOI. In some cases, recombinant viruses of this disclosure are $1\times10^8$ to $3\times10^{14}$ MOI, or are at most about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI. In some cases, a viral vector is introduced at a multiplicity of infection (MOI) from about $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$ $4\times10^6$, $5\times10^6$, $6\times10^6$, $7\times10^6$, $8\times10^6$, $9\times10^6$, $1\times10^7$, $2\times10^7$, $3\times10^7$, or up to about $9\times10^9$ genome copies/virus particles per cell.

The transfection efficiency of cells with any of the nucleic acid delivery platforms described herein, for example, transduction, can be or can be about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%. In some embodiments, a method can comprise adding an infective agent to a composition comprising a population of cells. An infective agent can comprise polybrene. In some aspects, an infective agent can enhance efficiency of viral infection. An infective agent can enhance viral infectivity from about 100 to 1,000 fold. Polybrene can be added to a composition at a concentration from about 5 ug to 10 ug per ml.

In some embodiments, a method provided herein can comprise a non-viral approach of introducing a cellular receptor to a cell. Non-viral approaches can include but are not limited to: CRISPR associated proteins (Cas proteins, e.g., Cas9), Zinc finger nuclease (ZFN), Transcription Activator-Like Effector Nuclease (TALEN), Argonaute nucleases, and meganucleases. Nucleases can be naturally existing nucleases, genetically modified, and/or recombinant. Non-viral approaches can also be performed using a transposon-based system (e.g. PiggyBac, Sleeping beauty).

In some embodiments, a method provided herein can utilize a PiggyBac system to introduce an exogenous polypeptide to a cell. A PiggyBac system comprises two components, a transposon and a transposase. The PiggyBac transposase facilitates the integration of the transposon specifically at 'TTAA' sites randomly dispersed in the genome. The predicted frequency of 'TTAA' in the genome is approximately 1 in every 256 base-pairs of DNA sequence. Unlike other transposons, the PB transposase also enables the excision of the transposon in a completely seamless manner, leaving no sequences or mutations behind. Furthermore, PiggyBac offers a large cargo-carrying capacity (over 200 kb has been demonstrated) with no known upper limit. PB performance levels can be increased by codon-optimization strategies, mutations, deletions, additions, substitutions, and any combination thereof. In some cases, PB can have a larger cargo (approximately 9.1-14.3 kb), a higher transposition activity, and its footprint-free characteristic can make it appealing as a gene editing tool. In some aspects, PB can comprise a few features: high efficiency transposition; large cargo; steady long-term expression; the trans-gene is integrated as a single copy; tracking the target gene in vivo by a noninvasive mark instead of traditional method such as PCR; easy to determine the integration site, and combinations thereof.

In some aspects, a method provided herein can utilize a Sleeping Beauty (SB) System to introduce a polypeptide coding for a cellular receptor to a cell. SB was engineered from ancient Tc1/mariner transposon fossils found within the Salmonid genomes by in vitro evolution. The SB ITRs (230 bp) contain imperfect direct repeats (DRs) of 32 bp in length that can serve as recognition signals for the transposase. Binding affinity and spacing between the DR elements within ITR has involved in transpositional activities. The SB transposase can be a 39 kDa protein that possess DNA binding polypeptide, a nuclear localization signal (NLS) and the catalytic domain, featured by a conserved amino acid motif (DDE). Various screens mutagenizing the primary amino acid sequence of the SB transposase resulted in hyperactive transposase versions. In some cases, a modified SB can be utilized. Modified SBs can contain mutations, deletions and additions within ITRs of the original SB transposon. Modified SBs can comprise: pT2, pT3, pT2B, pT4, SB100X, and combinations thereof. Non-limited examples of modified SBs can be selected from: SB10, SB11 (3-fold higher than SB10), SB12 (4-fold higher than SB10), HSB1-HSB5 (up to 10-fold higher than SB10), HSB13-HSB17 (HSB17 is 17-fold higher than SB10), SB100X (100-fold higher than SB10), SB150X (130-fold higher than SB10), and any combination thereof. In some cases, SB100X is 100-fold hyperactive compared to the originally resurrected transposase (SB10). In some aspects, SB transposition excision leaves a footprint (3 bp) at the cargo site. Integration occurs into TA dinucleotides of the genome, and results in target site duplications, generated by the host repair machinery. In some cases, SB appears to possess a nearly unbiased, close-to-random integration profile. Transposon integration can be artificially targeted (~10%) to a predetermined genomic locus in wildtype systems, however in chimeric systems provided herein, SB transposon integration can be directed to a predetermined locus with efficiencies over 10%.

In some aspects, a non-viral approach may be taken to introduce an exogenous polynucleic acid to a population of cells. In some aspects, a non-viral vector or nucleic acid may be delivered without the use of a virus and may be measured according to the quantity of nucleic acid. Generally, any suitable amount of nucleic acid can be used with the compositions and methods of this disclosure. In some cases, nucleic acid may be at least about 1 pg, 10 pg, 100 pg, 1 pg, 10 pg, 100 pg, 200 pg, 300 pg, 400 pg, 500 pg, 600 pg, 700 pg, 800 pg, 900 pg, 1 μg, 10 μg, 100 μg, 200 μg, 300 μg, 400 μg, 500 μg, 600 μg, 700 μg, 800 μg, 900 μg, 1 ng, 10 ng, 100 ng, 200 ng, 300 ng, 400 ng, 500 ng, 600 ng, 700 ng, 800 ng, 900 ng, 1 mg, 10 mg, 100 mg, 200 mg, 300 mg, 400 mg, 500 mg, 600 mg, 700 mg, 800 mg, 900 mg, 1 g, 2 g, 3 g, 4 g, or 5 g. In some cases, nucleic acid may be at most about 1 pg, 10 pg, 100 pg, 1 pg, 10 pg, 100 pg, 200 pg, 300 pg, 400 pg, 500 pg, 600 pg, 700 pg, 800 pg, 900 pg, 1 μg, 10 μg, 100 μg, 200 μg, 300 μg, 400 μg, 500 μg, 600 μg, 700 μg, 800 μg, 900 μg, 1 ng, 10 ng, 100 ng, 200 ng, 300 ng, 400 ng, 500 ng, 600 ng, 700 ng, 800 ng, 900 ng, 1 mg, 10 mg, 100 mg, 200 mg, 300 mg, 400 mg, 500 mg, 600 mg, 700 mg, 800 mg, 900 mg, 1 g, 2 g, 3 g, 4 g, or 5 g.

In some embodiments, a non-viral approach of introducing a CAR and/or TCR sequence to a cell can include electroporation. Electroporation can be performed using, for example, the Neon Transfection System (ThermoFisher Scientific) or a transfection system product sold under the trademark Amaxa® Nucleofector®. Electroporation parameters may be adjusted to optimize transfection efficiency and/or cell viability. Electroporation devices can have multiple electrical wave form pulse settings such as exponential decay, time constant and square wave. Every cell type has a unique optimal Field Strength (E) that is dependent on the pulse parameters applied (e.g., voltage, capacitance and resistance). Application of optimal field strength causes electropermeabilization through induction of transmembrane voltage, which allows nucleic acids to pass through the cell membrane. In some cases, the electroporation pulse voltage, the electroporation pulse width, number of pulses, cell density, and tip type may be adjusted to optimize transfection efficiency and/or cell viability.

In some embodiments, electroporation pulse voltage may be varied to optimize transfection efficiency and/or cell viability. In some cases, the electroporation voltage may be less than about 500 volts. In some cases, the electroporation voltage may be at least about 500 volts, at least about 600 volts, at least about 700 volts, at least about 800 volts, at least about 900 volts, at least about 1000 volts, at least about 1100 volts, at least about 1200 volts, at least about 1300 volts, at least about 1400 volts, at least about 1500 volts, at least about 1600 volts, at least about 1700 volts, at least about 1800 volts, at least about 1900 volts, at least about 2000 volts, at least about 2100 volts, at least about 2200 volts, at least about 2300 volts, at least about 2400 volts, at least about 2500 volts, at least about 2600 volts, at least about 2700 volts, at least about 2800 volts, at least about 2900 volts, or at least about 3000 volts. In some cases, the electroporation pulse voltage required for optimal transfection efficiency and/or cell viability may be specific to the cell type. For example, an electroporation voltage of 1900 volts may optimal (e.g., provide the highest viability and/or transfection efficiency) for macrophage cells. In another example, an electroporation voltage of about 1350 volts may optimal (e.g., provide the highest viability and/or transfection efficiency) for Jurkat cells or primary human cells such as T cells. In some cases, a range of electroporation voltages may be optimal for a given cell type. For example, an electroporation voltage between about 1000 volts and about 1300 volts may optimal (e.g., provide the highest viability and/or transfection efficiency) for human 578T cells. In some cases, a primary cell can be a primary lymphocyte. In some cases, a population of primary cells can be a population of lymphocytes.

In some embodiments, electroporation pulse width may be varied to optimize transfection efficiency and/or cell viability. In some cases, the electroporation pulse width may be less than about 5 milliseconds. In some cases, the electroporation width may be at least about 5 milliseconds, at least about 6 milliseconds, at least about 7 milliseconds, at least about 8 milliseconds, at least about 9 milliseconds, at least about 10 milliseconds, at least about 11 milliseconds, at least about 12 milliseconds, at least about 13 milliseconds, at least about 14 milliseconds, at least about 15 milliseconds, at least about 16 milliseconds, at least about 17 milliseconds, at least about 18 milliseconds, at least about 19 milliseconds, at least about 20 milliseconds, at least about 21 milliseconds, at least about 22 milliseconds, at least about 23 milliseconds, at least about 24 milliseconds, at least about 25 milliseconds, at least about 26 milliseconds, at least about 27 milliseconds, at least about 28 milliseconds, at least about 29 milliseconds, at least about 30 milliseconds, at least about 31 milliseconds, at least about 32 milliseconds, at least about 33 milliseconds, at least about 34 milliseconds, at least about 35 milliseconds, at least about 36 milliseconds, at least about 37 milliseconds, at least about 38 milliseconds, at least about 39 milliseconds, at least about 40 milliseconds, at least about 41 milliseconds, at least about 42 milliseconds, at least about 43 milliseconds, at least about 44 milliseconds, at least about 45 milliseconds, at least about 46 milliseconds, at least about 47 milliseconds, at least about 48 milliseconds, at least about 49 milliseconds, or at least about 50 milliseconds. In some cases, the electroporation pulse width required for optimal transfection efficiency and/or cell viability may be specific to the cell type. For example, an electroporation pulse width of 30 milliseconds may optimal (e.g., provide the highest viability and/or transfection efficiency) for macrophage cells. In another example, an electroporation width of about 10 milliseconds may optimal (e.g., provide the highest viability and/or transfection efficiency) for Jurkat cells. In some cases, a range of electroporation widths may be optimal for a given cell type. For example, an electroporation width between about 20 milliseconds and about 30 milliseconds may optimal (e.g., provide the highest viability and/or transfection efficiency) for human 578T cells.

In some embodiments, the number of electroporation pulses may be varied to optimize transfection efficiency and/or cell viability. In some cases, electroporation may comprise a single pulse. In some cases, electroporation may comprise more than one pulse. In some cases, electroporation may comprise 2 pulses, 3 pulses, 4 pulses, 5 pulses 6 pulses, 7 pulses, 8 pulses, 9 pulses, or 10 or more pulses. In some cases, the number of electroporation pulses required for optimal transfection efficiency and/or cell viability may be specific to the cell type. For example, electroporation with a single pulse may be optimal (e.g., provide the highest viability and/or transfection efficiency) for macrophage cells. In another example, electroporation with a 3 pulses may be optimal (e.g., provide the highest viability and/or transfection efficiency) for primary cells. In some cases, a range of electroporation widths may be optimal for a given cell type. For example, electroporation with between about 1 to about 3 pulses may be optimal (e.g., provide the highest viability and/or transfection efficiency) for human cells.

In some cases, the starting cell density for electroporation may be varied to optimize transfection efficiency and/or cell viability. In some cases, the starting cell density for electroporation may be less than about $1\times10^5$ cells. In some cases, the starting cell density for electroporation may be at least about $1\times10^5$ cells, at least about $2\times10^5$ cells, at least about $3\times10^5$ cells, at least about $4\times10^5$ cells, at least about $5\times10^5$ cells, at least about $6\times10^5$ cells, at least about $7\times10^5$ cells, at least about $8\times10^5$ cells, at least about $9\times10^5$ cells, at least about $1\times10^6$ cells, at least about $1.5\times10^6$ cells, at least about $2\times10^6$ cells, at least about $2.5\times10^6$ cells, at least about $3\times10^6$ cells, at least about $3.5\times10^6$ cells, at least about $4\times10^6$ cells, at least about $4.5\times10^6$ cells, at least about $5\times10^6$ cells, at least about $5.5\times10^6$ cells, at least about $6\times10^6$ cells, at least about $6.5\times10^6$ cells, at least about $7\times10^6$ cells, at least about $7.5\times10^6$ cells, at least about $8\times10^6$ cells, at least about $8.5\times10^6$ cells, at least about $9\times10^6$ cells, at least about $9.5\times10^6$ cells, at least about $1\times10^7$ cells, at least about $1.2\times10^7$ cells, at least about $1.4\times10^7$ cells, at least about $1.6\times10^7$ cells, at least about $1.8\times10^7$ cells, at least about $2\times10^7$ cells, at least about $2.2\times10^7$ cells, at least about $2.4\times10^7$ cells, at least about $2.6\times10^7$ cells, at least about $2.8\times10^7$ cells, at least about $3\times10^7$ cells, at least about $3.2\times10^7$ cells, at least about $3.4\times10^7$ cells, at least about $3.6\times10^7$ cells, at least about $3.8\times10^7$ cells, at least about $4\times10^7$ cells, at least about $4.2\times10^7$ cells, at least about $4.4\times10^7$ cells, at least about $4.6\times10^7$ cells, at least about $4.8\times10^7$ cells, or at least about $5\times10^7$ cells. In some cases, the starting cell density for electroporation required for optimal transfection efficiency and/or cell viability may be specific to the cell type. For example, a starting cell density for electroporation of $1.5\times10^6$ cells may optimal (e.g., provide the highest viability and/or transfection efficiency) for macrophage cells. In another example, a starting cell density for electroporation of $5\times10^6$ cells may optimal (e.g., provide the highest viability and/or transfection efficiency) for human cells. In some cases, a range of starting cell densities for electroporation may be optimal for a given cell type. For example, a starting cell density for electroporation between of $5.6\times10^6$ and $5\times10^7$ cells may optimal (e.g., provide the highest viability and/or transfection efficiency) for human cells such as T cells.

A method for treating a lymphoid malignancy is provided. The method can comprise administering to a patient in need thereof a population of engineered immune cells. An individual engineered immune cell of the population can comprise one or more chimeric antigen receptors (CARs) comprising a binding moiety, where the binding moiety can comprise an antigen binding domain capable of binding to an immune cell antigen, and where each CAR of the one or more CARs can further comprise a transmembrane domain and an intracellular signaling domain. An individual engineered immune cell of the population can further comprise an enhancer moiety capable of enhancing one or more activities of the engineered immune cell. An endogenous T cell receptor (TCR) of the engineered immune cell may be inactivated. In some cases, the number of affected cells in peripheral blood or the number of affected cells in bone marrow of the patient can be reduced by at least about 10%, 15%, 20%, 25%, 30%, 35%, 40%, 45%, 50%, 55%, 60%, 65%, 70%, 75%, 80%, 85%, 90%, 95% or more within a period (e.g., 3 weeks) after a last dosing of the engineered immune cells. In some cases, the period after a last dosing of the engineered immune cell can be about 1 week, 2 weeks, 3 weeks, 4 weeks, 5 weeks or more. The number of any one or more of autologous T cell, granulocyte, and NK cell in peripheral blood of the patient can start to increase within a period (e.g., 3 weeks) after a last dosing of the engineered immune cells. In some cases, the period after a last dosing of the engineered immune cell can be about 1 week, 2 weeks, 3 weeks, 4 weeks, 5 weeks or more.

The enhancer moiety can enhance one or more activities of the engineered immune cell. The enhancer moiety can be configured to constitutively enhance the one or more activities of the engineered immune cell. The enhancer moiety can be configured to constitutively upregulate one or more intracellular signaling pathways of the engineered immune cell. The one or more intracellular signaling pathways can be one or more cytokine signaling pathways. The enhancer moiety can be a cytokine or a cytokine receptor. The enhancer moiety can be selected from the group consisting of IL-2, IL-3, IL-4, IL-6, IL-7, IL-8, IL-10, IL-11, IL-12, IL-15, IL-17, IL-18, IL-21, IL-23, PD-1, PD-L1, CD122, CSF1R, CTAL-4, TIM-3, CCL21, CCL19, TGFR beta, receptors for the same, functional fragments thereof, functional variants thereof, and combinations thereof.

The engineered immune cell can further comprise an inducible cell death moiety capable of effecting death of the cell upon contacting the inducible cell death moiety with a cell death activator. The inducible cell death moiety can be selected from the group consisting of rapaCasp9, iCasp9, HSV-TK, ΔCD20, mTMPK, ΔCD19, RQR8, Her2t, CD30, BCMA, and EGFRt. For example, the inducible cell death moiety can be EGFRt, and the cell death activator can be an antibody or an antigen binding fragment thereof that binds EGFRt. For another example, the inducible cell death moiety can be HSV-TK, and the cell death activator can be GCV.

For another example, the inducible cell death moiety can be iCasp9, and the cell death activator can be AP1903.

A gene encoding an endogenous surface marker of the cell can be inactivated. The endogenous surface marker can be capable of binding to the first antigen binding domain when expressed. The endogenous surface marker can be CD2, CD3, CD4, CD5, CD7, CD8, CD16a, CD16b, CD25, CD27, CD28, CD30, CD38, CD45, CD48, CD50, CD52, CD56, CD57, CD62L, CD69, CD94, CD100, CD102, CD122, CD127, CD132, CD137, CD160, CD161, CD178, CD218, CD226, CD244, CD159a (NKG2A), CD159c (NKG2C), NKG2E, CD279, CD314 (NKG2D), CD305, CD335 (NKP46), CD337, CD319 (CS1), TCRα, TCRβ or SLAMF7.

The number of any one or more of autologous T cell, granulocyte, and NK cell in peripheral blood of the patient may start to increase before the number of affected cells in peripheral blood or the number of affected cells in bone marrow is reduced by at least about 10%, 15%, 20%, 25%, 30%, 35%, 40%, 45%, 50%, 55%, 60%, 65%, 70%, 75%, 80%, 85%, 90%, 95% or more. The number of any one or more of autologous T cell, granulocyte, and NK cell in peripheral blood may start to increase after the number of affected cells in peripheral blood or the number of affected cells in bone marrow is reduced by at least about 10%, 15%, 20%, 25%, 30%, 35%, 40%, 45%, 50%, 55%, 60%, 65%, 70%, 75%, 80%, 85%, 90%, 95% or more.

EXAMPLES

Example 1 Study of the U-CAR T Cells Expressing CD3+CD19 Dual CAR and EGFRt Switch with TCR Knockout General Materials and Methods Isolation of Peripheral Blood Mononuclear Cells (PBMCs) from Donor Blood and Expansion of T Cells Peripheral blood mononuclear cells (PBMCs) were isolated from donor blood by using Histopaque®-1077 (Sigma-Aldrich) through density gradient centrifuge. Then T cells were enriched, activated by magnetic beads coupled with anti-CD3/anti-CD28, cultured and expanded.

Cell Lines and the Culture of PBMCs

Raji cells (Burkitt's lymphoma cells, ATCC®-CCL-86™);

K562 cells (Human erythroleukemia cell line, ATCC®-CCL-243™);

Raji-ffluc cell line (obtained by screening Raji cells transfected with lentivirus having firefly luciferase);

293T cells (ATCC®-CRL-3216™)

Raji cells, K562 cells and Raji-ffluc cell line were cultured in RPMI1640 medium, and 293T cells were cultured in DMEM medium. Both RPMI1640 and DMEM were supplemented with 10% (v/v) fetal bovine serum and 100 U/ml penicillin and streptomycin, 2 mM glutamine and 1 mM sodium pyruvate. All of the cells were cultured in an incubator at 37° C., 5% $CO_2$.

T cells and the obtained CAR-T cells were cultured in X-vivo™ 15 medium (containing 5% FBS, 2 mM L-glutamine, 1 mM sodium pyruvate and 300 IU/ml rhIL2). The culture medium for CAR-T cells was further supplemented with rhIL-2 (ThermoFisher Scientific) at a final concentration of 300 IU/ml every two days. All of the cells were cultured in an incubator at 37° C., 5% $CO_2$.

1.1 Design of CAR and Package of the Virus

The structure of the chimeric antigen receptor is EGFRt-CD3 scFv-CD19 scFv-Hinge-TM-CD28-CD3ζ (tandem), tEGFR-CD19 scFv-CD28-CD3ζ-CD3 scFv-41BB-CD3ζ (Parallel), tEGFR-CD3 scFv-CD19 scFv41BB-CD3ζ (Tandem), and CD19VL-CD3VL-CD3VH-CD19VH-41BB-CD3ζ (Loop), wherein EGFRt (or tEGFR) is a truncated EGFR as a switch, CD3 scFv fragment is the heavy chain and light chain variable region of monoclonal antibody OKT3 or UCHT1 (connected by a GS linker), CD 19 scFv fragment is the heavy chain and light chain variable region of monoclonal antibody FMC63 (connected by a GS linker) containing a beacon sequence for CAR detection, and also included are hinge region, transmembrane region, human CD 28 intracellular co-stimulatory element and human CD3ζ intracellular region in tandem. An example construct of the chimeric antigen receptor is shown in FIG. 1.

The amino acid sequence of EGFRt-OKT3-FMC63-CD28z (SEQ ID NO.: 1) is as set forth below:

MLLLVTSLLLCELPHPAFLLIPRKVCNGIGIGEFKDSLSINATNIKHFK

NCTSISGDLHILPVAFRGDSFTHTPPLDPQELDILKTVKEITGFLLIQA

WPENRTDLHAFENLEIIRGRTKQHGQFSLAVVSLNITSLGLRSLKEISD

GDVIISGNKNLCYANTINWKKLFGTSGQKTKIISNRGENSCKATGQVCH

ALCSPEGCWGPEPRDCVSCRNVSRGRECVDKCNLLEGEPREFVENSECI

QCHPECLPQAMNITCTGRGPDNCIQCAHYIDGPHCVKTCPAGVMGENNT

LVWKYADAGHVCHLCHPNCTYGCTGPGLEGCPTNGPKIPSIATGMVGAL

LLLLVVALGIGLFMRAKRGSGATNFSLLKQAGDVEENPGPMALPVTALL

LPLALLLHAARPQVQLQQSGAELARPGASVKMSCKASGYTFTRYTMHWV

LPLALLLHAARPQVQLQQSGAELARPGASVKMSCKASGYTFTRYTMHWV

KQRPGQGLEWIGYINPSRGYTNYNQKFKDKATLTTDKSSSTAYMQLSSL

TSEDSAVYYCARYYDDHYCLDYWGQGTTLTVSSGSTSGGGSGGGSGGGG

-continued

SSQIVLTQSPAIMSASPGEKVTMTCSASSSVSYMNWYQQKSGTSPKRWI

YDTSKLASGVPAHFRGSGSGTSYSLTISGMEAEDAATYYCQQWSSNPFT

FGSGTKLEINRGGGGSGGGGSGGGGSDIQMTQTTSSLSASLGDRVTISC

RASQDISKYLNWYQQKPDGTVKLLIYHTSRLHSGVPSRFSGSGSGTDYS

LTISNLEQEDIATYFCQQGNTLPYTFGGGTKLEITGSTSGSGKPGSGEG

STKGEVKLQESGPGLVAPSQSLSVTCTVSGVSLPDYGVSWIRQPPRKGL

EWLGVIWGSETTYYNSALKSRLTIIKDNSKSQVFLKMNSLQTDDTAIYY

CAKHYYYGGSYAMDYWGQGTSVTVSSAAADYKDDDDKIEVMYPPPYLD

NEKSNGTIIHVKGKHLCPSPLFPGPSKPFWVLVVVGGVLACYSLLVTV

AFIIFWVRSKRSRLLHSDYMNMTPRRPGPTRKHYQPYAPPRDFAAYRS

RVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR.

In the EGFRt-OKT3-FMC63-CD28z amino acid sequence, the underlined part is the safety switch signal peptide region, the italic part is tEGFR, the italic underlined part is tEGFR TM, the curve underlined part is P2A, the italic curve underlined part is CAR signal peptide, the bold part is OKT3 VH, the dashed underlined part is a linking peptide, the bold underlined part is OKT3 VL, the bold italic part is FMC63 VL, the bold italic underlined part is FMC63 VH, the boxed part is CD28 hinge region transmembrane region and costimulatory domain, and the boxed italic part is CD3z.

The nucleotide acid sequence of EGFRt-OKT3-FMC63-CD28z is as set forth in SEQ ID NO.: 2.

```
SEQ ID NO.: 2:
ATGTTGCTCCTTGTGACGAGCCTCCTGCTCTGCGAGCTGCCCCATCCAGCCTTCCTCC

TCATCCCGCGGAAGGTGTGCAATGGCATAGGCATTGGCGAGTTTAAAGATTCTCTG

AGCATAAATGCTACGAATATTAAGCATTTCAAGAATTGTACTTCTATTAGTGGCGAC

CTCCATATTCTTCCGGTTGCCTTCAGGGGTGACTCTTTCACCCACACACCTCCATTGG

ATCCACAAGAACTTGACATCCTGAAGACGGTTAAAGAGATTACAGGCTTCCTCCTT

ATCCAAGCGTGGCCCGAGAACAGAACGGACTTGCACGCCTTTGAGAACCTCGAAAT

AATACGGGGTCGGACGAAGCAACACGGCCAATTTAGCCTTGCGGTTGTTAGTCTGA

ACATTACTTCTCTCGGCCTTCGCTCTTTGAAAGAAATCAGCGACGGAGATGTCATCA

TTAGTGGAAACAAGAACCTGTGCTACGCGAACACAATCAACTGGAAGAAGCTCTTC

GGTACTTCAGGCCAAAAGACAAAGATTATTAGTAACAGAGGAGAGAATAGCTGTA

AGGCTACCGGACAAGTTTGTCACGCCTTGTGTAGTCCAGAGGGTTGCTGGGGACCG

GAACCAAGGGATTGCGTCAGTTGCCGGAACGTGAGTCGCGGACGCGAGTGTGTGGA

TAAGTGCAATCTTCTGGAAGGGGAACCGCGAGAGTTTGTAGAAAATTCCGAATGTA

TACAGTGTCATCCCGAGTGTCTTCCACAAGCAATGAATATCACATGTACAGGGAGG

GGTCCTGATAACTGTATCCAATGTGCACACTACATAGATGGTCCTCACTGTGTAAAG

ACGTGCCCCGCCGGAGTAATGGGTGAAAACAACACCCTCGTGTGGAAGTACGCCGA

TGCCGGGCATGTCTGTCATTTGTGTCATCCCAACTGCACATATGGCTGTACCGGTCC

TGGATTGGAGGGCTGTCCAACAAACGGGCCGAAAATACCGAGTATCGCAACAGGC
```

-continued

ATGGTGGGAGCACTTTTGCTTCTCCTCGTTGTCGCCCTGGGCATCGGCTTGTTCATGC

GAGCTAAACGAGGCTCAGGCGCGACGAACTTTAGTTTGCTGAAGCAAGCTGGGGAT

GTAGAGGAAAATCCGGGTCCCATGGCCCTTCCAGTGACAGCCTTGTTGTTGCCACTT

GCTCTGCTGCTCCACGCTGCGCGGCCACAGGTCCAGTTGCAGCAGTCAGGCGCCGA

ATTGGCGCGACCAGGGGCAAGCGTAAAGATGAGCTGTAAGGCATCCGGGTACACGT

TCACTCGCTATACCATGCATTGGGTTAAACAACGGCCTGGGCAGGGCCTTGAGTGG

ATTGGGTATATCAACCCATCCCGGGGCTACACTAACTATAATCAAAAGTTTAAAGA

TAAAGCAACCCTTACGACCGACAAATCATCTTCTACCGCATACATGCAGCTCAGCTC

CCTCACCAGTGAAGATTCTGCCGTTTATTATTGTGCACGATACTATGACGATCACTA

TTGCCTGGACTACTGGGGTCAAGGCACCACACTTACTGTCAGTTCCGGAAGTACCA

GTGGGGGAGGTTCTGGCGGTGGCAGCGGGGGTGGGGGTAGCTCACAAATCGTGCTG

ACCCAGAGTCCCGCTATCATGAGCGCCTCCCCAGGGGAAAAGGTGACGATGACATG

CTCAGCCAGCTCCAGTGTATCCTACATGAATTGGTATCAACAGAAGAGTGGGACGT

CACCCAAAAGATGGATTTATGACACCAGCAAATTGGCCAGCGGAGTACCAGCGCAT

TTCAGAGGCAGTGGGAGTGGAACATCTTATTCTCTCACCATTAGCGGCATGGAAGC

AGAGGATGCAGCAACGTACTATTGTCAACAATGGAGCTCTAATCCCTTTACGTTCGG

CAGCGGCACTAAGCTCGAAATTAATAGGGGTGGCGGCGGCTCCGGCGGTGGCGGGT

CTGGAGGTGGGGGCAGTGACATCCAGATGACACAGACTACATCCTCCCTGTCTGCC

TCTCTGGGAGACAGAGTCACCATCAGTTGCAGGGCAAGTCAGGACATTAGTAAATA

TTTAAATTGGTATCAGCAGAAACCAGATGGAACTGTTAAACTCCTGATCTACCATAC

ATCAAGATTACACTCAGGAGTCCCATCAAGGTTCAGTGGCAGTGGGTCTGGAACAG

ATTATTCTCTCACCATTAGCAACCTGGAGCAAGAAGATATTGCCACTTACTTTTGCC

AACAGGGTAATACGCTTCCGTACACGTTCGGAGGGGGGACTAAGTTGGAAATAACA

GGCTCCACCTCTGGATCCGGCAAGCCCGGATCTGGCGAGGGATCCACCAAGGGCGA

GGTGAAACTGCAGGAGTCAGGACCTGGCCTGGTGGCGCCCTCACAGAGCCTGTCCG

TCACATGCACTGTCTCAGGGGTCTCATTACCCGACTATGGTGTAAGCTGGATTCGCC

AGCCTCCACGAAAGGGTCTGGAGTGGCTGGGAGTAATATGGGGTAGTGAAACCACA

TACTATAATTCAGCTCTCAAATCCAGACTGACCATCATCAAGGACAACTCCAAGAG

CCAAGTTTTCTTAAAAATGAACAGTCTGCAAACTGATGACACAGCCATTTACTACTG

TGCCAAACATTATTACTACGGTGGTAGCTATGCTATGGACTACTGGGGTCAAGGAA

CCTCAGTCACCGTCTCCTCAGCGGCCGCAGACTACAAAGACGATGACGACAAGATT

GAAGTTATGTATCCTCCTCCTTACCTAGACAATGAGAAGAGCAATGGAACCATTATC

CATGTGAAAGGGAAACACCTTTGTCCAAGTCCCCTATTTCCCGGACCTTCTAAGCCC

TTTTGGGTGCTGGTGGTGGTTGGGGGAGTCCTGGCTTGCTATAGCTTGCTAGTAACA

GTGGCCTTTATTATTTTCTGGGTGAGGAGTAAGAGGAGCAGGCTCCTGCACAGTGA

CTACATGAACATGACTCCCCGCCGCCCCGGGCCCACCCGCAAGCATTACCAGCCCT

ATGCCCCACCACGCGACTTCGCAGCCTATCGCTCCAGAGTGAAGTTCAGCAGGAGC

GCAGACGCCCCCGCGTACCAGCAGGGCCAGAACCAGCTCTATAACGAGCTCAATCT

AGGACGAAGAGAGGAGTACGATGTTTTGGACAAGAGACGTGGCCGGGACCCTGAG

ATGGGGGGAAAGCCGAGAAGGAAGAACCCTCAGGAAGGCCTGTACAATGAACTGC

AGAAAGATAAGATGGCGGAGGCCTACAGTGAGATTGGGATGAAAGGCGAGCGCCG

-continued

GAGGGGCAAGGGGCACGATGGCCTTTACCAGGGTCTCAGTACAGCCACCAAGGAC

ACCTACGACGCCCTTCACATGCAGGCCCTGCCCCCTCGCTAA

The amino acid sequence of EGFRt-UCHT1-FMC63-CD28z (SEQ ID NO.: 3) is as set forth below:

MLLLVTSLLLCELPHPAFLLIPRKVCNGIGIGEFKDSLSINATNIKHFK

NCTSISGDLHILPVAFRGDSFTHTPPLDPQELDILKTVKEITGFLLIQA

WPENRTDLHAFENLEIIRGRTKQHGQFSLAVVSLNITSLGLRSLKEISD

GDVIISGNKNLCYANTINWKKLFGTSGQKTKIISNRGENSCKATGQVCH

ALCSPEGCWGPEPRDCVSCRNVSRGRECVDKCNLLEGEPREFVENSECI

QCHPECLPQAMNITCTGRGPDNCIQCAHYIDGPHCVKTCPAGVMGENNT

LVWKYADAGHVCHLCHPNCTYGCTGPGLEGCPTNGPKIPSIATGMVGAL

LLLLVVALGIGLFMRAKRGSGATNFSLLKQAGDVEENPGPMALPVTALL

LPLALLLHAARPDIQMTQSPSSLSASVGDRVTITCRASQDIRNYLNWYQ

QKPGKAPKLLIYYTSRLESGVPSRFSGSGSGTDYTLTISSLQPEDFATY

YCQQGNTLPWTFGQGTKVEIKGGGGSGGGGSGGGGSEVQLVESGGGLVQ

PGGSLRLSCAASGYSFTGYTMNWVRQAPGKGLEWVALINPYKGVSTYNQ

KFKDRFTISVDKSKNTAYLQMNSLRAEDTAVYYCARSGYYGDSDWYFDV

WGQGTLVTVSSGGGGSGGGGSGGGGSEVKLQESGPGLVAPSQSLSVTCT

VSGVSLPDYGVSWIRQPPRKGLEWLGVIWGSETTYYNSALKSRLTIIKD

NSKSQVFLKMNSLQTDDTAIYYCAKHYYYGGSYAMDYWGQGTSVTVSSG

STSGSGKPGSGEGSTKGDIQMTQTTSSLSASLGDRVTISCRASQDISKY

LNWYQQKPDGTVKLLIYHTSRLHSGVPSRFSGSGSGTDYSLTISNLEQE

DIATYFCQQGNTLPYTFGGGTKLEITAAADYKDDDDKIEVMYPPPYL

DNEKSNGTIIHVKGKHLCPSPLFPGPSKPFWVLVVVGGVLACYSLLVT

VAFIIFWVRSKRSRLLHSDYMNMTPRRPGPTRKHYQPYAPPRDFAAYR

SRVKFSRSADAPAYQQGQNQLYNELNLGRREEYDVLDKRRGRDPEMGG

KPRRKNPQEGLYNELQKDKMAEAYSEIGMKGERRRGKGHDGLYQGLST

ATKDTYDALHMQALPPR.

In the amino acid sequence of EGFRt-UCHT1-FMC63-CD28z, the underlined part is the safety switch signal peptide (GMCSFR-L), the italic part is tEGFR, the italic underlined part is tEGFR TM, the curve underlined part is P2A, the italic curve underlined part is CAR signal peptide (CD8 L), the bold part is UCHT1 VL, the dashed underlined part is the linking peptide, the bold underlined part is UCHT1 VH, the bold italic part is FMC63 VH, the bold italic underlined part is FMC63 VL, the boxed part is CD28 hinge region transmembrane region and costimulatory domain, and the boxed italic part is CD3z.

The nucleotide acid sequence of EGFRt-UCHT1-FMC63-CD28z is as set forth in SEQ ID NO.: 4.

SEQ ID NO.: 4:
ATGCTGCTGCTCGTGACATCCCTCTTATTATGCGAACTCCCTCACCCCGCTTTTCTGC

TGATCCCCAGAAAGGTGTGCAACGGCATCGGCATTGGAGAGTTCAAGGATTCTTTA

-continued

AGCATCAACGCTACCAACATCAAACATTTCAAGAACTGTACCTCCATTTCCGGCGAT

TTACACATCCTCCCCGTTGCCTTTCGTGGCGATAGCTTCACACACACACCCCCTCTG

GACCCTCAAGAACTGGACATTTTAAAGACCGTGAAGGAGATCACTGGTTTTTTACTG

ATCCAAGCTTGGCCCGAAAATAGGACAGATCTCCACGCTTTCGAGAATTTAGAGAT

CATTCGTGGCAGAACCAAGCAGCACGGACAGTTCTCTTTAGCCGTCGTGTCTTTAAA

TATCACCTCTTTAGGTTTAAGATCTTTAAAAGAGATCAGCGATGGCGACGTCATCAT

CTCCGGCAACAAGAACCTCTGTTACGCCAACACCATTAATTGGAAAAAGCTGTTTG

GCACCTCCGGACAGAAGACCAAGATCATCAGCAACAGAGGCGAGAACAGCTGCAA

AGCTACCGGCCAAGTTTGCCACGCTCTGTGTAGCCCCGAAGGCTGCTGGGGACCCG

AACCTCGTGACTGTGTGAGCTGTAGGAACGTGTCTCGTGGTCGTGAGTGTGTGGATA

AGTGCAATTTACTCGAGGGCGAGCCCAGAGAGTTTGTGGAAAATAGCGAGTGCATC

CAGTGCCACCCCGAATGTCTGCCCCAAGCTATGAACATTACTTGTACTGGTCGTGGC

CCCGATAACTGTATCCAGTGCGCTCACTACATTGACGGCCCCCACTGCGTCAAGACA

TGCCCCGCTGGCGTGATGGGAGAAAACAACACACTGGTGTGGAAGTATGCCGATGC

CGGCCACGTCTGTCATCTGTGCCACCCTAACTGTACCTACGGCTGTACCGGACCCGG

ACTGGAGGGCTGTCCCACCAACGGACCCAAGATCCCTAGCATCGCCACCGGCATGG

TGGGAGCCTTACTGCTGTTACTGGTGGTGGCTCTGGGCATTGGTTTATTCATGAGGG

CCAAGAGAGGATCCGGCGCCACCAACTTTTCTTTACTGAAACAAGCTGGAGACGTC

GAGGAAAACCCCGGACCCATGGCTCTCCCCGTGACAGCTCTGCTGCTGCCTCTCGCT

TTATTACTGCACGCCGCTAGGCCCGATATTCAGATGACCCAAAGCCCTAGCTCTTTA

TCCGCCAGCGTCGGAGATAGAGTCACAATCACTTGTAGAGCCAGCCAAGATATTCG

TAATTATCTCAACTGGTACCAGCAGAAGCCCGGTAAAGCCCCCAAGCTGCTCATCT

ATTACACCTCTCGTCTGGAGAGCGGCGTGCCTTCCAGATTCAGCGGCTCCGGCAGCG

GCACCGACTATACACTCACCATTAGCTCTTTACAGCCCGAAGATTTCGCTACCTACT

ACTGCCAGCAAGGTAATACTTTACCTTGGACCTTCGGCCAAGGTACCAAGGTCGAA

ATCAAGGGCGGCGGCGGATCCGGCGGCGGTGGATCTGGTGGCGGCGGCTCCGAAGT

CCAGCTGGTCGAATCCGGAGGCGGACTGGTCCAGCCCGGTGGATCCCTCAGACTGA

GCTGCGCCGCTAGCGGCTATTCCTTCACCGGCTACACCATGAACTGGGTGAGACAA

GCTCCCGGCAAAGGACTGGAATGGGTGGCCCTCATCAACCCCTACAAGGGCGTGTC

CACATATAATCAAAAGTTTAAGGACAGATTCACCATCAGCGTCGACAAGTCCAAGA

ACACCGCTTATTTACAGATGAACTCTTTAAGAGCTGAGGATACCGCCGTGTACTATT

GTGCTAGGTCCGGCTACTACGGCGACAGCGACTGGTATTTTGACGTCTGGGGACAA

GGTACCCTCGTGACAGTGAGCAGCGGCGGTGGCGGTTCTGGCGGCGGAGGCTCCGG

AGGAGGCGGCAGCGAGGTGAAGCTGCAAGAAAGCGGACCCGGTCTCGTGGCTCCC

TCCCAATCTTTATCCGTGACTTGTACCGTGTCCGGAGTCTCTTTACCCGACTACGGC

GTGAGCTGGATTAGACAGCCCCCCAGAAAGGTTTAGAGTGGCTGGGCGTGATCTG

GGGATCCGAGACCACATACTACAACAGCGCTTTAAAGTCTCGTCTGACAATCATCA

AAGACAATTCCAAAAGCCAAGTTTTCCTCAAGATGAACTCTTTACAGACCGACGAC

ACAGCCATTTACTACTGCGCCAAGCATTATTACTACGGCGGCAGCTACGCTATGGAC

TACTGGGGCCAAGGTACAAGCGTCACAGTGAGCTCCGGCAGCACATCCGGAAGCGG

AAAGCCCGGCAGCGGAGAGGGCAGCACAAAGGGAGACATCCAGATGACCCAGACC

-continued

```
ACCTCCTCTTTAAGCGCCTCTTTAGGAGATAGGGTGACCATTAGCTGCAGAGCCTCC
CAAGACATCAGCAAGTATCTCAATTGGTACCAGCAAAAGCCCGATGGCACCGTCAA
GCTGCTGATCTACCACACCTCTCGTCTCCATTCCGGCGTGCCCAGCAGATTTAGCGG
AAGCGGATCCGGAACAGACTATTCTTTAACAATCAGCAATTTAGAGCAAGAAGACA
TCGCCACATATTTCTGCCAACAAGGTAACACTTTACCCTACACCTTCGGAGGCGGCA
CCAAACTGGAGATTACAGCGGCCGCAGACTACAAAGACGATGACGACAAGATTGA
AGTTATGTATCCTCCTCCTTACCTAGACAATGAGAAGAGCAATGGAACCATTATCCA
TGTGAAAGGGAAACACCTTTGTCCAAGTCCCCTATTTCCCGGACCTTCTAAGCCCTT
TTGGGTGCTGGTGGTGGTTGGGGGAGTCCTGGCTTGCTATAGCTTGCTAGTAACAGT
GGCCTTTATTATTTTCTGGGTGAGGAGTAAGAGGAGCAGGCTCCTGCACAGTGACT
ACATGAACATGACTCCCCGCCGCCCCGGGCCCACCCGCAAGCATTACCAGCCCTAT
GCCCCACCACGCGACTTCGCAGCCTATCGCTCCAGAGTGAAGTTCAGCAGGAGCGC
AGACGCCCCCGCGTACCAGCAGGGCCAGAACCAGCTCTATAACGAGCTCAATCTAG
GACGAAGAGAGGAGTACGATGTTTTGGACAAGAGACGTGGCCGGGACCCTGAGAT
GGGGGGAAAGCCGAGAAGGAAGAACCCTCAGGAAGGCCTGTACAATGAACTGCAG
AAAGATAAGATGGCGGAGGCCTACAGTGAGATTGGGATGAAAGGCGAGCGCCGGA
GGGGCAAGGGGCACGATGGCCTTTACCAGGGTCTCAGTACAGCCACCAAGGACACC
TACGACGCCCTTCACATGCAGGCCCTGCCCCCTCGCTAA
```

The CAR gene was cloned into the FUW lentiviral vector backbone under the promoter of EF1α (EF1α) to form Fuw-EF1α-CAR. Fuw-EF1α-CAR, lentiviral envelope plasmid pMD2.G (Addgene, Plasmid #12259) and lentiviral packaging plasmid psPAX2 (Addgene, Plasmid #12260) were transfected into 293 T cells by using Lipofectamine®3000 to prepare the whole lentiviral expression vector. The supernatant was collected at 48 and 72 h and subject to ultra-centrifuge (Merck Millipore) for concentration. The concentrated virus was ready for the transfection of T cells.

The result shows that the lentiviral vector was successfully constructed and expression of EGFRt and CD19+CD3 CAR were both detected as expected.

First, gRNA sequences targeting the first exon of the TCR conserved region were designed at http://crispr.mit.edu, and two gRNA sequences with scores above 80 were selected for higher knockout efficiency. For the gRNA primer, the forward primer comprises a T7 promotor followed by 20 bp of the target sequence, and the reverse primer has 20 bp of the complementary sequence. pX330 plasmid was used as the PCR template. After purification, T7-PCR product was further used as the template for MEGAshortscript® T7 kit to obtain RNA. The RNA was purified with a MEGAclear® column and eluted with RNA-free water. Cas9 plasmid was purchased from Addgene.

The gRNA targeting sequences are as below:

```
TRAC-gRNA:
                                        SEQ ID NO: 5
TGTGCTAGACATGAGGTCTA,;
```

Meanwhile, the knockout efficiency of the gRNA was analyzed by Surveyor assay, TIDE.

1.3 Preparation of CAR-T Cells

Cell Isolation and Activation

After apheresis, monocytes were isolated by using Histopaque®-1077 (Sigma-Aldrich) through density gradient centrifugation. Then T cells were enriched, activated by magnetic beads coupled with anti-CD3/anti-CD28, cultured and expanded.

X-vivo™ 15 with 5% FBS, 2 mM L-glutamine, 1 mM sodium pyruvate and 300 IU/ml rhIL2 was used as CAR-T cell medium. The cells were incubated and cultured at 37° C., 5% $CO_2$.

Cell line expressing CD 19: Raji (Burkitt's lymphoma cell line, ATCC®-CCL-86™); K562 cells (Human erythroleukemia cell line, ATCC®-CCL-243™); Raji-ffluc cell line was obtained by screening Raji cells transfected with lentivirus having firefly luciferase;

Cell line expressing CD3: Jurkat cell.

All of the cells were cultured in RPMI1640 medium and 293T cells (ATCC®-CRL-3216™) were cultured in DMEM medium. Both RPM11640 and DMEM were supplemented with 10% (v/v) fetal bovine serum and 100 U/ml penicillin and streptomycin, 2 mM glutamine and 1 mM sodium pyruvate.

Electroporation

Two days after enriching and activating T cells, the anti-CD3/anti-CD28 magnetic beads and the cells were collected into a tube and subject to centrifuge at 300 g for 5 min, and then washed twice with DPBS and re-suspended in opti-mem at a cell density of 1-3×$10^8$/ml. The amount of cas9/gRNA required was calculated based on the density of the cells, 30 μg/ml each. Cas9 and gRNA were 1:1 mixed, and incubated at room temperature for 10 mins and then transferred to electroporation buffer to further mix with the cells for electroporation by 4D-Nucleofector® System N (Lonza) system. Then the cells were re-suspended in a pre-warmed medium to a density of 1-2×$10^6$/ml, transferred to a plate and then cultured in an incubator at 37° C., 5% $CO_2$.

Lentiviral Transfection 1 day after electroporation, the cells were transfected by lentiviral vector at MOI of 2-8, transferred to a flask and cultured at 37° C., 5% $CO_2$.

Figure 2:
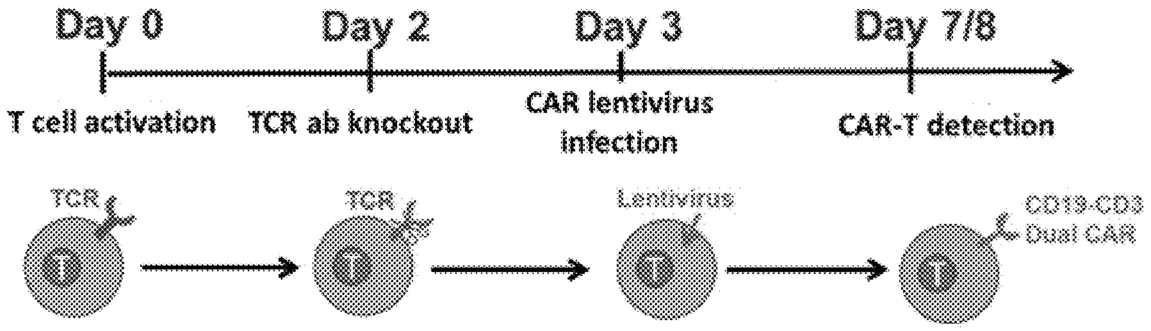
FIG. 2 illustrates an example preparation process of EGFRt-CD3-CD19 universal CAR-T.

Cell Proliferation and Detection of CAR Positive Ratio 3 days after the transfection, the number of cells and CAR positive cells were detected, and the positive ratio of CAR in T cells was calculated. The positive ratio of CD3 and PD1 was also detected to determine the knockout efficiency. Then the cells were continuously cultured in the incubator and half of the medium was replaced every 2-3 days till day 14, when the cells were ready for cryopreservation. An example workflow is shown in FIG. 2.

Figure 3:
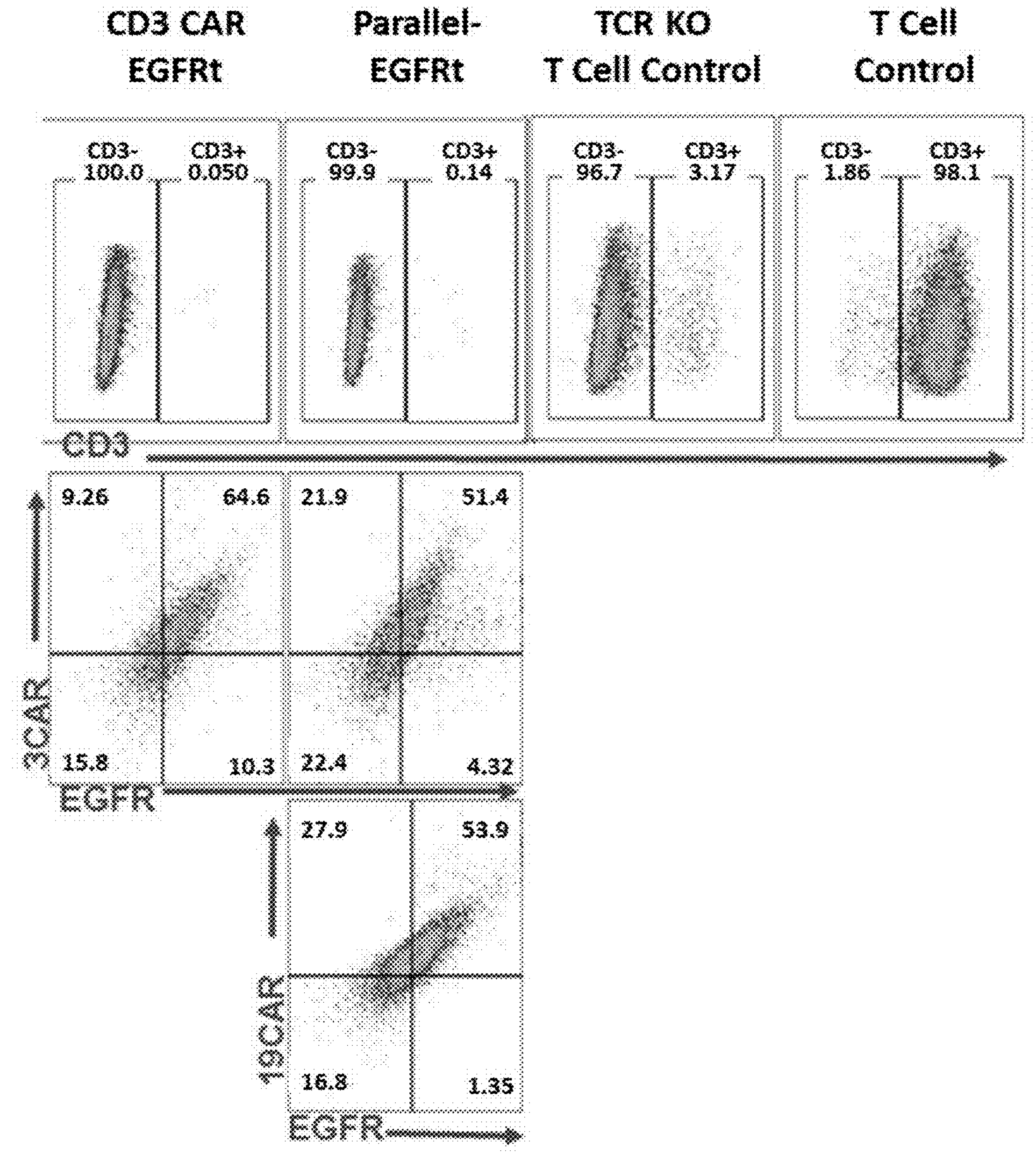
FIG. 3 illustrates expression of Parallel CAR (FMC63-OKT3) and the tEGFR switch.
Figure 4:
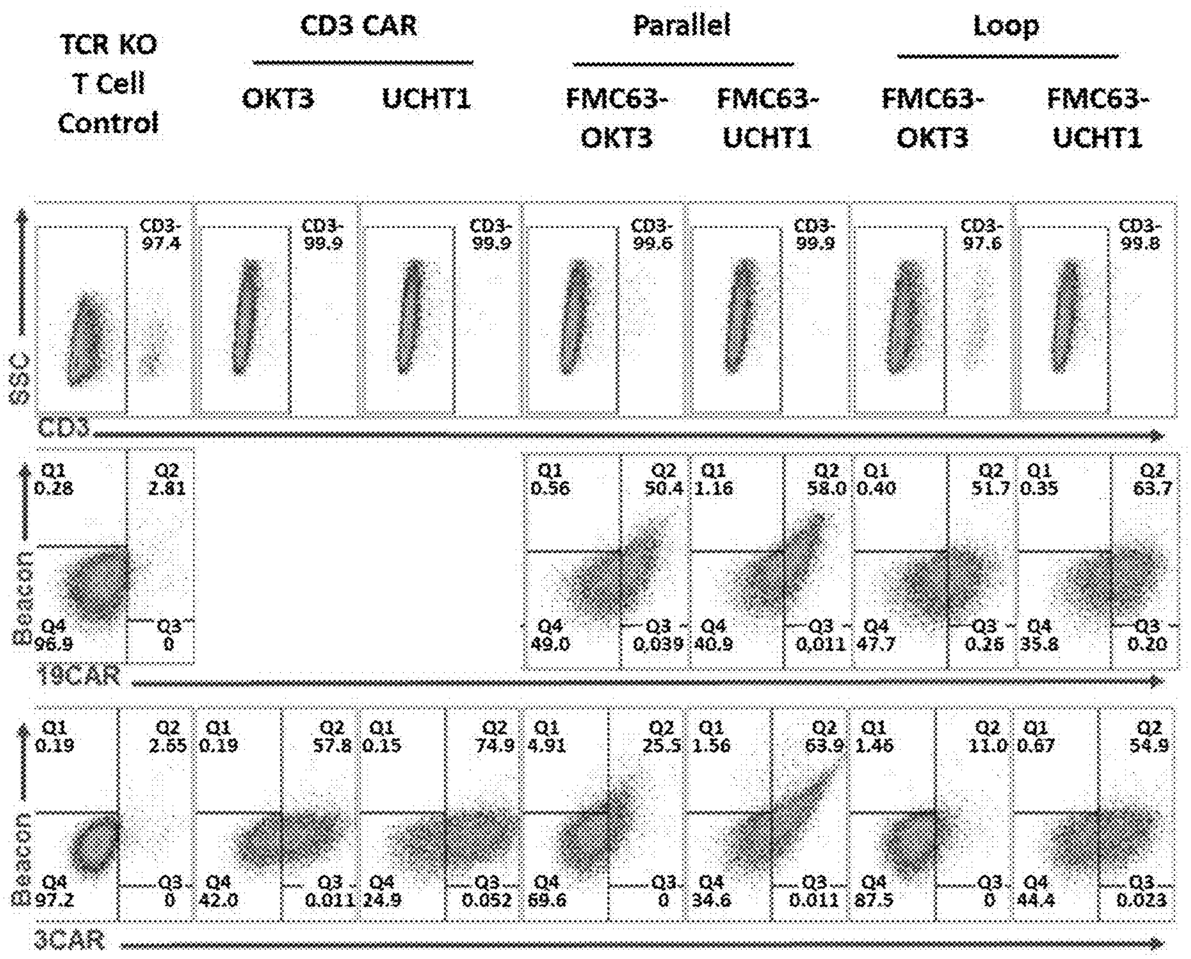
FIG. 4 illustrates expression of Parallel and Loop CARs.

FIG. 3 shows flow cytometry data of fractions of the engineered immune cells expressing dual-CARs or control cells with or without specified markers. For example, CD3 can be a marker indicative of endogenous TCR knockout efficiency, 3CAR (CAR targeting CD3) can be a marker indicative of CAR-T cells targeting CD3, 19CAR (CAR targeting CD19) can be a marker indicative of CAR-T cells targeting CD19, and EGFR can be a marker indicative of CAR-T expressing EGFRt. FIG. 4 shows another flow cytometry data of fractions of the engineered immune cells expressing dual-CARs or control cells with or without specified markers. In FIG. 4, the CAR targeting CD19 was a scFv of monoclonal antibody FMC63, and the CAR targeting CD3 was a scFv of monoclonal antibody OKT3 or UCHT1. The result shows that positive ratio of EGFR and CAR and negative ratio of CD3 were high in the prepared EGFRt-CD3-CD19 CAR-T cells, indicating the gene knockout dual CAR-T cells (e.g., parallel-EGFRt) with safety switch (e.g., EGFRt) were successfully prepared.

1.4 Release of the Cytokines

The dual CAR-T cells prepared in Example 1.3 and CD19 positive tumor cells (Raji), CD3 positive tumor cells (Jurkat) or primary allogeneic PBMCs, 100 ul each, were mixed in RPMI medium at 1:1 ratio to a density of 1×$10^6$/ml for each cell, and then cultured overnight in a 96-well plate. The medium was then collected and subject to centrifuge and the released cytokine IFN-γ and IL-2 were detected by Cytokine bead array kit (CBA kit, BD Biosciences).

The result shows that co-incubation of EGFRt-CD3-CD19 CAR-T cells with Raji, Jurkat or primary allogeneic PBMCs produce a large amount of IFN-γ and IL-2, indicating function of CAR-T against CD19 positive or CD3 positive target cells.

1.5 In Vitro Killing Activity

A stably transfected cell line was obtained by introducing the luciferase gene into the target cell followed by screening. After adding fluorescein, luciferase could react with the fluorescein to produce fluorescence. By detecting the intensity of the fluorescence, the activity of luciferase can be measured, and the survival of the cells can be detected so that to evaluate the killing effect of CART cells.

Figure 5A:
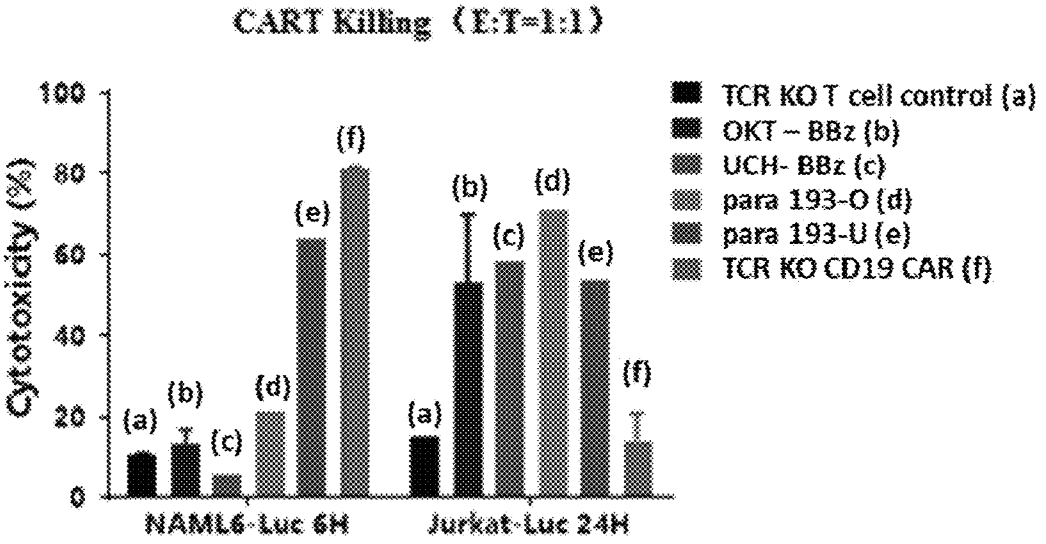
FIGS. 5A-C illustrate experimental data comparing the UCHT1 vs OKT3.
Figure 5B:
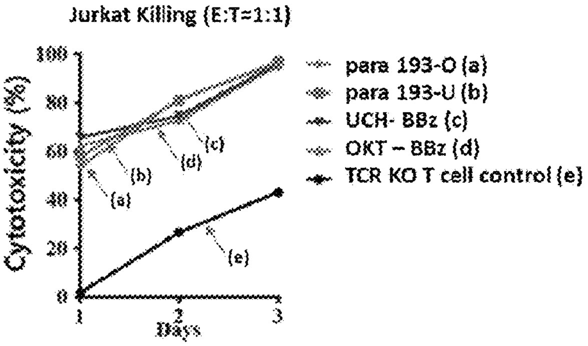
Figure 5C:
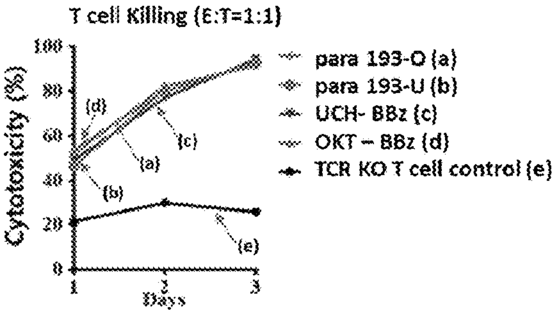

FIG. 5A shows bar-graphs of cytotoxicity of CAR-T cells, including CAR-T cells targeting CD3 with scFv of monoclonal antibody OKT3 or UCHT1, dual-specific CAR-T cells targeting CD19 and CD3 (para193-O and para193-U), CD19 CAR with endogenous TCR knocked out (TCR KO CD19 CAR), and T cells controls with endogenous TCR knocked out (TCR KO T cell control), toward CD19+ NALM6-Luc cells and CD3+ Jurkat-Luc cells at 1:1 E:T (Effector CAR-T cells to Target cancer cells) ratio for 6 hours and 24 hours, respectively. FIG. 5B shows cytotoxicity of CAR-T cells toward Jurket cells measured from Day 1 to Day3 of co-culture of Jurkat cells and CAR-T cells at 1:1 E:T ratio. FIG. 5C shows cytotoxicity of CAR-T cells toward T cells expressing CD3 measured from Day1 to Day 3 of co-culture of NALM6 cells and CAR-T cells at 1:1 E:T ratio.

Figure 6A:
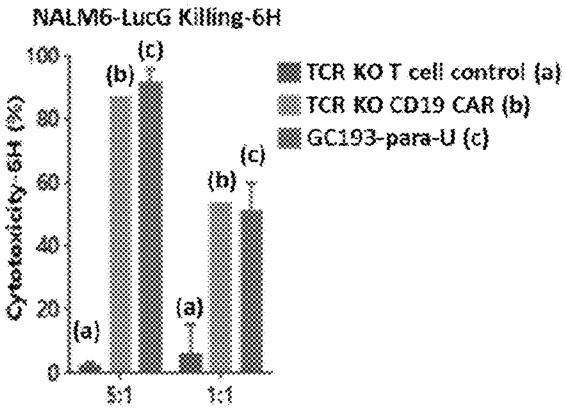
FIGS. 6A-C illustrate the anti-cancer function of parallel-UCHT1.
Figure 6B:
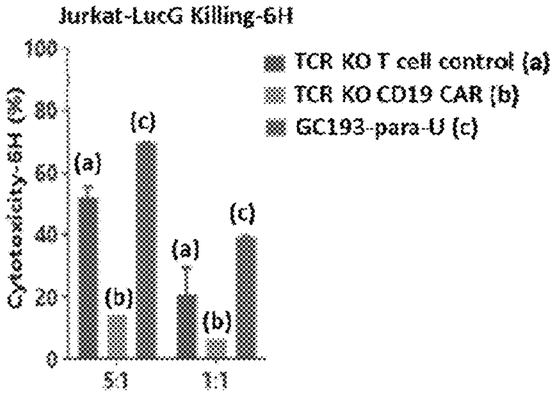
Figure 6C:
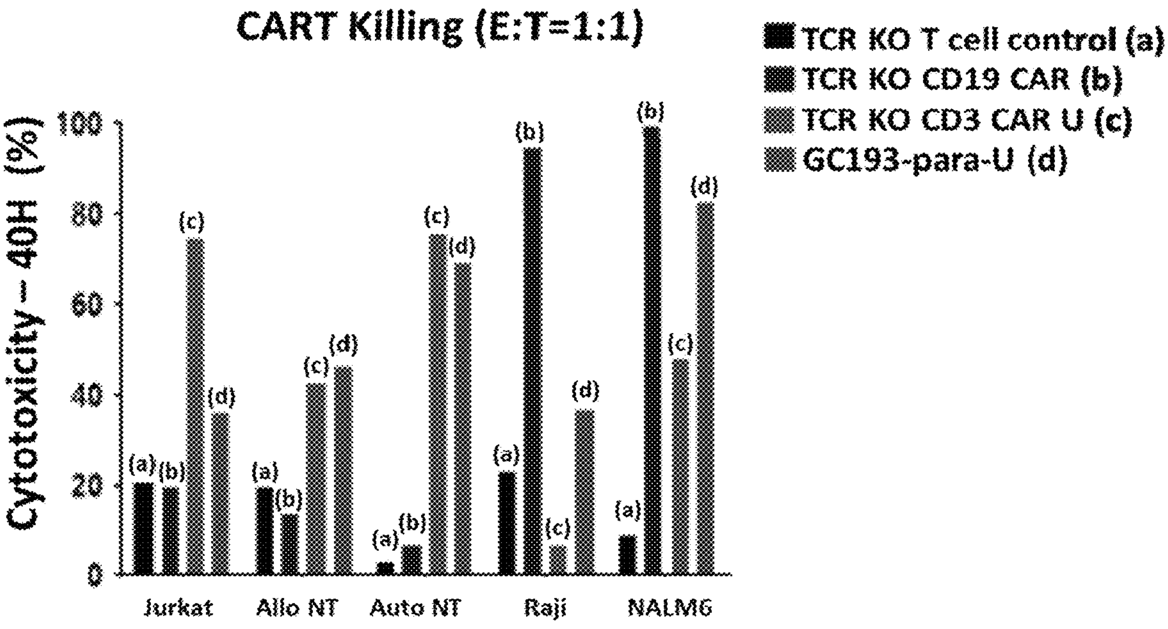
Figure 7A:
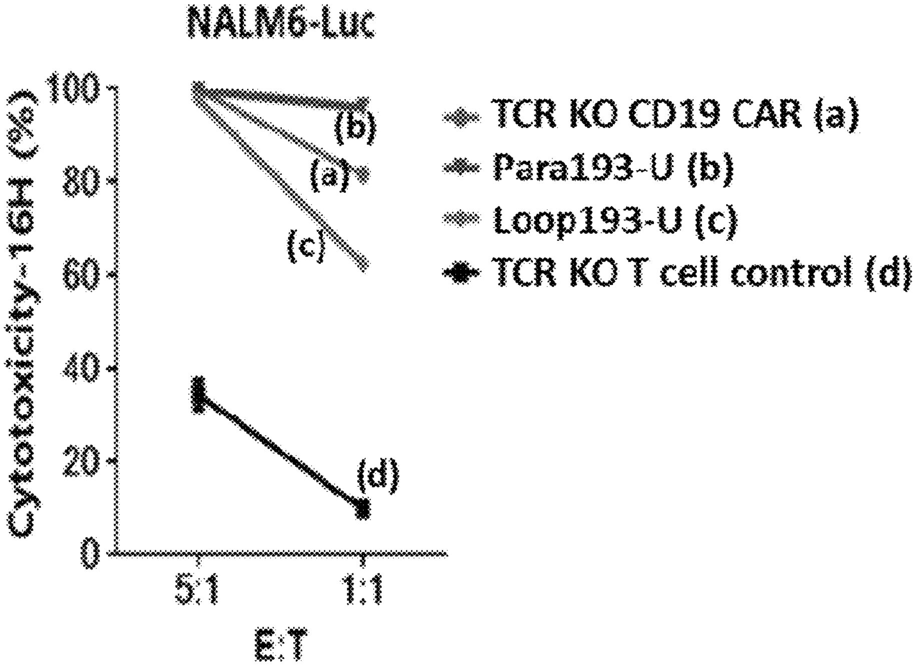
FIGS. 7A and 7B illustrate experimental data comparing the anti-cancer function of parallel CAR vs Loop CAR.
Figure 7B:
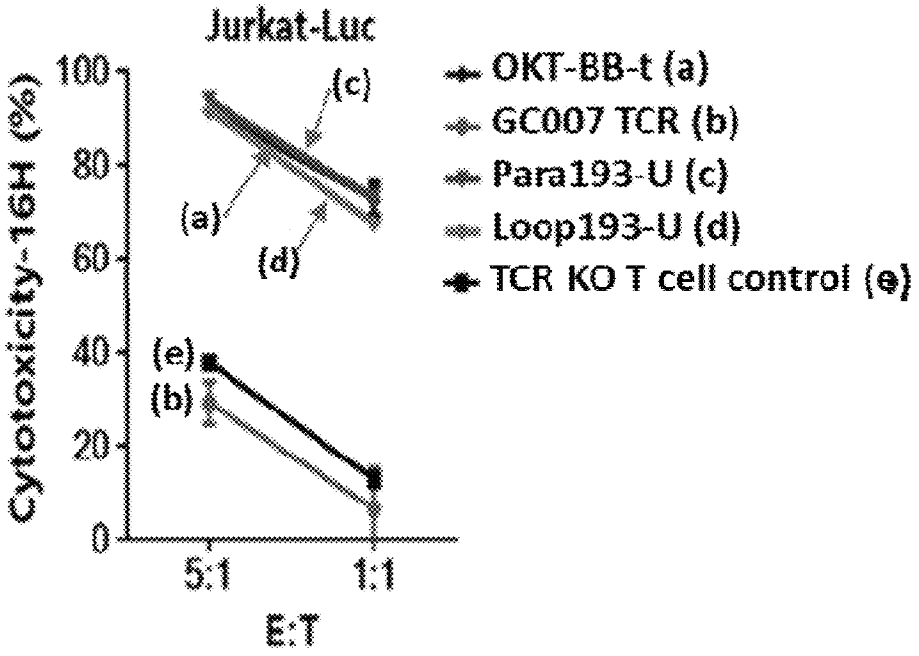

The cytotoxicity of the dual-specific CAR-T cells targeting CD19 and CD3 (e.g., dual-specific CAR-T cells in parallel form with scFv from monoclonal antibody UCHT1: GC193-para-U) were also tested against NALM6-LucG, Jurkat-LucG, Raji, allogeneic NTcells (non-treated T cells), and autologous NT cells. FIG. 6A shows 40 hour cytotoxicity of CAR-T cells toward NALM6 cells at different effector:target ratios. FIG. 6B shows 6 hour cytotoxicity of CAR-T cells toward Jurkat cells at different effector:target ratios. FIG. 6C shows 40 hour cytotoxicity of CAR-T cells toward Jurkat, allogeneic NT cells, autologous NT cells, Raji cells, and NALM6 cells. FIG. 7A shows 16 hour cytotoxicity of dual-specific CAR-T cells in parallel or loop form toward NALM6 cells. CD19-CD3 dual-specific CAR-T cells showed comparable anti-tumor efficacy to single CD19 CAR-T cells. FIG. 7B shows 16 hour cytotoxicity of dual-specific CAR-T cells in parallel or loop form toward Jurkat cells. CD19-CD3 dual-specific CAR-T cells showed comparable anti-tumor efficacy to single CD3 CAR-T cells. The result shows that EGFRt-CD3-CD19 CAR-T cells significantly killed Nalm6, Raji, Jurkat and primary allogeneic PBMCs, indicating the function of CAR-T against CD19-positive or CD3-positive target cells, and their capabilities of simultaneous targeting both CD19+ cancer cells and CD3+ killer T cells.

1.6 In Vivo Efficacy 6-12 weeks NOD-Prkdcscid Il2rgnull (NPG) mice were selected and intraperitoneally injected with 2×10' Raji-ffluc cells or Jurkat-ffluc cells, 50 μL DPBS and 50 μL Matrigel® matrix (Corning). Two days later, the tumor graft burden of the mice was measured, and the mice were divided into 4 groups based on the tumor burden. One day later, 200 μL DPBS, 5×$10^6$ NT cells and 5×$10^6$ EGFRt-CD3-CD19 CAR-T cells were respectively injected to each mouse. The tumor burden of the mice was further evaluated 7 days after the CAR-T treatment. Then each mouse was injected intraperitoneally with 3 mg d-luciferin for a 4-minutes reaction, and subsequently photographed by using a Xenogen IVIS® Imaging System with 30 s exposure.

The result shows that EGFRt-CD3-CD19 CAR-T significantly decreased the tumor burden compared to NT cells for tumors from by both Raji-ffluc and Jurkat-ffluc cells, indicating EGFRt-CD3-CD19 CAR-T can clear CD19 positive or CD3 positive target cells in vivo.

1.7 In Vivo GVHD Study

The mice were systemically treated with a sub-lethal dose of irradiation (175 cGy) first. Then CAR-T cells were re-suspended in PBS and injected into the thorax of the treated mice. The mice were observed 2-3 times a week by using GVHD clinical criteria including weight loss, arch-back, activity, fur texture, and skin integrity.

The result shows that mice without TCR knockout showed GVHD symptoms, however, no GVHD was detected in the EGFRt-CD3-CD19 CAR-T+TCR dual knockout group.

Figure 66A:
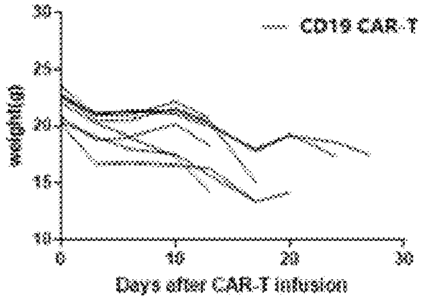
FIGS. 66A-C illustrate the in vivo GvHD study comparing CD19 CAR-T vs TCR KO CD19 CAR-T cells.
Figure 66B:
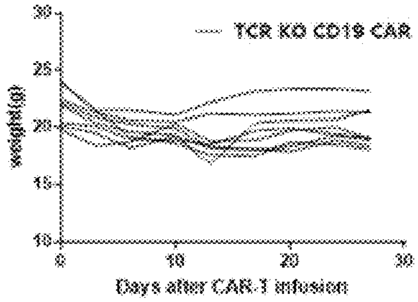
Figure 66C:
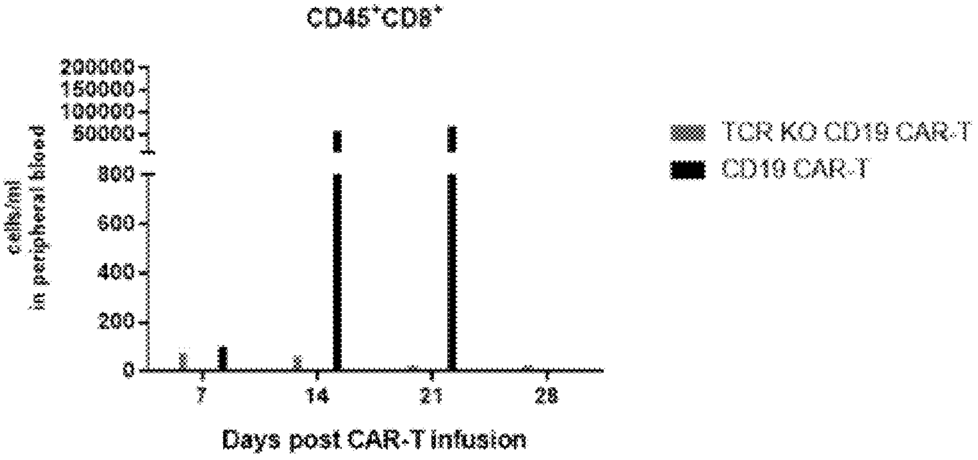
Figure 67A:
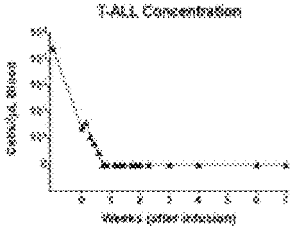
FIGS. 67A-E illustrate the clinical data of CAR7-C7R for treating T-acute lymphoblastic leukemia (T-ALL) patients.
Figure 67B:
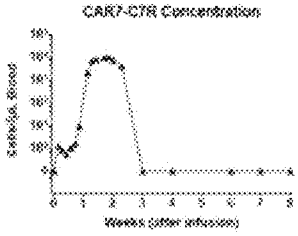
Figure 67C:
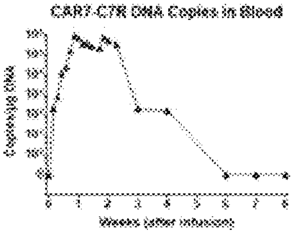
Figure 67D:
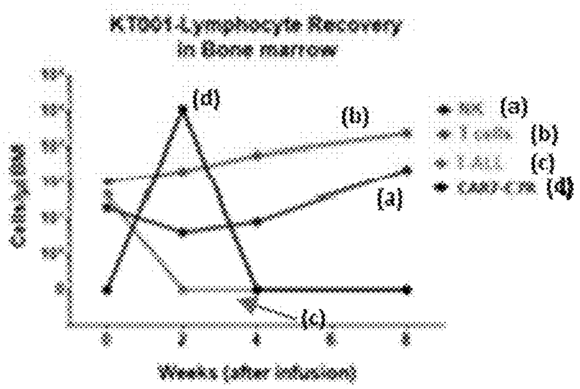
Figure 67E:
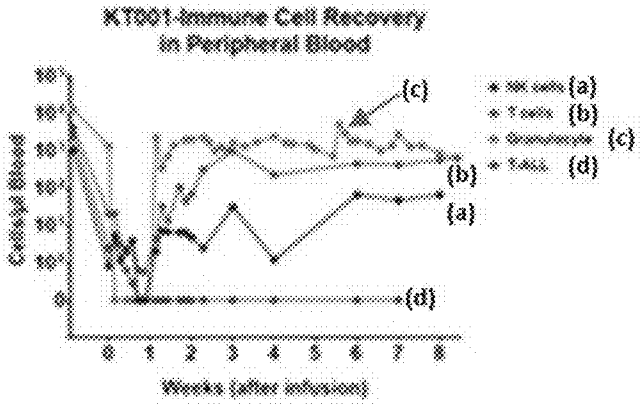

FIG. 66 shows the in vivo GvHD study comparing CD19 CAR-T vs TCR KO CD19 CAR-T cells. 2e7 CD19 CAR-T or TCR KO CD19 CAR-T cells were infused into each Raji-tumor bearing NOG mice to compare GvHD response. Mice from CD19 CAR-T group showed significant CAR-T expansion along with severe weight loss (>20%), arch-back, ruffled fur, and early death compared with TCR KO CAR-T cells. No GVHD was detected in any TCR KO CD19 CAR-T infused mice.

1.8 In Vitro HVG Study

EGFRt-CD3-CD19 CAR-T+TCR knockout and EGFRt-CD3-CD19 CAR-T+TCR/B2M dual knockout cells were 1:1 incubated with NK cells overnight to detect apoptosis and cytokine release (IFN-γ).

The results show that compared to the control group, EGFRt-CD3-CD19 CAR-T+TCR knockout group had almost no apoptosis, and the cytokine released was significantly less, indicating that the product of the present disclosure will not cause HVG reaction by NK cells. Meanwhile, the TCR/B2M dual knockout cells were significantly killed by NK cell and were not able to survive long.

HVG can also induce allogeneic T cells against HLA intact CAR-T cells. FIG. 6C shows that dual CAR-T cells can target allogeneic T cells within 40 hours, preventing CAR-T rejection by host allogeneic T cells, which usually takes 72 hours.

1.9 Clearance of EGFRt 2Ene-Mediated CAR-T Cells

NK cells were isolated from PBMCs as effector cells, and 1:1 co-cultured with CD19-28z CART or EGFRt-CD3-CD19 CAR-T, with or without Cetuximab at a final concentration of 10 μg/mL. 4 h and 24 h later, the expression of CD3 and CAR was detected by flow cytometry.

ADCC percentage=(1−monoclonal antibody group CAR positive ratio/no antibody group CAR positive ratio)*100%

The results show that, 4 h and 24 h later, in the presence of Cetuximab, NK cells significantly cleared EGFRt-CD3-CD19 CAR-T cells, but failed to clear CD19-28z CART. Without Cetuximab, NK failed to kill either of the cells. This indicates that Cetuximab functions as a safety switch, which binds to EGFRt-CD3-CD19 CAR-T, and allows NK to mediate the ADCC function so that to clear CART cells.

Figure 8A:
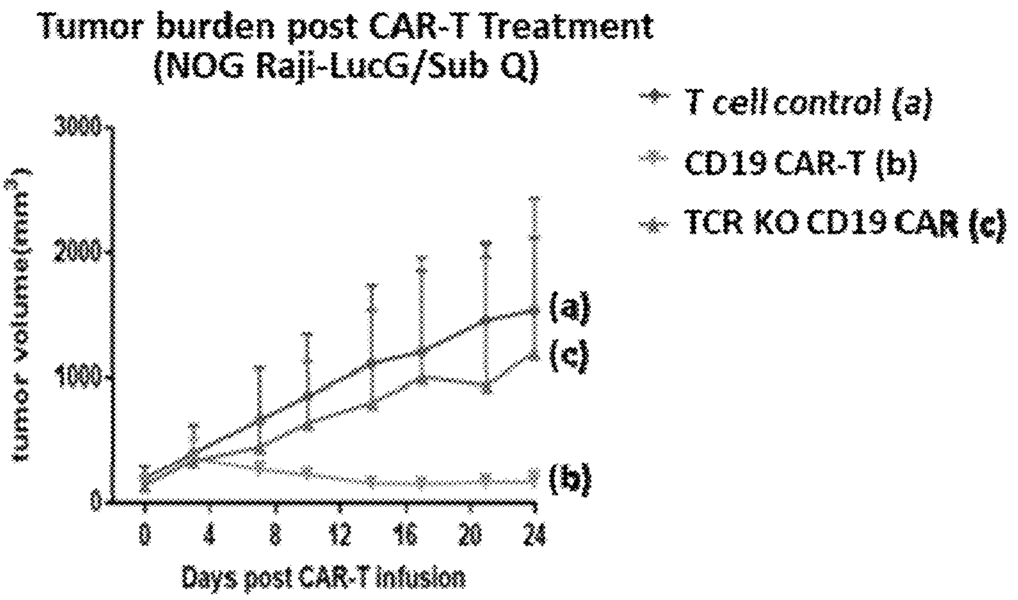
FIGS. 8A and 8B illustrate that TCR KO CD19 CAR-T cell showed a proliferation defect in subcutaneous tumor model. 5e5 Raji-luciferase cells were grafted into NOG mice by subcutaneous injection. 1e6 WT, TCR KO CD19 CAR-T cells were infused (IV) into Raji grafted mice. Tumor burden was assessed by caliper measurements of the actual tumor sizes. Although both were Raji based tumor bearing models, subcutaneous model generates solid tumors and has much higher requirements on CAR-T cell proliferation for controlling the tumors than intravenous model. TCR KO CAR-T cells showed a proliferation defects compared to WT CAR-T cells, consistent with their tumor control effects.
Figure 8B:
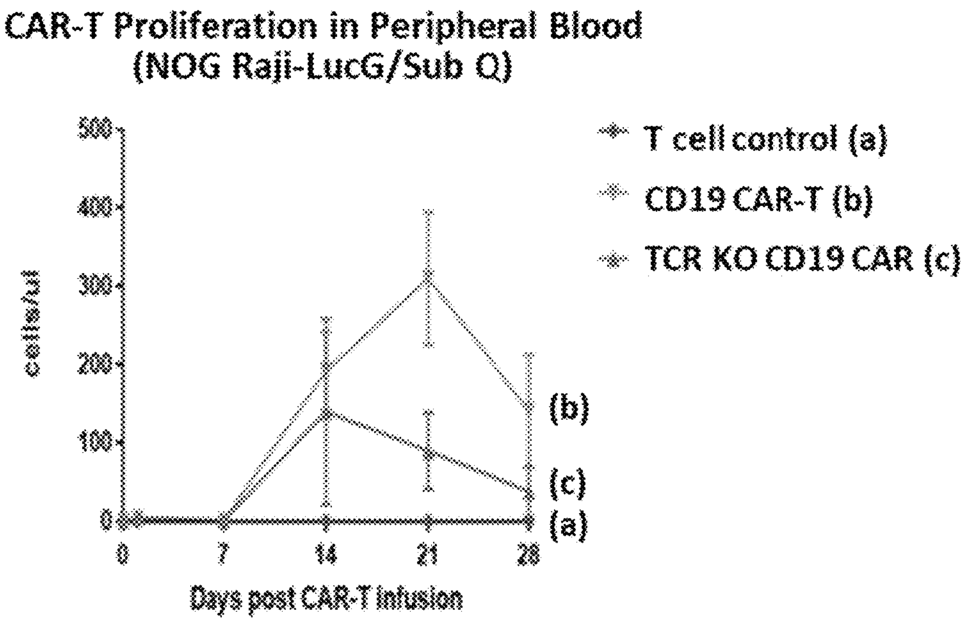

Example 2 Study of U-CAR-T Cells Expressing CAR19 and the Enhancer with TCR Knockout In this example, $5\times10^5$ Raji-luciferase cells were grafted into NOG mice by subcutaneous injection and grew till reach 100 $mm^3$. $1\times10^6$ wildtype or TCR KO CD19 CAR-T cells were intravenously infused (IV) into Raji grafted mice. Tumor burden was assessed by caliper measurements of the actual tumor sizes. CAR-T cell expansion in the peripheral blood was measured by flow cytometry analysis. FIG. 8A shows tumor burden post CAR-T treatment. TCR intact CD19 CAR-T cells were able to eliminate tumors, but TCR KO CD19 CAR-T wasn't able to control Raji tumor growth. Although both were Raji based tumor bearing models, subcutaneous model generates solid tumors and has much higher requirements on CAR-T cell proliferation for controlling the tumors than intravenous model. FIG. 8B shows CAR-T proliferation in peripheral blood. TCR KO CAR-T cells showed a proliferation defects compared to WT CAR-T cells, the peak of CAR-T cell expansion is much weaker than that of WT cells, which is consistent with their tumor control effects.

Figure 9A:
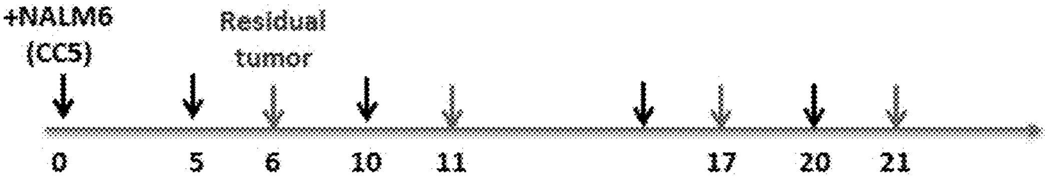
FIGS. 9A-C illustrate proliferation and killing efficacy of CAR-T cells with different enhancers after multiple rounds of stimulation by cancer cells.
Figure 9B:
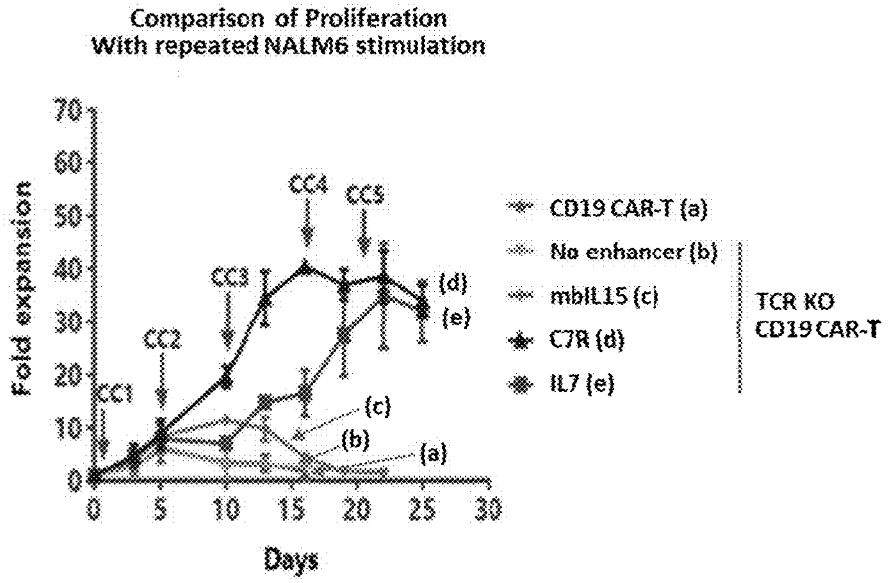
Figure 9C:
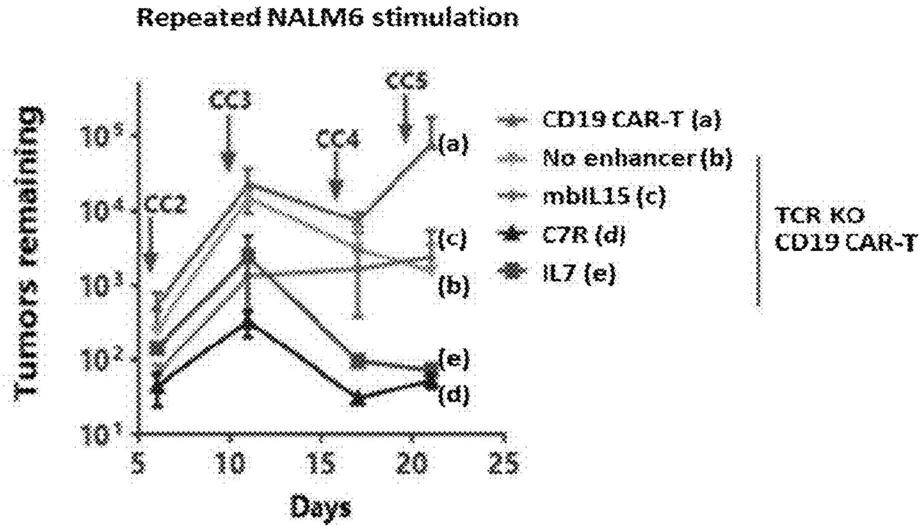

FIGS. 9A-9C show proliferation of CD19 CAR-T cells with TCR knockout. FIG. 9A shows an experimental timeline of repeated stimulations by NALM6 cells and measurements of residual tumor cells. FIG. 9B shows the proliferation data of CD19 CAR-T cells with TCR knockout and expression of different enhancers in comparison to CD19 CAR-T cells without TCR knockout and CD19 CAR-T cells with TCR knockout but without expression of the enhancers. Additions of NALM6 cells are indicated by arrows according to the experimental trimline in FIG. 9A. FIG. 9B shows the clearing activity of various CD19 CAR-T cells as indicated by the amount of residual tumor cells measured at the indicated days according to the experimental timeline in FIG. 9A. Under multiple rounds or repeated stimulations by NALM6 cells, the CD19 CAR-T cells with TCR knockout and C7R or IL7 exhibited persistent expansion and enhanced expansion ability compared with other cells tested in this experiment.

Figure 10A:
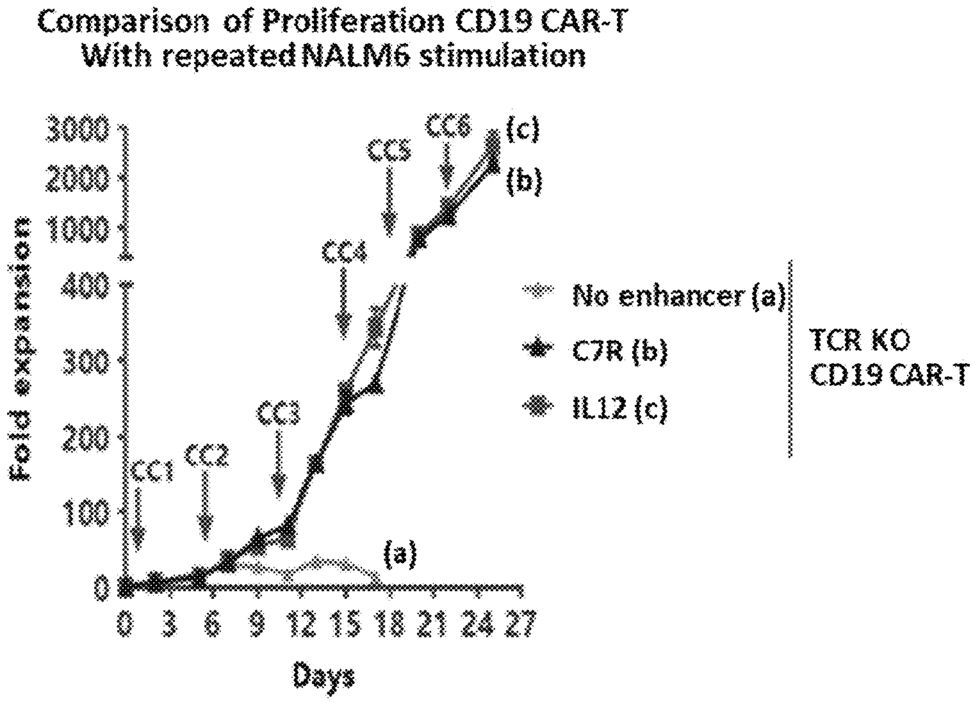
FIGS. 10A and 10B illustrate the proliferation of CAR-T cells with different enhancers after multiple rounds of stimulation by cancer cells.
Figure 10B:
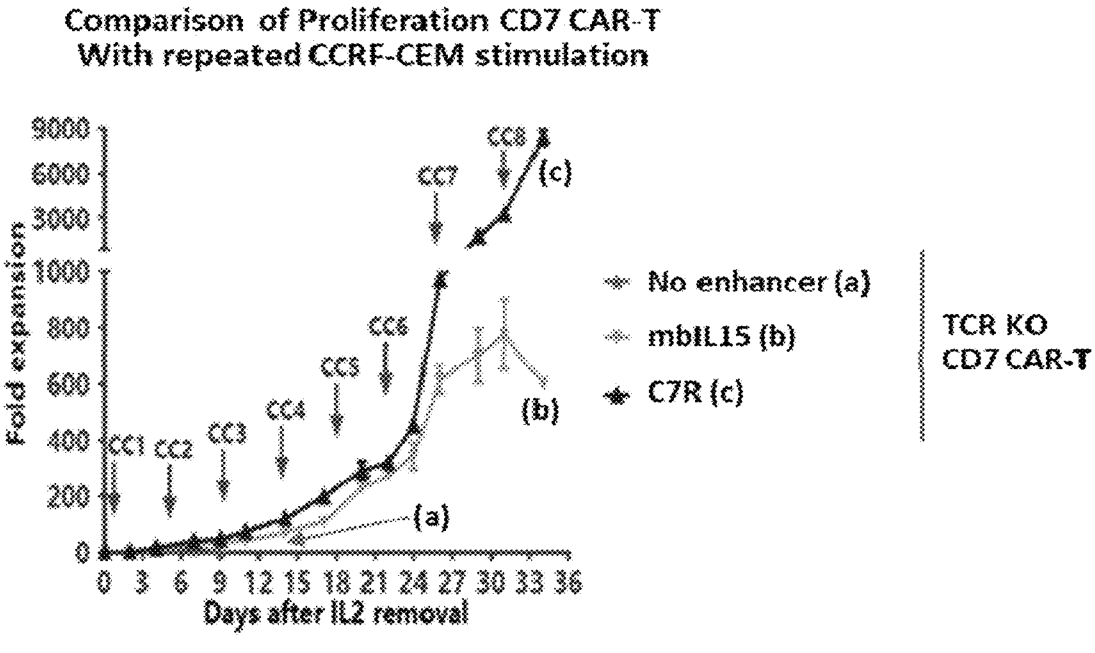

FIGS. 10A and 10B show additional proliferation data comparing expansion ability of engineered CAR-T cells. FIG. 10A shows proliferation data of CD19 CAR-T cells with TCR knockout and two different enhancers (C7R and IL2) in comparison to cells without the expression of the enhancer. The results showed that under multiple rounds or repeated stimulation by NALM6 cells, CD19 CAR-T cells with TCR knockout and C7R or IL2 exhibited persistent expansion and enhanced expansion ability compared with the cell without the expression of any enhancer. FIG. 10B shows proliferation data of CD7 CAR-T cells with TCR knockout and two different enhancers (C7R and mbIL15) in comparison to cells without the expression of the enhancer. The results showed that under multiple rounds or repeated stimulation by CCRF-CEM cells, CD7 CAR-T cells with TCR knockout and C7R or mbIL15 exhibited persistent expansion and enhanced expansion ability compared with the cell without the expression of any enhancer. The cells with the expression of C7R exhibited better expansion ability than the cells expressing mbIL15.

Figure 11:
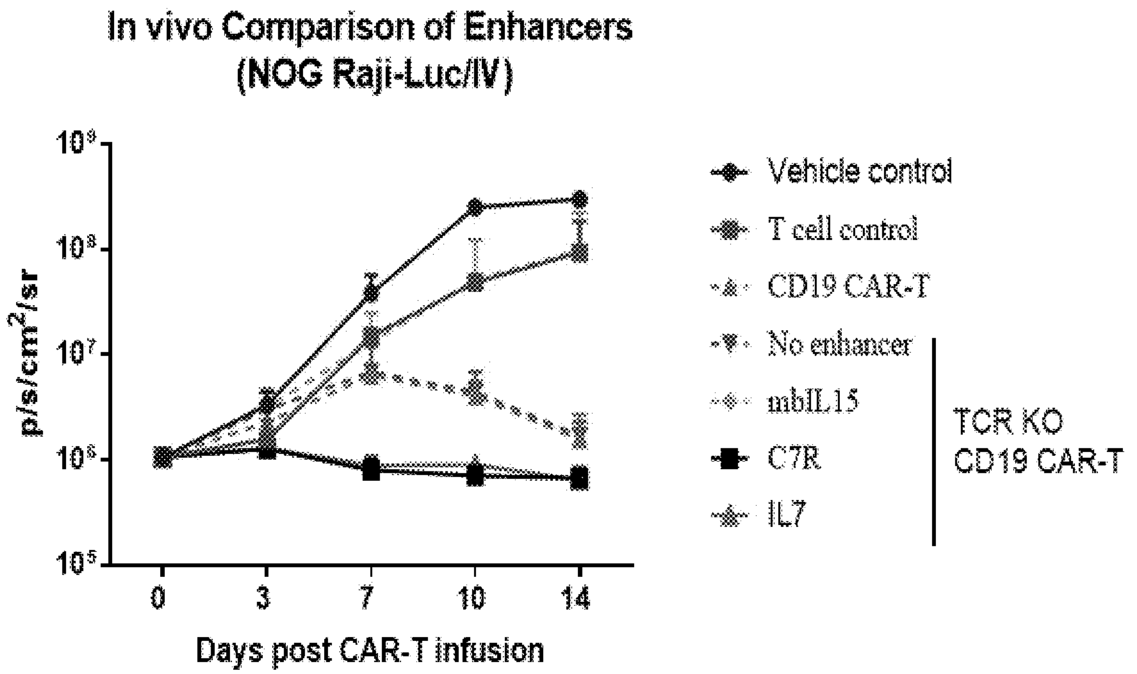
FIG. 11 illustrates In vivo comparison of enhancers in TCR KO CD19 CAR-T cells. 5e5 Raji-luciferase cells were grafted into NOG mice by intravenous (IV) injection. WT, TCR KO CD19 CAR-T cells with/without enhancers were infused (IV) into Raji grafted mice. Tumor burden was assessed by bioluminescence intensity (BLI).
Figure 12:
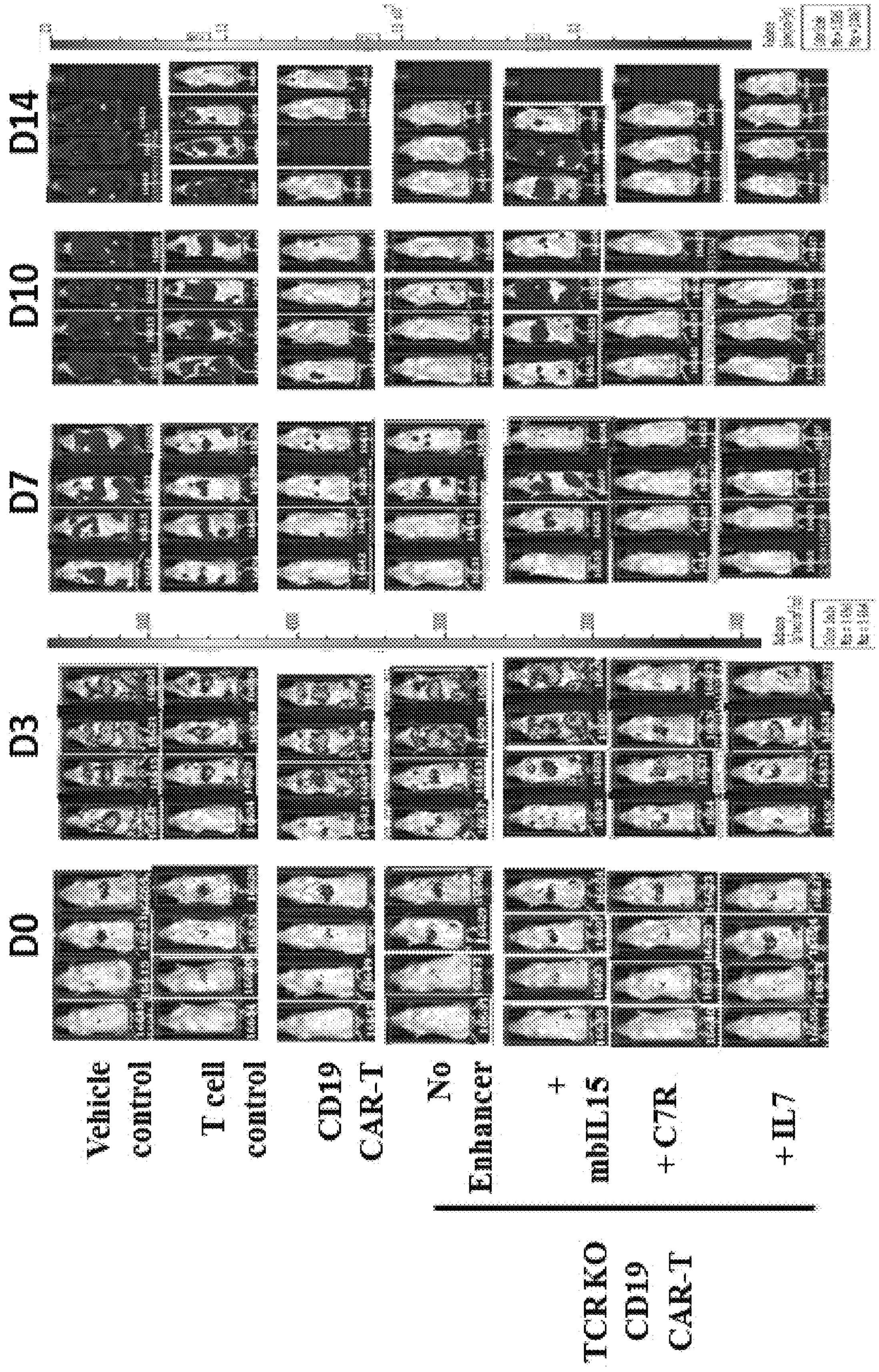
FIG. 12 illustrates in vivo comparison of enhancers in TCR KO CD19 CAR-T cells.

FIG. 11 shows an example of in vivo comparison of enhancers in TCR KO CD19 CAR-T cells. In this example, $5\times10^5$ Raji-luciferase cells were grafted into NOG mice by intravenous (IV) injection and grew for 5 days. TCR KO CD19 CAR-T cells (CD19 CAR-T cells with TCR knockout) with/without enhancers as well as vehicle and T cell controls were intravenously infused (IV) into Raji grafted mice. Tumor burden was assessed by bioluminescence intensity (BLI). The TCR KO CD19 CAR-T cells expressing enhancer C7R, IL7 exhibited the better tumor control in comparison to the cells without the expression of enhancers or with expression of mbIL15 or other control cells. FIG. 12 shows corresponding images of the NOG mice indicating tumor burden assessed by BLI.

Example 3 Study of U-CAR-T Cells Expressing CAR7 and the Enhancer with TCR and CD 7 Double Knockout, as Well as U-CAR-T Cells Expressing CD2 CAR and the Enhancer with TCR and CD 2 Double Knockout General Materials and Methods Isolation of Peripheral Blood Mononuclear Cells (PBMCs) from Donor Blood and Expansion of T Cells Peripheral blood mononuclear cells (PBMCs) were isolated from donor blood by using Histopaque®-1077 (Sigma-Aldrich) through density gradient centrifuge. Then T cells were enriched, activated by magnetic beads coupled with anti-CD3/anti-CD28, cultured and expanded.

Cell Lines and Culture of T Cells

CCRF-CEM (T lymphoblast, ATCC® CCL-119™);

CCRF-CEM-luc cells (obtained by screening CCRF-CEM cells transfected with lentivirus having firefly luciferase);

K562 cells (Human erythroleukemia cell line, ATCC®-CCL-243™);

293T cells (ATCC®-CRL-3216™);

NK92 cells (ATCC®-CRL-2407™)

The CCRF-CEM-luc cell line was cultured in RPMI1640 medium, and 293T cells were cultured in DMEM medium. Both RPMI1640 and DMEM were supplemented with 10% (v/v) fetal bovine serum and 100 U/ml penicillin and streptomycin, 2 mM glutamine and 1 mM sodium pyruvate. All of the cells were cultured in an incubator at 37° C., 5% $CO_2$.

NK92 cells were cultured in RPMI1640 medium supplemented with 10% (v/v) fetal bovine serum, 2 mM glutamine, 1 mM sodium pyruvate, 1% NEAA, 0.1 mM mercaptoethanol and 200 IU/ml rhIL2.

T cells and the obtained CAR-T cells were cultured in X-vivo™ 15 medium (containing 5% FBS, 2 mM L-glutamine, 1 mM sodium pyruvate and 300 IU/ml rhIL2). The culture medium for CAR-T cells was further supplemented with rhIL-2 (ThermoFisher Scientific) at a final concentration of 300 IU/ml every two days. All of the cells were cultured in an incubator at 37° C., 5% $CO_2$.

3.1 Design and Construction of CRISPR

CD7 and TCR gRNAs for gene editing were selected after evaluating gene editing efficiency and off-target risk at website http://crispr.mit.edu, www.idtdna.com and https://www.synthego.com.

gRNAs and HiFi-Cas9 protein used in the present disclosure were purchased from Integrated DNA Technologies, Inc (IDT).

For gene editing, 3 μg Cas9 protein and 1.5 μg gRNA were mixed in 20 μl and incubated at 37° C. or room temperature for 15 minutes to form ribonucleoprotein (RNP). Then RNP was transfected into T cells by Lonza 4D Nucleofector®. Gene knockout efficiency was determined by the ratio of the cells expressing the protein as detected by flow cytometry (FACS).

Figure 16:
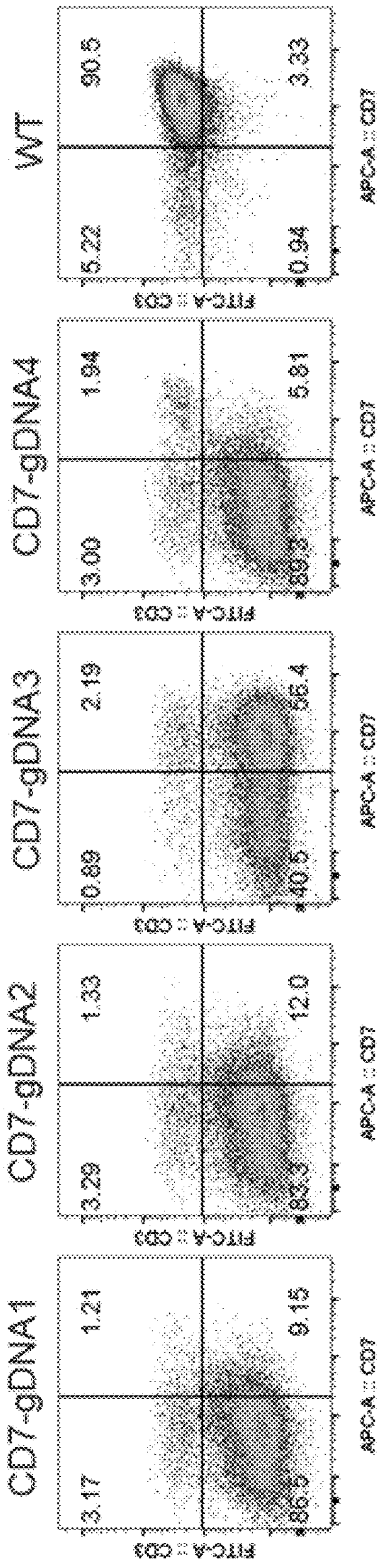
FIG. 16 illustrates an experimental data of CD7 gRNA screening.

Our previous study indicated that TRAC-gRNA1 has a higher knockout efficiency for TCR (the sequence is set forth as SEQ ID NO.: 20). When gRNA of CD7 and TRAC-gRNA were used together to knockout CD7 and TCR simultaneously, three of four CD7-gRNAs showed high efficiencies (as shown in FIG. 16). CD7-gRNA1 (SEQ ID NO.: 34) was selected as the gRNA to knockout CD7.

```
TRAC-gRNA1:
                                   SEQ ID NO 20
TTCGGAACCCAATCACTGAC,;

CD7-gRNA1:
                                   SEQ ID NO 25
GAGGTCAATGTCTACGGCTC,.
```

Figure 65:
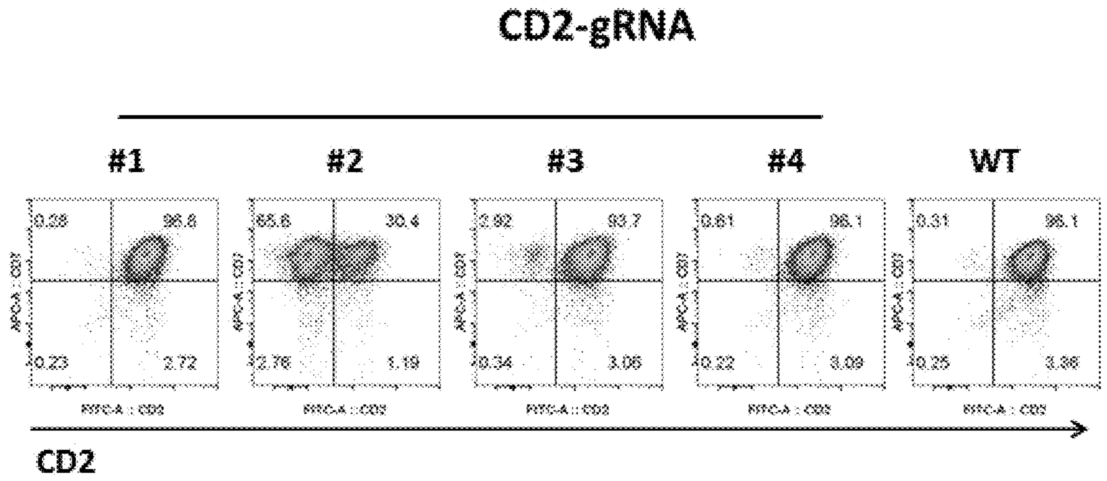
FIG. 65 illustrates CD2 gRNA screening.

The gDNA of CD2 were designed as below, and CD2 gRNA2 showed the highest CD2 knockout efficiencies (as shown in FIG. 65).

```
CD2-gRNA1:
                                (SEQ ID NO: 29)
CAAAGAGATTACGAATGCCT

CD2-gRNA2:
                                (SEQ ID NO: 30)
GTGCCACAAAGACCATCAAG

CD2-gRNA3:
                                (SEQ ID NO: 31)
AGAGGGTCATCACACACAAG

CD2-gRNA4:
                                (SEQ ID NO: 32)
CTTGTAGATATCCTGATCAT
```

3.2 Design of CAR and Cytokine and Package of the Virus

Figure 17:
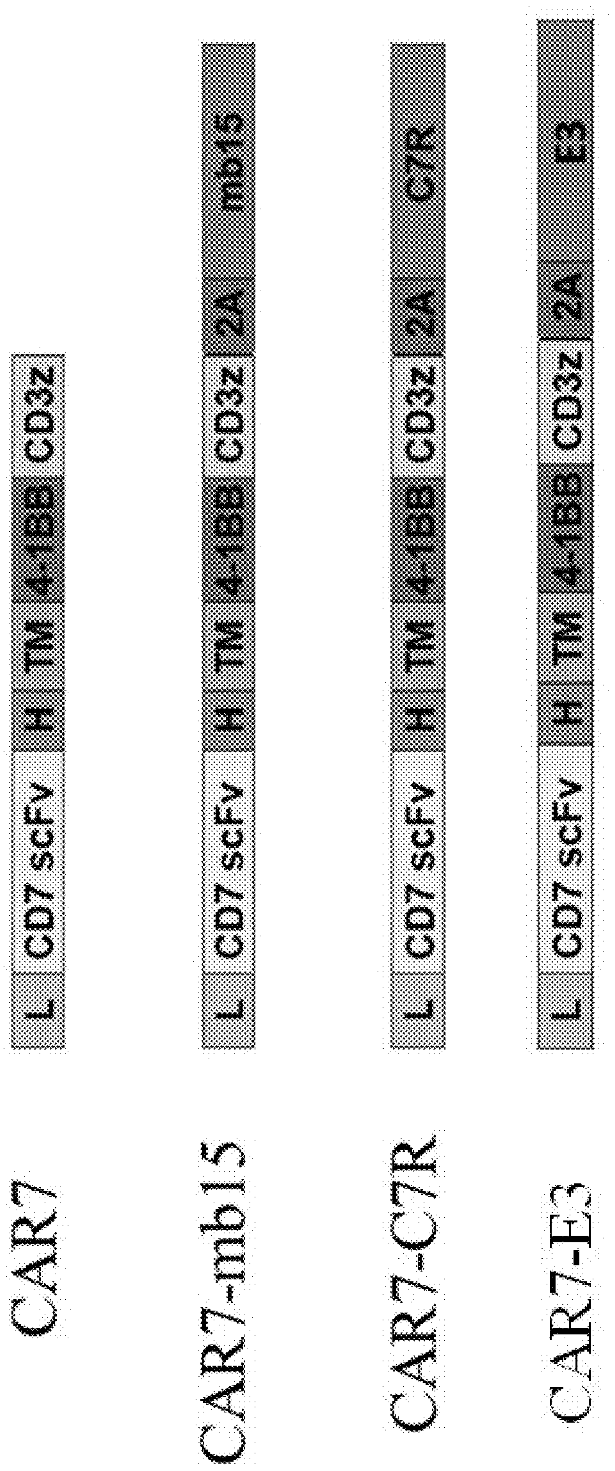
FIG. 17 illustrates example structures of CAR7, CAR7-mb15 and CAR7-C7R. 1

The structure of the chimeric antigen receptor and the cytokines are: CAR7, CAR7-mb15 and CAR7-C7R (as shown in FIG. 17). The nucleotide sequences and amino acid sequences are set forth as SEQ ID NO.: 35-40.

```
CAR7 (SEQ ID NO 35):
atggcactccctgtaactgcacttcttttgccacttgccttgctcctgcacgcagcgcggccggacatcgagctgacccagagc

cccgccatcatgagcgccagcctgggcgaggagatcaccctgacctgcagcgccagcagcagcgtgagctacatgcactggtaccagc

agaagagcggcaccagccccaagctgctgatctacagcaccagcaacctggccagcggcgtgcccagcaggttcagcggcagcggca

gcggcaccttctacagcctgaccatcagcagcgtggaggccgaggacgccgccgactactactgccaccagtggagcagctacaccttc

ggcggcggcaccaagctggagatcaagaggggcggcggcggcagcggcggcggcagcggcggcggcggcagccaggtgaa

gctgcaggagagcggcggcggcctggtgaagcccggcggcagcctgaagctgagctgcgccgccagcggcttcaccttcagcagcta

cgccatgagctgggtgaggcagacccccgagaagaggctggagtgggtggccaccatcagcagcggcggcagctacacctactaccc

cgacagcgtgaagggcaggttcaccatcagcagggacaacgccaagaacaccctgtacctgcagatgagcagcctgaggagcgagga

caccgccatgtactactgcgccaggcaggacggctactaccccggctggttcgccaactggggccagggcaccaccgtgaccgtgagc

agctccggaacaacgacaccagcaccacggccacccactcctgctccgacaattgcgtctcagcccctttcccttcgacccgaagcttgtc

gccctgctgcgggaggagcggtccacacgcgcgggcttgacttcgcttgcgacatctacatttgggcacccttggccgggacatgcggc

gtcttgctcctgagtctggttataacgctgtattgtaagcgaggtcggaagaagcttttgtatatctttaaacagccctttatgaggcccgtaca

aaccacacaagaggaggatgggtgctcatgcagatttcctgaagaggaagagggcggttgcgaacttagagtcaaattcagccgctccgc

agatgcacctgcttataaacagggtcagaatcaattgtataatgaacttaatctcgggaggcgcgaggagtatgatgtgctggacaagcgac

ggggtcgagacccagagatgggcggtaaaccccgccgaaagaacccccaggagggactgtataatgagctgcaaaaggacaaaatgg

cagaagcctattccgaaatagggatgaagggagagcggcggcgaggtaagggacatgacggtctttatcaaggtcttagtactgcaacta

aggacacctatgacgcgctgcatatgcaggctctcccacctagataa
```

-continued

CAR7 (SEQ ID NO 36):
MALPVTALLLPLALLLHAARPDIELTQSPAIMSASLGEEITLTCSASSSVSYMHW

YQQKSGTSPKLLIYSTSNLASGVPSRFSGSGSGTFYSLTISSVEAEDAADYYCHQWSSYT

FGGGTKLEIKRGGGGSGGGGSGGGGSQVKLQESGGGLVKPGGSLKLSCAASGFTFSSY

AMSWVRQTPEKRLEWVATISSGGSYTYYPDSVKGRFTISRDNAKNTLYLQMSSLRSED

TAMYYCARQDGYYPGWFANWGQGTTVTVSSSGTTTPAPRPPTPAPTIASQPLSLRPEAC

RPAAGGAVHTRGLDFACDIYIWAPLAGTCGVLLLSLVITLYCKRGRKKLLYIFKQPFMR

PVQTTQEEDGCSCRFPEEEEGGCELRVKFSRSADAPAYKQGQNQLYNELNLGRREEYD

VLDKRRGRDPEMGGKPRRKNPQEGLYNELQKDKMAEAYSEIGMKGERRRGKGHDGL

YQGLSTATKDTYDALHMQALPPR

CAR7-mb15 (SEQ ID NO 37):
atggcactccctgtaactgcacttcttttgccacttgccttgctcctgcacgcagcgcggccggacatcgagctgacccagagc cccgccatcatgagcgccagcctgggcgaggagatcaccctgacctgcagcgccagcagcagcgtgagctacatgcactggtaccagc agaagagcggcaccagccccaagctgctgatctacagcaccagcaacctggccagcggcgtgcccagcaggttcagcggcagcggca gcggcaccttctacagcctgaccatcagcagcgtggaggccgaggacgccgccgactactactgccaccagtggagcagctacaccttc ggcggcggcaccaagctggagatcaagaggggcggcggcggcagcggcggcggcggcagcggcggcggcggcagccaggtgaa gctgcaggagagcggcggcggcctggtgaagcccggcggcagcctgaagctgagctgcgccgccagcggcttcaccttcagcagcta cgccatgagctgggtgaggcagacccccgagaagaggctggagtgggtggccaccatcagcagcggcggcagctacacctactaccc cgacagcgtgaagggcaggttcaccatcagcagggacaacgccaagaacaccctgtacctgcagatgagcagcctgaggagcgagga caccgccatgtactactgcgccaggcaggacggctactaccccggctggttcgccaactggggccagggcaccaccgtgaccgtgagc agctccggaacaacgacaccagcaccacggccacccactcctgctccgacaattgcgtctcagcccctttcccttcgacccgaagcttgtc gccctgctgcgggaggagcggtccacacgcgcgggcttgacttcgcttgcgacatctacatttgggcacccttggccgggacatgcggc gtcttgctcctgagtctggttataacgctgtattgtaagcgaggtcggaagaagcttttgtatatctttaaacagccctttatgaggcccgtaca aaccacacaagaggaggatgggtgctcatgcagatttcctgaagaggaagagggcggttgcgaacttagagtcaaattcagccgctccgc agatgcacctgcttataaacagggtcagaatcaattgtataatgaacttaatctcgggaggcgcgaggagtatgatgtgctggacaagcgac ggggtcgagacccagagatgggcggtaaaccccgccgaaagaacccccaggagggactgtataatgagctgcaaaaggacaaaatgg cagaagcctattccgaaatagggatgaagggagagcggcggcgaggtaagggacatgacggtctttatcaaggtcttagtactgcaacta aggacacctatgacgcgctgcatatgcaggctctcccacctagacgagctaaacgaggctcaggcgcgacgaactttagtttgctgaagc aagctggggatgtagaggaaaatccgggtcccatggattggacttggattttgttcctcgttgccgcagcgactcgcgtccatagtaattgg gtgaacgtaattagtgacttgaaaaaaattgaggaccttatacaaagtatgcatatcgatgcaacactgtacacggagtccgacgtgcaccc aagctgcaaggtcaccgcaatgaaatgctttttgctcgaattgcaagttatctcacttgagtcaggggacgcttcaatccatgatactgtggag aatttgataatcctggcgaacaatagccttagttcaaatggcaacgtcactgagtcaggctgcaaggaatgtgaggaattggaagaaaaaa tatcaaggaattttgcaatcttttgttcacatagttcagatgttcattaacactagttccgggggcggcagtggaggtggcggtagcggcggg ggtggctctggtggaggcggctctgggggcggaagtctgcagataacatgcccccccacctatgagtgttgaacatgctgatatctgggtta aatcttactccctttacagtcgagaaaggtacatttgcaactccggctttaaacgcaaagccgggactagttcactgactgaatgtgtattgaat aaagcgacaaatgtcgcacactggactaccccttccctcaaatgcattcgcgatcctgccttggtgcatcagcgaccagcaccgccgtcca cggtaactaccgcaggagtaacaccgcagcccgagagcctttcccctcaggcaaagagccggccgcatcctccccatcttccaataata ccgcagctaccaccgcagcaatcgtacccggatcccagctgatgcccagcaaaagtccgagtactggaacgactgaaatctccagtcac gagtcttctcatggaactccgagtcaaactacagcaaagaattgggagctgactgcttccgcttcacaccagccgccaggcgtttatcctca gggacactcagataccacggtggcgattagcacaagcaccgtcctcctgtgtgggctgagtgcagtgtcacttctcgcctgctaccttaagt ccagacagacacccccttttggcaagcgttgaaatggaagccatggaagccttgcctgtcacatgggggacttcatcccgcgatgaagactt ggagaactgctcacaccatctt -continued CAR7-mb15 (SEQ ID NO 38):
MALPVTALLLPLALLLHAARPDIELTQSPAIMSASLGEEITLTCSASSSVSYMHW

YQQKSGTSPKLLIYSTSNLASGVPSRFSGSGSGTFYSLTISSVEAEDAADYYCHQWSSYT

FGGGTKLEIKRGGGGSGGGGSGGGGSQVKLQESGGGLVKPGGSLKLSCAASGFTFSSY

AMSWVRQTPEKRLEWVATISSGGSYTYYPDSVKGRFTISRDNAKNTLYLQMSSLRSED

TAMYYCARQDGYYPGWFANWGQGTTVTVSSSGTTTPAPRPPTPAPTIASQPLSLRPEAC

RPAAGGAVHTRGLDFACDIYIWAPLAGTCGVLLLSLVITLYCKRGRKKLLYIFKQPFMR

PVQTTQEEDGCSCRFPEEEEGGCELRVKFSRSADAPAYKQGQNQLYNELNLGRREEYD

VLDKRRGRDPEMGGKPRRKNPQEGLYNELQKDKMAEAYSEIGMKGERRRGKGHDGL

YQGLSTATKDTYDALHMQALPPRRAKRGSGATNFSLLKQAGDVEENPGPMDWTWILF

LVAAATRVHSNWVNVISDLKKIEDLIQSMHIDATLYTESDVHPSCKVTAMKCFLLELQV

ISLESGDASIHDTVENLIILANNSLSSNGNVTESGCKECEELEEKNIKEFLQSFVHIVQMFI

NTSSGGGSGGGGSGGGGSGGGGSGGGSLQITCPPPMSVEHADIWVKSYSLYSRERYICN

SGFKRKAGTSSLTECVLNKATNVAHWTTPSLKCIRDPALVHQRPAPPSTVTTAGVTPQP

ESLSPSGKEPAASSPSSNNTAATTAAIVPGSQLMPSKSPSTGTTEISSHESSHGTPSQTTAK

NWELTASASHQPPGVYPQGHSDTTVAISTSTVLLCGLSAVSLLACYLKSRQTPPLASVE

MEAMEALPVTWGTSSRDEDLENCSHHL

CAR7-C7R (SEQ ID NO 39):
atggcactccctgtaactgcacttcttttgccacttgccttgctcctgcacgcagcgcggccggacatcgagctgacccagagc cccgccatcatgagcgccagcctgggcgaggagatcaccctgacctgcagcgccagcagcagcgtgagctacatgcactggtaccagc agaagagcggcaccagccccaagctgctgatctacagcaccagcaacctggccagcggcgtgcccagcaggttcagcggcagcggca gcggcaccttctacagcctgaccatcagcagcgtggaggccgaggacgccgccgactactactgccaccagtggagcagctacaccttc ggcggcggcaccaagctggagatcaagaggggcggcggcggcagcggcggcggcggcagcggcggcggcggcagccaggtgaa gctgcaggagagcggcggcggcctggtgaagcccggcggcagcctgaagctgagctgcgccgccagcggcttcaccttcagcagcta cgccatgagctgggtgaggcagacccccgagaagaggctggagtgggtggccaccatcagcagcggcggcagctacacctactaccc cgacagcgtgaagggcaggttcaccatcagcagggacaacgccaagaacaccctgtacctgcagatgagcagcctgaggagcgagga caccgccatgtactactgcgccaggcaggacggctactaccccggctggttcgccaactggggccagggcaccaccgtgaccgtgagc agctccggaacaacgacaccagcaccacggccacccactcctgctccgacaattgcgtctcagcccctttcccttcgacccgaagcttgtc gccctgctgcgggaggagcggtccacacgcgcgggcttgacttcgcttgcgacatctacatttgggcacccttggccgggacatgcggc gtcttgctcctgagtctggttataacgctgtattgtaagcgaggtcggaagaagcttttgtatatctttaaacagccctttatgaggcccgtaca aaccacacaagaggaggatgggtgctcatgcagatttcctgaagaggaagagggcggttgcgaacttagagtcaaattcagccgctccgc agatgcacctgcttataaacagggtcagaatcaattgtataatgaacttaatctcgggaggcgcgaggagtatgatgtgctggacaagcgac ggggtcgagacccagagatgggcggtaaaccccgccgaaagaacccccaggagggactgtataatgagctgcaaaaggacaaaatgg cagaagcctattccgaaatagggatgaagggagagcggcggcgaggtaagggacatgacggtctttatcaaggtcttagtactgcaacta aggacacctatgacgcgctgcatatgcaggctctcccacctagaggctcaggcgcgacgaactttagtttgctgaagcaagctggggatgt agaggaaaatccgggtcccatgttggtgcgccgaggcgcacgagcaggacctcggatgccgcgaggctggacagccctctgtctcctct ctttgcttccatccgggttcatgagtctcgacaataatggtacggcaaccccggaactcccgacccaaggaacctttagtaacgtttcaacca atgtgtcctatcaggagacaacaacccccttctacactgggcagtaccagcttgcatcccgtcagccaacacggcaacgaggcaacaacta acatcacagagactacggtcaagtttactagtacttccgtaatcacgtctgtgtacgggaatacaaattcatcagttcagagtcaaacgtcagt tatatctacagtcttcactactcccgcgaatgtatccaccccagaaaccaccctcaaaccttctcttagtccaggaaatgttagcgatttgtcaa cgacgagcacgagtttggcgactagtccaacgaaaccgtacacttccagcagtcccatactgtccgacattaaggcagaaataaaatgttct -continued gggatcagggaggtcaagcttacgcagggaatatgtcttgagcaaaataagacgtcctcatgcgcagaattcaagaaagatcgcggcgaa ggtctggccagagtcctctgtggagaggagcaggcggatgctgacgcaggagcgcaggtttgtagtctcctgctcgcgcaaagtgaagtt aggccccaatgtctcttgttggtactggctaaccgaactgaaattagcagcaagcttcaactcatgaaaaaacaccagagtgatttgaaaaaa cttgggatacttgacttcacggagcaagacgttgcgtctcaccaatcctactcacagaaaaccccgatactgttgacatgccccaccatatca atcttgtctttcttcagtgtggctcttctggtgatcttggcgtgcgtgctgtggaaaaaaaggattaaaccgatcgtttggcctagtctgccgga tcacaaaaagacactggagcacctctgcaagaagccacgaaaaaacctgaatgtgagctttaaccccgagtctttttttggactgtcagataca ccgagtcgacgatatacaggcaagagatgaggttgagggtttcctgcaagacacattcccgcaacaactcgaagaatccgagaaacagc gccttggtggagatgtccagtctccgaactgtccgagcgaggacgtagtaattaccccagaaagcttcggtcgagatagtagccttacgtgt ctcgccgggaacgtgtcagcgtgtgacgcgcctattctttcaagttcacgcagtttggactgtcgagaatcagggaaaaacggacctcacgt gtatcaggatctccttctcagcctgggcacgacaaacagtaccttgcctcctccgttttccctgcagtcaggtattctgacgctcaatccagtc gcacaagggcaacctatcctgacctccttgggttctaaccaggaagaggcatacgtcactatgtccagcttctatcagaatcag

CAR-C7R (SEQ ID NO 40):
MALPVTALLLPLALLLHAARPDIELTQSPAIMSASLGEEITLTCSASSSVSYMHW

YQQKSGTSPKLLIYSTSNLASGVPSRFSGSGSGTFYSLTISSVEAEDAADYYCHQWSSYT

FGGGTKLEIKRGGGGSGGGGSGGGGSQVKLQESGGGLVKPGGSLKLSCAASGFTFSSY

AMSWVRQTPEKRLEWVATISSGGSYTYYPDSVKGRFTISRDNAKNTLYLQMSSLRSED

TAMYYCARQDGYYPGWFANWGQGTTVTVSSSGTTTPAPRPPTPAPTIASQPLSLRPEAC

RPAAGGAVHTRGLDFACDIYIWAPLAGTCGVLLLSLVITLYCKRGRKKLLYIFKQPFMR

PVQTTQEEDGCSCRFPEEEEGGCELRVKFSRSADAPAYKQGQNQLYNELNLGRREEYD

VLDKRRGRDPEMGGKPRRKNPQEGLYNELQKDKMAEAYSEIGMKGERRRGKGHDGL

YQGLSTATKDTYDALHMQALPPRGSGATNFSLLKQAGDVEENPGPMLVRRGARAGPR

MPRGWTALCLLSLLPSGFMSLDNNGTATPELPTQGTFSNVSTNVSYQETTTPSTLGSTSL

HPVSQHGNEATTNITETTVKFTSTSVITSVYGNTNSSVQSQTSVISTVFTTPANVSTPETT

LKPSLSPGNVSDLSTTSTSLATSPTKPYTSSSPILSDIKAEIKCSGIREVKLTQGICLEQNKT

SSCAEFKKDRGEGLARVLCGEEQADADAGAQVCSLLLAQSEVRPQCLLLVLANRTEISS

KLQLMKKHQSDLKKLGILDFTEQDVASHQSYSQKTPILLTCPTISILSFFSVALLVILACV

LWKKRIKPIVWPSLPDHKKTLEHLCKKPRKNLNVSFNPESFLDCQIHRVDDIQARDEVE

GFLQDTFPQQLEESEKQRLGGDVQSPNCPSEDVVITPESFGRDSSLTCLAGNVSACDAPI

LSSSRSLDCRESGKNGPHVYQDLLLSLGTTNSTLPPPFSLQSGILTLNPVAQGQPILTSLG

SNQEEAYVTMSSFYQNQ

The amino acid sequence of two CD2 scFv constructed to single or a dual CAR are as below:

CD2 scFv1 VH:
(SEQ ID NO: 95)
QLQQPGAELVRPGSSVKLSCKASGYTFTRYWIHWVKQRPIQGLEWIGNI
DPSDSETHYNQKFKDKATLTVDKSSGTAYMQLSSLTSEDSAVYYCATED
LYYAMEYWGQGTSVTVSS

CD2 scFv1 VL:
(SEQ ID NO: 96)
DIMMTQSPSSLAVSAGEKVTMTCKSSQSVLYSSNQKNYLAWYQQKPGQS
PKLLIYWASTRESGVPDRFTGSGSGTDFTLTISSVQPEDLAVYYCHQYL
SSHTFGGGTKLEIKR

CD2 scFv2 VH:
(SEQ ID NO: 97)
QVQLQQPGTELVRPGSSVKLSCKASGYTFTSYWVNWVKQRPDQGLEWIG
RIDPYDSETHYNQKFTDKAISTIDTSSNTAYMQLSTLTSDASAVYYCSR
SPRDSSTNLADWGQGTLVTVSS

-continued

CD2 scFv2 VL:
(SEQ ID NO: 98)
DIVMTQSPATLSVTPGDRVSLSCRASQSISDYLHWYQQKSHESPRLLIK
YASQSISGIPSRFSGSGSGSDFTLSINSVEPEDVGVYYCQNGHSFPLTF
GAGTKLELRR

The CAR genes were cloned into the FUW lentiviral vector backbone under the promoter of EF1α (EF-1α) to form Fuw-EF1α-CAR. Fuw-EF1α-CAR, lentiviral envelope plasmid pMD2.G (Addgene, Plasmid #12259) and lentiviral packaging plasmid psPAX2 (Addgene, Plasmid #12260) were transfected into 293 T cells by using Lipofectamine®3000 to prepare the whole lentiviral expression vector. The supernatant was collected at 48 and 72 h and subject to ultra-centrifuge (Merck Millipore) for concentration.

3.3 Preparation of UCAR-T Cells

Figure 15:
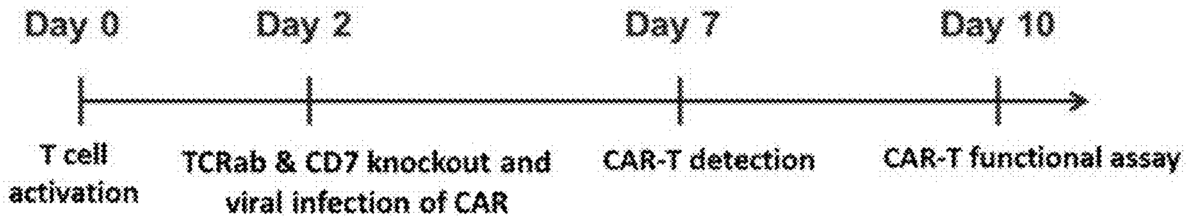
FIG. 15 illustrates an example preparation of CD7 CAR-T.

The whole preparation process is illustrated in FIG. 15.

Cell Isolation and Activation

After apheresis, monocytes were isolated using Histopaque®-1077 (Sigma-Aldrich) by density gradient centrifugation. T cells were then enriched, activated by magnetic beads coupled with anti-CD3/anti-CD28, cultured and expanded.

X-vivo™ 15 with 5% FBS, 2 mM L-glutamine, 1 mM sodium pyruvate and 300 IU/ml rhIL2 was used as UCAR-T cell medium. The cells were incubated and cultured at 37° C., 5% $CO_2$.

Electroporation and Lentivirus Infection

Two days after enriching and activating the T cells, the anti-CD3/anti-CD28 magnetic beads were removed and the cells were collected into a tube and subject to centrifuge at 300 g for 5 min, and then washed twice with DPBS and re-suspended in opti-mem at a cell density of $50\times10^6$/ml. The amount of cas9/gRNA RNP required was calculated based on the density of the cells, and then mixed with cells and transferred for electroporation by 4D-Nucleofector® System N (Lonza) system. Then the cells were re-suspended in a pre-warmed medium to a density of $2\times10^6$/ml. The cells were further subject to lentiviral transfection at MOI of 2-8, transferred to a flask and cultured in an incubator at 37° C., 5% $CO_2$.

Cell Proliferation and Detection of CAR Positive Ratio 3 days after the transfection, the number of cells and CAR positive cells were detected, and the positive ratio of CAR in T cells was calculated. The positive ratio of TCR (or CD3) and CD7 was also detected to determine the knockout efficiency. Then cells were continuously cultured in the incubator for 10 days and then the cells were ready for cryopreservation.

Figure 18:
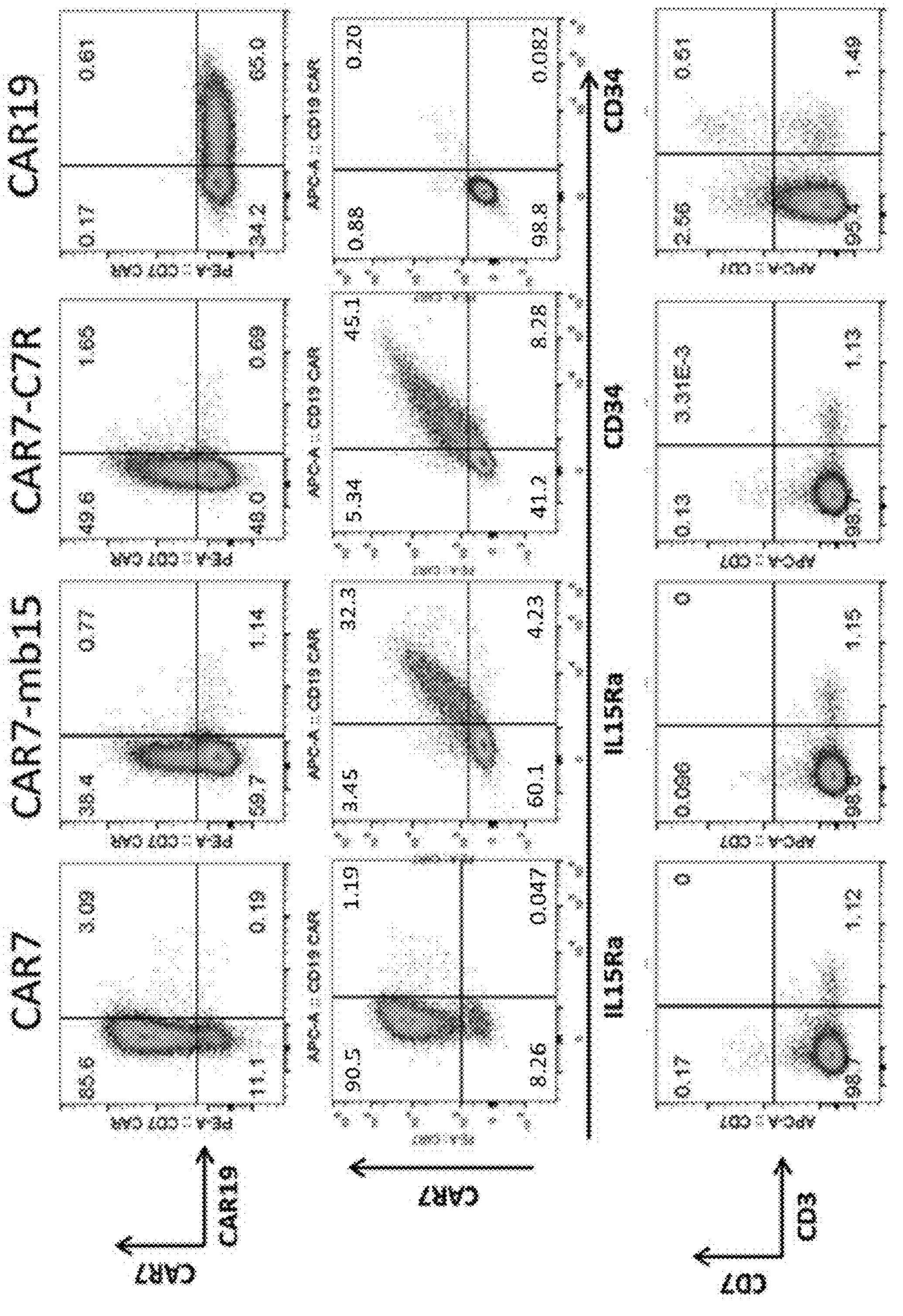
FIG. 18 illustrates experimental data of CAR expression of CAR7, CAR7-mb15, CAR7-C7R and control CAR19, expression of IL15Ra and CD34, and the knockout efficiency of CD7 and CD3.

The result shows that (FIG. 18) the expression of CAR, IL15Rα or C7R (CD34) was successfully detected by flow cytometry for CAR7, CAR7-mb15 and CAR7-C7R, and the positive ratio was higher than 30%. The negative ratio of CD3/CD7 was up to about 98%, indicating that the TCR knockout enhanced and universal UCAR-T cells were successfully prepared.

Figure 19:
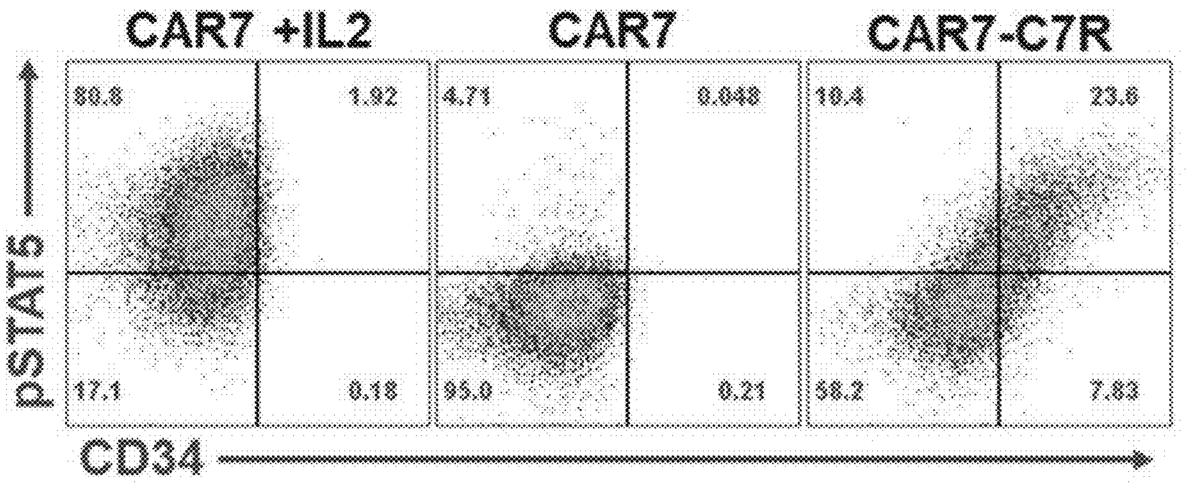
FIG. 19 illustrates experimental data of the activation of STAT5 in UCAR-T cells. Adding IL-2 activated the STAT5 of CAR7 T cells and remove of IL-2 significantly decreased pSTAT5 level. In CAR7-C7R, the level of pSTAT5 was at high level with or without exogenous IL-2.

As shown in FIG. 19, after removing exogenous IL-2, pSTAT5 level of CAR7 went down to basal level. However, the level of pSTAT5 in CAR7-C7R T cells (CD34+ cells) or CAR7-T cells with exogenous IL2 addition were at quite high levels, indicating expression of C7R and exogenously added IL-2 can both enhance the activation of STAT5 signaling pathway.

3.4 In Vitro Killing Effect

A stably transfected CCRF-CEM-luc cell line was obtained by introducing the luciferase gene into the target cell CCRF-CEM followed by screening. After adding fluorescein, luciferase could react with the fluorescein to produce fluorescence. By detecting the intensity of the fluorescence, the activity of luciferase can be measured, and the survival of the cells can be detected so that to evaluate the killing effect of UCAR-T cells.

Figure 20:
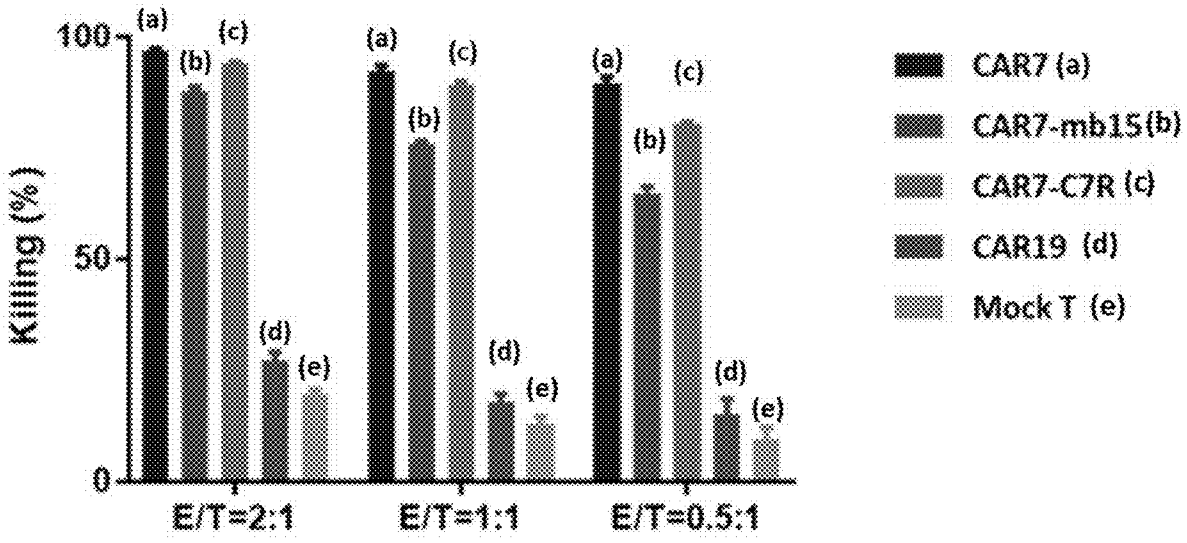
FIG. 20 illustrates experimental data of the killing effect of UCAR-T cells on CCRF-CEM-luc cell line.

The UCAR-T cells prepared in Example 3.3 were mixed with CD-7 positive T cell CCRF-CEM-luc, 100 ul each, in RPMI medium at 1:1 ratio to a density of 1×106/ml for each cell, and then cultured for a certain period of time in a 96-well plate. The medium was then collected and subject to centrifuge and the cytokine IFN-γ and IL-2 were detected by Cytokine bead array kit (CBA kit, BD Biosciences). In addition, fluorescein substrate was added to the cell culture to detect the killing effect of the UCAR-T cells. The result shows that UCAR-T has a significant killing effect on CCRF-CEM tumor within 24 hours (FIG. 20).

Figure 21:
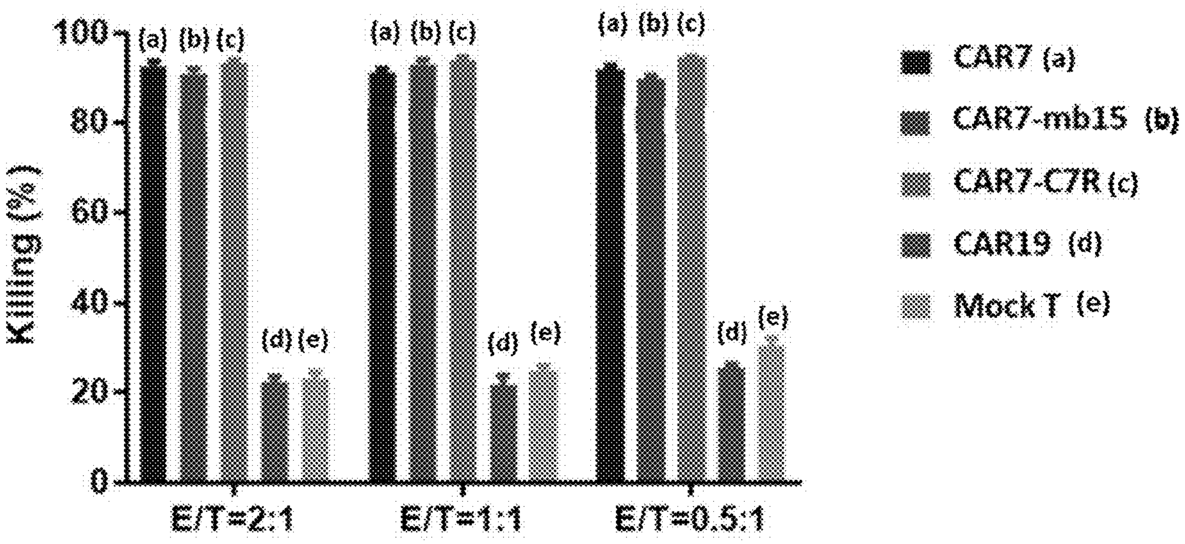
FIG. 21 illustrates experimental data of the killing effect of UCAR-T cells on alloreactive T (allo-T) cells.

The killing effect of UCAR-T on allogeneic T cells: allogeneic T cells were labeled with CFSE and incubated with CAR-T for a predetermined period of time. Then changes in the number of CFSE positive cells were analyzed by flow cytometry. The result shows that CAR-T cells efficiently killed allogeneic T cells within 24 hours, which is much shorter than the time for allo-T cell mediated HVG to happen, and thus CAR7 can effectively protect CAR-T cells from allogeneic T cell killing (FIG. 21).

Figure 22:
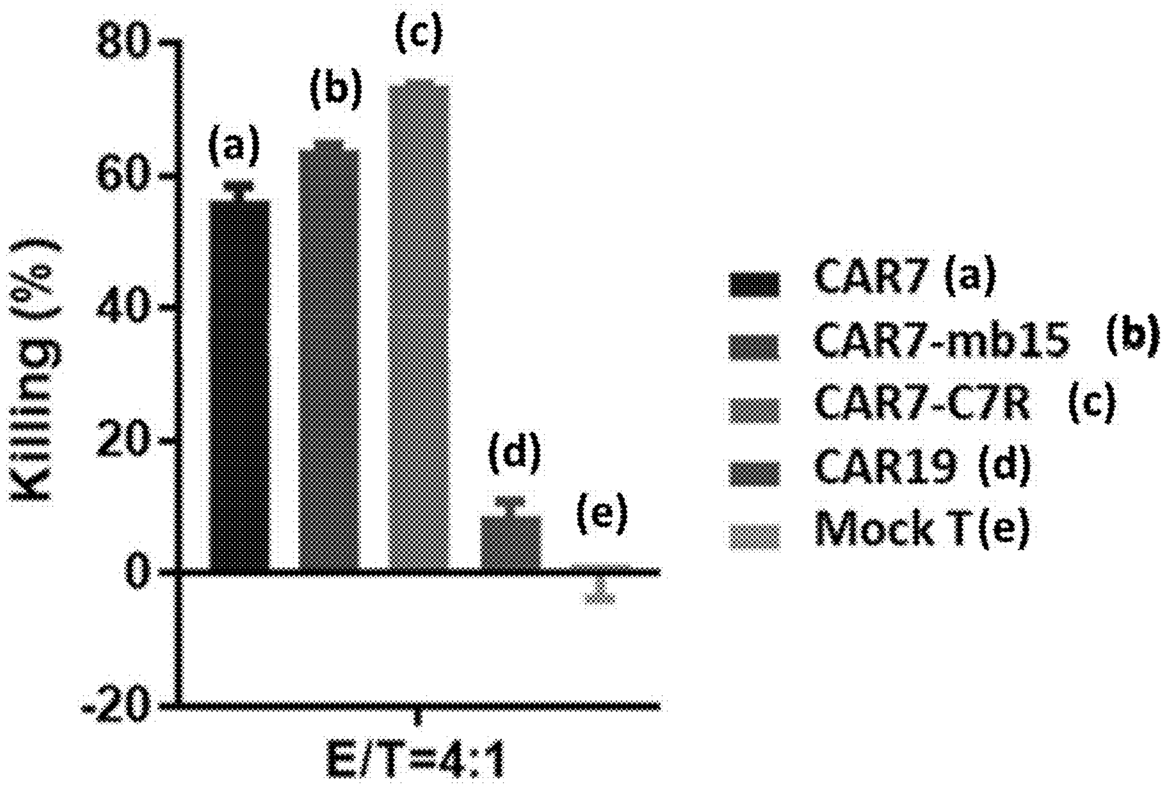
FIG. 22 illustrates the killing effect of UCAR-T cells on NK92 cell line in 24 hours.

The 24 hour killing effect of UCAR-T on NK tumor cell line (NK92): NK92 was labeled with carboxyfluorescein succinimidyl ester (CFSE) and incubated with UCAR-T for a predetermined period of time. Then changes in the number of CFSE positive cells were analyzed by flow cytometry, so that to calculate the in vitro killing effect of UCAR-T on NK92 tumor cell line (FIG. 22).

3.5 Proliferation of CAR-T Cells

IL-2 was removed from CAR-T. CAR-T cells were continuously cultured for 2 weeks and counted twice a week to measure the proliferation.

Figure 23A:
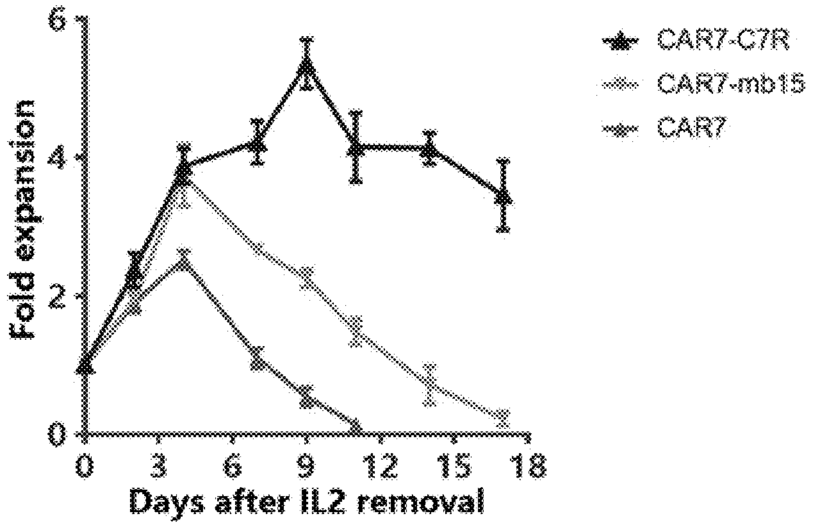
FIG. 23A illustrates experimental data of in vitro expansion of several UCAR-T cells, where the UCAR-T cells expressing enhancers survived longer.
Figure 23B:
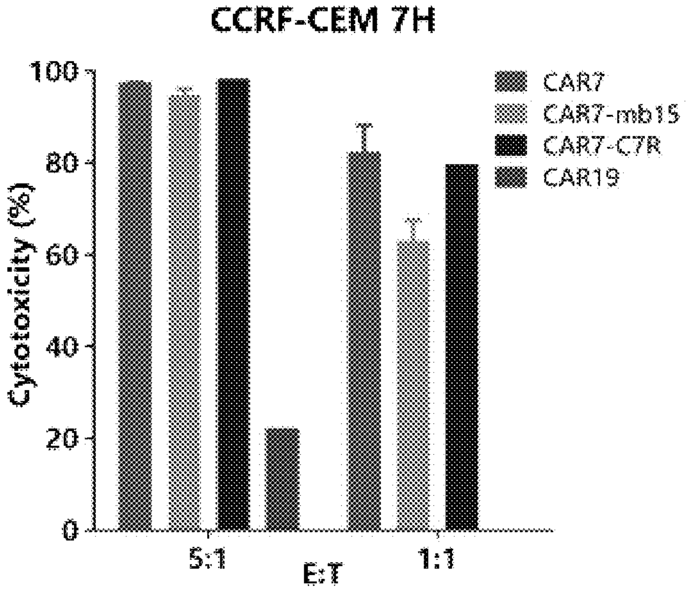
FIG. 23B illustrates experimental data of comparison of their killing effects on CCRF-CEM tumor cells after removing IL-2.

The result in FIGS. 23A and 23B shows that CAR7-mb15 and CAR7-C7R CAR-T cells had stronger proliferation rate than CAR7 CAR-T cells, and in absence of IL-2, they still had higher survival ratio within 2 weeks. CAR7-C7R showed better survival than CAR7-mb15. In vitro killing assay indicates that the UCAR-T cells have superior killing effect against T-ALL cell line CCRF-CEM within 7 hours.

3.6 Re-Activation of Cells In Vitro

Figure 24A:
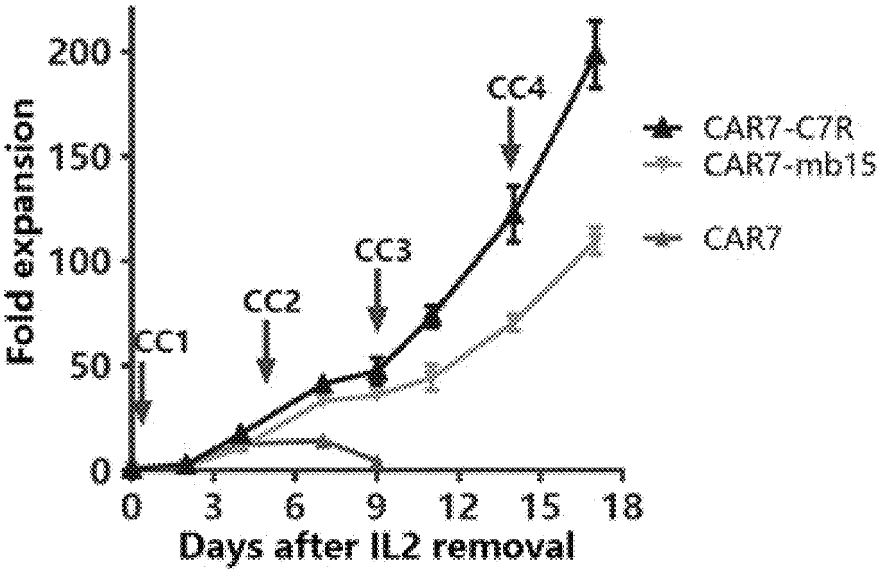
FIG. 24A illustrates experimental data of in vitro expansion of several UCAR-T cells.
Figure 24B:
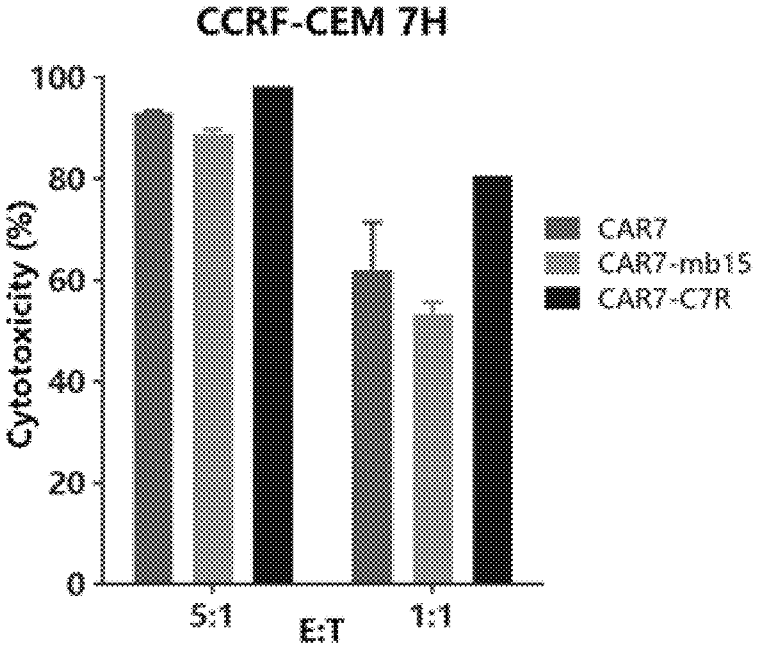
FIG. 24B illustrates experimental data of comparison of their killing effects on CCRF-CEM tumor cells after removing IL-2 and co-culturing with CCRF-CEM for multiple rounds, where the UCAR-T cells expressing enhancers showed stronger expansion under the stimulation of tumor antigens.

IL-2 was removed from UCAR-T. CCRF-CEM was added twice a week at 1:1 effector: target ratio and counted twice a week to measure the proliferation. 4 FIGS. 24A and 24B show that after adding CCRF-CEM, CAR7-mb15 and CAR7-C7R UCAR-T cells showed significantly stronger proliferation than CAR7 UCAR-T and CAR7-C7R UCAR-T cells proliferated better than CAR7-mbIL15 UCAR-T cells. After repeated stimulation, UCAR-T cells still showed significant ability to remove tumor cells, indicating after repeated antigen stimulation, the cytokine-related signaling pathway enhanced UCAR-T cells has a higher proliferation rate, and can survive better.

3.7 Proliferation and Efficacy of UCAR-T Cells in Tumor Bearin2 Mice 6-12 weeks NOD/Shi-scid/IL-2Rγnull (NOG) mice were selected and intraperitoneally injected with $2\times10^6$ CCRF-CEM-luc cells. Two days later, the tumor graft burden of the mice was measured, and the mice were divided into 5 groups based on the tumor burden. 6 days after the tumor implantation, $1\times10^6$ UCAR-T or control was injected intravenously to each mouse, and the tumor burden was further evaluated every 1-2 weeks. Each mouse was injected intraperitoneally with 3 mg D-luciferin for a 4-minutes reaction, and then photographed using a Xenogen IVIS® Imaging System with 30 s exposure (BLI). UCAR-T cell number in peripheral blood was counted every week.

Figure 25:
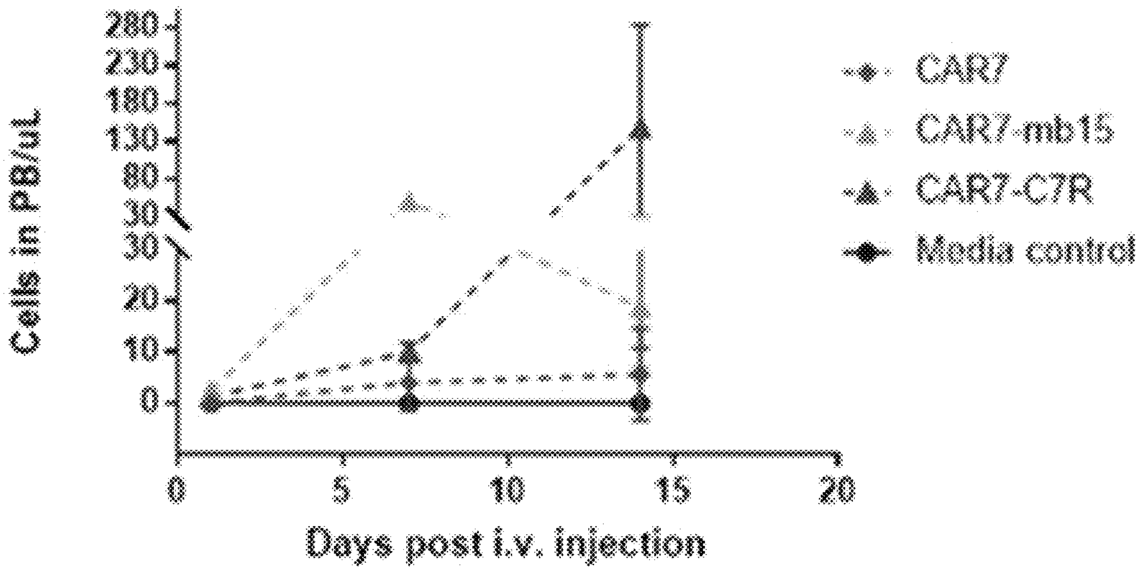
FIG. 25 illustrates experimental data of expansion of UCAR-T cells expressing enhancers in immuno-deficient mice carrying CCRF-CEM tumor.
Figure 26:
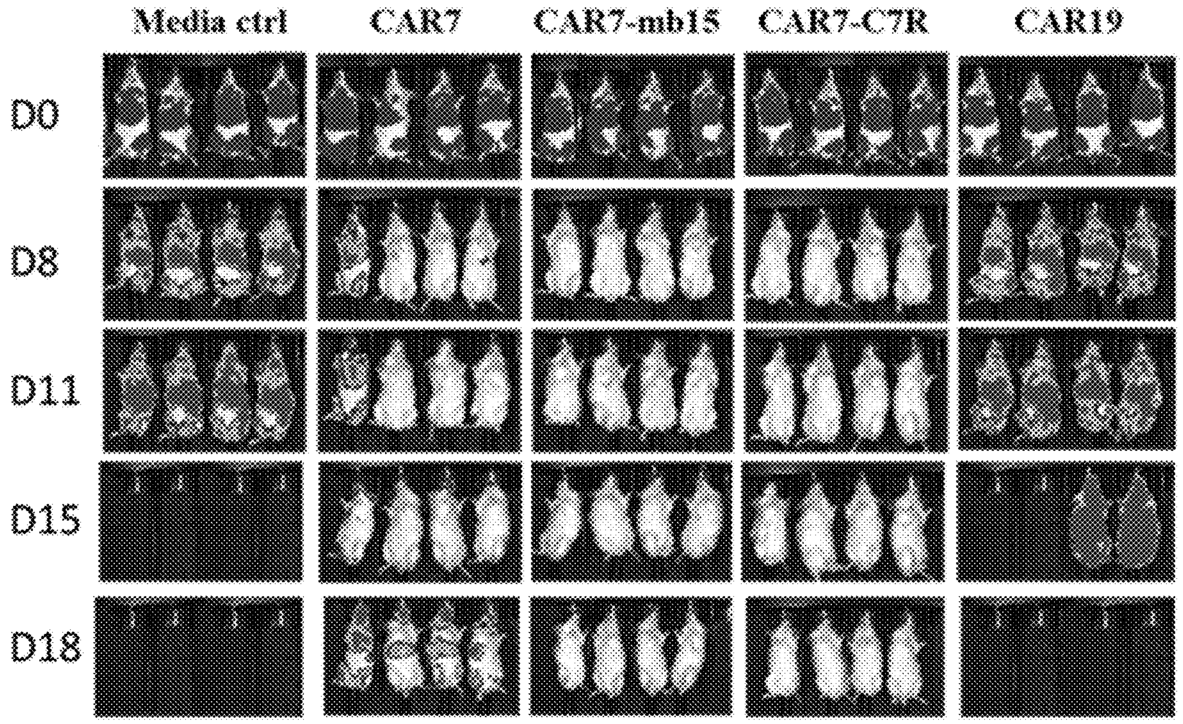
FIG. 26 illustrates experimental data of the killing effect of UCAR-T cells expressing enhancers on CCRF-CEM tumor in mice.

FIG. 25 shows that CAR7-mb15 and CAR7-C7R UCAR-T had significant expansion, and CAR7 UCAR-T did not show any significant expansion. FIG. 26 shows the result of BLI imaging, and it can be seen that CAR7-mb15 and CAR7-C7R UCAR-T cells had better effect on tumor clearance than CAR7 UCAR-T cells.

Figure 27:
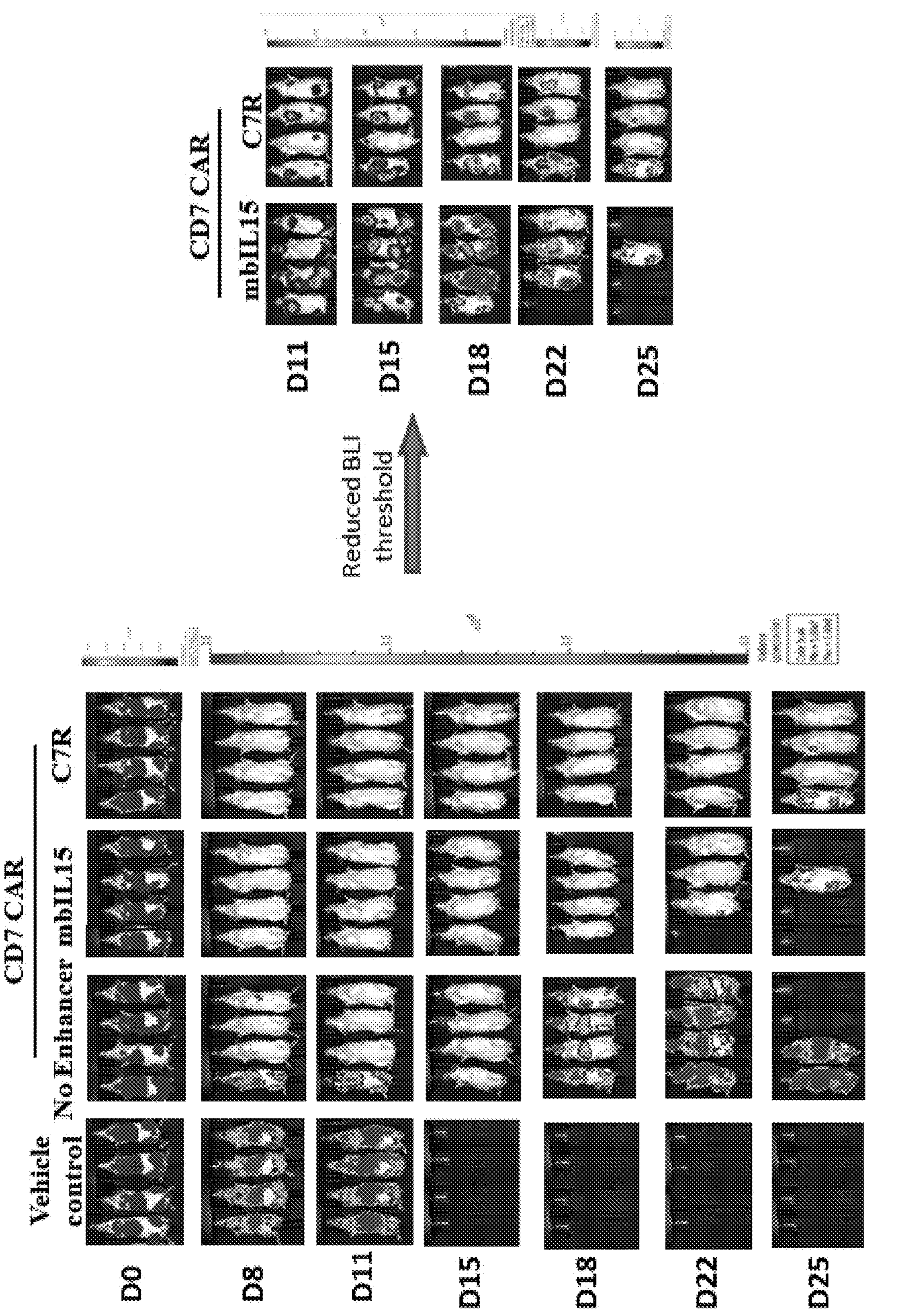
FIG. 27 illustrates in vivo comparison of enhancers in TCR KO CD7 CAR-T cells.

FIG. 27 shows BLI images of the mice treated with vehicle control or CAR7 UCAR-T cells with TCR knockout and with or without expression of enhancers. CAR7 UCAR-T cells with TCR knockout and the expression of C7R or mbIL15 exhibited better efficiency on tumor clearance in comparison to vehicle control and TCR KO CAR7 UCAR-T cells without the expression of any enhancers.

C7R expressing CAR7 cells showed better tumor control and mouse survival than that expressing mbIL15. As used herein, "CAR7," "CAR7 UCAR-T," or CD7 CAR-T" can be used interchangeably to indicate an engineered CAR-T cell comprising a CAR targeting CD7.

Figure 28A:
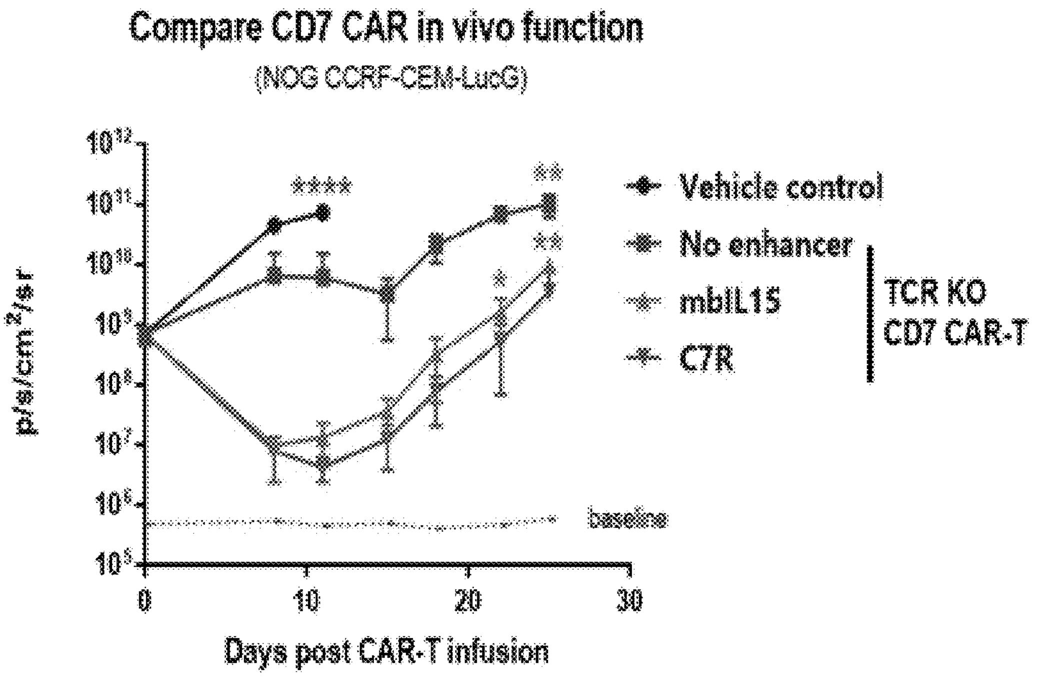
FIGS. 28A and 28B illustrate in vivo comparison of enhancers in TCR KO CD7 CAR-T cells.
Figure 28B:
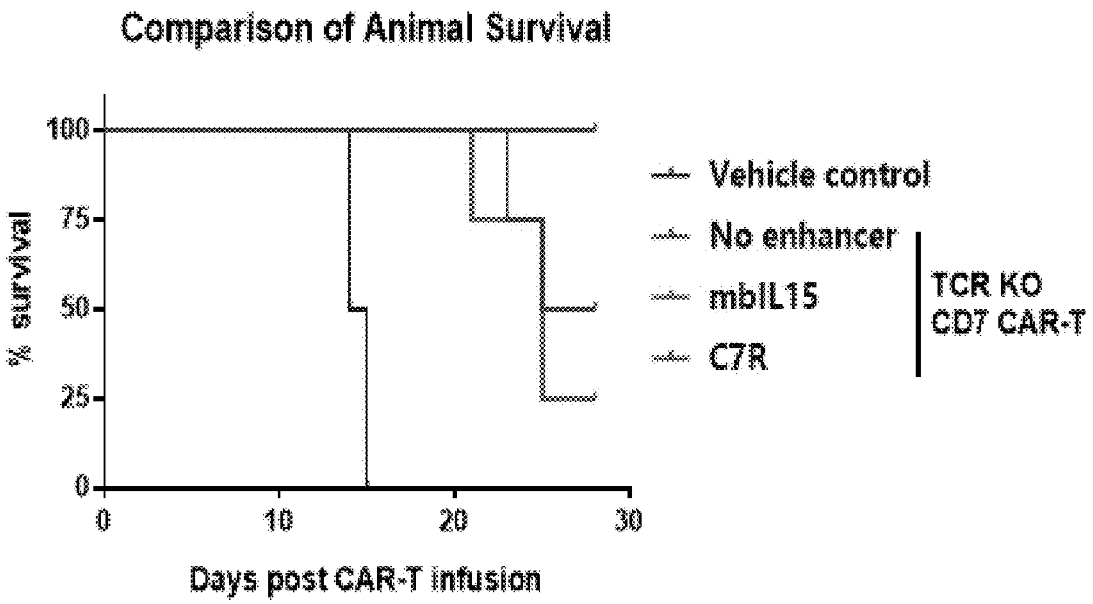

FIG. 28A BLI imaging shows in vivo function of CD7 CAR-T cells in clearing tumor cells. TCR KO CD7 CAR-T cells with the expression C7R or mbIL15 exhibited better in vivo efficiency on tumor clearance in comparison to vehicle control and TCR KO CD7 CAR-T cells without the expression of any enhancers. FIG. 28B shows animal survival data of the NOG mice treated with TCR KO CD7 CAR-T with or without the expression of enhancer and vehicle control. Percentage of survived mice were measured against days after CAR-T cell infusion. Mice treated with TCR KO CD7 CAR-T with expression of C7R or mbIL15 had a better survival rate in comparison to mice treated with CAR-T cells without the expression enhancer or vehicle control. C7R expressing CAR7 cells showed better tumor control and mouse survival than that expressing mbIL15.

Figure 55A:
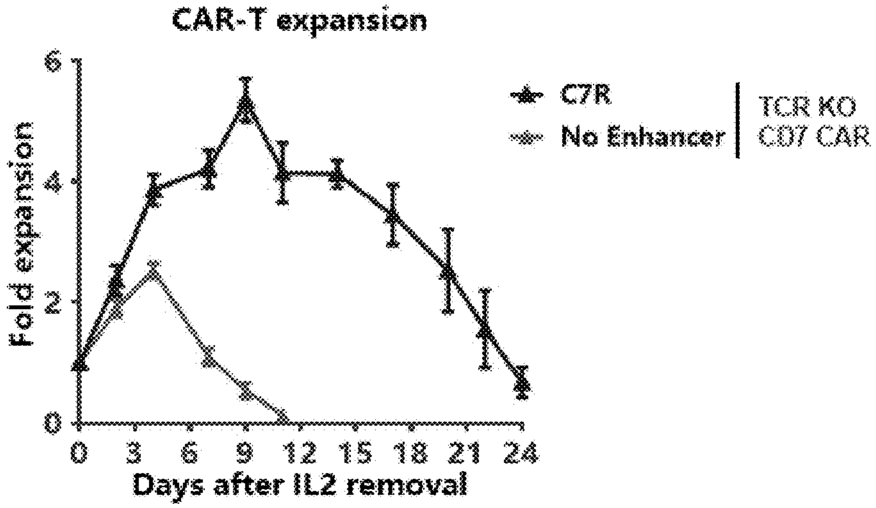
FIGS. 55A and 55B illustrate experimental data showing effects of C7R on TCR knockout (KO) CD7 CAR-T cells (e.g., a CAR-T cell having a CAR targeting CD7, also referred to as UCART7 cells or CAR7 cells) expansion and persistence.
Figure 55B:
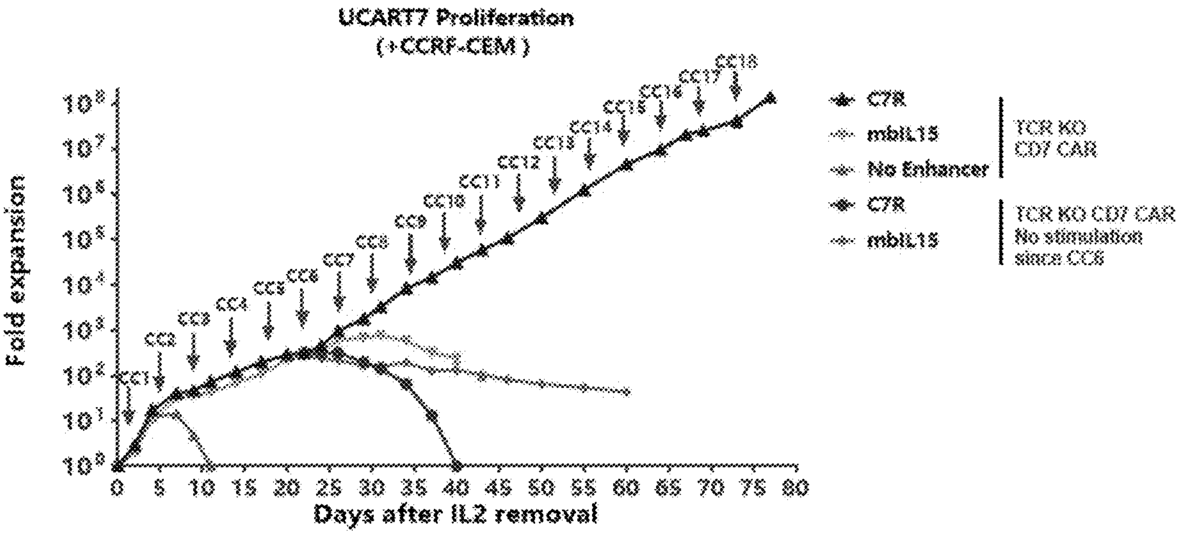

FIG. 55A shows expansion data of CAR-T cells. Freshly prepared CD7 CAR-T cells expressing C7R were cultured in T cell culture media without supplement of IL2 or antigen stimulation, compared to control cells that do not have C7R or any enhancer expression, CD7 CAR-T cells expressing C7R maintained better expansion and persisted in culture. FIG. 55B shows proliferation of CAR-T cells in the presence of stimulation. CD7 CAR-T (or UCART7), CD7 CAR-T expressing mbIL15 or C7R were repetitively stimulated by CCRF-CEM (CD7+ T-ALL cells). The CD7 CAR-T expressing C7R showed the best persistence and proliferation. CD7 CAR-T expressing mbIL15/C7R stopped proliferation when antigen stimulation was removed at round 6 of stimulation (CC6). "CC," as used herein, indicates co-culture with cancer cells.

3.8 In Vivo GVHD Study

The mice were systemically treated with a sub-lethal dose of irradiation (175 cGy) first. Then CAR-T cells were re-suspended in PBS and injected into the thorax of the treated mice. The mice were observed 2-3 times a week by using GVHD clinical criteria including weight loss, arch-back, activity, fur texture, and skin integrity.

The result shows that mice in groups without TCR knockout all showed symptoms of GVHD, however, no GVHD was detected in TCR knockout group.

3.9 Effect of TCR Knockout

Figure 54A:
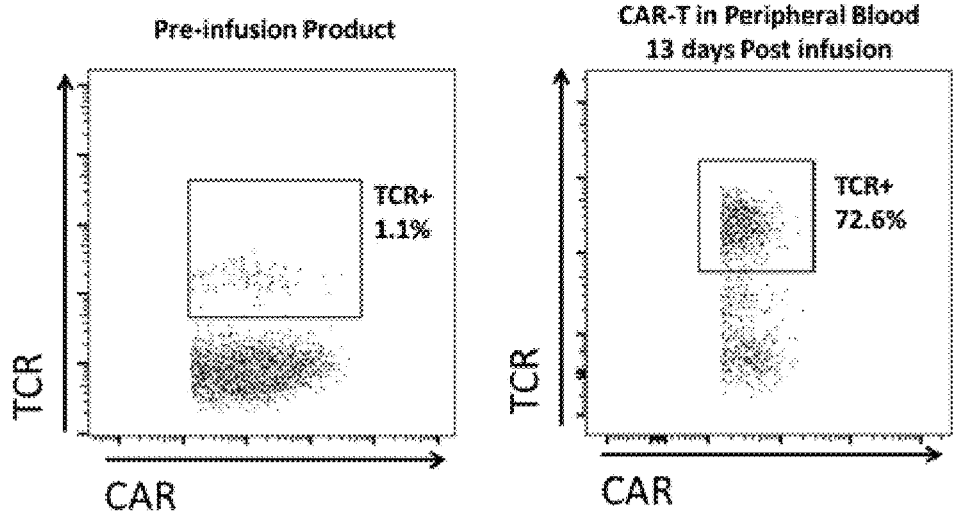
FIGS. 54A-C illustrate experimental data showing defects in cell expansion of TCR knockout autologous CAR-T cells.
Figure 54B:
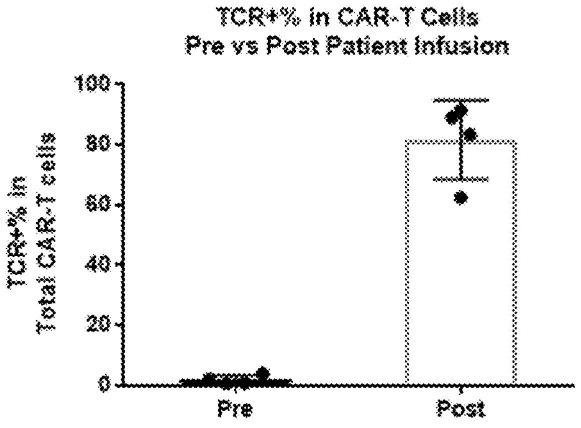
Figure 54C:
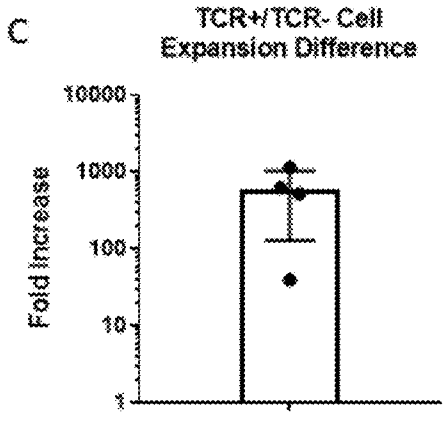

FIGS. 54A-C show the effect of TCR knockout in the CAR-T cells. In an investigator initiated clinical trial, TCR expression in Mesothelin CAR-T cells were impaired to avoid TCR related adverse event. However, TCR KO CAR-T cells unexpectedly showed significant expansion defects after infusion into the patients. FIG. 54A shows example of TCR KO efficiency in autologous Mesothelin (MSLN) CAR+ T cells (left), and CAR+ T cells in patient's peripheral blood CAR-T cells at 13 days post infusion (right). FIG. 54B shows TCR disruption efficiencies in autologous MSLN CAR-T products were highly effective, with less than 5% TCR+ cells remaining in the product. However, after infusion into patients, majority of the CAR-T cells detected in the peripheral blood were TCR+ cells. FIG. 54C shows that TCR+ cells showed 40 to ~1000 fold more expansion than TCR-cells in cancer patients. Therefore, even in autologous CAR-T applications, where there is no cell survival and expansion pressure from allogeneic killer cells, TCR disruption dramatically impaired CAR-T cell expansion.

3.10 Sequences of Construct Designs

CD7CAR-mbIL15 construct design: CD7CAR-mbIL15 amino acid sequence (mbIL15=IgE signal peptide+IL15+IL15Rα)

```
                                              (SEQ ID NO: 99)
MALPVTALLLPLALLLHAARPDIELTQSPAIMSASLGEEITLTCSASSS
VSYMHWYQQKSGTSPKLLIYSTSNLASGVPSRFSGSGSGTFYSLTISSV
EAEDAADYYCHQWSSYTFGGGTKLEIKRGGGGSGGGGSGGGGSQVKLQE
SGGGLVKPGGSLKLSCAASGFTFSSYAMSWVRQTPEKRLEWVATISSGG
SYTYYPDSVKGRFTISRDNAKNTLYLQMSSLRSEDTAMYYCARQDGYYP
GWFANWGQGTTVTVSSSGTTTPAPRPPTPAPTIASQPLSLRPEACRPAA
GGAVHTRGLDFACDIYIWAPLAGTCGVLLLSLVITLYCKRGRKKLLYIF
KQPFMRPVQTTQEEDGCSCRFPEEEEGGCELRVKFSRSADAPAYKQGQN
QLYNELNLGRREEYDVLDKRRGRDPEMGGKPRRKNPQEGLYNELQKDKM
AEAYSEIGMKGERRRGKGHDGLYQGLSTATKDTYDALHMQALPPRGSGA
TNFSLLKQAGDVEENPGPMDWTWILFLVAAATRVHSNWVNVISDLKKIE
DLIQSMHIDATLYTESDVHPSCKVTAMKCFLLELQVISLESGDASIHDT
VENLIILANNSLSSNGNVTESGCKECEELEEKNIKEFLQSFVHIVQMFI
NTSSGGGSGGGGSGGGGSGGGGSGGGSLQITCPPPMSVEHADIWVKSYS
LYSRERYICNSGFKRKAGTSSLTECVLNKATNVAHWTTPSLKCIRDPAL
VHQRPAPPSTVTTAGVTPQPESLSPSGKEPAASSPSSNNTAATTAAIVP
GSQLMPSKSPSTGTTEISSHESSHGTPSQTTAKNWELTASASHQPPGVY
PQGHSDTTVAISTSTVLLCGLSAVSLLACYLKSRQTPPLASVEMEAMEA
LPVTWGTSSRDEDLENCSHHL
```

CD7CAR-C7R construct design: CD7CAR-C7R amino acid sequence (C7R=CD34 ecto domain+constitutively active IL7Rα)

```
                                              (SEQ ID NO: 40)
MALPVTALLLPLALLLHAARPDIELTQSPAIMSASLGEEITLTCSASSS
VSYMHWYQQKSGTSPKLLIYSTSNLASGVPSRFSGSGSGTFYSLTISSV
EAEDAADYYCHQWSSYTFGGGTKLEIKRGGGGSGGGGSGGGGSQVKLQE
SGGGLVKPGGSLKLSCAASGFTFSSYAMSWVRQTPEKRLEWVATISSGG
SYTYYPDSVKGRFTISRDNAKNTLYLQMSSLRSEDTAMYYCARQDGYYP
GWFANWGQGTTVTVSSSGTTTPAPRPPTPAPTIASQPLSLRPEACRPAA
GGAVHTRGLDFACDIYIWAPLAGTCGVLLLSLVITLYCKRGRKKLLYIF
KQPFMRPVQTTQEEDGCSCRFPEEEEGGCELRVKFSRSADAPAYKQGQN
QLYNELNLGRREEYDVLDKRRGRDPEMGGKPRRKNPQEGLYNELQKDKM
AEAYSEIGMKGERRRGKGHDGLYQGLSTATKDTYDALHMQALPPRGSGA
TNFSLLKQAGDVEENPGPMLVRRGARAGPRMPRGWTALCLLSLLPSGFM
SLDNNGTATPELPTQGTFSNVSTNVSYQETTTPSTLGSTSLHPVSQHGN
EATTNITETTVKFTSTSVITSVYGNTNSSVQSQTSVISTVFTTPANVST
PETTLKPSLSPGNVSDLSTTSTSLATSPTKPYTSSSPILSDIKAEIKCS
GIREVKLTQGICLEQNKTSSCAEFKKDRGEGLARVLCGEEQADADAGAQ
```

-continued

VCSLLLAQSEVRPQCLLLVLANRTEISSKLQLMKKHQSDLKKLGILDFT

EQDVASHQSYSQKTPILLTCPTISILSFFSVALLVILACVLWKKRIKPI

VWPSLPDHKKTLEHLCKKPRKNLNVSFNPESFLDCQIHRVDDIQARDEV

EGFLQDTFPQQLEESEKQRLGGDVQSPNCPSEDVVITPESFGRDSSLTC

LAGNVSACDAPILSSSRSLDCRESGKNGPHVYQDLLLSLGTTNSTLPPP

FSLQSGILTLNPVAQGQPILTSLGSNQEEAYVTMSSFYQNQ

Example 4 Study of U-CAR T Cells Expressing the Enhancer Together with the Safety-Switch 4.1 Design of CAR and Package of the Virus The structure of the chimeric antigen receptor is:

1) RQR8-CD19CAR-mbIL15;
2) RQR8-CD19CAR-mbIL15-IL7;
3) RQR8-CD19CAR-C7R;
4) RQR8-CD19CAR-mbIL7;

wherein RQR8 is a safety switch, and the CD19CAR fragment is the heavy chain and light chain variable region of monoclonal antibody FMC63 (connected by a GS linker), and also included are hinge region and transmembrane region, human CD 28 intracellular co-stimulatory element, and human CD3ζ intracellular region in tandem; mbIL15 consists of IL15+IL15Rα in tandem; C7R is a constitutively activated IL7 receptor consisting of CD34 extracellular domain and IL7 receptor transmembrane and intracellular domains; IL7 consists of IL7 signal peptide and mature peptide; mbIL7 consists of IL7+IL7Ra in tandem. Examples of the constructs described herein are shown in FIG. 29.

The amino acid sequence of RQR8 is as set forth below (SEQ ID NO.: 7):

MGTSLLCWMALCLLGADHADACPYSNPSLCSGGGGSELPTQGTFSNVST

NVSPAKPTTTACPYSNPSLCSGGGGSPAPRPPTPAPTIASQPLSLRPEA

CRPAAGGAVHTRGLDFACDIYIWAPLAGTCGVLLLSLVITLYCNHRNRR

RVCKCPRPVV

The DNA sequence of RQR8 is as set forth below (SEQ ID NO.: 8):

ATGGGCACCTCTCTGCTGTGCTGGATGGCTCTGTGTCTGCTGGGCGCTG

ACCATGCTGATGCTTGCCCCTATTCCAACCCCTCTCTGTGCTCCGGAGG

AGGAGGATCCGAACTGCCTACCCAAGGCACCTTCAGCAACGTGTCCACC

AACGTGAGCCCCGCTAAGCCTACCACCACCGCTTGCCCTTACTCCAATC

CCAGCCTCTGCTCCGGAGGCGGAGGATCCCCCGCCCCCAGACCTCCTAC

ACCCGCTCCCACAATCGCCAGCCAGCCTCTGTCTCTGAGACCCGAAGCT

TGCAGACCCGCTGCCGGAGGAGCTGTGCATACAAGAGGACTGGATTTCG

CTTGCGACATCTACATCTGGGCCCCTCTGGCTGGCACATGTGGCGTGCT

GCTGCTGTCTCTGGTCATTACACTGTACTGCAACCATAGAAATAGAAGA

AGGGTGTGCAAGTGTCCCAGACCCGTGGTGGGCAGCGGAGAAGGAAGAG

GCTCTCTGCTGACATGCGGAGACGTGGAAGAGAACCCCGGCCCC

The amino acid sequence of CD19CAR is as set forth below (SEQ ID NO.: 9):

MLLLVTSLLLCELPHPAFLLIPDIQMTQTTSSLSASLGDRVTISCRASQ

DISKYLNWYQQKPDGTVKLLIYHTSRLHSGVPSRFSGSGSGTDYSLTIS

NLEQEDIATYFCQQGNTLPYTFGGGTKLEITGSTSGSGKPGSGEGSTKG

EVKLQESGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTSVTVSSAAADYKDDDDKIEVMYPPPYLDNEKSN

GTIIHVKGKHLCPSPLFPGPSKPFWVLVVVGGVLACYSLLVTVAFIIFW

VRSKRSRLLHSDYMNMTPRRPGPTRKHYQPYAPPRDFAAYRSRVKFSRS

ADAPAYQQGQNQLYNELNLGRREEYDVLDKRRGRDPEMGGKPRRKNPQE

GLYNELQKDKMAEAYSEIGMKGERRRGKGHDGLYQGLSTATKDTYDALH

MQALPPR

The DNA sequence of CD19CAR is as set forth below (SEQ ID NO.: 10):

ATGCTTCTCCTGGTGACAAGCCTTCTGCTCTGTGAGTTACCACACCCAG

CATTCCTCCTGATCCCAGACATCCAGATGACACAGACTACATCCTCCCT

GTCTGCCTCTCTGGGAGACAGAGTCACCATCAGTTGCAGGGCAAGTCAG

GACATTAGTAAATATTTAAATTGGTATCAGCAGAAACCAGATGGAACTG

TTAAACTCCTGATCTACCATACATCAAGATTACACTCAGGAGTCCCATC

AAGGTTCAGTGGCAGTGGGTCTGGAACAGATTATTCTCTCACCATTAGC

AACCTGGAGCAAGAAGATATTGCCACTTACTTTTGCCAACAGGGTAATA

CGCTTCCGTACACGTTCGGAGGGGGGACTAAGTTGGAAATAACAGGCTC

CACCTCTGGATCCGGCAAGCCCGGATCTGGCGAGGGATCCACCAAGGGC

GAGGTGAAACTGCAGGAGTCAGGACCTGGCCTGGTGGCGCCCTCACAGA

GCCTGTCCGTCACATGCACTGTCTCAGGGGTCTCATTACCCGACTATGG

TGTAAGCTGGATTCGCCAGCCTCCACGAAAGGGTCTGGAGTGGCTGGGA

GTAATATGGGGTAGTGAAACCACATACTATAATTCAGCTCTCAAATCCA

GACTGACCATCATCAAGGACAACTCCAAGAGCCAAGTTTTCTTAAAAAT

GAACAGTCTGCAAACTGATGACACAGCCATTTACTACTGTGCCAAACAT

TATTACTACGGTGGTAGCTATGCTATGGACTACTGGGGTCAAGGAACCT

CAGTCACCGTCTCCTCAGCGGCCGCAGACTACAAAGACGATGACGACAA

GATTGAAGTTATGTATCCTCCTCCTTACCTAGACAATGAGAAGAGCAAT

GGAACCATTATCCATGTGAAAGGGAAACACCTTTGTCCAAGTCCCCTAT

TTCCCGGACCTTCTAAGCCCTTTTGGGTGCTGGTGGTGGTTGGGGGAGT

CCTGGCTTGCTATAGCTTGCTAGTAACAGTGGCCTTTATTATTTTCTGG

GTGAGGAGTAAGAGGAGCAGGCTCCTGCACAGTGACTACATGAACATGA

CTCCCCGCCGCCCCGGGCCCACCCGCAAGCATTACCAGCCCTATGCCCC

ACCACGCGACTTCGCAGCCTATCGCTCCAGAGTGAAGTTCAGCAGGAGC

GCAGACGCCCCCGCGTACCAGCAGGGCCAGAACCAGCTCTATAACGAGC

-continued

TCAATCTAGGACGAAGAGAGGAGTACGATGTTTTGGACAAGAGACGTGG
CCGGGACCCTGAGATGGGGGGAAAGCCGAGAAGGAAGAACCCTCAGGAA
GGCCTGTACAATGAACTGCAGAAAGATAAGATGGCGGAGGCCTACAGTG
AGATTGGGATGAAAGGCGAGCGCCGGAGGGGCAAGGGGCACGATGGCCT
TTACCAGGGTCTCAGTACAGCCACCAAGGACACCTACGACGCCCTTCAC
ATGCAGGCCCTGCCCCCTCGC

The amino acid sequence of mbIL15 is as set forth below (SEQ ID NO.: 11):

MDWTWILFLVAAATRVHS*NWVNVISDLKKIEDLIQSMHIDATLYTESDV*
*HPSCKVTAMKCFLLELQVISLESGDASIHDTVENLIILANNSLSSNGNV*
*TESGCKECEELEEKNIKEFLQSFVHIVQMFINTSS*GGGSGGGGSGGGGS
GGGGSGGGSLQITCPPPMSVEHADIWVKSYSLYSRERYICNSGFKRKAG
TSSLTECVLNKATNVAHWTTPSLKCIRDPALVHQRPAPPSTVTTAGVTP
QPESLSPSGKEPAASSPSSNNTAATTAAIVPGSQLMPSKSPSTGTTEIS
SHESSHGTPSQTTAKNWELTASASHQPPGVYPQGHSDTTVAISTSTVLL
CGLSAVSLLACYLKSRQTPPLASVEMEAMEALPVTWGTSSRDEDLENCS
HHL

In the amino acid sequence of mbIL15, the underlined part is the signal peptide region, the italic part is IL-15, the bold part is the linking region, and the dashed underlined part is IL-15 receptor α.

The DNA sequence of mbIL15 is as set forth below (SEQ ID NO.: 12):

ATGGATTGGACTTGGATTTTGTTCCTCGTTGCCGCAGCGACTCGCGTCC
ATAGTAATTGGGTGAACGTAATTAGTGACTTGAAAAAAATTGAGGACCT
TATACAAAGTATGCATATCGATGCAACACTGTACACGGAGTCCGACGTG
CACCCAAGCTGCAAGGTCACCGCAATGAAATGCTTTTTGCTCGAATTGC
AAGTTATCTCACTTGAGTCAGGGGACGCTTCAATCCATGATACTGTGGA
GAATTTGATAATCCTGGCGAACAATAGCCTTAGTTCAAATGGCAACGTC
ACTGAGTCAGGCTGCAAGGAATGTGAGGAATTGGAAGAAAAAAATATCA
AGGAATTTTTGCAATCTTTTGTTCACATAGTTCAGATGTTCATTAACAC
TAGTTCCGGGGGCGGCAGTGGAGGTGGCGGTAGCGGCGGGGGTGGCTCT
GGTGGAGGCGGCTCTGGGGGCGGAAGTCTGCAGATAACATGCCCCCCAC
CTATGAGTGTTGAACATGCTGATATCTGGGTTAAATCTTACTCCCTTTA
CAGTCGAGAAAGGTACATTTGCAACTCCGGCTTTAAACGCAAAGCCGGG
ACTAGTTCACTGACTGAATGTGTATTGAATAAAGCGACAAATGTCGCAC
ACTGGACTACCCCTTCCCTCAAATGCATTCGCGATCCTGCCTTGGTGCA
TCAGCGACCAGCACCGCCGTCCACGGTAACTACCGCAGGAGTAACACCG
CAGCCCGAGAGCCTTTCCCCCTCAGGCAAAGAGCCGGCCGCATCCTCCC
CATCTTCCAATAATACCGCAGCTACCACCGCAGCAATCGTACCCGGGTC

-continued

CCAGCTGATGCCCAGCAAAAGTCCGAGTACTGGAACGACTGAAATCTCC
AGTCACGAGTCTTCTCATGGAACTCCGAGTCAAACTACAGCAAAGAATT
GGGAGCTGACTGCTTCCGCTTCACACCAGCCGCCAGGCGTTTATCCTCA
GGGACACTCAGATACCACGGTGGCGATTAGCACAAGCACCGTCCTCCTG
TGTGGGCTGAGTGCAGTGTCACTTCTCGCCTGCTACCTTAAGTCCAGAC
AGACACCCCCTTTGGCAAGCGTTGAAATGGAAGCCATGGAAGCCTTGCC
TGTCACATGGGGGACTTCATCCCGCGATGAAGACTTGGAGAACTGCTCA
CACCATCTTTGA

The amino acid sequence of IL7 is as set forth below (SEQ ID NO.: 13):

MFHVSFRYIFGLPPLILVLLPVASSDCDIEGKDGKQYESVLMVSIDQLL
DSMKEIGSNCLNNEFNFFKRHICDANKEGMFLFRAARKLRQFLKMNSTG
DFDLHLLKVSEGTTILLNCTGQVKGRKPAALGEAQPTKSLEENKSLKEQ
KKLNDLCFLKRLLQEIKTCWNKILMGTKEH

The DNA sequence of IL7 is as set forth below (SEQ ID NO.: 14):

GAATTCGGCAGCGGCGTCAAGCAGACACTGAACTTCGATCTGCTGAAGC
TGGCCGGAGACGTCGAGAGCAACCCCGGCCCTATGTTCCACGTGAGCTT
TAGATACATCTTCGGACTGCCCCCTCTGATTCTGGTGCTGCTGCCCGTG
GCCAGCAGCGACTGCGATATCGAGGGCAAGGACGGCAAGCAGTATGAGT
CCGTGCTGATGGTCTCCATCGATCAGCTGCTGGACAGCATGAAGGAGAT
CGGCTCCAACTGCCTCAACAACGAGTTCAACTTTTTCAAGAGGCACATC
TGCGACGCCAACAAGGAGGGCATGTTTCTGTTTAGAGCCGCTAGAAAGC
TGAGGCAGTTTCTGAAGATGAACAGCACCGGCGACTTTGATCTGCATCT
GCTGAAAGTGAGCGAGGGCACCACCATTCTGCTGAACTGCACCGGCCAA
GTGAAAGGAAGAAAGCCCGCCGCTCTGGGCGAGGCTCAGCCTACCAAGT
CTCTGGAAGAGAACAAGTCTCTGAAGGAGCAGAAGAAGCTCAACGATCT
GTGCTTCCTCAAGAGGCTGCTGCAAGAGATCAAGACATGCTGGAACAAG
ATCCTCATGGGCACCAAGGAACACTG

The amino acid sequence of C7R is as set forth below (SEQ ID NO.: 15):

MLVRRGARAGPRMPRGWTALCLLSLLPSGFMSLDNNGTATPELPTQGTFS
NVSTNVSYQETTTPSTLGSTSLHPVSQHGNEATTNITETTVKFTSTSVIT
SVYGNTNSSVQSQTSVISTVFTTPANVSTPETTLKPSLSPGNVSDLSTTS
TSLATSPTKPYTSSSPILSDIKAEIKCSGIREVKLTQGICLEQNKTSSCA
EFKKDRGEGLARVLCGEEQADADAGAQVCSLLLAQSEVRPQCLLLVLANR
TEISSKLQLMKKHQSDLKKLGILDFTEQDVASHQSYSQKT*PILLTCPTIS*
*ILSFFSVALLVIL*ACVLWKKRIKPIVWPSLPDHKKTLEHLCKKPRKNLNV
SFNPESFLDCQIHRVDDIQARDEVEGFLQDTFPQQLEESEKQRLGGDVQS

-continued

PNCPSEDVVITPESFGRDSSLTCLAGNVSACDAPILSSSRSLDCRESGKN

GPHVYQDLLLSLGTTNSTLPPPFSLQSGILTLNPVAQGQPILTSLGSNQE

EAYVTMSSFYQNQ.

In the amino acid sequence of the constitutively activated IL-7 receptor (C7R), the underlined part is CD34 extracellular region, the italic part is IL-7 receptor α transmembrane region, and the bold part is IL-7 receptor α intracellular region.

The DNA sequence of C7R is as set forth below (SEQ ID NO.: 16):

GGAAGCGGCGCCACAAACTTTTCTCTGCTGAAGCAAGCCGGCGACGTCG

AAGAGAACCCCGGCCCTATGCTGGTGAGGAGAGGCGCTAGGGCTGGACC

CAGAATGCCCAGAGGCTGGACCGCTCTGTGTCTGCTGTCTCTGCTGCCC

AGCGGCTTCATGAGCCTCGATAATAACGGCACCGCTACCCCCGAGCTGC

CCACACAAGGCACCTTCTCCAATGTGAGCACCAACGTGTCCTACCAAGA

GACCACCACCCCTTCCACACTGGGAAGCACATCTCTGCATCCCGTCTCC

CAGCACGGCAATGAAGCCACCACAAACATCACCGAGACCACCGTGAAGT

TCACCAGCACCTCCGTCATTACCAGCGTGTACGGCAACACCAATAGCTC

CGTGCAAAGCCAGACATCCGTGATTTCCACCGTGTTTACCACCCCCGCC

AATGTCAGCACACCCGAGACAACACTGAAACCTTCTCTGTCCCCCGGAA

ACGTGAGCGATCTGAGCACAACCAGCACCAGCCTCGCCACCAGCCCCAC

AAAGCCTTACACAAGCAGCAGCCCCATTCTGAGCGACATCAAGGCCGAA

ATCAAGTGCTCCGGAATTAGAGAGGTCAAGCTGACCCAAGGAATCTGTC

TGGAGCAGAATAAGACCAGCAGCTGCGCCGAGTTCAAGAAAGACAGAGG

CGAAGGACTGGCCAGAGTGCTCTGCGGCGAGGAACAAGCCGATGCCGAT

GCCGGAGCTCAAGTGTGCAGCCTCCTCCTCGCTCAGAGCGAGGTCAGAC

CCCAATGTCTGCTGCTCGTGCTGGCCAATAGGACCGAGATCTCCTCCAA

ACTGCAGCTGATGAAGAAGCACCAGAGCGACCTCAAGAAGCTCGGCATC

CTCGACTTTACCGAGCAAGACGTGGCCTCCCATCAATCCTATAGCCAGA

AGACCCCCATTCTGCTGACATGTCCCACAATCAGCATCCTCAGCTTCTT

CAGCGTCGCTCTGCTCGTCATTCTGGCTTGTGTGCTGTGGAAGAAGAGG

ATCAAGCCTATTGTGTGGCCCTCTCTGCCCGACCACAAGAAGACCCTCG

AACACCTCTGCAAGAAACCTAGAAAGAACCTCAACGTGAGCTTCAACCC

CGAGTCCTTTCTGGACTGTCAAATCCATAGGGTGGATGACATCCAAGCT

AGAGACGAGGTCGAGGGCTTTCTGCAAGACACCTTCCCTCAGCAGCTGG

AAGAAAGCGAGAAGCAAAGACTGGGCGGAGATGTGCAGTCCCCTAATTG

CCCCTCCGAGGACGTGGTGATTACCCCCGAGAGCTTCGGAAGAGACAGC

TCTCTGACATGTCTGGCCGGAAATGTGTCCGCTTGCGATGCCCCTATTC

TGAGCAGCTCCAGATCTCTGGACTGCAGAGAGTCCGGCAAGAACGGCCC

TCATGTGTACCAAGATCTGCTGCTGTCTCTGGGAACCACAAACTCCACA

CTGCCTCCCCCCTTTAGCCTCCAGTCCGGCATTCTGACACTGAACCCCG

-continued

TGGCTCAAGGCCAACCTATCCTCACATCCCTCGGCTCCAATCAAGAGGA

AGCCTACGTGACCATGAGCTCCTTCTATCAGAACCAGTGA

The amino acid sequence of mbIL7 is as set forth below (SEQ ID NO.: 17):

MALPVTALLLPLALLLHAARP*DCDIEGKDGKQYESVLMVSIDQLLDSMK*

*EIGSNCLNNEFNFFKRHICDANKEGMFLFRAARKLRQFLKMNSTGDFDL*

*HLLKVSEGTTILLNCTGQVKGRKPAALGEAQPTKSLEENKSLKEQKKLN*

*DLCFLKRLLQEIKTCWNKILMGTKEH*GGGSGGGGSGGGGSGGGGSGGGS

ESGYAQNGDLEDAELDDYSFSCYSQLEVNGSQHSLTCAFEDPDVNITNL

EFEICGALVEVKCLNFRKLQEIYFIETKKFLLIGKSNICVKVGEKSLTC

KKIDLTTIVKPEAPFDLSVVYREGANDFVVTFNTSHLQKKYVKVLMHDV

AYRQEKDENKWTHVNLSSTKLTLLQRKLQPAAMYEIKVRSIPDHYFKGF

WSEWSPSYYFRTPEINNSSGEMDPILLTISILSFFSVALLVILACVLWK

KRIKPIVWPSLPDHKKTLEHLCKKPRKNLNVSFNPESFLDCQIHRVDDI

QARDEVEGFLQDTFPQQLEESEKQRLGGDVQSPNCPSEDVVITPESFGR

DSSLTCLAGNVSACDAPILSSSRSLDCRESGKNGPHVYQDLLLSLGTTN

STLPPPFSLQSGILTLNPVAQGQPILTSLGSNQEEAYVTMSSFYQNQ

In the amino acid sequence of mbIL7, the underlined part is the signal peptide region, the italic part is IL-7, the bold part is the linking region and the dashed underlined part is IL-7 receptor α.

The DNA sequence of mbIL7 is as set forth below (SEQ ID NO.: 18):

ATGGCTCTGCCTGTTACAGCTCTGCTGCTGCCTCTGGCTCTGCTTCTGC

ATGCCGCCAGACCTGACTGTGACATCGAGGGCAAAGACGGCAAGCAGTA

CGAGAGCGTGCTGATGGTGTCCATCGACCAGCTGCTGGACAGCATGAAG

GAAATCGGCAGCAACTGCCTGAACAACGAGTTCAACTTCTTCAAGCGGC

ACATCTGCGACGCCAACAAAGAAGGCATGTTCCTGTTCAGAGCCGCCAG

AAAGCTGCGGCAGTTCCTGAAGATGAACAGCACCGGCGACTTCGACCTG

CATCTGCTGAAAGTGTCTGAGGGCACCACCATCCTGCTGAATTGCACCG

GCCAAGTGAAGGGCAGAAAGCCTGCTGCTCTGGGAGAAGCCCAGCCTAC

CAAGAGCCTGGAAGAGAACAAGTCCCTGAAAGAGCAGAAGAAGCTGAAC

GACCTCTGCTTCCTGAAGCGGCTGCTGCAAGAGATCAAGACCTGCTGGA

ACAAGATCCTGATGGGCACCAAAGAGCACGGCGGAGGATCTGGCGGAGG

TGGAAGCGGCGGAGGCGGTAGCGGTGGCGGAGGAAGTGGTGGCGGATCT

GAATCTGGCTACGCCCAGAACGGCGACCTGGAAGATGCCGAGCTGGACG

ACTACAGCTTCAGCTGCTACAGCCAGCTGGAAGTGAACGGCAGCCAGCA

CTCTCTGACCTGCGCCTTTGAAGATCCCGACGTGAACATCACCAACCTT

GAGTTCGAGATTTGTGGCGCCCTGGTGGAAGTCAAGTGCCTGAATTTCC

-continued

```
GGAAGCTGCAAGAAATCTACTTTATCGAGACAAAGAAGTTCCTGCTGAT
CGGCAAGAGCAACATCTGTGTGAAAGTGGGCGAGAAAAGCCTGACCTGC
AAGAAGATCGACCTGACCACCATCGTGAAGCCCGAGGCTCCTTTCGATC
TGAGCGTGGTGTATAGAGAGGGCGCCAACGACTTCGTGGTCACCTTCAA
CACCAGCCACCTCCAAAAGAAATACGTGAAGGTGCTGATGCACGACGTG
GCCTACCGGCAAGAGAAGGACGAGAACAAATGGACCCACGTGAACCTGA
GCAGCACCAAGCTGACCCTGCTGCAGAGAAAACTGCAGCCTGCCGCTAT
GTACGAGATCAAAGTGCGGAGCATCCCCGACCACTACTTTAAAGGCTTT
TGGAGCGAGTGGTCCCCTAGCTACTACTTCAGAACCCCTGAGATCAACA
ACTCCAGCGGCGAGATGGACCCCATTCTGCTGACAATCAGCATCCTGAG
CTTTTTCAGCGTGGCCCTGCTGGTCATCCTGGCCTGTGTGCTGTGGAAG
AAGCGGATCAAGCCCATCGTGTGGCCCAGCCTGCCTGACCACAAGAAAA
CCCTGGAACACCTGTGCAAGAAGCCCCGGAAAAACCTGAACGTGTCCTT
CAATCCCGAGAGCTTCCTGGACTGCCAGATCCACAGAGTGGACGACATC
CAGGCCAGGGACGAAGTGGAAGGATTTCTGCAGGACACATTCCCTCAGC
AGCTCGAAGAGAGCGAGAAGCAAAGACTCGGAGGCGACGTGCAGAGCCC
TAATTGCCCTTCTGAGGACGTGGTCATCACCCCAGAGAGCTTCGGCAGA
GATAGCAGCCTGACATGTCTGGCCGGCAATGTGTCCGCCTGTGATGCCC
CTATCCTGTCCTCTAGCAGAAGCCTGGATTGCAGAGAGAGCGGCAAGAA
CGGCCCTCACGTGTACCAGGATCTGCTCCTGTCTCTGGGCACCACAAAC
AGCACACTGCCTCCACCATTCAGCCTGCAGAGCGGCATCCTGACACTGA
ACCCTGTTGCTCAGGGCCAGCCTATCCTGACAAGCCTGGGCAGCAATCA
AGAAGAGGCCTACGTCACCATGAGCAGCTTCTACCAGAACCAG
```

The above CAR genes were cloned into the FUW lentiviral vector backbone under the promoter of EF1α (EF-1α) to form Fuw-EF1α-CAR. Fuw-EF1α-CAR, lentiviral envelope plasmid pMD2.G (Addgene, Plasmid #12259) and lentiviral packaging plasmid psPAX2 (Addgene, Plasmid #12260) were transfected into 293 T cells by using Lipofectamine®3000 to prepare the whole lentiviral expression vector. The supernatant was collected at 48 and 72 h and subject to ultra-centrifuge (Merck Millipore) for concentration. The concentrated virus was ready for the transfection of T cells.

The result shows that expression of RQR8, CAR, IL15Ra or C7R was successfully detected by flow cytometry for RQR8-CD19CAR-MBIL15, RQR8-CD19CAR-MBIL15-IL7, RQR8-CD19CAR-C7R cells; secretion of IL-7 was detected by ELISA. The lentiviral vectors were successfully constructed. All of the structures could be expressed simultaneously without interference with each other.

4.2 Design and Construction of CRISPR

First, gRNA sequences targeting the exon of the TCR conserved region were designed at http://crispr.mit.edu, and two gRNA sequences with scores above 80 were selected for higher knockout efficiency. For the gRNA primer, the forward primer comprises a T7 promotor followed by 20 bp of the target sequence, and the reverse primer has 20 bp of the complementary sequence. Plasmids were used as PCR template. After purification, T7-PCR product was further used as the template for MEGAshortscript® T7 kit to obtain RNA. The RNA was purified with a MEGAclear® column and eluted with RNA-free water. Cas9 plasmid was purchased from Addgene.

The gRNA targeting sequences are as below:

```
TRAC-gRNA:
                                        SEQ ID NO.: 5
TGTGCTAGACATGAGGTCTA,
```

Meanwhile, the knockout efficiency of the gRNA was analyzed by T7E1, TIDE and flow cytometry.

The result shows that the TCR gene was successfully knocked out with a knockout efficiency of higher than 90%.

4.3 Preparation of CAR-T Cells

Cell Isolation and Activation

After apheresis, monocytes were isolated using Histopaque®-1077 (Sigma-Aldrich) by density gradient centrifugation. Then T cells were enriched, activated by magnetic beads coupled with anti-CD3/anti-CD28, cultured and expanded.

X-vivo™ 15 with 5% FBS, 2 mM L-glutamine, 1 mM sodium pyruvate and 300 IU/ml rhIL2 was used as CAR-T cell medium. The cells were incubated and cultured at 37° C., 5% $CO_2$.

Cell line expressing CD 19: Raji (Burkitt's lymphoma cell line, ATCC®-CCL-86™); K562 cells (Human erythroleukemia cell line, ATCC®-CCL-243™); Raji-ffluc cell line was obtained by screening Raji cells transfected with lentivirus having firefly luciferase;

All of the cells were cultured in RPMI1640 medium and 293T cells (ATCC®-CRL-3216™) were cultured in DMEM medium. Both RPM11640 and DMEM were supplemented with 10% (v/v) fetal bovine serum and 100 U/ml penicillin and streptomycin, 2 mM glutamine and 1 mM sodium pyruvate.

4 Electroporation

Two days after enriching and activating the T cells, the anti-CD3/anti-CD28 magnetic beads were removed and the cells were collected into a tube. Cas9 and gRNA as needed were mixed, incubated at room temperature and then transferred to electroporation buffer to further mix with the cells for electroporation by 4D-Nucleofector® System N (Lonza) system. Then the cells were re-suspended in a pre-warmed medium to a density of $1\text{-}2\times10^6$/ml, transferred to a plate and cultured in an incubator at 37° C., 5% $CO_2$.

Lentiviral Transfection 1 day after electroporation, the cells were transfected by lentiviral vector at MOI of 2-8, transferred to a flask and cultured at 37° C., 5% $CO_2$.

Cell Proliferation and Detection of CAR Positive Ratio 3 days after the transfection, the number of cells and CAR positive cells were detected, and the positive ratio of CAR in T cells was calculated. The positive ratio of CD3 was also detected to determine the knockout efficiency. Then cells were continuously cultured in the incubator and half of the medium was replaced every 2-3 days till day 14 when the cells were ready for cryopreservation.

The result shows that that expression of RQR8, CAR, IL15Ra or C7R was successfully detected by flow cytometry for RQR8-CD19CAR-mbIL15, RQR8-CD19CAR-mbIL15-IL7, RQR8-CD19CAR-C7R CAR-T; secretion of IL-7 was detected by ELISA. The CD3 negative ratio was higher than 90%, indicating that the TCR knockout CAR-T with enhanced cytokine-related signaling pathway and the safety switch was successfully constructed, and each of the elements does not interfere with each other.

4.4 Release of the Cytokines

The CAR-T cells prepared in Example 3 and CD19 positive tumor cells (Raji, NALM6), 100 ul each, were mixed in RPMI medium at 1:1 ratio to a density of $1\times10^6$/ml for each cell, and then cultured overnight in a 96-well plate. The medium was collected and subject to centrifuge and the released cytokine IFN-γ and IL-2 were detected by Cytokine bead array kit (CBA kit, BD Biosciences).

The result shows that incubation of RQR8-CD19CAR-MBIL15, RQR8-CD19CAR-MBIL15-IL7, RQR8-CD19CAR-C7R CAR-T cells with Raji, NALM6 produced a large amount of IFN-γ and IL-2, indicating function of the cytokine-related signaling pathway enhanced CART against CD19 positive target cells, and the secretion of cytokines by the cytokine-related signaling pathway enhanced CART was increased compared to conventional CAR-T.

4.5 Expression of CD107a after Co-Culture of CAR-T Cells with the Target Cells $2*10^5$ CAR-T/NT cells and $2*10^5$ target cells (Raji, NALM6)/control cells (K562) were added to a v-bottom 96 well plate, and re-suspended in 200 μl X-VIVO™ complete medium without IL-2. 1 μl BD GolgiStop™ (containing monesin) was added to each 1 ml medium and 2 μl CD107a antibody (1:50) was added to each well. The cells were then cultured at 37° C. for 4 hours and further subject to collection.

The sample was centrifuged to remove the medium, washed once with PBS, and then centrifuged at 400 g, 4° C. for 5 minutes. The supernatant was removed and specific surface antibodies CAR, CD3, CD4, and CD8 were added to each tube. Then the cells were re-suspended in 100 μl and put on ice for 30 minutes in dark.

Each tube was washed once with 3 mL PBS, and then the sample was centrifuged at 400 g for 5 minutes. The supernatant was carefully removed and the pellet was re-suspended in PBS. CAR, CD3, CD4, CD8, and CD107a were detected by flow cytometry.

The result shows that incubation of RQR8-CD19CAR-MBIL15, RQR8-CD19CAR-MBIL15-IL7, RQR8-CD19CAR-C7R CAR-T cells with Raji, NALM6 produced a large amount of CD107a, indicating function of the cytokine-related signaling pathway enhanced CART against CD19 positive target cells in vitro.

4.6 In Vitro Killing Activity

A stably transfected cell line was obtained by introducing the luciferase gene into the target cell followed by screening. The CAR-T cells prepared in Example 3 were mixed with CD19-positive tumor cells (Raji-luc, NALM6-luc) at different effector:target ratios. After adding fluorescein, luciferase could react with the fluorescein to produce fluorescence. By detecting the intensity of the fluorescence, the activity of luciferase can be measured, and the survival of the cells can be detected so that to evaluate the killing effect of CART cells.

The result shows that RQR8-CD19CAR-MBIL15, RQR8-CD19CAR-MBIL15-IL7, RQR8-CD19CAR-C7R CAR-T cells significantly killed Raji and NALM6, and the cytokine-related signaling pathway enhanced CART showed a more significant killing effect, which is correlated with the effector:target ratio.

4.7 Proliferation of CAR-T Cells

IL-2 was removed from CAR-T. CAR-T cells were continuously cultured for 2 weeks and counted twice a week to measure the proliferation.

The result shows that RQR8-CD19CAR-MBIL15, RQR8-CD19CAR-MBIL15-IL7, RQR8-CD19CAR-C7R CAR-T cells had stronger proliferation rate than CD19 CAR-T. Without IL-2, they still had high survival ratio after 2 weeks. CFSE showed certain proliferation and CD19 CAR-T could not survive after 2 weeks.

4.8 Re-Activation of Cells In Vitro

IL-2 was removed from CAR-T. K562-CD19 was added twice a week at 2:1 effector:target ratio. The cells were cultured for 2 weeks and counted twice a week to measure cell proliferation The result shows that after adding K562-CD19, RQR8-CD19CAR-MBIL15, RQR8-CD19CAR-MBIL15-IL7, RQR8-CD19CAR-C7R CAR-T cells showed significantly stronger proliferation rate than CD19 CAR-T. After the stimulation, the cell survival ratio was higher than CD19 CAR-T, indicating the cytokine-related signaling pathway enhanced CART has a higher proliferation rate, and can survive better.

4.9 In Vivo Efficacy 6-12 weeks NOD-Prkdcscid Il2rgnull (NOG) mice were selected and intraperitoneally injected with 2×10' Raji-ffluc cells, 50 μL DPBS and 50 μL matrigel Matrix® (Corning). Two days later, the tumor graft burden of the mice was measured, and the mice were divided into 4 groups based on the tumor burden. One day later, 200 μL DPBS, $5\times10^6$NT cells, $5\times10^6$ CD19 CAR-T cells, RQR8-CD19CAR-MBIL15, RQR8-CD19CAR-MBIL15-IL7, RQR8-CD19CAR-C7R CAR-T cells were respectively injected to each mouse. The tumor burden of the mice was further evaluated 7 days after the CAR-T treatment. Each mouse was injected intraperitoneally with 3 mg d-luciferin for a 4-minutes reaction, and then photographed by using a Xenogen IVIS® Imaging System with 30 s exposure.

The result shows that after two weeks, RQR8-CD19CAR-MBIL15, RQR8-CD19CAR-MBIL15-IL7 and RQR8-CD19CAR-C7R CAR-T cells significantly decreased the tumor burden compared to NT and CD19 CAR-T cells, and T cells could still be detected in peripheral blood. Mice in the cytokine-related signaling pathway enhanced CART groups overall had longer survival.

4.10 In Vivo GVHD Study

The mice were systemically treated with a sub-lethal dose of irradiation (175 cGy) first. Then CAR-T cells were re-suspended in PBS and injected into the thorax of the treated mice. The mice were observed 2-3 times a week by using GVHD clinical criteria including weight loss, arch-back, activity, fur texture, and skin integrity.

The result shows that mice in the group without TCR knockout all showed symptoms of GVHD reaction, and no GVHD reaction was detected in TCR single knockout CAR-T cell groups.

4.11 Clearance of 11 RQR8 Gene-Mediated CAR-T Cells

NK cells were isolated from PBMCs as effector cells, and 1:1 co-cultured with CAR-T, with or without rituximab (Rutiximab) at a final concentration of 10 μg/mL. 4 h and 24 h later, the expression CAR was detected by flow cytometry.

ADCC percentage=(1−monoclonal antibody group CAR positive ratio/no antibody group CAR positive ratio)*100%

The results show that, 4 h and 24 h later, NK cells significantly cleared RQR8-CD19CAR-MBIL15, RQR8-CD19CAR-MBIL15-IL7 and RQR8-CD19CAR-C7R CAR-T cells in the presence of Rutiximab, but failed to clear CD19 CAR-T. Without Rutiximab, NK failed to kill any of the cells. This indicates that Rutiximab can function as a safety switch, which binds to RQR8, and allows NK to mediate the ADCC function so that to clear CART cells.

Example 5 Study of U-CAR T Cells Expressing E3

Figure 30:
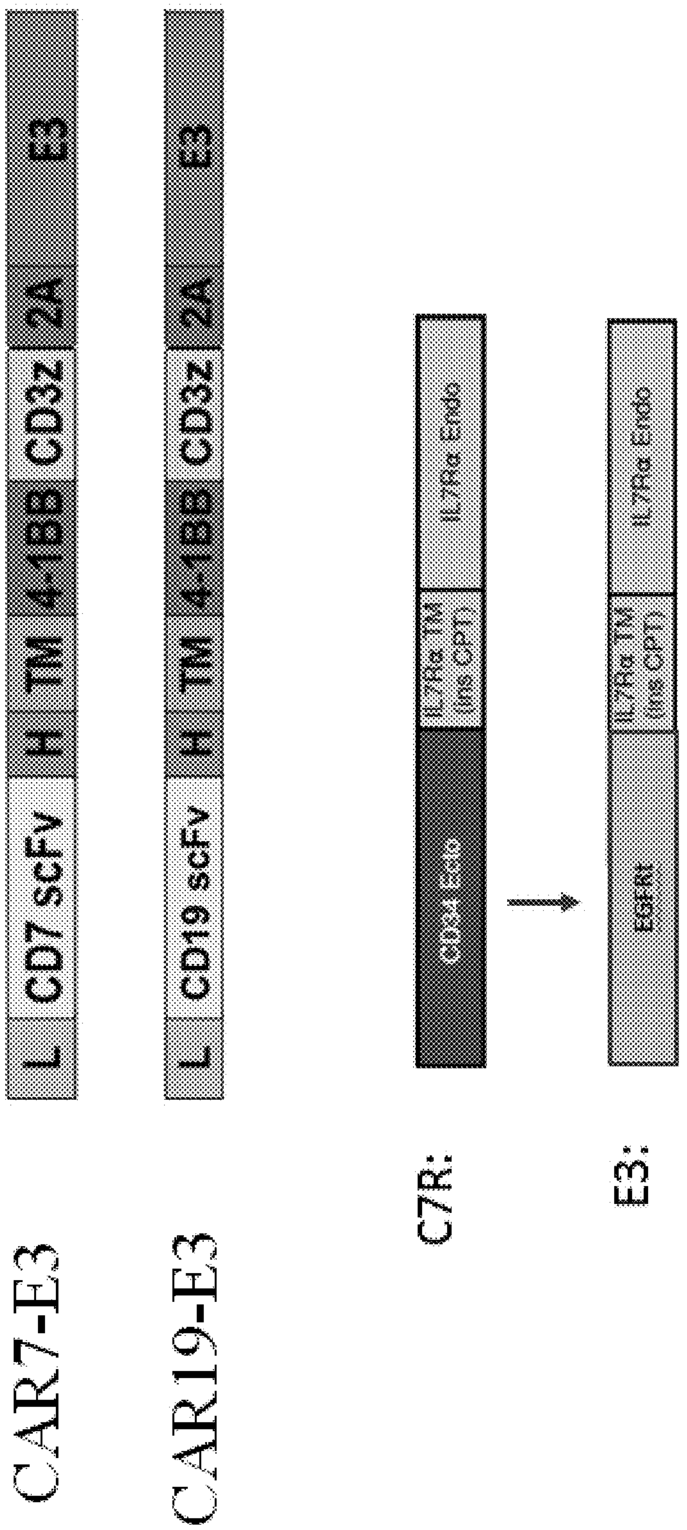
FIG. 30 illustrates a design of E3: constitutive active IL7Rα based enhancer+safety switch.

FIG. 30 shows an example design of CAR-T cells expressing of enhancer E3. In E3, the ecto domain of C7R is replaced by a safety switch, such as EGFRt or Her2t or other peptides described in the present disclosure.

Figure 31:
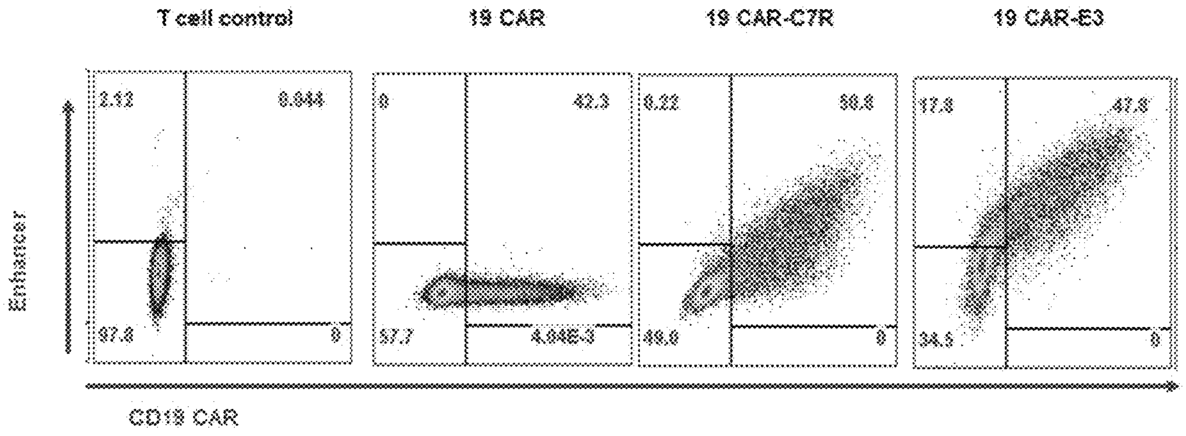
FIG. 31 illustrates expression of CAR and the enhancer.

FIG. 31 shows flow cytometry data of fractions of CAR-T cells expressing CD19 CAR and the enhancer C7R or E3.

Figures 32A, 32B:
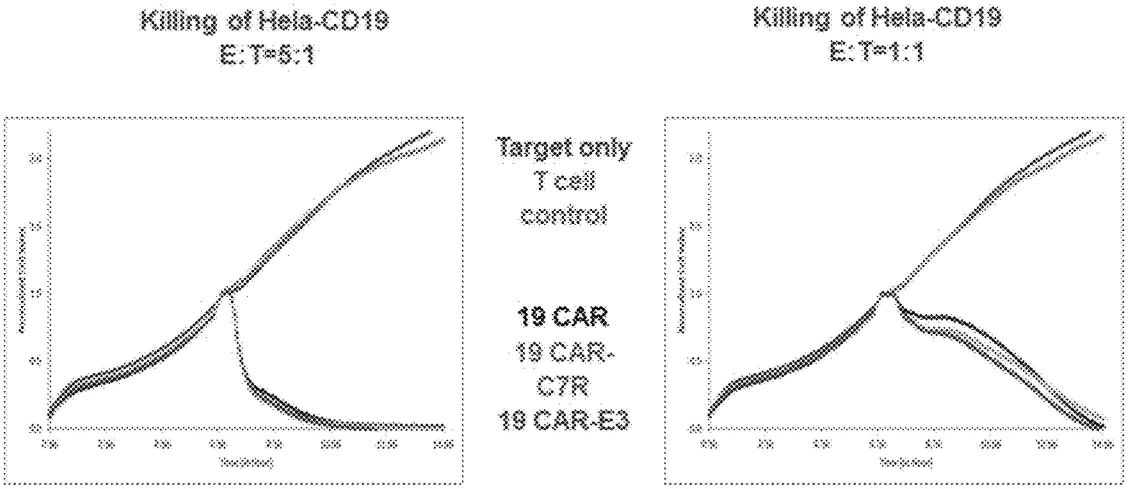
FIGS. 32A and 32B illustrate test of CAR-T function.

FIGS. 32A and 32B show in vitro killing activity of CAR-T cells toward HeLa cells expressing a CD19 antigen. FIG. 32A shows in vitro killing activity of CD19 CAR-T cells expressing C7R or E3 in comparison with target only or T cell controls. The effector:target ratio in this experiment is 5:1. FIG. 32B shows in vitro killing activity of CD19 CAR-T cells expressing C7R or E3 in comparison with target only or T cell controls. The effector:target ratio in this experiment is 1:1.

Figure 33A:
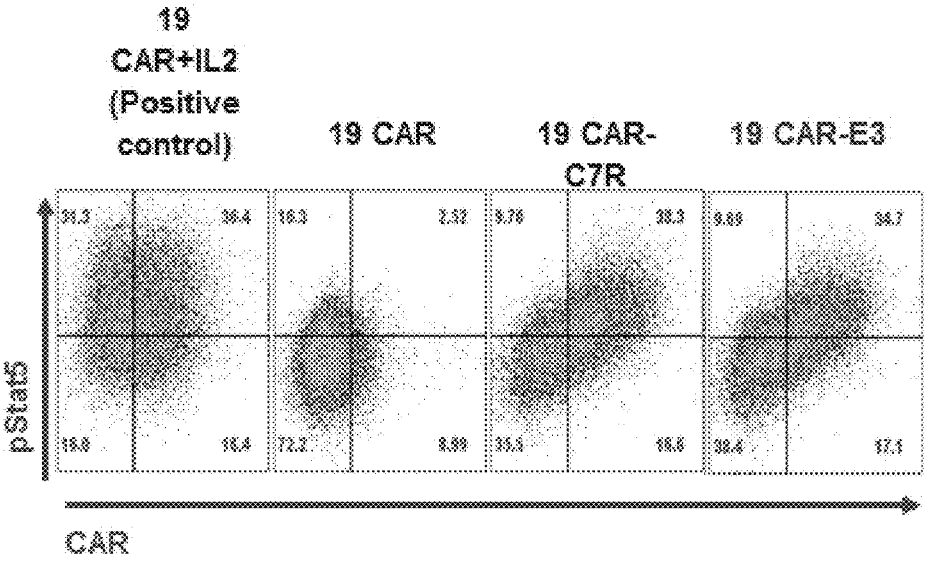
FIGS. 33A and 33B illustrate test of enhancer function.
Figure 33B:
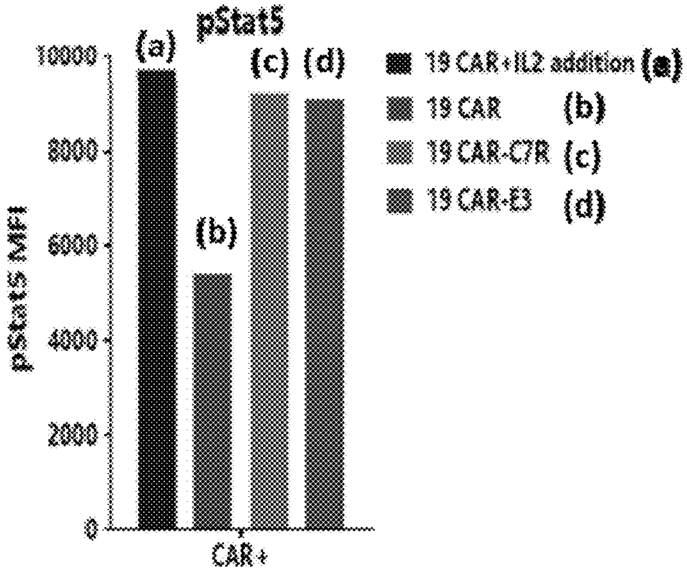

FIGS. 33A and 33B show expression of phosphorylated STAT5 (pSTAT5) and CD19 CAR in the tested engineered cells. FIG. 33A shows flow cytometry data of fractions of CAR-T cells expressing CD19 CAR and pSTAT5. FIG. 33B shows corresponding mean fluorescent index (MFI) of pSTAT5 of the data in FIG. 33A.

Figure 34A:
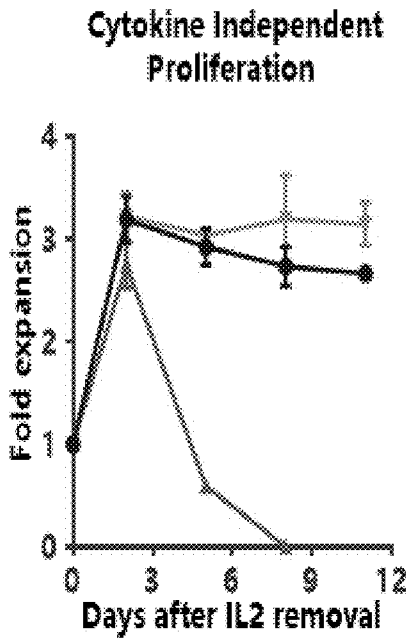
FIGS. 34A-C illustrate test of enhancer function.
Figure 34B:
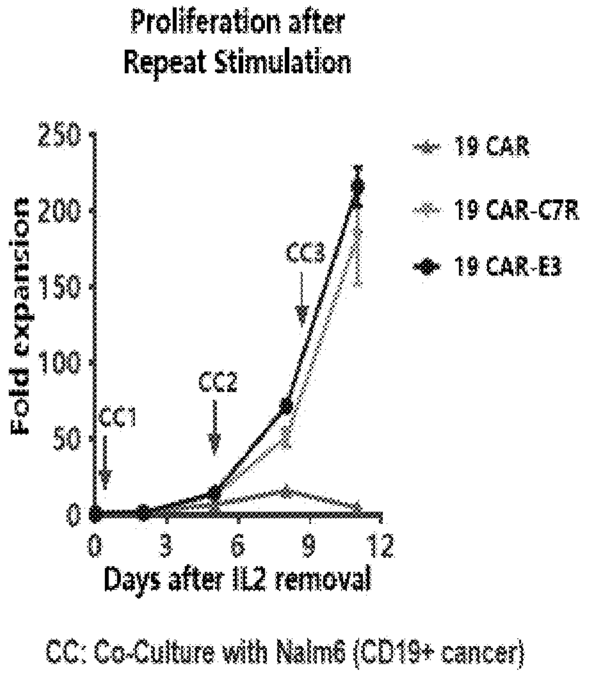
Figure 34C:
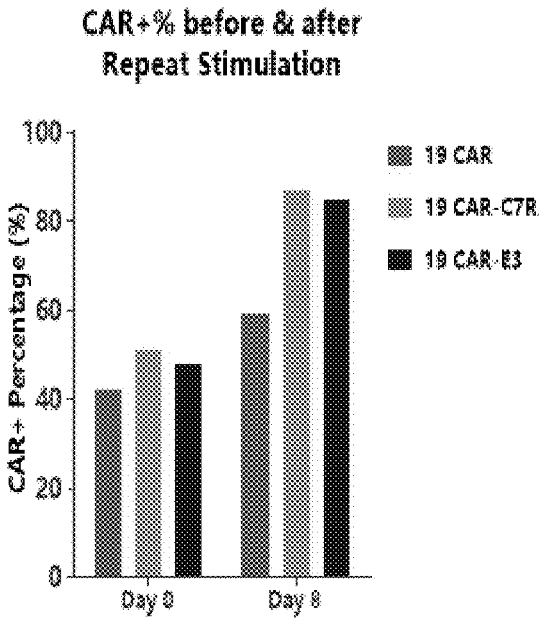

FIGS. 34A-C show proliferation data of CD19 CAR-T cells expressing C7R or E3 in comparison to CD19 CAR-T without enhancer. FIG. 34A shows cytokine independent proliferation of the three different cells. FIG. 34B shows proliferation under repeated NALM6 stimulations. FIG. 34C shows percentage of CAR-T cells before and after the stimulation by NALM6. CAR stimulation enriched CAR+ cells.

Figure 35A:
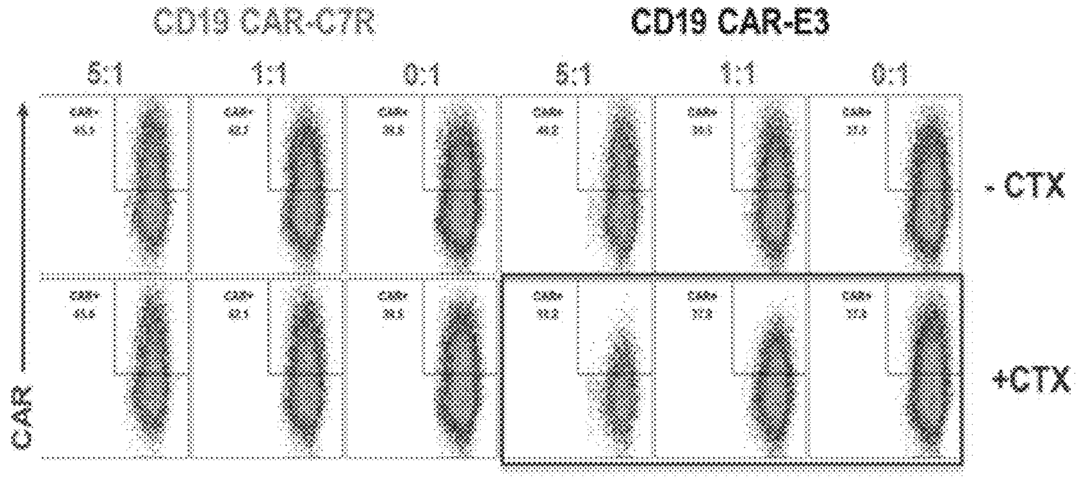
FIGS. 35A-C illustrate test of safety switch by ADCC.
Figure 35B:
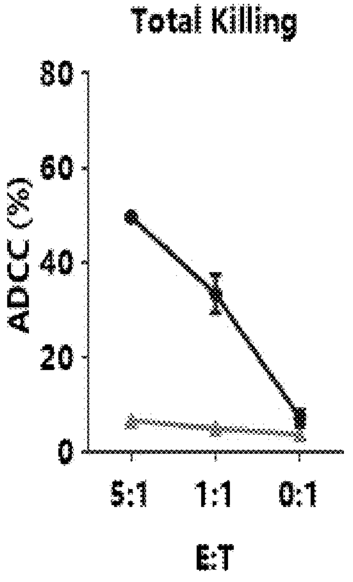
Figure 35C:
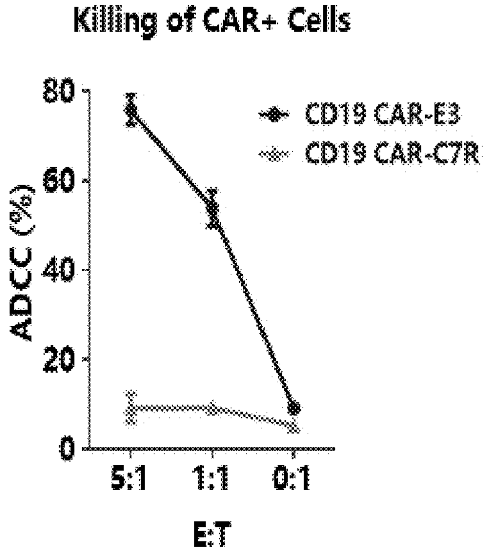

FIG. 35A shows flow cytometry data of fractions of CAR-T cells co-cultured with NK cells at different effector: target ratios in the presence or absence of Cetuximab (CTX, anti-EGFR Antibody). The data showed that in the presence of CTX, the CD19 CAR-T expressing E3 can be effectively killed by NK cells via NK Cell-Mediated Antibody-Dependent Cellular Cytotoxicity (ADCC), indicating that E3 functions as an effective safety switch and has been effectively turned off. FIG. 35B shows the total killing activity of NK cells toward other cells. FIG. 35C shows the killing activity of NK cells toward CAR-T cells.

Figure 36A:
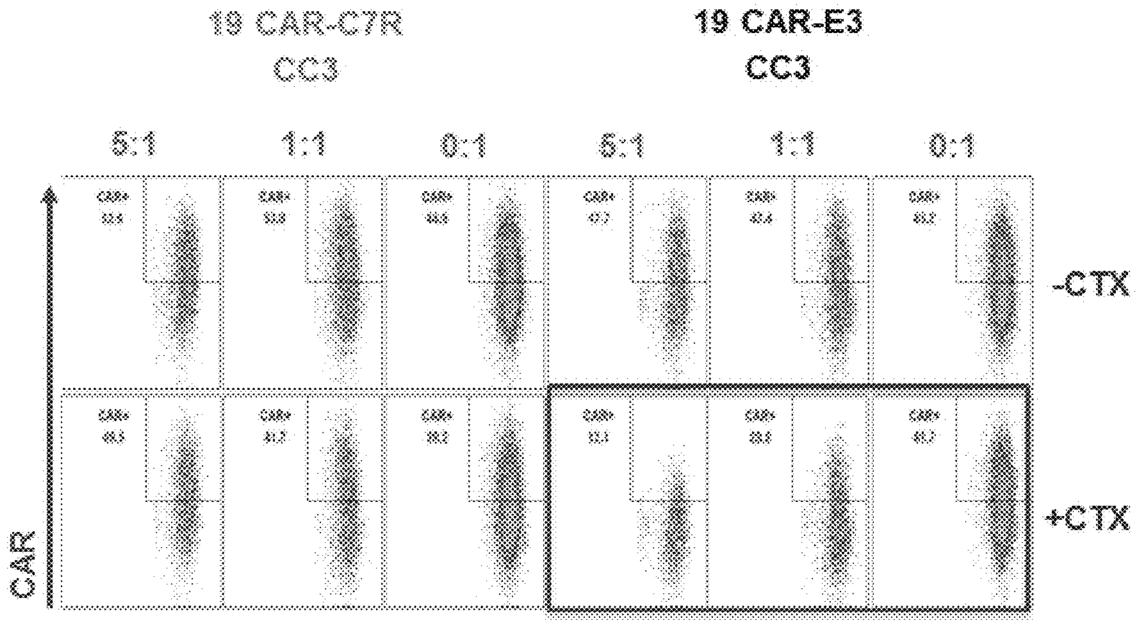
FIGS. 36A and 36B illustrate test of safety switch by ADCC after repeat stimulations.
Figure 36B:
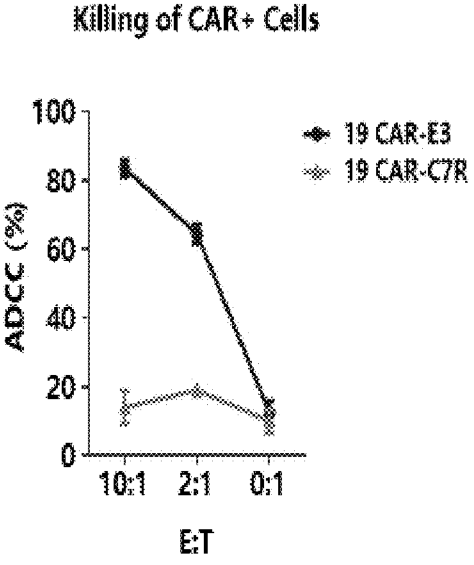

FIGS. 36A and 36B show test of safety switch by ADCC after repeated stimulation. FIG. 36A shows flow cytometry data of fractions of CAR-T cells co-cultured with NK cells at different effector:target ratios in the presence or absence of CTX. The cells shown in this example were repeated stimulated. FIG. 36B shows killing activity of NK cells toward CAR-T cells.

Figure 56A:
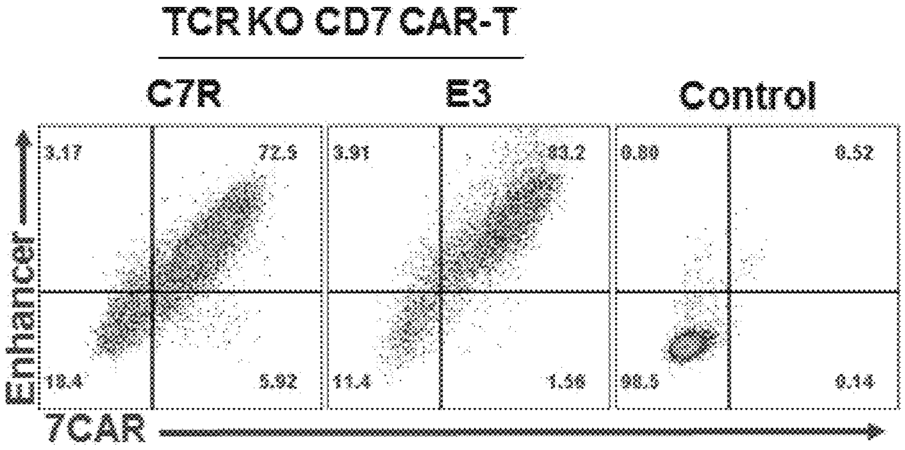
FIGS. 56A-E illustrate experimental data showing STAT5 phosphorylation, cell persistence and cytotoxicity of TCR KO CD7 CAR-T cells expressing enhancer C7R or E3 (EGFRt+IL7R$\alpha$).
Figure 56B:
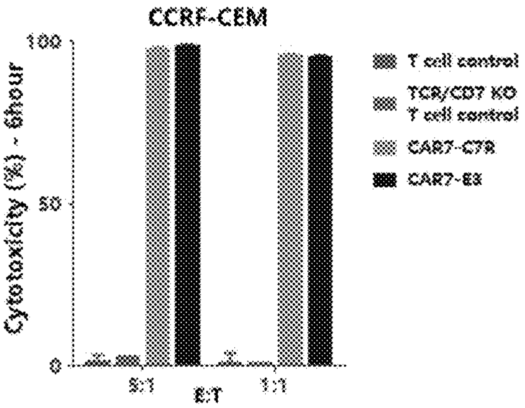
Figure 56C:
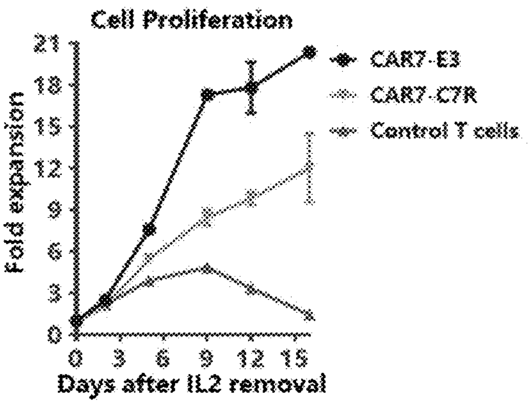

FIG. 56A shows flow cytometry data of fractions of TCR KO CD7 CAR-T cells expressing CD7 CAR and enhancer C7R or E3 (EGFRt+IL7Rα) at day 12 of cell culture. FIG. 56B shows 6-hour cytotoxicity of TCR KO CD7 CAR-T cells expressing CD7 CAR and enhancer C7R or E3 (EGFRt+IL7Rα) toward CCRF-CEM cells. The effector:target ratios tested in this experiment are 5:1 and 1:1. FIG. 56C shows proliferation of TCR KO CD7 CART cells expressing C7R or E3 (EGFRt+IL7Rα). The CAR-T cells were cultured in T cell culture media without supplement of IL2 and monitored for fold of cell expansion. The results show that TCR KO CD7 CART cells expressing C7R or E3 displayed better cell expansion and cell stability than control T cells. E3 (EGFRt+IL7Rα) has better enhancer expression and thus maintained better cell persistence and expansion than C7R.

Figure 56D:
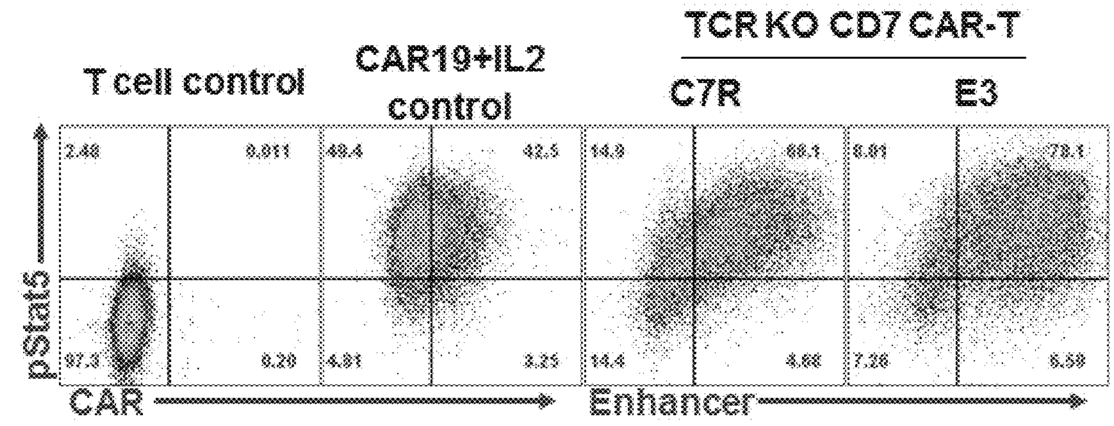
Figure 56E:
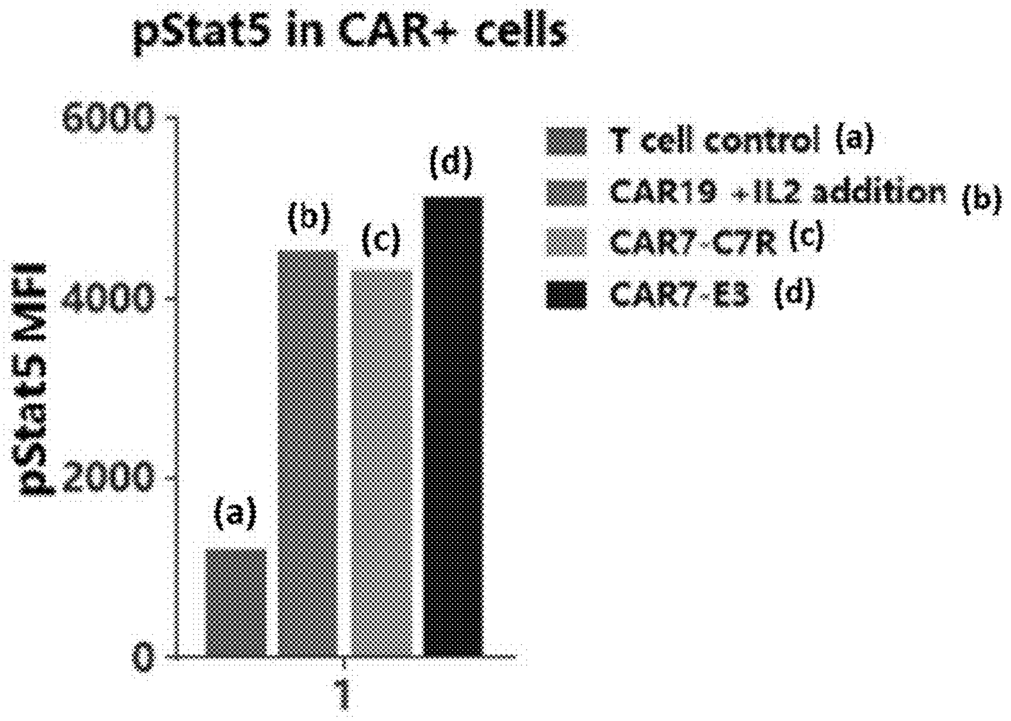

FIG. 56D shows flow cytometry data of fractions of TCR KO CD7 CAR-T cells expressing phosphorylated STAT5 (pSTAT5) and C7R or E3. pSTAT5 was highly upregulated in TCR KO CD7 CAR-T cells expressing C7R or E3. CAR19 plus IL2 stimulation were used as positive control for pSTAT5. FIG. 56E shows corresponding mean fluorescent index (MFI) of pSTAT5 of the data in FIG. 56D.

Sequence of construct design: The etcodomain of C7R can replaced by a safety switch, such as truncated EGFR or truncated Her2.

CD7CAR-E3 amino acid sequence (E3=EGFRt+constitutively active IL7Rα TM and endo domain)

```
                                         (SEQ ID NO: 100)
MALPVTALLLPLALLLHAARPDIELTQSPAIMSASLGEEITLTCSASSSV
SYMHWYQQKSGTSPKLLIYSTSNLASGVPSRFSGSGSGTFYSLTISSVEA
EDAADYYCHQWSSYTFGGGTKLEIKRGGGGSGGGGSGGGGSQVKLQESGG
GLVKPGGSLKLSCAASGFTFSSYAMSWVRQTPEKRLEWVATISSGGSYTY
YPDSVKGRFTISRDNAKNTLYLQMSSLRSEDTAMYYCARQDGYYPGWFAN
WGQGTTVTVSSSGTTTPAPRPPTPAPTIASQPLSLRPEACRPAAGGAVHT
RGLDFACDIYIWAPLAGTCGVLLLSLVITLYCKRGRKKLLYIFKQPFMRP
VQTTQEEDGCSCRFPEEEEGGCELRVKFSRSADAPAYKQGQNQLYNELNL
GRREEYDVLDKRRGRDPEMGGKPRRKNPQEGLYNELQKDKMAEAYSEIGM
KGERRRGKGHDGLYQGLSTATKDTYDALHMQALPPRGSGATNFSLLKQAG
DVEENPGPMLLLVTSLLLCELPHPAFLLIPRKVCNGIGIGEFKDSLSINA
TNIKHFKNCTSISGDLHILPVAFRGDSFTHTPPLDPQELDILKTVKEITG
FLLIQAWPENRTDLHAFENLEIIRGRTKQHGQFSLAVVSLNITSLGLRSL
KEISDGDVIISGNKNLCYANTINWKKLFGTSGQKTKIISNRGENSCKATG
QVCHALCSPEGCWGPEPRDCVSCRNVSRGRECVDKCNLLEGEPREFVENS
ECIQCHPECLPQAMNITCTGRGPDNCIQCAHYIDGPHCVKTCPAGVMGEN
NTLVWKYADAGHVCHLCHPNCTYGCTGPGLEGCPTNGPKIPSPILLTCPT
ISILSFFSVALLVILACVLWKKRIKPIVWPSLPDHKKTLEHLCKKPRKNL
NVSFNPESFLDCQIHRVDDIQARDEVEGFLQDTFPQQLEESEKQRLGGDV
QSPNCPSEDVVITPESFGRDSSLTCLAGNVSACDAPILSSSRSLDCRESG
KNGPHVYQDLLLSLGTTNSTLPPPFSLQSGILTLNPVAQGQPILTSLGSN
QEEAYVTMSSFYQNQ
```

CD7CAR-E3 (E3=Her2t+constitutively active IL7Rα TM and endo domain)

```
                                         (SEQ ID NO: 101)
MALPVTALLLPLALLLHAARPDIELTQSPAIMSASLGEEITLTCSASSSV
SYMHWYQQKSGTSPKLLIYSTSNLASGVPSRFSGSGSGTFYSLTISSVEA
EDAADYYCHQWSSYTFGGGTKLEIKRGGGGSGGGGSGGGGSQVKLQESGG
GLVKPGGSLKLSCAASGFTFSSYAMSWVRQTPEKRLEWVATISSGGSYTY
YPDSVKGRFTISRDNAKNTLYLQMSSLRSEDTAMYYCARQDGYYPGWFAN
WGQGTTVTVSSSGTTTPAPRPPTPAPTIASQPLSLRPEACRPAAGGAVHT
RGLDFACDIYIWAPLAGTCGVLLLSLVITLYCKRGRKKLLYIFKQPFMRP
```

-continued

```
VQTTQEEDGCSCRFPEEEEGGCELRVKFSRSADAPAYKQGQNQLYNELNL

GRREEYDVLDKRRGRDPEMGGKPRRKNPQEGLYNELQKDKMAEAYSEIGM

KGERRRGKGHDGLYQGLSTATKDTYDALHMQALPPRGSGATNFSLLKQAG

DVEENPGPMLLLVTSLLLCELPHPAFLLIPCHPECQPQNGSVTCFGPEAD

QCVACAHYKDPPFCVARCPSGVKPDLSYMPIWKFPDEEGACQPCPINCTH

SCVDLDDKGCPAEQRASPLTGGGSGGGSPILLTCPTISILSFFSVALLVI

LACVLWKKRIKPIVWPSLPDHKKTLEHLCKKPRKNLNVSFNPESFLDCQI

HRVDDIQARDEVEGFLQDTFPQQLEESEKQRLGGDVQSPNCPSEDVVITP

ESFGRDSSLTCLAGNVSACDAPILSSSRSLDCRESGKNGPHVYQDLLLSL

GTTNSTLPPPFSLQSGILTLNPVAQGQPILTSLGSNQEEAYVTMSSFYQN

Q
```

Figure 68:
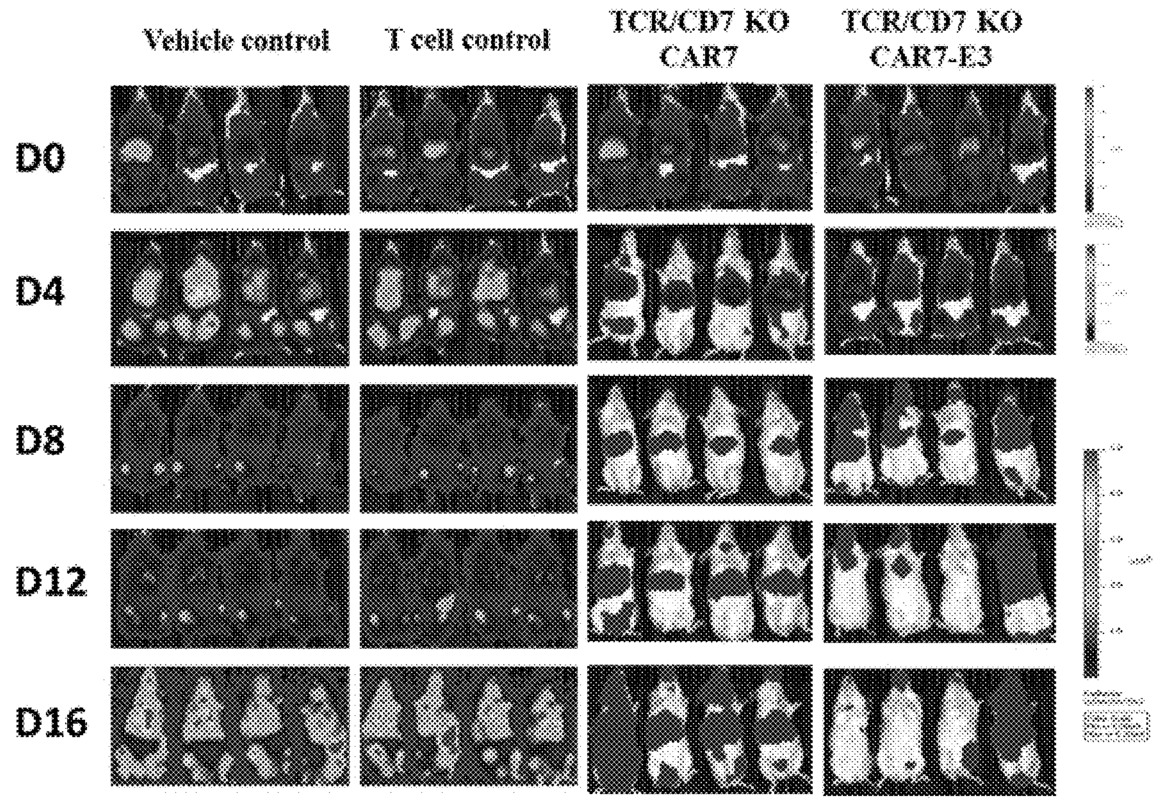
FIG. 68 illustrates BLI imaging of the in vivo efficacy of CAR7 and CAR7-E3 UCAR-T cells.

FIG. 68 shows BLI imaging of the in vivo efficacy of CAR7 and CAR7-E3 UCAR-T in CCRF-CEM (T-ALL) murine xenograft model. Each mouse was inoculated intravenously with $3\times10^5$ CCRF-CEM cells. Four days later, CAR-T cells were intravenously infused ($1\times10^6$ cells per mouse). BLI imaging indicates CAR7-E3 UCAR-T cells had better effect on tumor clearance than CAR7 UCAR-T cells.

Example 6 Study of U-CAR T Cells Expressing Dual CAR

General Materials and Methods

Isolation of Peripheral Blood Mononuclear Cells (PBMCs) from Donor Blood and Expansion of T Cells Peripheral blood mononuclear cells (PBMCs) were isolated from donor blood by using Histopaque®-1077 (Sigma-Aldrich) through density gradient centrifuge. Then T cells were enriched, activated by magnetic beads coupled with anti-CD3/anti-CD28, cultured and expanded.

Cell Lines and Culture of PBMCs

- Raji cells (Burkitt's lymphoma cells, ATCC®-CCL-86™);
- K562 cells (Human erythroleukemia cell line, ATCC®-CCL-243™);
- Raji-ffluc cell line (obtained by screening Raji cells transfected with lentivirus having firefly luciferase);
- 293T cells (ATCC®-CRL-3216™);
- CCRF-CEM cells (ATCC®-CCL-119™);
- PBNK: peripheral blood NK sorted from PBMC by using CD56 microbeads and cultured in NK serum free medium kit II (Cyagen Biosciences)+10% FBS+900 IU/ml IL2 (PeproTech);
- NK92 cells (ATCC®-CRL-2407™);
- NK92-ffluc cells (obtained by screening NK92 cells transfected with lentivirus having firefly luciferase);
- Raji cells, Raji-ffluc cell line, and K562 cells were cultured in RPM11640 medium, and 293T cells were cultured in DMEM medium. Both RPM11640 and DMEM were supplemented with 10% (v/v) fetal bovine serum and 100 U/ml penicillin and streptomycin, 2 mM glutamine and 1 mM sodium pyruvate. All of the cells were cultured in an incubator at 37° C., 5% $CO_2$.

NK92 cells were cultured in RPMI1640 medium supplemented with 10% (v/v) fetal bovine serum, 2 mM glutamine, 1 mM sodium pyruvate, 1% NEAA, 0.1 mM mercaptoethanol and 200 IU/ml rhIL2.

T cells and the obtained CAR-T cells were cultured in X-vivo™15 medium (containing 5% FBS, 2 mM L-glutamine, 1 mM sodium pyruvate and 300 IU/ml rhIL2). The culture medium for CAR-T cells was further supplemented with rhIL-2 (ThermoFisher Scientific) at a final concentration of 300 IU/ml every two days. All of the cells were cultured in an incubator at 37° C., 5% $CO_2$.

6.1 Design and Construction of CRISPR

CD7, CD2, TCR gRNAs for gene editing were selected after evaluating gene editing efficiency and off-target risk at website http://crispr.mit.edu, www.idtdna.com and https://www.synthego.com.

gRNAs used in the present disclosure were either synthesized by Integrated DNA Technologies, Inc (IDT) or prepared by in vitro transcription (See Shi et al., 2017, J Vis Exp. doi: 10.3791/55267). HiFi-Cas9 was purchased from IDT.

For gene editing, 3 μg Cas9 protein and 1.5 μg gRNA were mixed in 20 μl and incubated at 37° C. or room temperature for 15 minutes to form ribonucleoprotein (RNP). Then RNP was transfected into T cells by Lonza 4D Nucleofector®. Gene knockout efficiency was determined by the ratio of the cells expressing the protein as detected by flow cytometry.

gRNA targeting sequences used are as below:

```
TRAC-gRNA1:                              SEQ ID NO: 20
TTCGGAACCCAATCACTGAC,

TRAC-gRNA2:                              SEQ ID NO: 21
TCAGGGTTCTGGATATCTGT,

TRAC-gRNA3:                              SEQ ID NO: 22
AAGTTCCTGTGATGTCAAGC,

CD7-gRNA1:                               SEQ ID NO: 25
GAGGTCAATGTCTACGGCTC,

CD7-gRNA2:                               SEQ ID NO: 26
ATCACGGAGGTCAATGTCTA,

CD7-gRNA3:                               SEQ ID NO: 27
GTAGACATTGACCTCCGTGA,

CD7-gRNA4:                               SEQ ID NO: 28
GGAGCAGGTGATGTTGACGG,

CD2-gRNA1:                               SEQ ID NO: 29
CAAAGAGATTACGAATGCCT,

CD2-gRNA2:                               SEQ ID NO: 30
GTGCCACAAAGACCATCAAG,

CD2-gRNA3:                               SEQ ID NO: 31
AGAGGGTCATCACACACAAG,

CD2-gRNA4:                               SEQ ID NO: 32
CTTGTAGATATCCTGATCAT,
```

After screening, gRNA with high knockout efficiency was found for each gene and high efficiency was also observed when knocking out two genes, TCR/CD7 or TCR/CD2, wherein TRAC-gRNA2 and CD7-gRNA1 are gRNAs with high knockout efficiencies. FIG. 16 shows efficiencies of CD7 knockout by using different CD7-gRNAs with TRAC-gRNA1, and CD7-gRNA1 and CD7-gRNA4 were obviously better, and CD7-gRNA1 was used in subsequent experiments.

6.2 Design of CD7 CAR and Package of the Virus

The scFv of the CD7 single CAR is derived from TH69, 3Ale and SDZCHH380 antibodies. The scFv in the CAR is designed as 3Ale-LH, TH69-LH, SDZ-LH, SDZ-HL. The amino acid sequence of the CAR is as set forth in SEQ ID NO: 75-78.

```
3A1e-LH
                                         (SEQ ID NO 75)
MALPVTALLLPLALLLHAARPDIELTQSPAIMSASLGEEITLTCSASSSV

MHSYWYQQKSGTSPKLLIYSTSNLASGVPSRFSGSGSGTFYSLTISSVEA

EDAADYYCHQWSSYTFGGGTKLEIKRGGGGSGGGGSGGGGSQVKLQESGG

GLVKPGGSLKLSCAASGFTFSSYAMSWVRQTPEKRLEWVATISSGGSYTY

YPDSVKGRFTISRDNAKNTLYLQMSSLRSEDTAMYYCARQDGYYPGWFAN

WGQGTTVTVSSSGTTTPAPRPPTPAPTIASQPLSLRPEACRPAAGGAVHT

RGLDFACDIYIWAPLAGTCGVLLLSLVITLYCKRGRKKLLYIFKQPFMRP

VQTTQEEDGCSCRFPEEEEGGCELRVKFSRSADAPAYKQGQNQLYNELNL

GRREEYDVLDKRRGRDPEMGGKPRRKNPQEGLYNELQKDKMAEAYSEIGM

KGERRRGKGHDGLYQGLSTATKDTYDALHMQALPPR*

TH69-LH
                                         (SEQ ID NO 76)
MALPVTALLLPLALLLHAARPAAYKDIQMTQTTSSLSASLGDRVTISCSA

SQGISNYLNWYQQKPDGTVKLLIYYTSSLHSGVPSRFSGSGSGTDYSLTI

SNLEPEDIATYYCQQYSKLPYTFGGGTKLEIKRGGGGSGGGGSGGGGSEV

QLVESGGGLVKPGGSLKLSCAASGLTFSSYAMSWVRQTPEKRLEWVASIS

SGGFTYYPDSVKGRFTISRDNARNILYLQMSSLRSEDTAMYYCARDEVRG

YLDVWGAGTTVTVSSSGTTTPAPRPPTPAPTIASQPLSLRPEACRPAAGG

AVHTRGLDFACDIYIWAPLAGTCGVLLLSLVITLYCKRGRKKLLYIFKQP

FMRPVQTTQEEDGCSCRFPEEEEGGCELRVKFSRSADAPAYKQGQNQLYN

ELNLGRREEYDVLDKRRGRDPEMGGKPRRKNPQEGLYNELQKDKMAEAYS

EIGMKGERRRGKGHDGLYQGLSTATKDTYDALHMQALPPR*

SDZ-LH
                                         (SEQ ID NO 77)
MALPVTALLLPLALLLHAARPDIQMTQSPASLSASVGETVTITCRASGNI

HNYLAWYQQKQGKSPQLLVYNAKTLADGVPSRFSGSGSGTQYSLKINSLQ

PEDFGSYYCQHFWTTPPWTFGGGTKLEIKGGGGSGGGGSGGGGSQIQLVQ

KSGPELKPGETVKISCKASGYTFTNYGMNWVKQAPGKGLKWMGWINTYNG

EPTYADDFKGRFDFSLETSASTAYLQINNLKNEDTATYFCARRGYYYGSR

YGAMDYWGQGTSVTVSSSGTTTPAPRPPTPAPTIASQPLSLRPEACRPAA

GGAVHTRGLDFACDIYIWAPLAGTCGVLLLSLVITLYCKRGRKKLLYIFK

QPFMRPVQTTQEEDGCSCRFPEEEEGGCELRVKFSRSADAPAYKQGQNQL

YNELNLGRREEYDVLDKRRGRDPEMGGKPRRKNPQEGLYNELQKDKMAEA

YSEIGMKGERRRGKGHDGLYQGLSTATKDTYDALHMQALPPR*
```

-continued

```
SDZ-HL
                                         (SEQ ID NO 78)
MALPVTALLLPLALLLHAARPQIQLVQSGPELKKPGETVKISCKASGYTF

TNYGMNWVKQAPGKGLKWMGWINTYNGEPTYADDFKGRFDFSLETSASTA

YLQINNLKNEDTATYFCARRGYYYGSRYGAMDYWGQGTSVTVSSGGGGSG

GGGSGGGGSDIQMTQSPASLSASVGETVTITCRASGNIHNYLAWYQQKQG

KSPQLLVYNAKTLADGVPSRFSGSGSGTQYSLKINSLQPEDFGSYYCQHF

WTTPPWTFGGGTKLEIKSGTTTPAPRPPTPAPTIASQPLSLRPEACRPAA

GGAVHTRGLDFACDIYIWAPLAGTCGVLLLSLVITLYCKRGRKKLLYIFK

QPFMRPVQTTQEEDGCSCRFPEEEEGGCELRVKFSRSADAPAYKQGQNQL

KYNELNLGRREEYDVLDRRGRDPEMGGKPRRKNPQEGLYNELQKDKMAEA

YSEIGMKGERRRGKGHDGLYQGLSTATKDTYDALHMQALPPR*
```

The CAR gene was cloned into the FUW lentiviral vector backbone under the promoter of EF1α (EF-1α) to form Fuw-EF1α-CAR. Fuw-EF1α-CAR, lentiviral envelope plasmid pMD2.G (Addgene, Plasmid #12259) and lentiviral packaging plasmid psPAX2 (Addgene, Plasmid #12260) were transfected into 293 T cells by using Lipofectamine®3000 or PEI to prepare the whole expression vector. The supernatant was collected at 48 and 72 h and subject to ultra-centrifuge (Merck Millipore) for concentration. The concentrated virus was ready for the transfection of T cells.

6.3 Preparation of CAR-T Cells

Cell Isolation and Activation

After apheresis, monocytes were isolated using Histopaque®-1077 (Sigma-Aldrich) by density gradient centrifugation. Then T cells were enriched, activated by magnetic beads coupled with anti-CD3/anti-CD28, cultured and expanded.

X-vivo™ 15 with 5% FBS, 2 mM L-glutamine, 1 mM sodium pyruvate and 300 IU/ml rhIL2 was used as CAR-T cell medium. The cells were incubated and cultured at 37° C., 5% $CO_2$.

Cell line expressing CD 19: Raji (Burkitt's lymphoma cell line, ATCC®-CCL-86™); K562 (ATCC®-CCL-243™); Raji-ffluc and NK92 cell lines was obtained by screening cells transfected with lentivirus having firefly luciferase;

Cell line expressing CD7 and CD2: Jurkat cell, CCRF-CEM and NK92 cells.

All of the cells were cultured in RPMI1640 medium and 293T cells (ATCC®-CRL-3216™) were cultured in DMEM medium. Both RPMI1640 and DMEM were supplemented with 10% (v/v) fetal bovine serum and 100 U/ml penicillin and streptomycin, 2 mM glutamine and 1 mM sodium pyruvate.

Electroporation and Lentivirus Infection

Two days after enriching and activating the T cells, the anti-CD3/anti-CD28 magnetic beads were removed and the cells were collected into a tube and subject to centrifuge at 300 g for 5 min, and then washed twice with DPBS and re-suspended in opti-mem at a cell density of $50\times10^6$/ml. The amount of cas9/gRNA RNP required was calculated based on the density of the cells, and then mixed with cells and transferred for electroporation by 4D-Nucleofector® System N (Lonza) system. Then the cells were re-suspended in a pre-warmed medium to a density of $1\text{-}2\times10^6$/ml. The cells were further subject to lentiviral transfection at MOI of 2-8, transferred to a flask and cultured in an incubator at 37° C., 5% $CO_2$.

Cell Proliferation and Detection of CAR Positive Ratio 3 days after the transfection, the number of cells and CAR positive cells were detected, and the positive ratio of CAR in T cells was calculated. The positive ratio of TCR (or CD3), and CD7 was also detected to determine the knockout efficiency. Then the cells were continuously cultured in the incubator and half of the medium was replaced every 2-3 days till day 10 when the cells were ready for cryopreservation.

6.4 Screening of CD7 CAR Structure

Figure 38A:
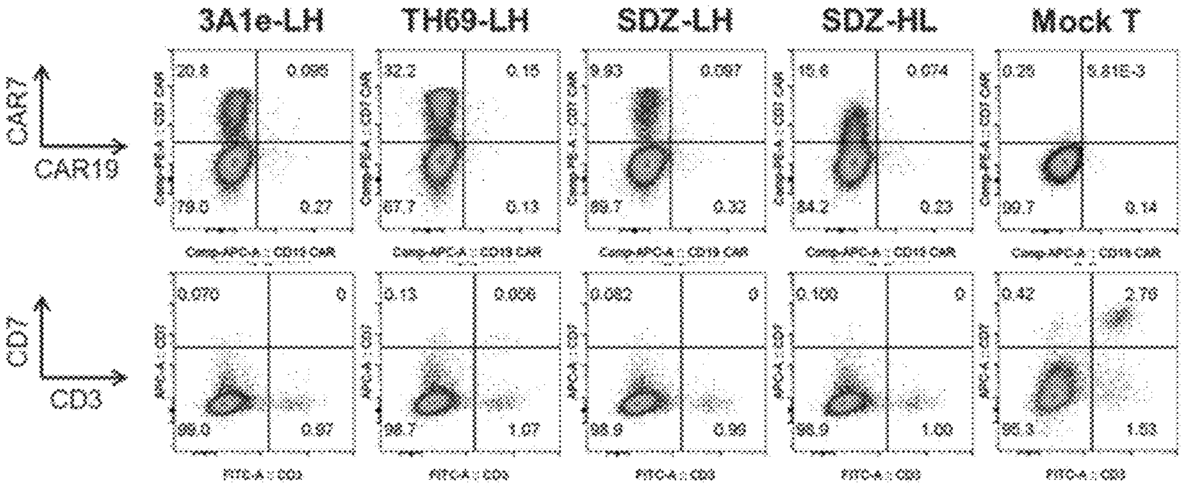
FIGS. 38A and 38B illustrate an experimental data of the expression of CD7 single CARs constructed with scFvs of different antibodies and the knockout efficiencies of CD7/CD3 (TRAC) (FIG. 38A), as well as the killing effects of CARs on CD7+ cells (FIG. 38B). LH represents VLVH, and HL represents VHVL.
Figure 38B:

As shown in FIG. 38A, the expression of anti-CD7 CAR was successfully detected, among which TH69-LH shows the strongest expression, followed by 3Ale-LH, then SDZ-LH, and SDZ-HL. In terms of function, as shown in FIG. 38B, 3Ale-LH, CARs all showed the best killing effects on CD7-positive T cells, while TH69-LH, SDZ-LH and SDZ-HL CARs were less effective. Therefore, the scFv of 3Ale was selected for CD7 CAR in the dual CAR.

6.5 Design of CD19-CD7 Dual CAR Structure

Figure 37:
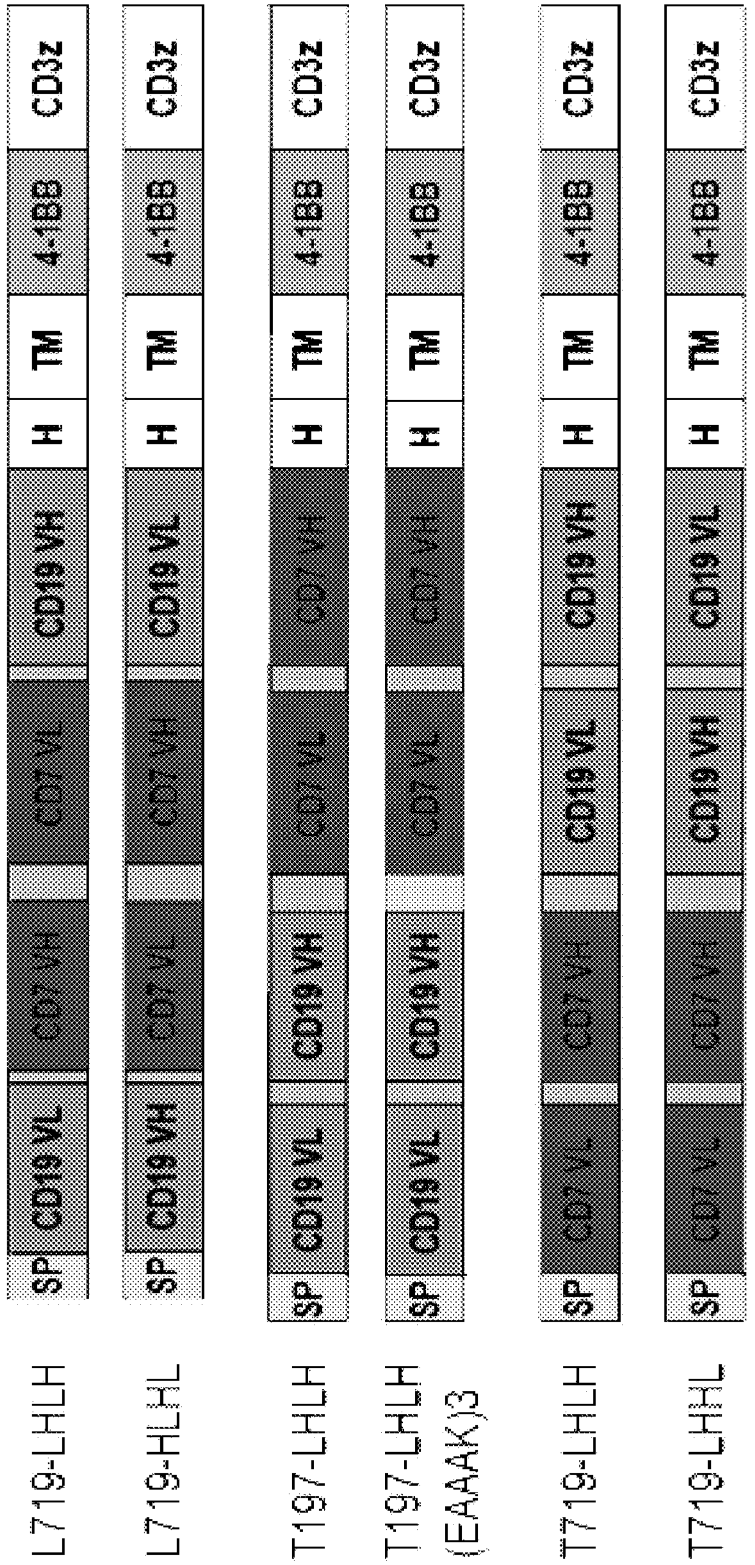
FIG. 37 illustrates examples of the design of CD7-CD19 dual CARs. L719 represents Loop-CAR, LHLH═VLVH—VLVH, HLHL═VHVL—VHVL; T197 and T719 are Tandem-CARs, EAAAK is the linker (SEQ ID NO: 92) between two LH. SP: signaling peptide; H: hinge; TM: transmembrane domain.

The structure of CD19-CD7 dual CAR targeting CD19 and CD7 is as illustrated in FIG. 37 and below:

Loop: L719-LHLH and L719-HLHL, sequence as set forth in SEQ ID NO 79 and 80;

L719-LHLH
(SEQ ID NO. 79)

MALPVTALLLPLALLLHAARPDIQMTQTTSSLSASLGDRVTISCRASQDI
SKYLNWYQQKPDGTVKLLIYHTSRLHSGVPSRFSGSGSGTDYSLTISNLE
QEDIATYFCQQGNTLPYTFGGGTKLEITGGGGSQVKLQESGGGLVKPGGS
LKLSCAASGFTFSSYAMSWVRQTPEKRLEWVATISSGGSYTYYPDSVKGR
FTISRDNAKNTLYLQMSSLRSEDTAMYYCARQDGYYPGWFANWGQGTTVT
VSSGSTSGSGKPGSGEGSTKGDIELTQSPAIMSASLGEEITLTCSASSSV
SYMHWYQQKSGTSPKLLIYSTSNLASGVPSRFSGSGSGTFYSLTISSVEA
EDAADYYCHQWSSYTFGGGTKLEIKRGGGGSEVKLQESGPGLVAPSQSLS
VTCTVSGVSLPDYGVSWIRQPPRKGLEWLGVIWGSETTYYNSALKSRLTI
IKDNSKSQVFLKMNSLQTDDTAIYYCAKHYYYGGSYAMDYWGQGTSVTVS
SSGTTTPAPRPPTPAPTIASQPLSLRPEACRPAAGGAVHTRGLDFACDIY
IWAPLAGTCGVLLLSLVITLYCKRGRKKLLYIFKQPFMRPVQTTQEEDGC
SCRFPEEEEGGCELRVKFSRSADAPAYKQGQNQLYNELNLGRREEYDVLD
KRRGRDPEMGGKPRRKNPQEGLYNELQKDKMAEAYSEIGMKGERRRGKGH
DGLYQGLSTATKDTYDALHMQALPPR*

L719-HLHL
(SEQ ID NO. 80)

MALPVTALLLPLALLLHAARPEVKLQESGPGLVAPSQSLSVTCTVSGVSL
PDYGVSWIRQPPRKGLEWLGVIWGSETTYYNSALKSRLTIIKDNSKSQVF
LKMNSLQTDDTAIYYCAKHYYYGGSYAMDYWGQGTSVTVSSGGGGSDIEL
TQSPAIMSASLGEEITLTCSASSSVSYMHWYQQKSGTSPKLLIYSTSNLA
SGVPSRFSGSGSGTFYSLTISSVEAEDAADYYCHQWSSYTFGGGTKLEIK
RGSTSGSGKPGSGEGSTKGQVKLQESGGGLVKPGGSLKLSCAASGFTFSS
YAMSWVRQTPEKRLEWVATISSGGSYTYYPDSVKGRFTISRDNAKNTLYL
QMSSLRSEDTAMYYCARQDGYYPGWFANWGQGTTVTVSSGGGGSDIQMTQ
TTSSLSASLGDRVTISCRASQDISKYLNWYQQKPDGTVKLLIYHTSRLHS

-continued

GVPSRFSGSGSGTDYSLTISNLEQEDIATYFCQQGNTLPYTFGGGTKLEI
TSGTTTPAPRPPTPAPTIASQPLSLRPEACRPAAGGAVHTRGLDFACDIY
IWAPLAGTCGVLLLSLVITLYCKRGRKKLLYIFKQPFMRPVQTTQEEDGC
SCRFPEEEEGGCELRVKFSRSADAPAYKQGQNQLYNELNLGRREEYDVLD
KRRGRDPEMGGKPRRKNPQEGLYNELQKDKMAEAYSEIGMKGERRRGKGH
DGLYQGLSTATKDTYDALHMQALPPR*

Tandem: T197-LHLH, T197-LHLH-EAAAK3 (by using a linker with three connected EAAAK (SEQ ID NO: 102)), T719-LHLH, T719-LHHL, sequence as set forth in SEQ ID NO 81-84;

T197-LHLH
(SEQ ID NO. 81)

MALPVTALLLPLALLLHAARPDIQMTQTTSSLSASLGDRVTISCRASQDI
SKYLNWYQQKPDGTVKLLIYHTSRLHSGVPSRFSGSGSGTDYSLTISNLE
QEDIATYFCQQGNTLPYTFGGGTKLEITGGGGSGGGGSGGGGSEVKLQES
GPGLVAPSQSLSVTCTVSGVSLPDYGVSWIRQPPRKGLEWLGVIWGSETT
YYNSALKSRLTIIKDNSKSQVFLKMNSLQTDDTAIYYCAKHYYYGGSYAM
DYWGQGTSVTVSSGSTSGSGKPGSGEGSTKGDIELTQSPAIMSASLGEEI
TLTCSASSSVSYMHWYQQKSGTSPKLLIYSTSNLASGVPSRFSGSGSGTF
YSLTISSVEAEDAADYYCHQWSSYTFGGGTKLEIKRGGGGSGGGGSGGGG
SQVKLQESGGGLVKPGGSLKLSCAASGFTFSSYAMSWVRQTPEKRLEWVA
TISSGGSYTYYPDSVKGRFTISRDNAKNTLYLQMSSLRSEDTAMYYCARQ
DGYYPGWFANWGQGTTVTVSSSGTTTPAPRPPTPAPTIASQPLSLRPEAC
RPAAGGAVHTRGLDFACDIYIWAPLAGTCGVLLLSLVITLYCKRGRKKLL
YIFKQPFMRPVQTTQEEDGCSCRFPEEEEGGCELRVKFSRSADAPAYKQG
QNQLYNELNLGRREEYDVLDKRRGRDPEMGGKPRRKNPQEGLYNELQKDK
MAEAYSEIGMKGERRRGKGHDGLYQGLSTATKDTYDALHMQALPPR*

T197-LHLH-(EAAAK)3
(SEQ ID NO. 82)

MALPVTALLLPLALLLHAARPDIQMTQTTSSLSASLGDRVTISCRASQDI
SKYLNWYQQKPDGTVKLLIYHTSRLHSGVPSRFSGSGSGTDYSLTISNLE
QEDIATYFCQQGNTLPYTFGGGTKLEITGGGGSGGGGSGGGGSEVKLQES
GPGLVAPSQSLSVTCTVSGVSLPDYGVSWIRQPPRKGLEWLGVIWGSETT
YYNSALKSRLTIIKDNSKSQVFLKMNSLQTDDTAIYYCAKHYYYGGSYAM
DYWGQGTSVTVSSEAAAKEAAAKEAAAKDIELTQSPAIMSASLGEEITLT
CSASSSVSYMHWYQQKSGTSPKLLIYSTSNLASGVPSRFSGSGSGTFYSL
TISSVEAEDAADYYCHQWSSYTFGGGTKLEIKRGGGGSGGGGSGGGGSQV
KLQESGGGLVKPGGSLKLSCAASGFTFSSYAMSWVRQTPEKRLEWVATIS
SGGSYTYYPDSVKGRFTISRDNAKNTLYLQMSSLRSEDTAMYYCARQDGY
YPGWFANWGQGTTVTVSSSGTTTPAPRPPTPAPTIASQPLSLRPEACRPA
AGGAVHTRGLDFACDIYIWAPLAGTCGVLLLSLVITLYCKRGRKKLLYIF
KQPFMRPVQTTQEEDGCSCRFPEEEEGGCELRVKFSRSADAPAYKQGQNQ

-continued

LYNELNLGRREEYDVLDKRRGRDPEMGGKPRRKNPQEGLYNELQKDKMAE

AYSEIGMKGERRRGKGHDGLYQGLSTATKDTYDALHMQALPPR*

T719-LHLH (SEQ ID NO. 83)

MALPVTALLLPLALLLHAARPDIELTQSPAIMSASLGEEITLTCSASSSV

SYMHWYQQKSGTSPKLLIYSTSNLASGVPSRFSGSGSGTFYSLTISSVEA

EDAADYYCHQWSSYTFGGGTKLEIKRGGGGSGGGGSGGGGSQVKLQESGG

GLVKPGGSLKLSCAASGFTFSSYAMSWVRQTPEKRLEWVATISSGGSYTY

YPDSVKGRFTISRDNAKNTLYLQMSSLRSEDTAMYYCARQDGYYPGWFAN

WGQGTTVTVSSGSTSGSGKPGSGEGSTKGDIQMTQTTSSLSASLGDRVTI

SCRASQDISKYLNWYQQKPDGTVKLLIYHTSRLHSGVPSRFSGSGSGTDY

SLTISNLEQEDIATYFCQQGNTLPYTFGGGTKLEITGGGGSGGGGSGGGG

SEVKLQESGPGLVAPSQSLSVTCTVSGVSLPDYGVSWIRQPPRKGLEWLG

TVIWGSETTYYNSALKSRLIIKDNSKSQVFLKMNSLQTDDTAIYYCAKHY

YYGGSYAMDYWGQGTSVTVSSSGTTTPAPRPPTPAPTIASQPLSLRPEAC

RPAAGGAVHTRGLDFACDIYIWAPLAGTCGVLLLSLVITLYCKRGRKKLL

YIFKQPFMRPVQTTQEEDGCSCRFPEEEEGGCELRVKFSRSADAPAYKQG

QNQLYNELNLGRREEYDVLDKRRGRDPEMGGKPRRKNPQEGLYNELQKDK

MAEAYSEIGMKGERRRGKGHDGLYQGLSTATKDTYDALHMQALPPR*

T719-LHHL (SEQ ID NO. 84)

MALPVTALLLPLALLLHAARPDIELTQSPAIMSASLGEEITLTCSASSSV

SYMHWYQQKSGTSPKLLIYSTSNLASGVPSRFSGSGSGTFYSLTISSVEA

EDAADYYCHQWSSYTFGGGTKLEIKRGGGGSGGGGSGGGGSQVKLQESGG

GLVKPGGSLKLSCAASGFTFSSYAMSWVRQTPEKRLEWVATISSGGSYTY

YPDSVKGRFTISRDNAKNTLYLQMSSLRSEDTAMYYCARQDGYYPGWFAN

WGQGTTVTVSSGSTSGSGKPGSGEGSTKGEVKLQESGPGLVAPSQSLSVT

CTVSGVSLPDYGVSWIRQPPRKGLEWLGVIWGSETTYYNSALKSRLTIIK

DNSKSQVFLKMNSLQTDDTAIYYCAKHYYYGGSYAMDYWGQGTSVTVSSG

GGGSGGGGSGGGGSDIQMTQTTSSLSASLGDRVTISCRASQDISKYLNWY

HQQKPDGTVKLLIYHTSRLSGVPSRFSGSGSGTDYSLTISNLEQEDIATY

TFCQQGNTLPYTFGGGTKLEISGTTTPAPRPPTPAPTIASQPLSLRPEAC

RPAAGGAVHTRGLDFACDIYIWAPLAGTCGVLLLSLVITLYCKRGRKKLL

YIFKQPFMRPVQTTQEEDGCSCRFPEEEEGGCELRVKFSRSADAPAYKQG

QNQLYNELNLGRREEYDVLDKRRGRDPEMGGKPRRKNPQEGLYNELQKDK

MAEAYSEIGMKGERRRGKGHDGLYQGLSTATKDTYDALHMQALPPR*

Loop dual CAR connected with a constitutively activated IL7 receptor C7R: L719-C7R, amino acid sequence as set forth in SEQ ID NO 85.

L719-C7R (SEQ ID NO 85)

MALPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

-continued

QEDIATYFCQQGNTLPYTFGGGTKLEITGGGGSQVKLQESGGGLVKPGGS

LKLSCAASGFTFSSYAMSWVRQTPEKRLEWVATISSGGSYTYYPDSVKGR

FTISRDNAKNTLYLQMSSLRSEDTAMYYCARQDGYYPGWFANWGQGTTVT

VSSGSTSGSGKPGSGEGSTKGDIELTQSPAIMSASLGEEITLTCSASSSV

SYMHWYQQKSGTSPKLLIYSTSNLASGVPSRFSGSGSGTFYSLTISSVEA

EDAADYYCHQWSSYTFGGGTKLEIKRGGGGSEVKLQESGPGLVAPSQSLS

VTCTVSGVSLPDYGVSWIRQPPRKGLEWLGVIWGSETTYYNSALKSRLTI

IKDNSKSQVFLKMNSLQTDDTAIYYCAKHYYYGGSYAMDYWGQGTSVTVS

SSGTTTPAPRPPTPAPTIASQPLSLRPEACRPAAGGAVHTRGLDFACDIY

IWAPLAGTCGVLLLSLVITLYCKRGRKKLLYIFKQPFMRPVQTTQEEDGC

SCRFPEEEEGGCELRVKFSRSADAPAYKQGQNQLYNELNLGRREEYDVLD

KRRGRDPEMGGKPRRKNPQEGLYNELQKDKMAEAYSEIGMKGERRRGKGH

DGLYQGLSTATKDTYDALHMQALPPRGSGATNFSLLKQAGDVEENPGPML

VRRGARAGPRMPRGWTALCLLSLLPSGFMSLDNNGTATPELPTQGTFSNV

STNVSYQETTTPSTLGSTSLHPVSQHGNEATTNITETTVKFTSTSVITSV

YGNTNSSVQSQTSVISTVFTTPANVSTPETTLKPSLSPGNVSDLSTTSTS

LATSPTKPYTSSSPILSDIKAEIKCSGIREVKLTQGICLEQNKTSSCAEF

KKDRGEGLARVLCGEEQADADAGAQVCSLLLAQSEVRPQCLLLVLANRTE

ISSKLQLMKKHQSDLKKLGILDFTEQDVASHQSYSQKTPILLTCPTISIL

SFFSVALLVILACVLWKKRIKPIVWPSLPDHKKTLEHLCKKPRKNLNVSF

NPESFLDCQIHRVDDIQARDEVEGFLQDTFPQQLEESEKQRLGGDVQSPN

CPSEDVVITPESFGRDSSLTCLAGNVSACDAPILSSSRSLDCRESGKNGP

HVYQDLLLSLGTTNSTLPPPFSLQSGILTLNPVAQGQPILTSLGSNQEEA

YVTMSSFYQNQ*

6.6 Test for the Dual CAR Structure-1

1) Expression of the Dual CARs and the Knockout Efficiency

Figure 39:
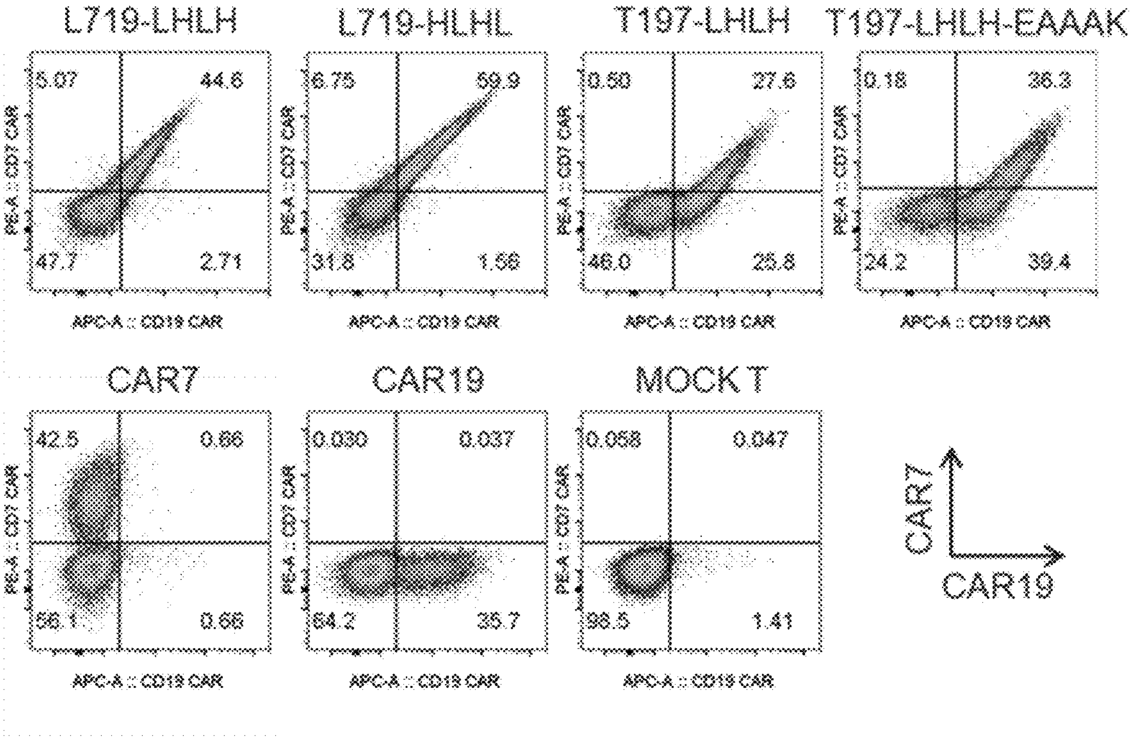
FIG. 39 illustrates experimental data of the expressions of Loop-CARs and Tandem-CARs. CAR7 and CAR19 are single CAR controls, and Mock T is negative control.
Figure 40:
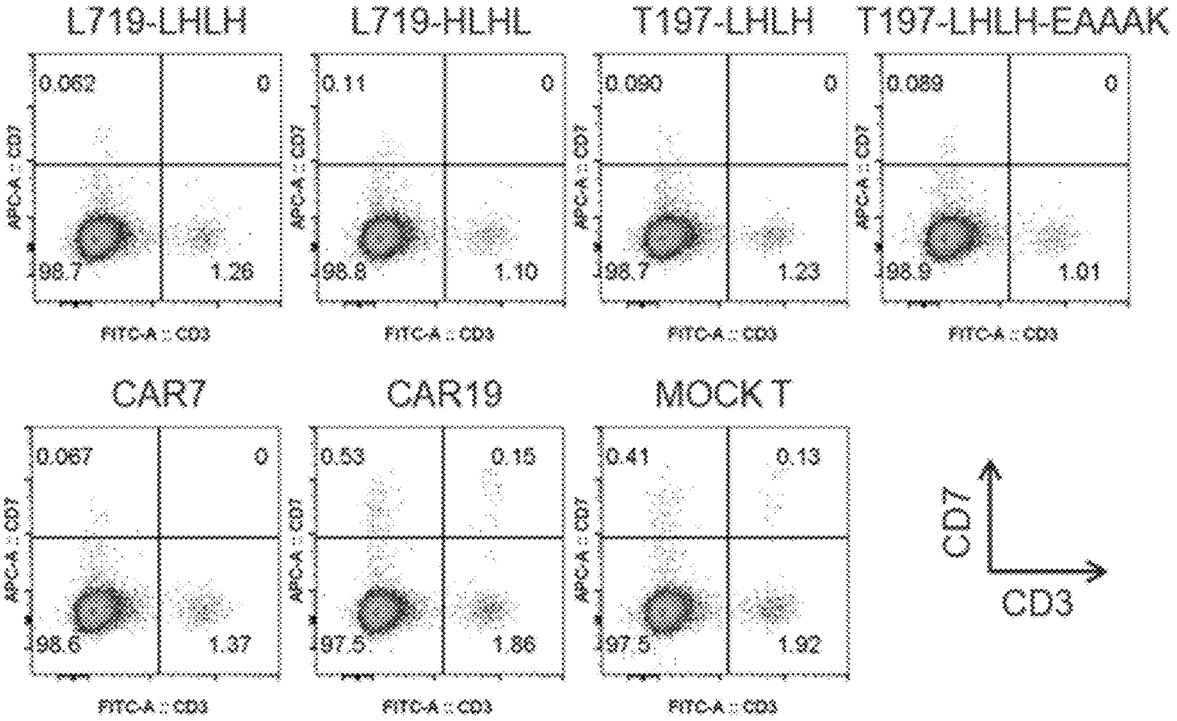
FIG. 40 illustrates experimental data of the knockout efficiencies of CD7 and CD3 (TRAC) and clearances of CD7+ cells by CARs.

We compared two Loop CARs (L719-LHLH and L719-HLHL) and two Tandem CARs (T197-LHLH and T197-LHLH-(EAAAK3)3), where CAR7 and CAR19 were used as single CAR control, and Mock T was a negative control. As shown in FIG. 39, the expression of the two Loop dual CARs was diagonally distributed, indicating successful expression of the dual CARs. CD19 CAR of the Tandem dual CARs showed strong expression, however, CD7 CAR was weakly detected. FIG. 40 shows the knockout efficiencies of CD7 and CD3 (TRAC), and it can be seen that in Mock T and CAR19, the knockout efficiencies were up to 98%. In the other two groups including CD7 single CAR and CD7/CD19 dual CAR, the ratio of CD7+ cells was significantly lower than those in Mock T and CAR 19 groups, indicating the function of CD7 CAR.

2) In Vitro Killing Effects of Dual CARs on CD19+ Cells and CD7+ Cells

Figure 41:
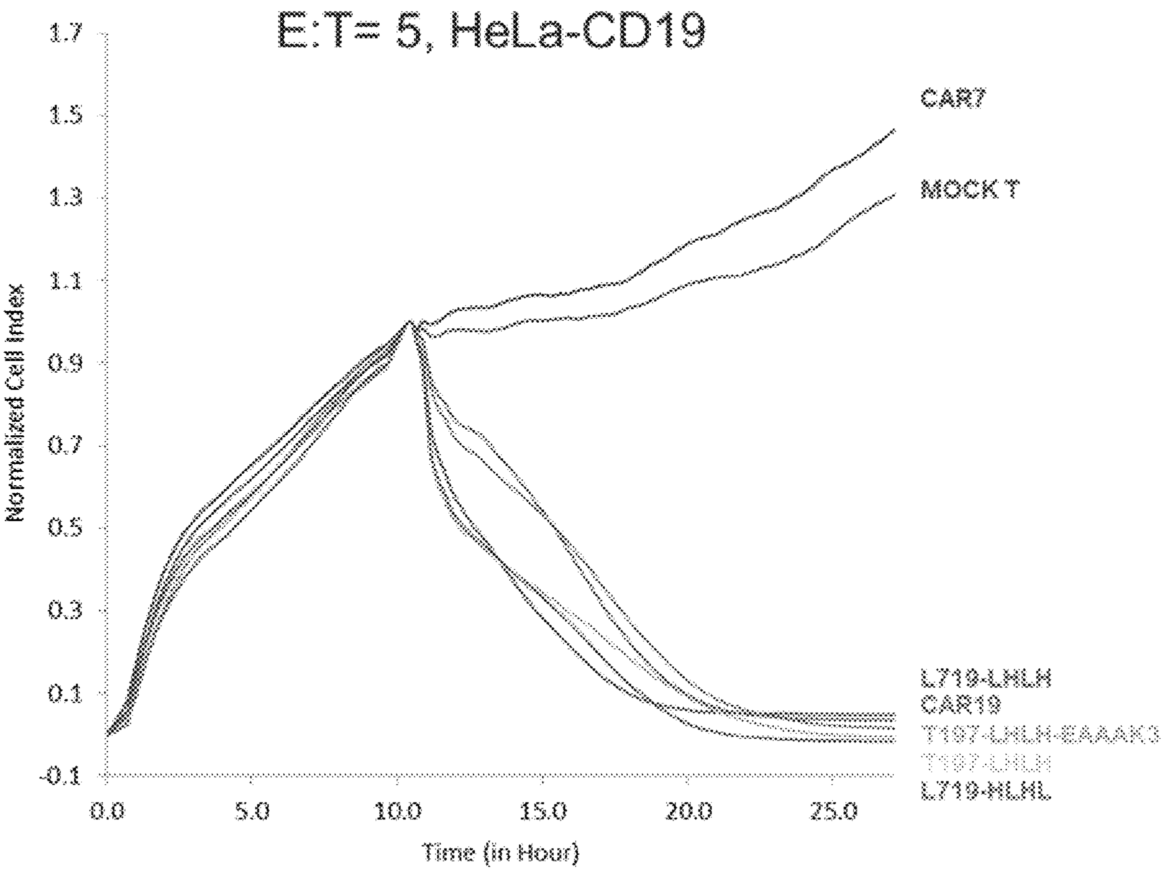
FIG. 41 illustrates experimental data of the clearance of HeLa-CD19+ cells by Loop-CARs and Tandem CARs.

First, we compared the killing effects of different CARs on CD 19 target. xCELLigence Real-Time Cell Analyzer (RTCA) experiment showed that two Loop CARs and two Tandem CARs both had potent killing effects on HeLa-CD19+ cells, similar as CD19 single CAR (CAR19) (FIG. 41).

Figure 42A:
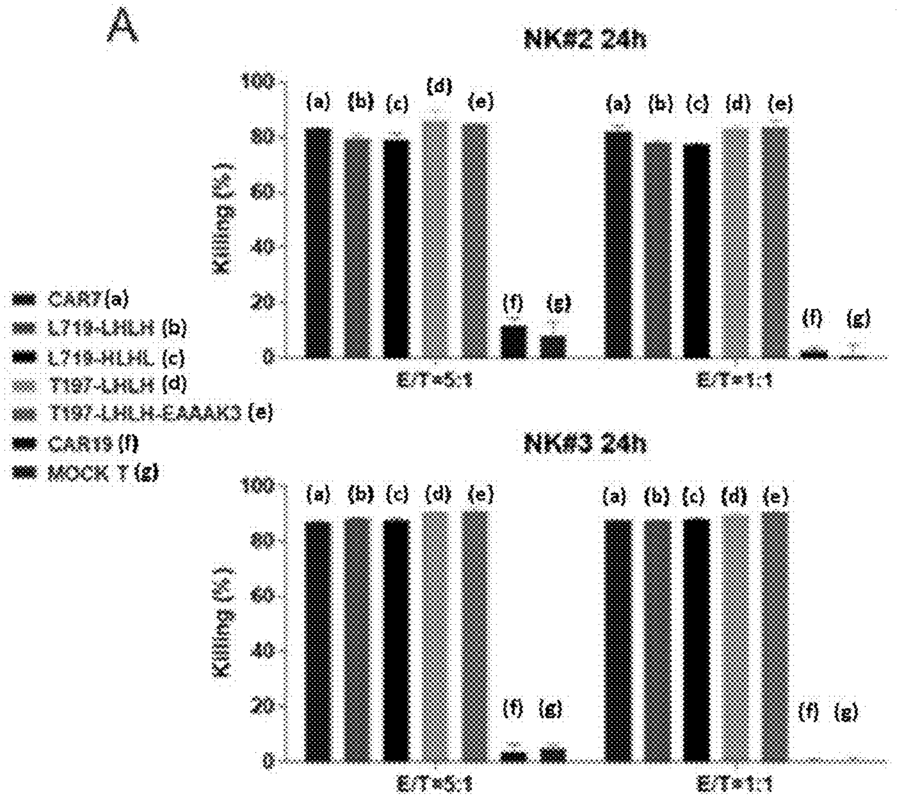
FIGS. 42A and 42B illustrate experimental data of the complete killing of NK by CD7 single CAR and CD7-CD19 dual CARs.

Subsequently, we compared the killing effects of different CARs on CD7+ NK cells from peripheral blood (FIG. 42A).

Figure 42B:
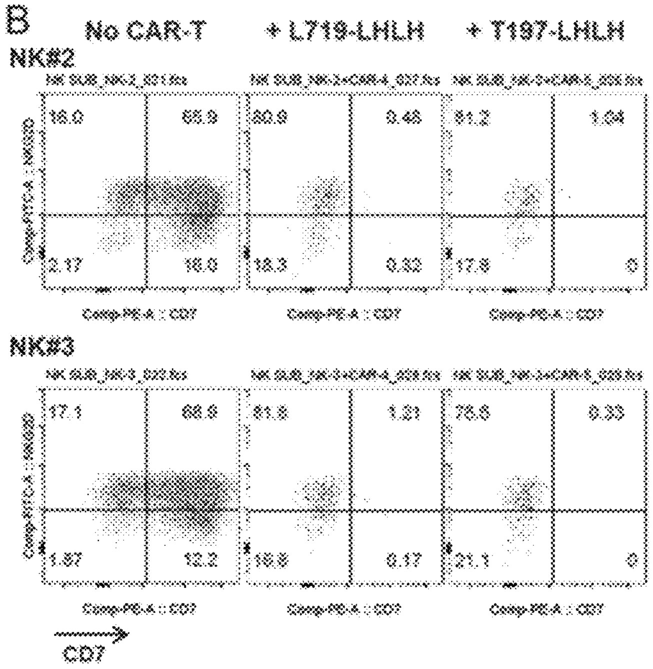

In vivo expanded PBNK cells (ratio of CD7+ cell was ~80%) were labelled with carboxyfluorescein succinimidyl ester (CFSE), and incubated with CAR-T cells for 1 day. Then the cells were subject to flow cytometry to analyze the change in ratio of CFSE positive cells. FIG. 42A shows that dual CARs and CD7 single CAR had significant killing effects on NK cells, and CD19 single CAR and Mock T did not show any killing effect. FIG. 42B shows that $CD7^+$ cells in NK almost disappeared after co-culturing with dual CARs (L719-LHLH and T197-LHLH), indicating CAR7 and dual CARs completely killed the CD7+ cells in NK.

Figure 43:
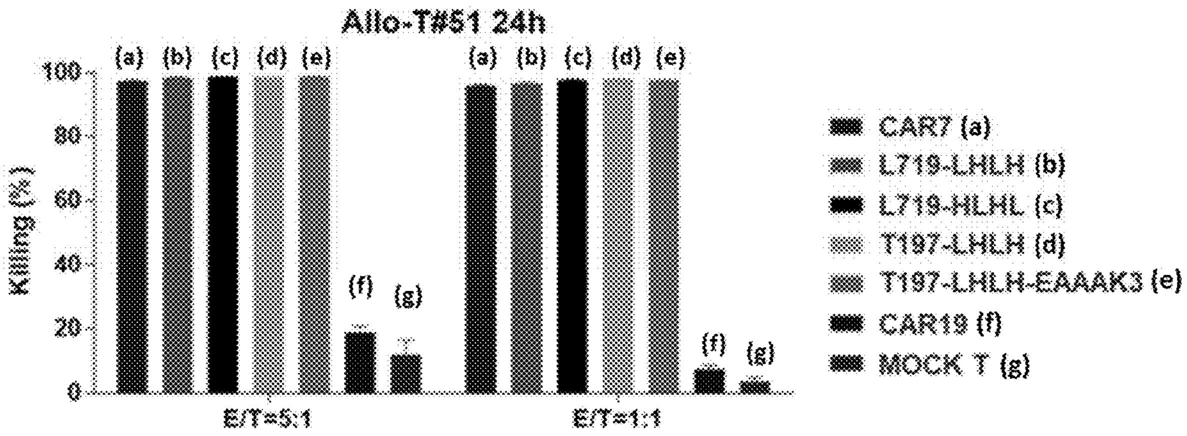
FIG. 43 illustrates experimental data of the rapid killing of allogeneic T cells by CD7 single CAR and CD7-CD19 dual CARs. 1077

Furthermore, we compared the killing effects of different CARs on allogeneic T cells (CD7+) (FIG. 43). The result shows that the allogeneic T cells were completely killed by CAR7 and dual CARs, while CAR19 did not show any killing effect on allogeneic T cells.

3) In Vivo Clearance of CD19+ Raji Tumor by Dual CARs

Figure 44:
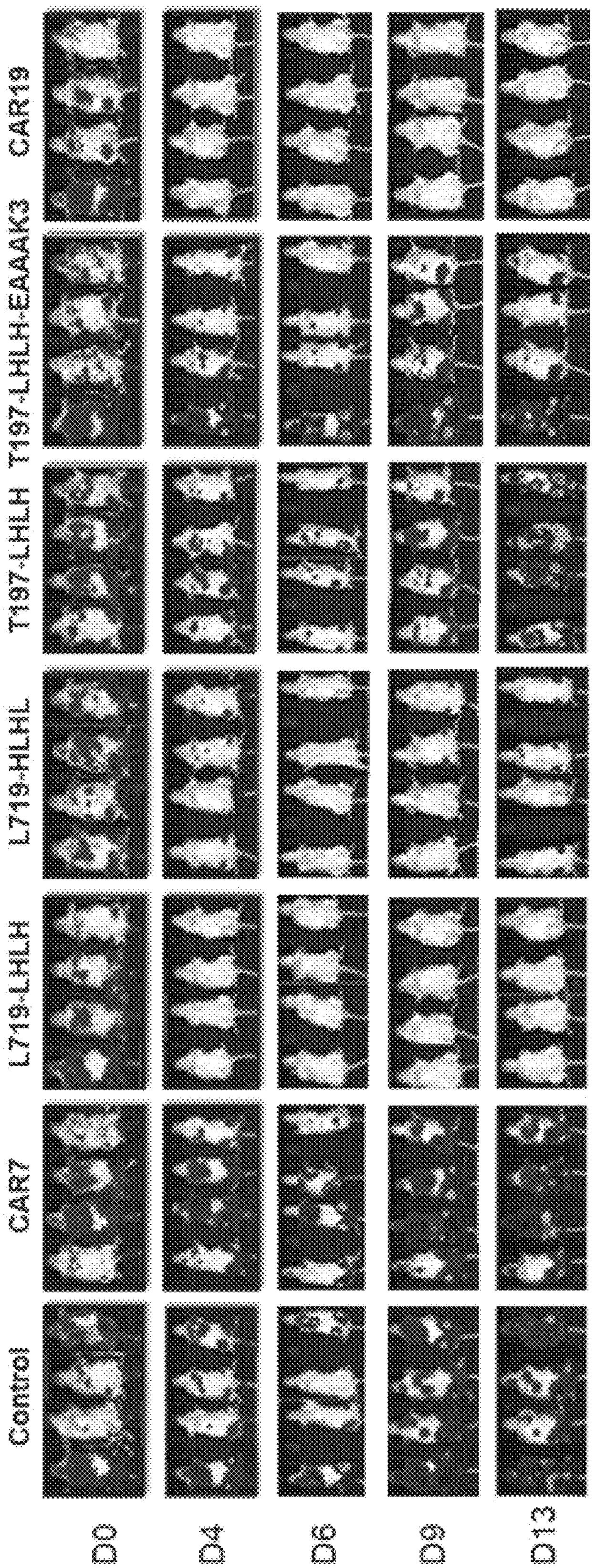
FIG. 44 illustrates experimental data of the in vivo functions of dual CARs. Loop CARs and Tandem CARs both showed potent killing effects on Raji tumor cells.

Each mouse was inoculated intravenously with $3\times10^5$ tumor cells. 6 days later, CAR-T cells were intravenously infused ($3\times10^6$ cells per mouse). BLI imaging indicates that Loop CARs and Tandem CARs both cleared Raji tumors to certain extent, and L719-LHLH showed the best in vivo tumor control (FIG. 44).

6.7 Test for Dual CAR Structure-2

Two other Tandem dual CAR structures: T719-LHLH and T719-LHHL were designed and compared with Loop CAR (L719-LHLH, also named as L719).

Figure 45A:
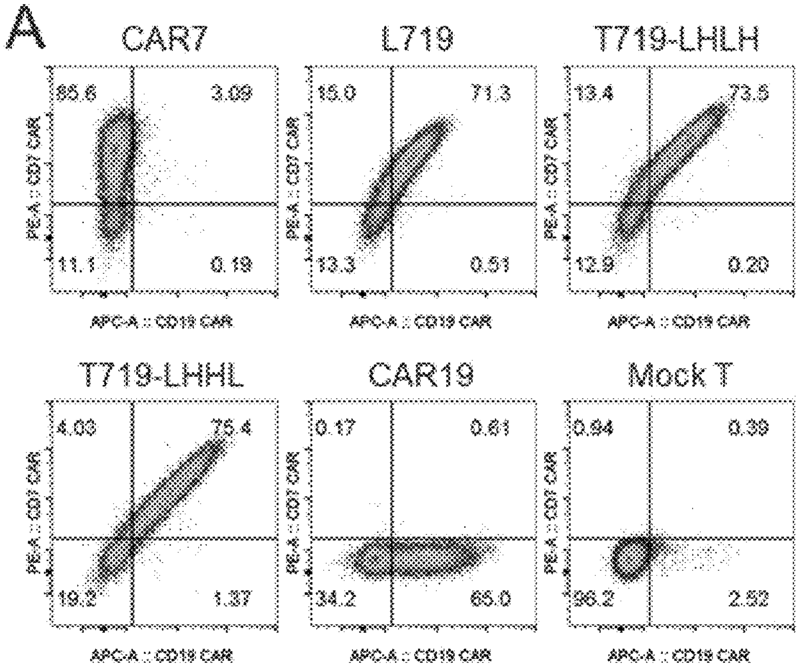
FIGS. 45A and 45B illustrate experimental data comparing two Tandem CARs.
Figure 45B:
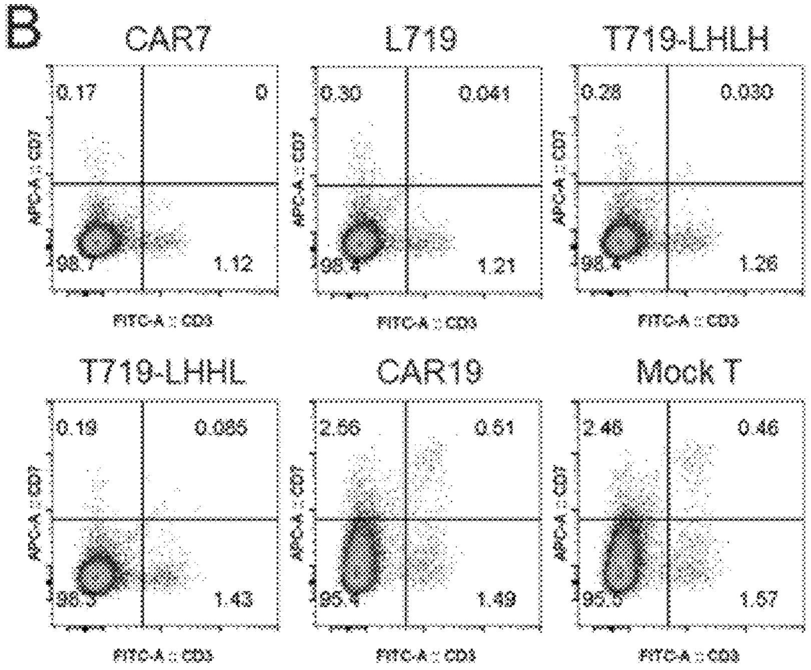

FIGS. 45A and 45B show that new Tandem dual CARs were successfully expressed (FIG. 45A), and also had significant killing effects on the remaining CD7+ cells after gene knockout (FIG. 45B).

Figure 46:
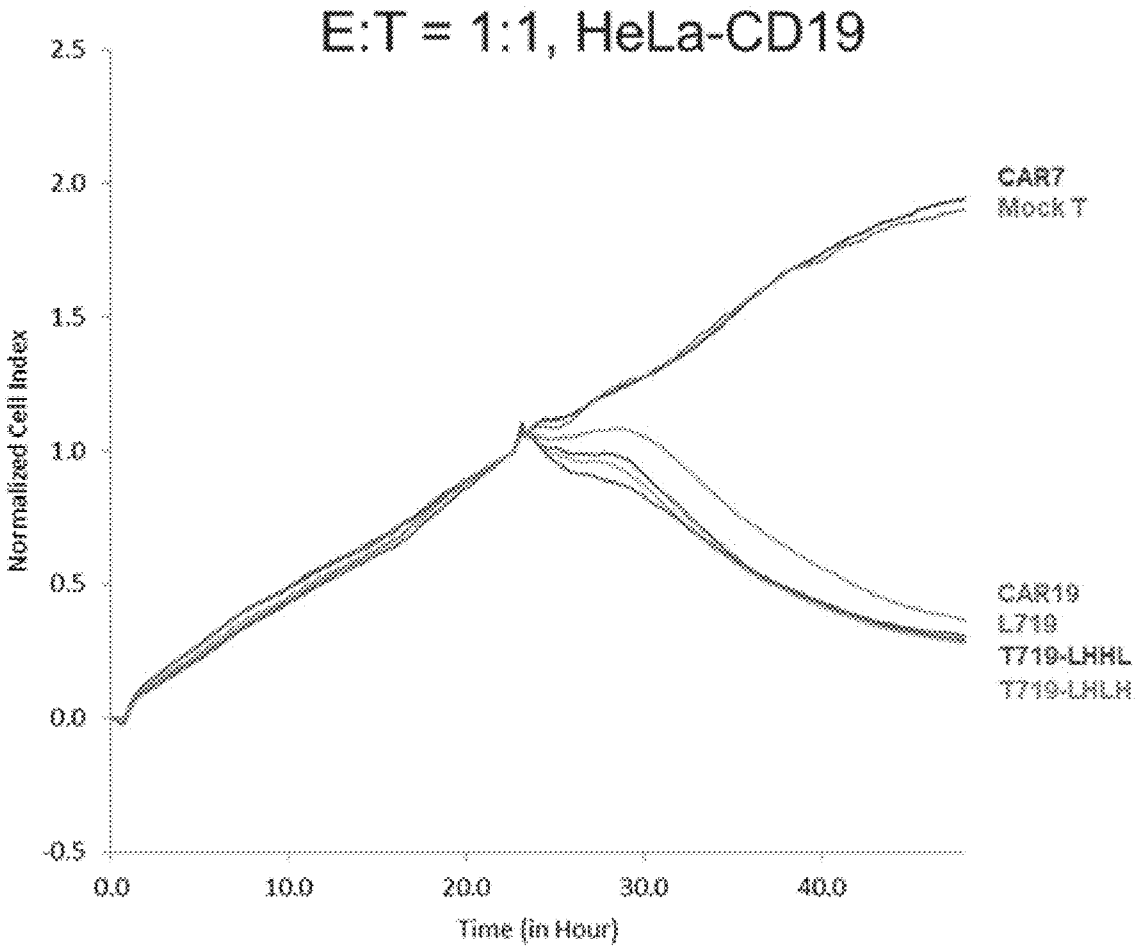
FIG. 46 illustrates experimental data of the two Tandem CARs showing similar clearance effects on HeLa-CD19+ cells as L719.

Real-time Cell Analysis (RTCA) shows that (FIG. 46), Tandem dual CARs had similar killing effects on HeLa-CD19 cells as L719.

Figure 47A:
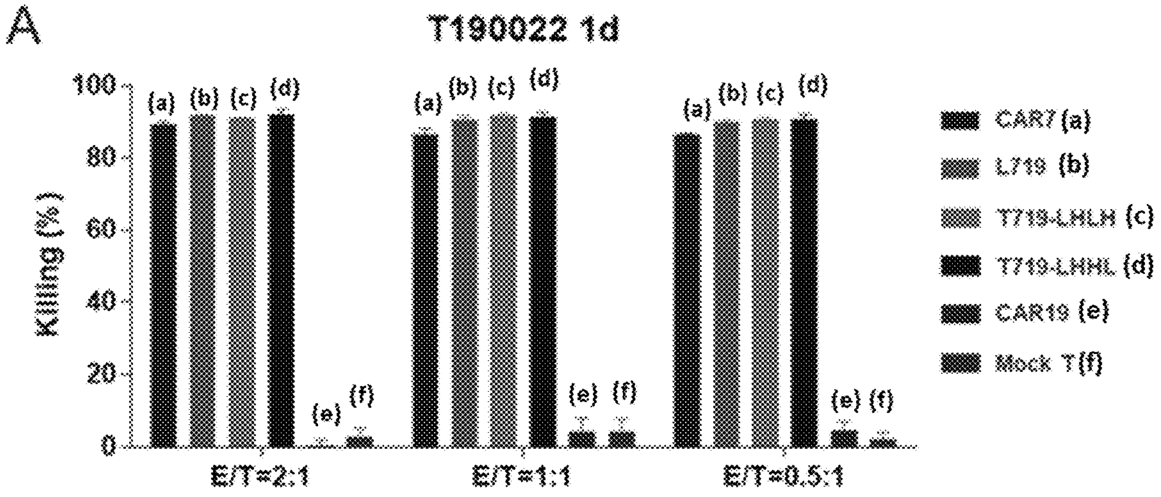
FIGS. 47A and 47 B illustrate experimental data of the two Tandem CARs showing similar clearance effects on allogeneic T cells (FIG. 47A) and NK cells (FIG. 47B) as L719.
Figure 47B:
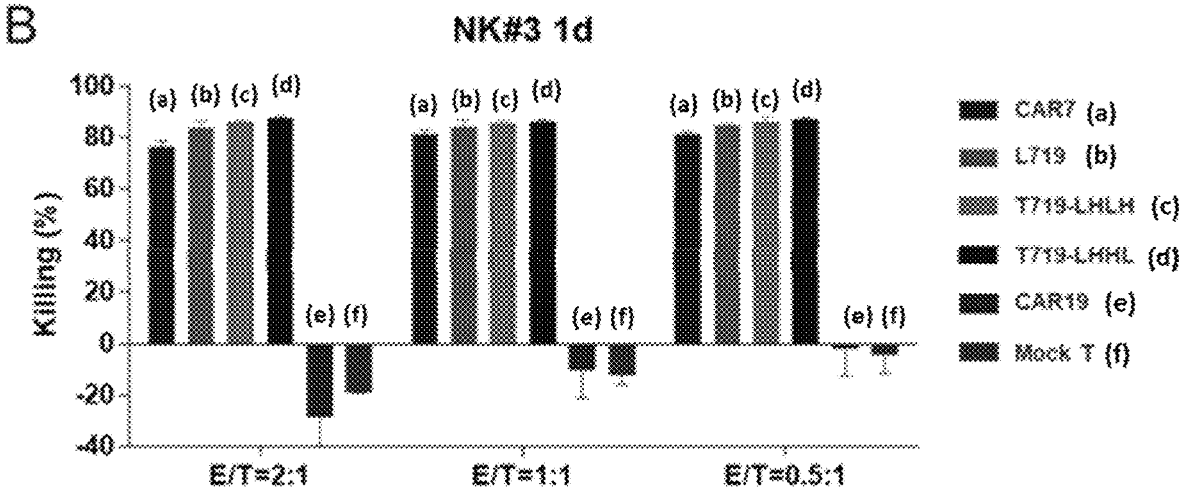

FIGS. 47A and 47B shows that, Tandem dual CARs also had similar strong killing effects on allogeneic T cells and NK cells as L719 over 24 hours.

Figure 48:
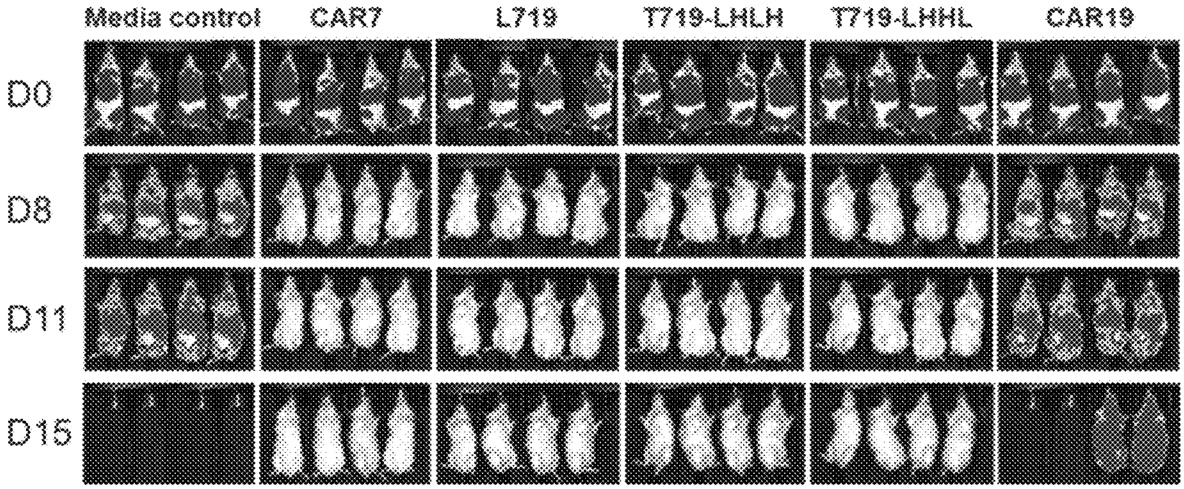
FIG. 48 illustrates experimental data of the in vivo functional screening of dual CARs. Both Loop and Tandem dual CARs showed potent killing effects on CCRF-CEM tumor cells in vivo.
Figure 49:
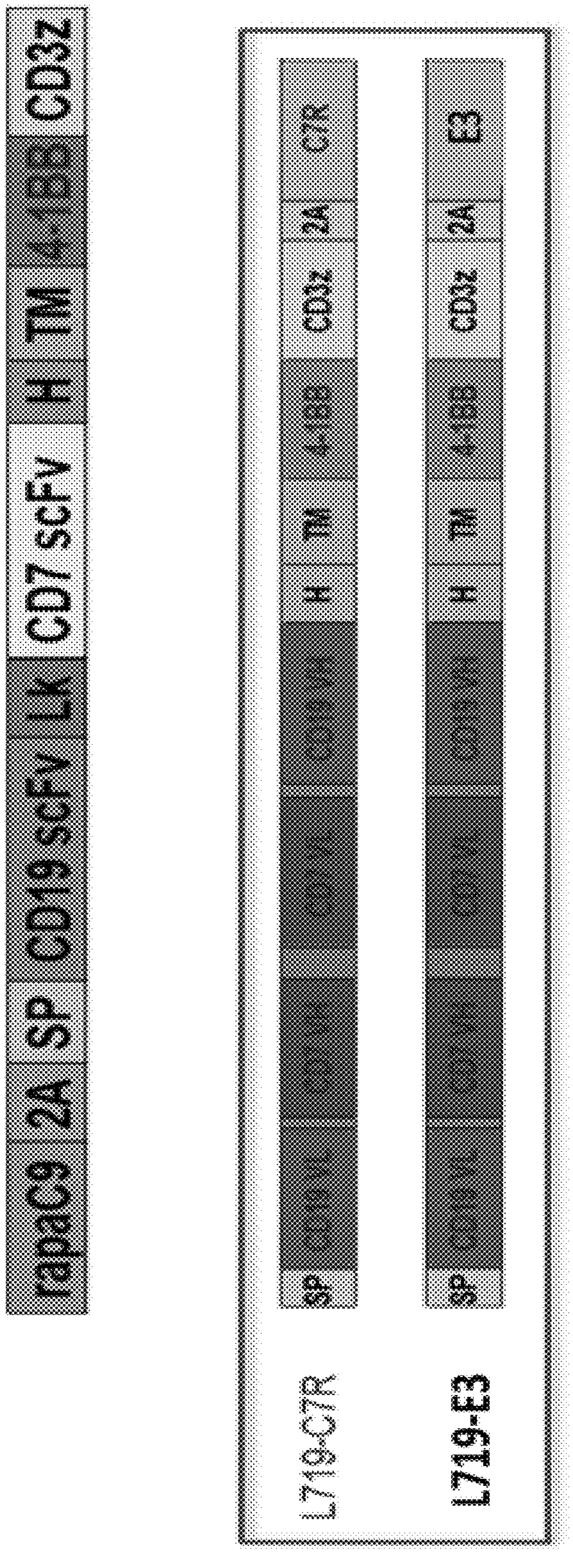
FIG. 49 illustrates the structure of rapaC, L719-C7R, and L719-E3.

FIG. 48 shows that L719 and Tandem (T719-LHLH and T719-LHHL) dual CARs both greatly cleared the CCRF-CEM tumors in vivo (CCRF-CEM intravenous model in NOG mice).

6.8 Release of the Cytokines

The dual CAR-T cells prepared in Example 6.3 and CD19 positive tumor cells (Raji), CD7 positive tumor cells (Jurkat) or primary allogeneic PBMCs or NK, 100 ul each, were mixed in RPMI medium at 1:1 ratio to a density of $1\times10^6$/ml for each cell, and then cultured overnight in a 96-well plate. The medium was then collected and subject to centrifuge and the released cytokine IFN-γ and IL-2 were detected by Cytokine bead array kit (CBA kit, BD Biosciences).

The result shows that incubation of CD19-CD7 CAR-T cells with Raji, Jurka, primary allogeneic PBMCs or NK cells produces a large amount of IFN-γ and IL-2, indicating function of CAR-T against CD19 positive or CD7 positive target cells.

6.9 In Vivo GVHD Study

The mice were systemically treated with a sub-lethal dose of irradiation (175 cGy) first. Then CAR-T cells were re-suspended in PBS and injected into the thorax of the treated mice. The mice were observed 2-3 times a week by using GVHD clinical criteria including weight loss, arch-back, activity, fur texture, and skin integrity.

The result shows that mice without TCR knockout showed GVHD symptoms, however, no GVHD was detected in the CD7-CD19 CAR-T+ TCR/CD7 double knockout group.

6.10 In Vitro HVG Study

CD7 CAR can effectively and rapidly clear CD7+ cells, and in vitro experiments showed that allogeneic T cells did not display significant rejection on CAR-T cells expressing CD7 CAR, but displayed strong rejection on CAR-T cells expressing CAR19 only.

The allogeneic NK cells showed significantly less rejection on CAR-T cells expressing CD7 CAR than CAR-T cells without CD7 CAR.

6.11 Clearance of CAR-T Cells by AP1903 or Rapamycin 10 nM AP1903 or Rapamycin was added to the medium of rapaCasp9-L719 CAR-T (sequence as set forth in SEQ ID NO: 86) cells. 1, 6 and 24 hours later, apoptosis and survival of the CAR-T cells were detected by flow cytometry.

The result shows that AP1903 and Rapamycin rapidly cleared rapaCasp9-L719 CAR-T cells but fails to clear CD19 control CART, indicating the specificity of the safety switch.

```
rapaC9-L719
                                                  (SEQ ID NO. 86)
MASRILWHEMWHEGLEEASRLYFGERNVKGMFEVLEPLHAMMERGPQTLK
ETSFNQAYGRDLMEAQEWCRKYMKSGNVKDLLQAWDLYYHVFRRISKLEY
SGGGSLEGVQVETISPGDGRTFPKRGQTCVVHYTGMLEDGKKFDSSRDRN
KPFKFMLGKQEVIRGWEEGVAQMSVGQRAKLTISPDYAYGATGHPGIIPP
HATLVFDVELLKLESGGGGSGGGGSGGGGSGVDGFGDVGALESLRGNADL
AYILSMEPCGHCLIINNVNFCRESGLRTRTGSNIDCEKLRRRFSSLHFMV
EVKGDLTAKKMVLALLELAQQDHGALDCCVVVILSHGCQASHLQFPGAVY
GTDGCPVSVEKIVNIFNGTSCPSLGGKPKLFFIQACGGEQKDHGFEVAST
SPEDESPGSNPEPDATPFQEGLRTFDQLDAISSLPTPSDIFVSYSTFPGF
VSWRDPKSGSWYVETLDDIFEQWAHSEDLQSLLLRVANAVSVKGIYKQMP
GCFNFLRKKLFFKTSGSGATNFSLLKQAGDVEENPGPMALPVTALLLPLA
LLLHAARPDIQMTQTTSSLSASLGDRVTISCRASQDISKYLNWYQQKPDG
TVKLLIYHTSRLHSGVPSRFSGSGSGTDYSLTISNLEQEDIATYFCQQGN
TLPYTFGGGTKLEITGGGGSQVKLQESGGGLVKPGGSLKLSCAASGFTFS
YSYAMSWVRQTPEKRLEWVATISSGGSYTYPDSVKGRFTISRDNAKNTLY
LQMSSLRSEDTAMYYCARQDGYYPGWFANWGQGTTVTVSSGSTSGSGKPG
SGEGSTKGDIELTQSPAIMSASLGEEITLTCSASSSVSYMHWYQQKSGTS
PKLLIYSTSNLASGVPSRFSGSGSGTFYSLTISSVEAEDAADYYCHQWSS
YTFGGGTKLEIKRGGGGSEVKLQESGPGLVAPSQSLSVTCTVSGVSLPDY
GVSWIRQPPRKGLEWLGVIWGSETTYYNSALKSRLTIIKDNSKSQVFLKM
NSLQTDDTAIYYCAKHYYYGGSYAMDYWGQGTSVTVSSSGTTTPAPRPPT
PAPTIASQPLSLRPEACRPAAGGAVHTRGLDFACDIYIWAPLAGTCGVLL
LSLVITLYCKRGRKKLLYIFKQPFMRPVQTTQEEDGCSCRFPEEEEGGCE
LRVKFSRSADAPAYKQGQNQLYNELNLGRREEYDVLDKRRGRDPEMGGKP
RRKNPQEGLYNELQKDKMAEAYSEIGMKGERRRGKGHDGLYQGLSTATKD
TYDALHMQALPPR*
```

Figure 61A:
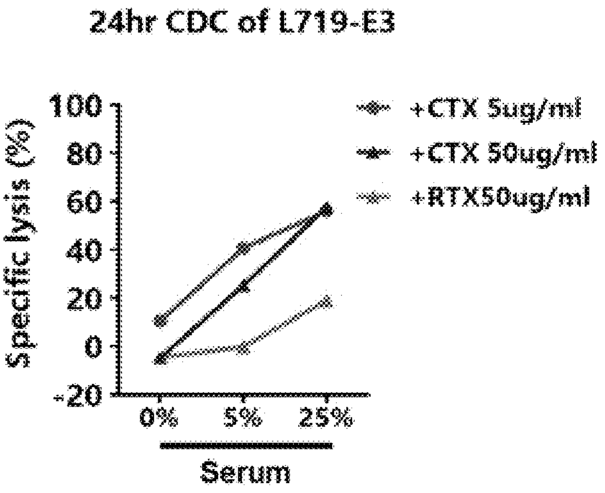
FIGS. 61A and 61B illustrate safety switch function of E3 in L719-E3 cells by Complement deepened cytotoxicity assay (CDC assay).
Figure 61B:
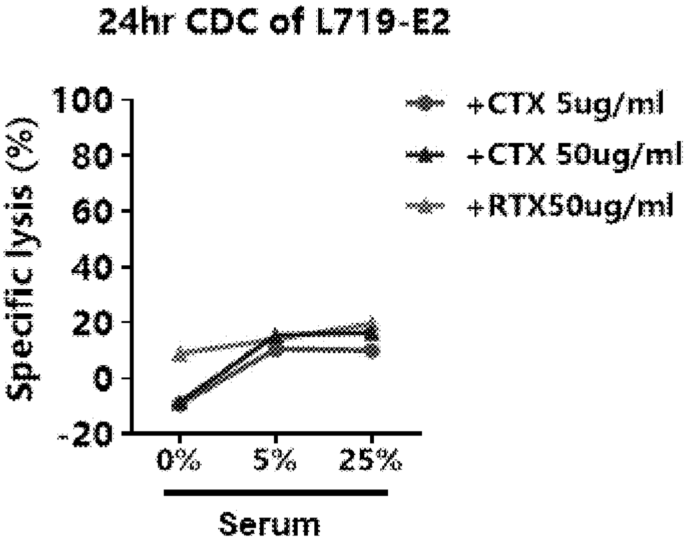

Safety switch functions of E3 in L719-E3 cells were determined by 24 hr Complement dependent cytotoxicity assay (CDC assay). Briefly, TCR/CD7 double knockout L719-E3 cells or L718-E2 cells were incubated in media containing 0%, 5% or 25% donor serum. 24 hr CDC effects were examined by adding 5 or 50 ug/ml of Cetuximab (CTX). Rituximab (RTX), which targeting CD20, was used as negative control. As shown in FIG. 61, L719-E3 cells were specifically lysed by cetuximab in the presence of serum (FIG. 61 A), and no CDC effect was observed in L719-E2 cells without EGFRt or CD20 extracellular domain (FIG. 61 B).

Figure 62A:
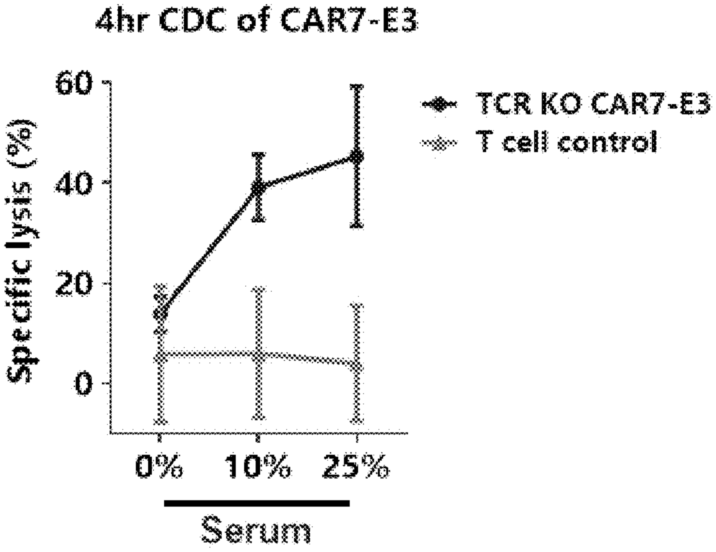
FIGS. 62A and 62B illustrate safety switch function of E3 tested in CAR7-E3 and L719-E3 by CDC assay.
Figure 62B:
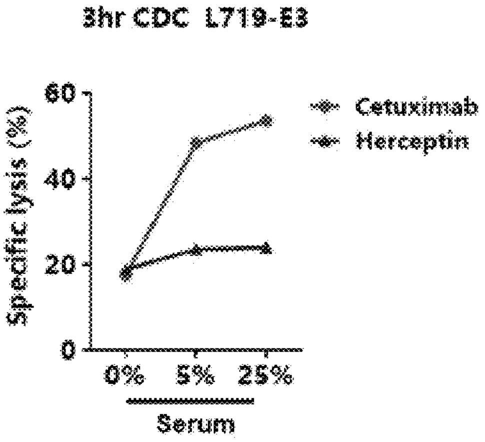

Safety switch functions of E3 in TCR/CD7 double knockout CAR7-E3 cells or L719-E3 cells were further determined by Complement dependent cytotoxicity assay (CDC assay). Cells were incubated in media containing 0%, 5% or 25% Guinea pig serum. Then CDC effects were detected in the presence of 5 ug/ml of Cetuximab. As shown in FIG. 62 A, the CDC effects corresponded to the concentrations of the serum (complement), and were specific for E3 expressing CAR7-E3 cells but not control T cells. The CDC effects were also examined on L719-E3 cells in the presence of either 5 ug/ml Cetuximab or Herceptin®. As shown in FIG. 62B, the CDC effects were only observed in the presence of Cetuximab.

6.12 Cytokine Receptor C7R or E3 Enhanced the Function of Dual CAR

Figure 50A:
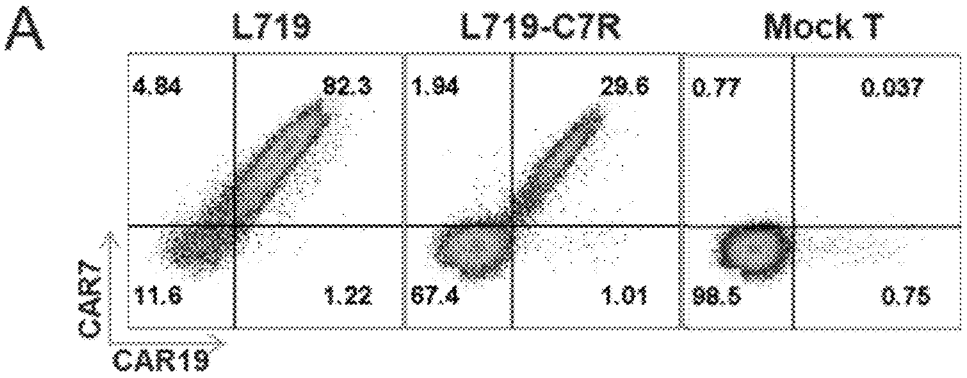
FIGS. 50A-J illustrate experimental data of the effects of cytokine signaling on the functions of dual CARs.
Figure 50B:
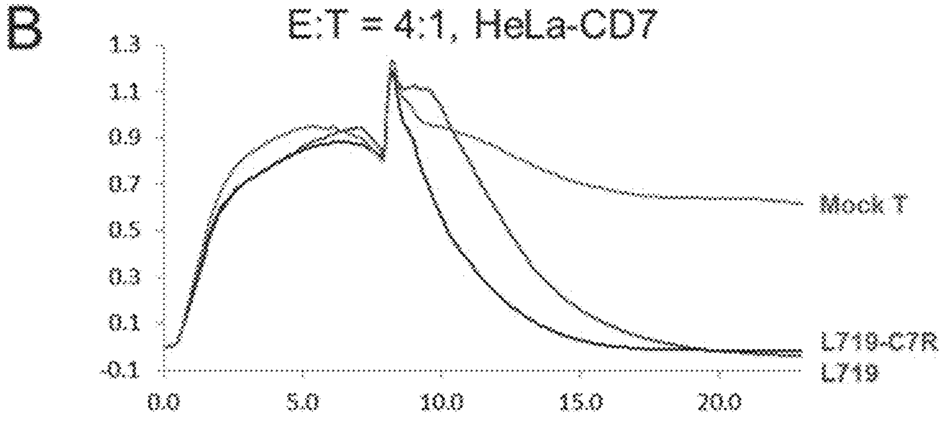
Figure 50C:
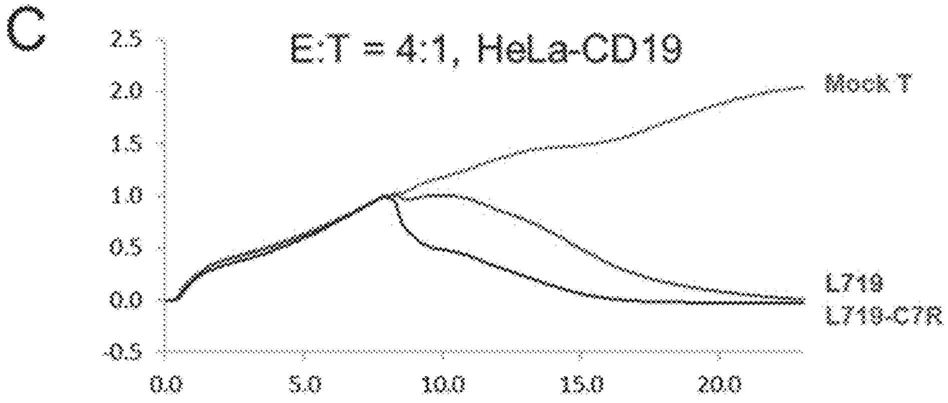
Figure 50D:
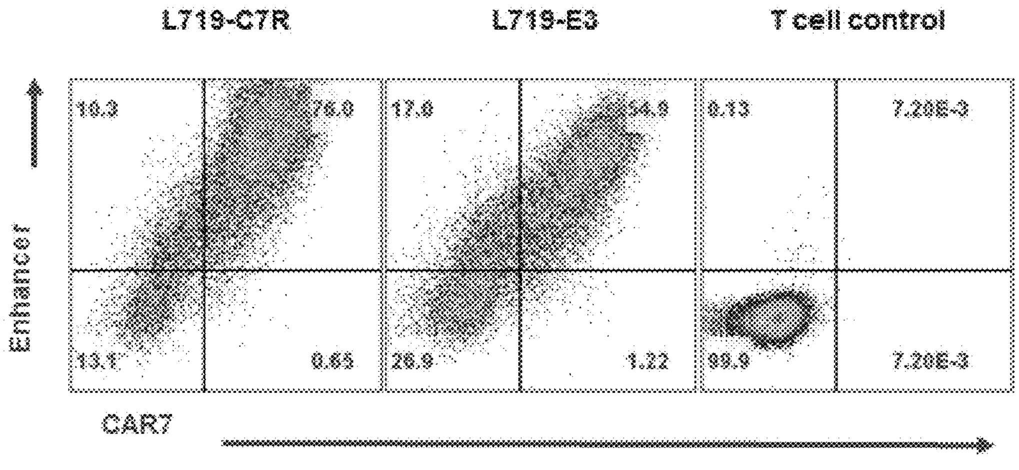
Figure 50E:
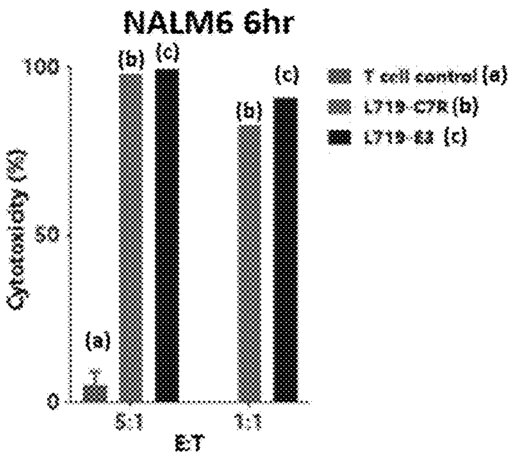
Figure 50F:
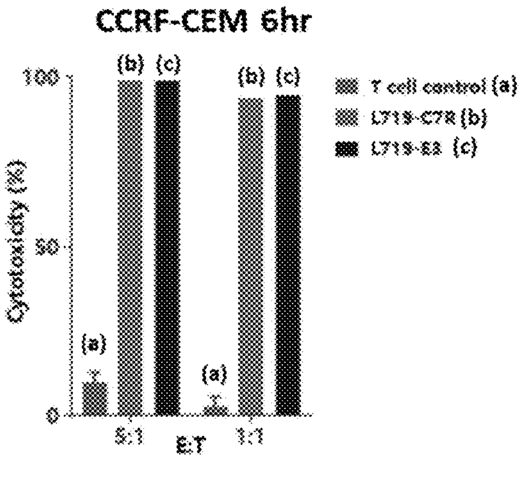
Figure 50G:
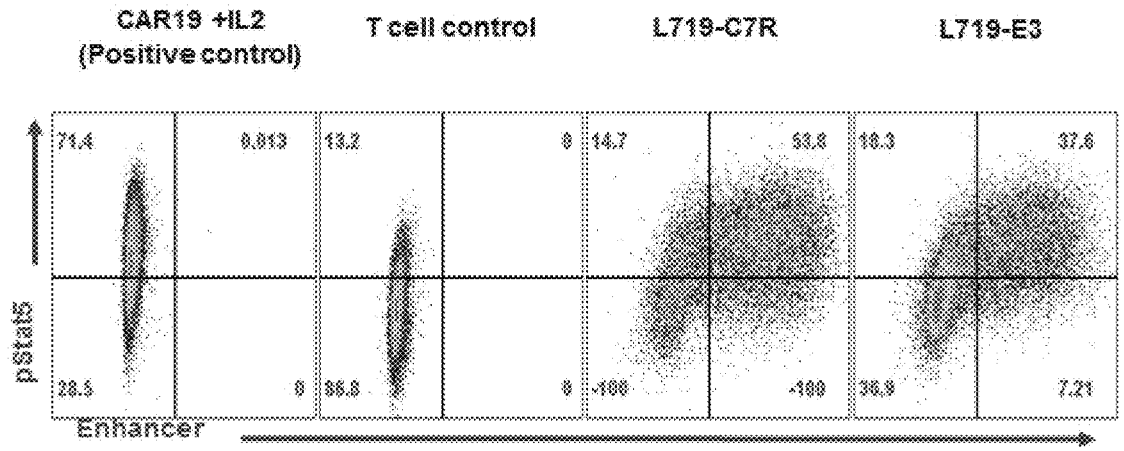
Figure 50H:
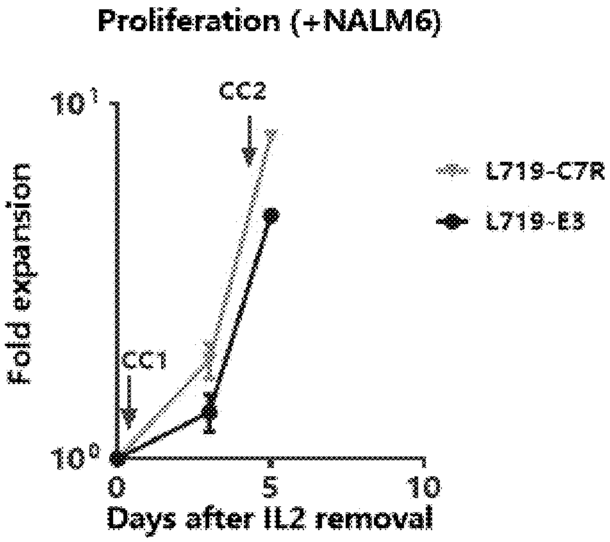

To further enhance the survival of the universal CAR-T cells in vivo, a constitutive signal factor IL7 receptor (C7R) or E3 was linked to the L719 dual CAR by 2A to activate the pSTAT5 signaling pathway. FIG. 50A shows the expression of CD19 and CD7 antigen binding domains in L719 and L719-C7R dual CAR-T cells. FIG. 50B shows cytotoxicity of L719 dual CAR-T cells with or without C7R expression toward HeLa cells expressing CD7 (HeLa-CD7). FIG. 50C show cytotoxicity of L719 dual CAR-T cells with or without C7R expression toward HeLa cells expressing CD19 co(HeLa-CD19). The effector:target ratio tested in FIGS. 50B and 50C is 4:1. FIGS. 50B and 50C show that both L719 and L719-C7R effectively killed HeLa-CD7 and HeLa-CD19. FIG. 50D shows flow cytometry data of fractions of L719 dual CAR-T cells expressing both an enhancer (C7R or E3) and CD7. FIG. 50E shows 6-hour cytotoxicity data of L719 dual CAR-T cells expressing C7R or E3 toward NALM6 cells. The effector:target ratios tested in this experiment are 5:1 and 1:1. FIG. 50F shows 6-hour cytotoxicity data of L719 dual CAR-T cells expressing C7R or E3 toward CCRF-CEM cells. The effector:target ratios tested in this experiment are 5:1 and 1:1. FIG. 50G shows flow cytometry data of fractions of L719 dual CAR-T cells expressing phosphorylated STAT5 (pSTAT5) and C7R or E3. pSTAT5 was highly upregulated in L719 dual CAR-T cells expressing C7R or E3. CAR19 plus IL2 stimulation were used as positive control for pSTAT5. Non-engineered T cells were used as negative control for pSTAT5. FIG. 50H shows proliferation of L719 dual CAR-T cells expressing C7R or E3 after IL-2 removal. The CAR-T cells were treated with two rounds of stimulations by NALM6 cells.

Figure 50I:
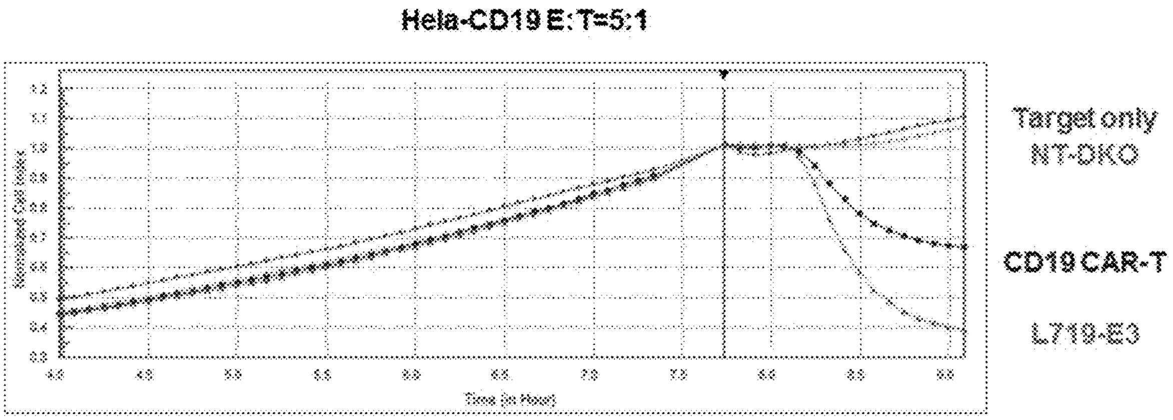
Figure 50J:
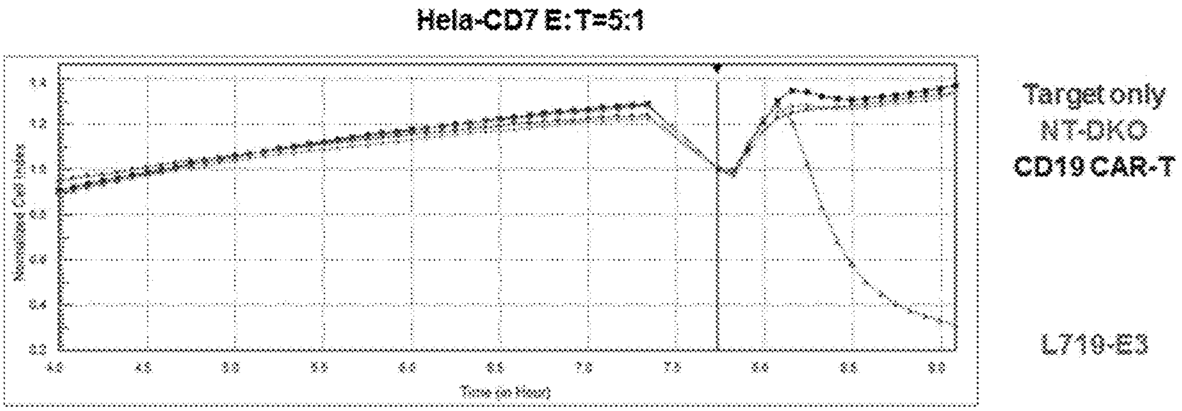

FIG. 50I shows cytotoxicity of L719 dual CAR-T cells expressing E3 (L719-E3) toward CD19 expressing HeLa cells (HeLa-CD19). The L719-E3 cells were compared with control groups including target cells only, non-transduced TCR/CD7 double knockout cells (NT-DKO), and CD19 CAR-T cells, and L719-E3 showed better cytotoxicity toward HeLa-CD19 cells. The effector:target ratio tested in this experiment is 5:1. FIG. 50J shows cytotoxicity of L719 dual CAR-T cells expressing E3 (L719-E3) toward CD7 expressing HeLa cells (HeLa-CD7). The L719-E3 cells were compared with control groups including target cells only, non-transduced TCR/CD7 double knockout cells (NT-DKO), and CD19 CAR-T cells, and L719-E3 showed better cytotoxicity toward HeLa-CD7 cells. The effector:target ratio tested in this experiment is 5:1.

Figure 63A:
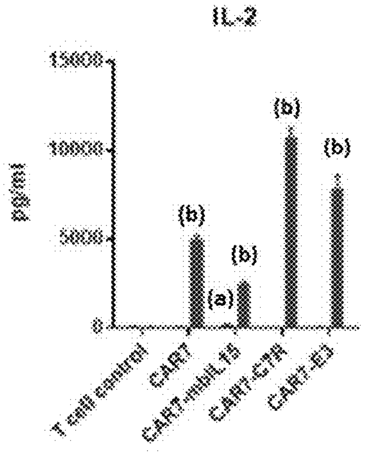
FIGS. 63A and 63B illustrate expression of IL2 and IFN γ in TCR/CD7 double knockout CAR7 cells with no cytokine signaling enhancement, or with mbIL15, C7R, or E3 expression.
Figure 63B:
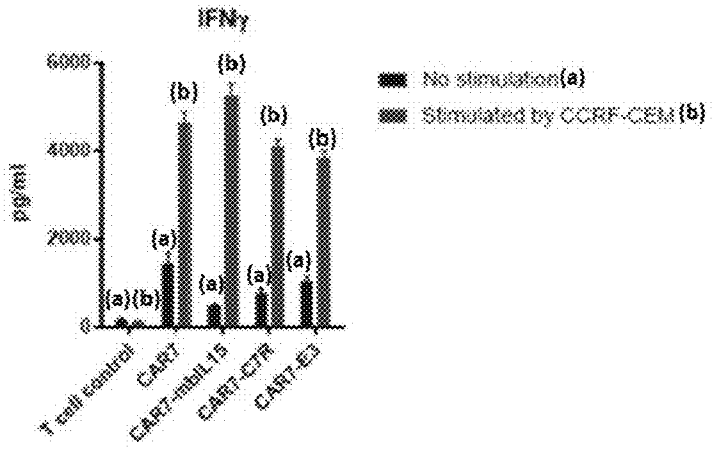

FIG. 63 shows the expression of IL2 and IFN-γ in TCR/CD7 double knockout CAR7 cells with no cytokine signaling enhancement, or with mbIL15, C7R, or E3 expression. Cells were stimulated by CCRF-CEM cells at 1:1 effector:target cell ratio for 24 hours. Supernatant were collected and measured for IL12 and IFNγ expression by cytokine bead array. As shown in FIG. 63, CAR7 cells expressing C7R and E3 showed enhanced IL-2 production.

Figure 64:
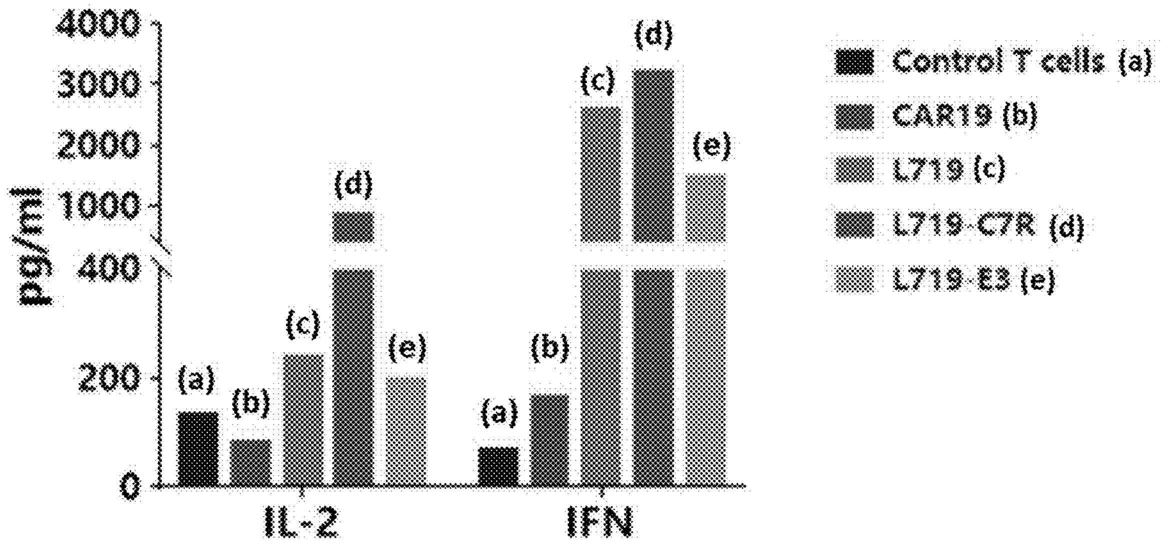
FIG. 64 illustrates expression of IL2 and IFNγ in TCR/CD7 double knockout CD19/CD7 dual CAR-L719 cells with no cytokine signaling enhancement, or with C7R, or E3 expression.

FIG. 64 shows the expression of IL2 and IFN-γ in TCR/CD7 double knockout CD19/CD7 dual CAR-L719 cells with no cytokine signaling enhancement, or with C7R, or E3 expression.

Cells were stimulated by CCRF-CEM cells at 1:2 effector:target cell ratio for 24 hours. Supernatant were collected and measured for IL12 and IFNγ expression by cytokine bead array. As shown in FIG. 64, CAR7 cells expressing C7R showed enhanced IL-2 production.

6.13 Additional Sequences Used to Construct CARs as Described Herein

FMC63 scFv $V_L$ (SEQ ID NO 87)

DIQMTQTTSSLSASLGDRVTISCRASQDISKYLNWYQQKPDGTVKLLIYH

RTSLHSGVPSRFSGSGSGTDYSLTISNLEQEDIATYFCQQGNTLPYTFGG

GTKLEIT

FMC63 scFv $V_H$ (SEQ ID NO 88)

EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSS

FMC63 CD19CAR (SEQ ID NO 89)

MALPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

QEDIATYFCQQGNTLPYTFGGGTKLEITGSTSGSGKPGSGEGSTKGEVKL

QESGPGLVAPSQSLSVTCTVSGVSLPDYGVSWIRQPPRKGLEWLGVIWGS

ETTYYNSALKSRLTIIKDNSKSQVFLKMNSLQTDDTAIYYCAKHYYYGGS

YAMDYWGQGTSVTVSSSGTTTPAPRPPTPAPTIASQPLSLRPEACRPAAG

GAVHTRGLDFACDIYIWAPLAGTCGVLLLSLVITLYCKRGRKKLLYIFKQ

PFMRPVQTTQEEDGCSCRFPEEEEGGCELRVKFSRSADAPAYKQGQNQLY

NELNLGRREEYDVLDKRRGRDPEMGGKPRRKNPQEGLYNELQKDKMAEAY

SEIGMKGERRRGKGHDGLYQGLSTATKDTYDALHMQALPPR*

3A1e CD7 scFv $V_L$ (SEQ ID NO 90)

DIELTQSPAIMSASLGEEITLTCSASSSVSYMHWYQQKSGTSPKLLIYST

SNLASGVPSRFSGSGSGTFYSLTISSVEAEDAADYYCHQWSSYTFGGGTK

LEIKR

3A1e CD7 scFv $V_H$ (SEQ ID NO 91)

QVKLQESGGGLVKPGGSLKLSCAASGFTFSSYAMSWVRQTPEKRLEWVAT

ISSGGSYTYYPDSVKGRFTISRDNAKNTLYLQMSSLRSEDTAMYYCARQD

Figure 57A:
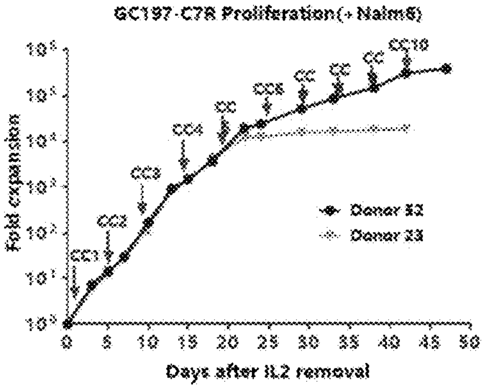
FIGS. 57A and 57B illustrate experimental data showing expansion and persistence of UCAR-T GC197 cells (e.g., multi-specific CAR-T cells having CARs targeting both CD19 and CD7).
Figure 57B:
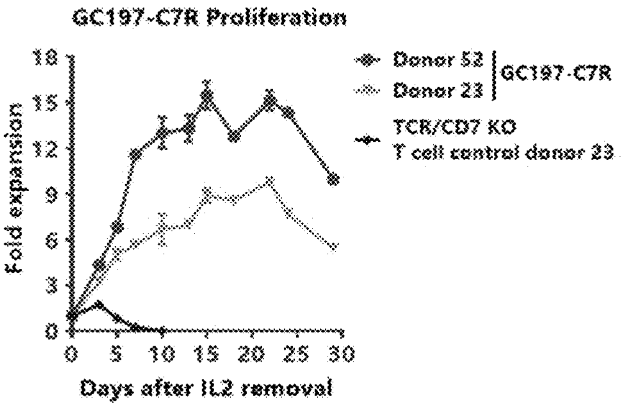

GYYPGWFANWGQGTTVTVSS 6.14 Proliferation of CD19 and CD7 Dual Specific CAR-T Cells FIG. 57A shows proliferation of CD19 and CD7 dual specific CAR-T cells expressing C7R (GC197-C7R). The engineered dual specific CAR-T cells were prepared from two different T cell donors. CAR-T cells from both donors displayed superior persistence and proliferation in response to repetitive cancer antigen stimulation. FIG. 57B shows proliferation of GC197-C7R cells without stimulation. Freshly prepared GC197-C7R were cultured in T cell culture media without supplement of IL2 or antigen stimulation, compared to control T cells, GC197-C7R maintained better expansion, and persisted in culture.

Figure 58A:
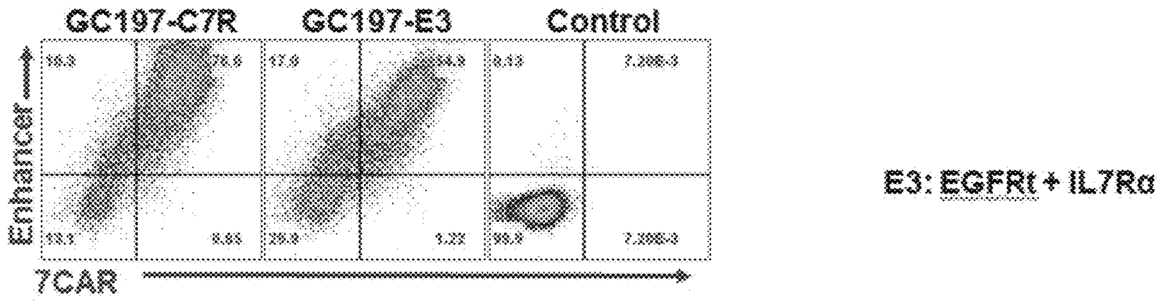
FIGS. 58A-C illustrate experimental data showing expansion and persistence of UCAR-T GC197 cells.
Figure 58B:
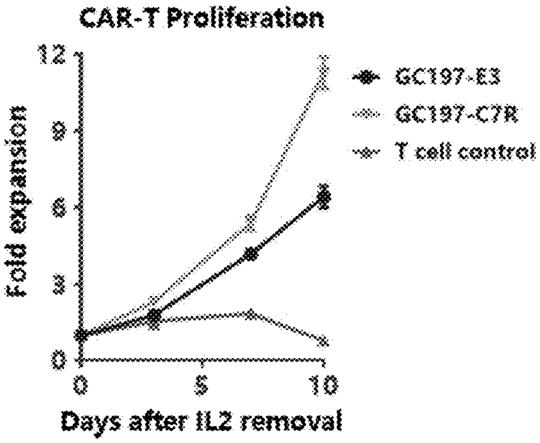
Figure 58C:
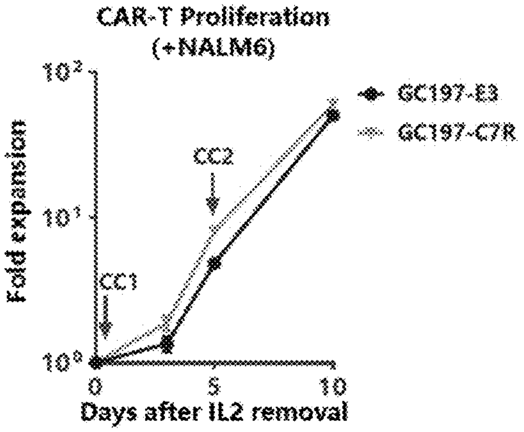

FIG. 58A shows expression of CD7 CAR and enhancer in GC197-C7R and GC197-E3 at day 12 of cell culture. FIG. 58B shows proliferation of GC197 cells expressing C7R (GC197-C7R) or E3 (GC197-E3) without stimulation. GC197-C7R or GC197-E3 cells were cultured in T cell culture media without supplement of IL2 and monitored for fold of cell expansion and persistence. FIG. 58C shows proliferation of GC197-C7R and GC197-E3 in the presence of antigen stimulation. The cells were repeated stimulated by Nalm6 (CD19+ B-ALL cell line) and monitored for fold of cell expansion. The data showed that GC197-C7R/E3 displayed comparably superior cell expansion and cell stability either with or without cytokine or antigen stimulation.

6.15 In Vivo Efficacy

Figure 69:
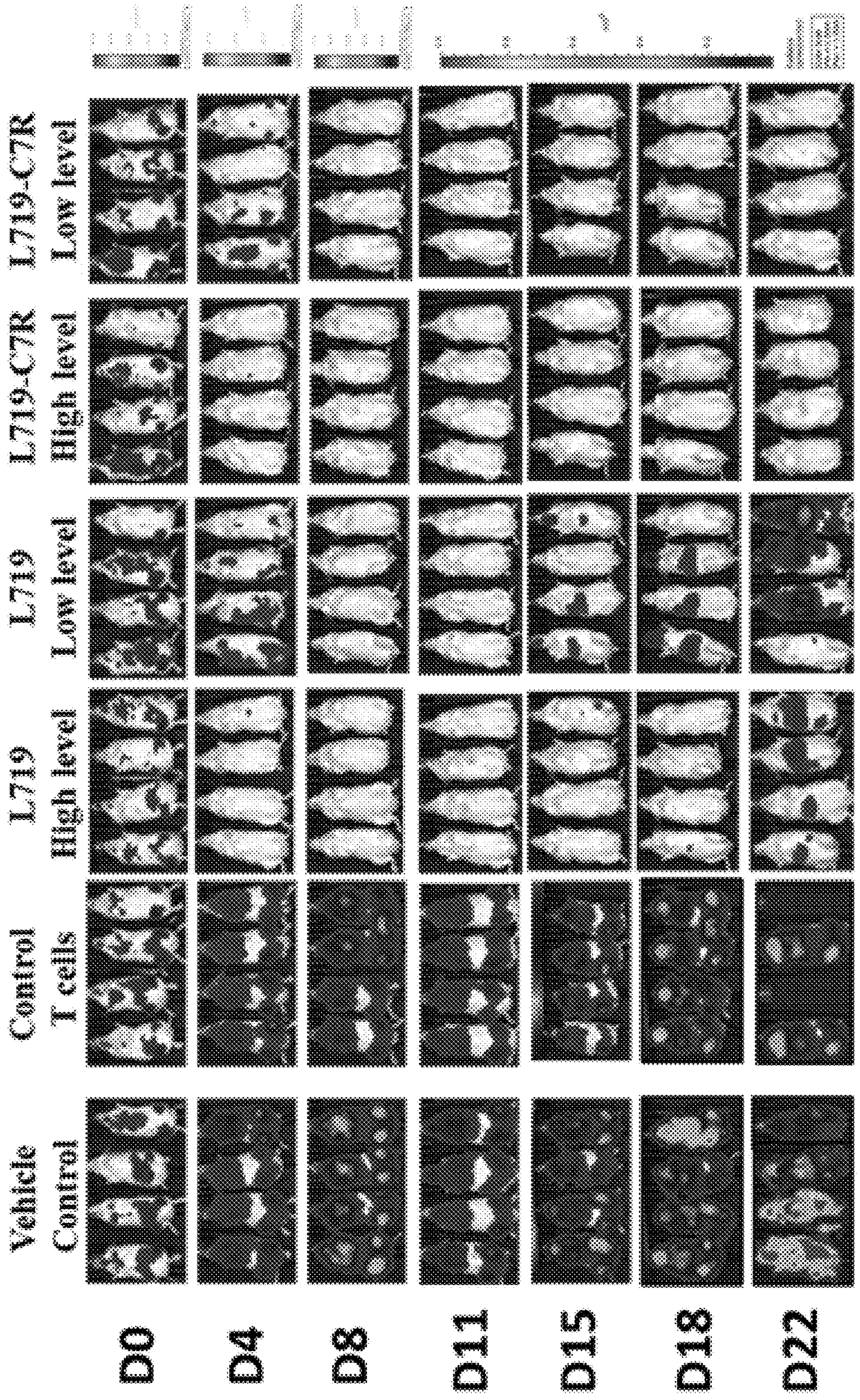
FIG. 69 illustrates BLI imaging of the in vivo efficacy of L719 and L719-C7R UCAR-T cells.

FIG. 69 shows BLI imaging of the in vivo efficacy of L719 and L719-C7R UCAR-T in Nalm6 (B-ALL) murine xenograft model. Each mouse was inoculated intravenously with $1\times10^6$ Nalm6 cells. Four days later, CAR-T cells were intravenously infused (high dose: $1\times10^6$ or low dose: $3\times10^5$ cells per mouse). BLI imaging indicates L719-C7R UCAR-T cells had better effect on tumor clearance than L719 UCAR-T cells.

Example 7 Study of U-CAR T Cells with CD137 and CD19 Dual CAR

General Materials and Methods

Isolation Of Peripheral Blood Mononuclear Cells (PBMCs) from Donor Blood and Expansion of T Cells Peripheral blood mononuclear cells (PBMCs) were isolated from donor blood by using Histopaque®-1077 (Sigma-Aldrich) through density gradient centrifuge. Then T cells were enriched, activated by magnetic beads coupled with anti-CD3/anti-CD28, cultured and expanded.

6 Cell Lines and Culture of Pbmc and Peripheral Blood Primary Nk (Pbnk) Cells

- Raji cells (Burkitt's lymphoma cells, ATCC®-CCL-86™);
- K562 cells (Human erythroleukemia cell line, ATCC®-CCL-243™);
- Raji-ffluc cell line (obtained by screening Raji cells transfected with lentivirus having firefly luciferase);
- 293T cells (ATCC®-CRL-3216™);
- NK92 cells (ATCC®-CRL-2407™);
- NK92-ffluc cells (obtained by screening NK92 cells transfected with lentivirus having firefly luciferase)
- Raji cells, K562 cells and Raji-ffluc cell line were cultured in RPMI1640 medium, and 293T cells were cultured in DMEM medium. Both RPMI1640 and DMEM were supplemented with 10% (v/v) fetal bovine serum and 100 U/ml penicillin and streptomycin, 2 mM glutamine and 1 mM sodium pyruvate. All of the cells were cultured in an incubator at 37° C., 5% $CO_2$.

NK92 cells and NK92-ffluc cells were cultured in RPMI1640 medium supplemented with 10% (v/v) fetal bovine serum, 2 mM glutamine, 1 mM sodium pyruvate, 1% NEAA, 0.1 mM mercaptoethanol and 200 IU/ml rhIL2. PBNKs was sorted from PBMCs by using CD56 microbeads, and then cultured in above medium and expanded under the stimulation of K562 expressing 4-1BBL-mbIL15.

T cells and the obtained CAR-T cells were cultured in X-vivo™ 15 medium (containing 5% FBS, 2 mM L-glutamine, 1 mM sodium pyruvate and 300 IU/ml rhIL2). The culture medium for CAR-T cells was supplemented with rhIL-2 (ThermoFisher Scientific) at a final concentration of 300 IU/ml every two days. All of the cells were cultured in an incubator at 37° C., 5% $CO_2$.

7.1 Design of CD19-CD137 Dual CAR and Package of the Virus

Figure 52:
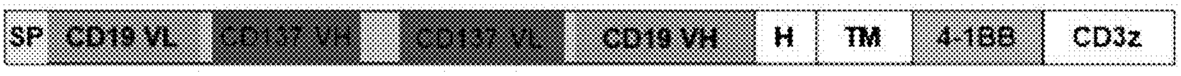
FIG. 52 illustrates an example structural diagram of CD137-CD19 AAC/CAR.

The structure of CD19 CAR is SP-CD19 scFv VL-Linker-CD19 scFv VH-Hinge-TM-4-1BB-CD3ζ; and the loop of CD19 and CD137 targeting dual CAR (CD19-CD7 dual-CAR) is SP-CD19 scFv VL-Linker-CD137 scFv VH-linker-CD137 scFv VL-Linker-CD19 scFv VH-Hinge-TM-4-1BB-CD3ζ(as shown in FIG. 52). The nucleotide sequence of CD19-CD137-loop-CAR is set forth as SEQ ID NO.: 41.

```
CD19-CD137-Loop-CAR (SEQ ID NO 41):
ATGGCACTCCCTGTAACTGCACTTCTTTTGCCACTTGCCTTGCTCCTGCA

CGCAGCGCGGCCGGATATTCAAATGACACAAACTACCAGCTCCCTTTCAG

CATCTTTGGGCGATAGAGTAACTATAAGTTGCCGCGTCCCAAGACATC

TCTAAGTACCTTAACTGGTATCAACAAAAACCGGACGGGACGGTCAAACT

GTTGATCTATCACACATCCAGATTGCACTCAGGCGTGCCGAGCAGGTTCA

GTGGGAGTGGGTCAGGAACGGATTACAGCTTGACGATTAGTAACCTGGAG

CAAGAAGACATTGCCACCTACTTCTGCCAGCAAGGTAACACTCTCCCATA

TACGTTCGGGGGTGGCACCAAGCTGGAAATCACTGGCGGCGGAGGATCCG

AGGTGCAGCTGGTGCAGAGCGGCGCCGAGGTGAAGAAGCCCGGCGAGAGC

CTGAGGATCAGCTGCAAGGGCAGCGGCTACAGCTTCAGCACCTACTGGAT

CAGCTGGGTGAGGCAGATGCCCGGCAAGGGCCTGGAGTGGATGGGCAAGA

TCTACCCCGGCGACAGCTACACCAACTACAGCCCCAGCTTCCAGGGCCAG

GTGACCATCAGCGCCGACAAGAGCATCAGCACCGCCTACCTGCAGTGGAG

CAGCCTGAAGGCCAGCGACACCGCCATGTACTACTGCGCCAGGGGCTACG

GCATCTTCGACTACTGGGGCCAGGGCACCCTGGTGACCGTGAGCAGCGGC

AGCACAAGCGGCTCTGGCAAGCCTGGATCTGGCGAGGGCTCTACCAAGGG

CATGAGCTACGAGCTGACCCAGCCCCCCAGCGTGAGCGTGAGCCCCGGCC

AGACCGCCAGCATCACCTGCAGCGGCGACAACATCGGCGACCAGTACGCC

CACTGGTACCAGCAGAAGCCCGGCCAGAGCCCCGTGCTGGTGATCTACCA

GGACAAGAACAGGCCCAGCGGCATCCCCGAGAGGTTCAGCGGCAGCAACA

GCGGCAACACCGCCACCCTGACCATCAGCGGCACCCAGGCCATGGACGAG

GCCGACTACTACTGCGCCACCTACACCGGCTTCGGCAGCCTGGCCGTGTT

CGGCGGCGGCACCAAGCTGACCGTGCTGGGGGGAGGCGGCAGCGAGGTGA

AACTGCAGGAGTCCGGGCCCGGTCTCGTGGCACCTTCCCAGTCACTGTCC

GTGACCTGCACCGTATCTGGGGTAAGTCTGCCGGATTATGGGGTTTCATG
```

-continued

```
GATCCGGCAACCTCCGAGGAAAGGGTTGGAATGGCTGGGAGTCATCTGGG
GAAGCGAGACAACTTATTATAATTCTGCTTTGAAGAGCCGCTTGACGATA
ATCAAGGACAACAGTAAGAGTCAGGTTTTCTTGAAGATGAATTCTCTTCA
GACAGATGACACCGCTATTTATTATTGTGCAAAACATTATTATTACGGAG
GATCCTACGCGATGGACTATTGGGGACAGGGTACCTCTGTTACGGTGTCC
TCATCCGGAACAACGACACCAGCACCACGGCCACCCACTCCTGCTCCGAC
AATTGCGTCTCAGCCCCTTTCCCTTCGACCCGAAGCTTGTCGCCCTGCTG
CGGGAGGAGCGGTCCACACGCGCGGGCTTGACTTCGCTTGCGACATCTAC
ATTTGGGCACCCTTGGCCGGGACATGCGGCGTCTTGCTCCTGAGTCTGGT
TATAACGCTGTATTGTAAGCGAGGTCGGAAGAAGCTTTTGTATATCTTTA
AACAGCCCTTTATGAGGCCCGTACAAACCACACAAGAGGAGGATGGGTGC
TCATGCAGATTTCCTGAAGAGGAAGAGGGCGGTTGCGAACTTAGAGTCAA
ATTCAGCCGCTCCGCAGATGCACCTGCTTATAAACAGGGTCAGAATCAAT
TGTATAATGAACTTAATCTCGGGAGGCGCGAGGAGTATGATGTGCTGGAC
AAGCGACGGGGTCGAGACCCAGAGATGGGCGGTAAACCCCGCCGAAAGAA
CCCCCAGGAGGGACTGTATAATGAGCTGCAAAAGGACAAAATGGCAGAAG
CCTATTCCGAAATAGGGATGAAGGGAGAGCGGCGGCGAGGTAAGGGACAT
GACGGTCTTTATCAAGGTCTTAGTACTGCAACTAAGGACACCTATGACGC
GCTGCATATGCAGGCTCTCCCACCTAGATAA
```

The CAR gene was cloned into the FUW lentiviral vector backbone under the promoter of EF1α (EF-1α) to form Fuw-EF1α-CAR. Fuw-EF1α-CAR, lentiviral envelope plasmid pMD2.G (Addgene, Plasmid #12259) and lentiviral packaging plasmid psPAX2 (Addgene, Plasmid #12260) were transfected into 293 T cells by using Lipofectamine®3000 to prepare the whole lentiviral expression vector. The supernatant was collected at 48 and 72 h and subject to ultra-centrifuge (Merck Millipore) for concentration. The concentrated virus was ready for the transfection of T cells.

The result shows that the lentiviral vector was successfully constructed and expressions of anti-CD19 and anti-CD19/CD137 of the dual CAR were detected as expected.

7.2 Design and Construction of CRISPR

CD137 and TCR gRNAs for gene editing were selected after evaluating gene editing efficiency and off-target risk at website http://crispr.mit.edu, www.idtdna.com and https://www.synthego.com.

gRNAs used in the present disclosure were synthesized by Integrated DNA Technologies, Inc (IDT). HiFi-Cas9 was purchased from IDT.

For gene editing, 3 μg Cas9 protein and 1.5 μg gRNA were mixed in 20 μl and incubated at 37° C. or room temperature for 15 minutes to form ribonucleoprotein (RNP). Then RNP was transfected into T cells by Lonza 4D Nucleofector®. Gene knockout efficiency was determined by the ratio of the cells expressing the protein as detected by flow cytometry. gRNA targeting sequences used are as below:

```
TRAC-gRNA1:
                                    SEQ ID NO: 20
TTCGGAACCCAATCACTGAC,
```

-continued

```
TRAC-gRNA2:
                                    SEQ ID NO: 21
TCAGGGTTCTGGATATCTGT,

TRAC-gRNA3:
                                    SEQ ID NO: 22
AAGTTCCTGTGATGTCAAGC,

CD137-gRNA1:
                                    SEQ ID NO: 45
AACGTGGCATCTGTCGACCC,

CD137-gRNA2:
                                    SEQ ID NO: 46
GCGCTGGAGAAACTATTTGG,

CD137-gRNA3:
                                    SEQ ID NO: 47
ACATTTAACGATCAGAAACG,

CD137-gRNA4:
                                    SEQ ID NO: 48
GGTCCTTTGTCCACCTGCGC,

CD137-gRNA5:
                                    SEQ ID NO: 49
GAGAAACTATTTGGAGGACA,

CD137-gRNA6:
                                    SEQ ID NO: 50
GGAGAAACTATTTGGAGGAC,
```

After screening, gRNA with high knockout efficiency was found for each gene and high efficiency was also observed when knocking out two genes, TCR/CD137.

7.3 Preparation of CAR-T Cells

Cell Isolation and Activation

After apheresis, monocytes were isolated using Histopaque®-1077 (Sigma-Aldrich) by density gradient centrifugation. Then T cells were enriched, activated by magnetic beads coupled with anti-CD3/anti-CD28, cultured and expanded. 4 X-vivo™ 15 with 5% FBS, 2 mM L-glutamine, 1 mM sodium pyruvate and 300 IU/ml rhIL2 was used as CAR-T cell medium. The cells were incubated and cultured at 37° C., 5% $CO_2$.

Allogeneic T cells were activated by using anti-CD3/anti-CD28 magnetic beads.

Allogeneic PBNK cells were activated by co-culturing K562 cells with PBNKs.

The expression of CD137 on the cell surface before and after the activation was determined by flow cytometry.

Electroporation and Lentivirus Infection

Two days after enriching and activating the T cells, the anti-CD3/anti-CD28 magnetic beads were removed and the cells were collected into a tube and subject to centrifuge at 300 g for 5 min, and then washed twice with DPBS and re-suspended in opti-mem at a cell density of 50×106/ml. The amount of cas9/gRNA RNP required was calculated based on the density of the cells, and then mixed with cells and transferred for electroporation by 4D-Nucleofector® System N (Lonza) system. Then the cells were re-suspended in a pre-warmed medium to a density of 1-2×106/ml. The cells were further subject to lentiviral transfection at MOI of 2-8, and then transferred to a flask and cultured in an incubator at 37° C., 5% $CO_2$.

Figure 53:
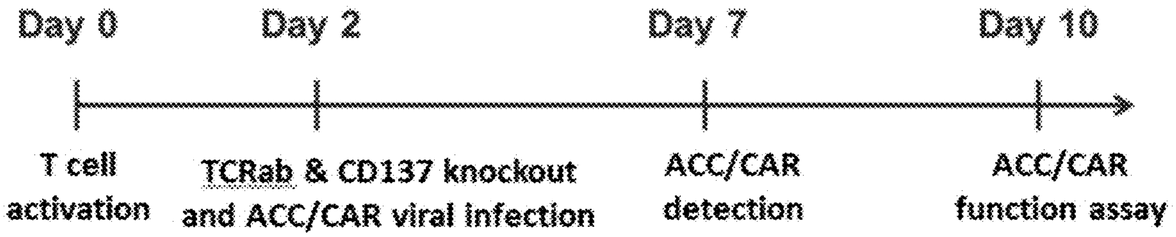
FIG. 53 illustrates an example preparing process of CD137-CD19 universal CAR-T.

Cell Proliferation and Detection of CAR Positive Ratio 4 days after the transfection, the number of cells and CAR positive cells were detected, and the positive ratio of CAR in T cells was calculated. The positive ratio of TCR (or CD3) and CD137 was also detected to determine the knockout efficiency. Then cells were continuously cultured in the incubator and half of the medium was replaced every 2-3 days till day 10 when the cells were ready for cryopreservation. An example workflow is shown in FIG. 53.

The result shows that positive ratio of CAR and negative ratio of CD3 were both high in the prepared CD19-CD137 CAR-T cells.

7.4 In Vitro Killing Effect and Release of the Cytokines

The dual CAR-T cells prepared in Example 7.3 and CFSE labeled CD19 positive tumor cells (Raji) and CD137 positive cells (activated allogeneic T cells or activated allogeneic PBNK or NK92), 100 ul each, were mixed in RPMI medium at 1:1 ratio to a density of $1\times10^6$/ml for each cell, and then cultured from overnight to 1 week in a 96-well plate. The number of CAR-T cells and CFSE-labeled target cells was detected by flow cytometry, so that to determine the killing effect between CAR-T cells and target cells during co-culture. Furthermore, the co-culture medium was also collected and subject to centrifuge and the released cytokine IFN-γ and IL-2 were detected by Cytokine bead array kit (CBA kit, BD Biosciences).

The result shows that incubation of CD19-CD137 CAR-T cells with Raji, allo-T or allo-NK cells produces a large amount of IFN-γ and IL-2, indicating function of CAR-T against CD19 positive or CD137 positive target cells. The flowcytometry result also indicates that the killing effects of allo-T and allo-NK on CD19-CD137 dual CAR T cells were significantly less than that on CD19 single CAR T cells.

Additional experiments show that CD19-CD137 dual CAR T cells only clear CD137 positive cells and NK cells, but fails to show any significant killing effect on CD137 negative inactivated T cells or NK cells, indicating the specificity of CD137 CAR.

7.5 In Vivo Efficacy 6-12 weeks NOD/Shi-scid/IL-2Rγnull (NOG) mice were selected and intravenously injected with 2×10' Raji-ffluc cells and allo-T cells. 5 days later, the tumor graft burden of the mice was measured, and the mice were divided into 4 groups based on the tumor burden. One day later, 200 μL DPBS, $0.5\times10^6$ CD19 CAR-T cells and $0.5\times10^6$ CD19-CD137 CAR-T cells were respectively injected to each mouse. The tumor burden of the mice was further evaluated every 7 days after the CAR-T treatment. Each mouse was injected intraperitoneally with 3 mg d-luciferin for a 4-minutes reaction, and then photographed using a Xenogen IVIS® Imaging System with 30 s exposure.

The result shows that CD19-CD137 CAR-T significantly decreased the tumor burden compared to CD19 CAR-T cells, and CD19-CD137 CAR-T cells showed significant better in vivo expansion than CD19 CAR-T cells, indicating the CD19-CD137 CAR-T cells survive better and have a stronger ability to clear CD19 positive tumor cells in vivo.

7.6 In Vivo GVHD Study

The mice were systemically treated with a sub-lethal dose of irradiation (175 cGy) first. Then CAR-T cells were re-suspended in PBS and injected into the thorax of the treated mice. The mice were observed 2-3 times a week by using GVHD clinical criteria including weight loss, arch-back, activity, fur texture, and skin integrity.

The result shows that mice without TCR knockout all showed GVHD symptoms, however, no GVHD was detected in the TCR/CD137 dual knockout CD19-CD137 CAR-T cell group.

7.7 Additional Sequences Used in Constructing CARs as Described Herein 4-1BB-L (SEQ ID NO: 51)

MEYASDASLDPEAPWPPAPRARACRVLPWALVAGLLLLLLLAAACAVFLACP

WAVSGARASPGSAASPRLREGPELSPDDPAGLLDLRQGMFAQLVAQNVLLIDGPLSWY

SDPGLAGVSLTGGLSYKEDTKELVVAKAGVYYVFFQLELRRVVAGEGSGSVSLALHLQ

PLRSAAGAAALALTVDLPPASSEARNSAFGFQGRLLHLSAGQRLGVHLHTEARARHAW

QLTQGATVLGLFRVTPEIPAGLPSPRSE 4-1BB PF-05082566 scFv VH (SEQ ID NO: 52)

EVQLVQSGAEVKKPGESLRISCKGSGYSFSTYWISWVRQMPGKGLEWMGKIYP

GDSYTNYSPSFQGQVTISADKSISTAYLQWSSLKASDTAMYYCARGYGIFDYWGQGTL

VTVSS 4-1BB PF-05082566 scFv VL (SEQ ID NO: 53)

MSYELTQPPSVSVSPGQTASITCSGDNIGDQYAHWYQQKPGQSPVLVIYQDKN

RPSGIPERFSGSNSGNTATLTISGTQAMDEADYYCATYTGFGSLAVFGGGTKLTVL 4-1BB BMS-663513 scFv VH (SEQ ID NO: 54)

QVQLQQWGAG LLKPSETLSL TCAVYGGSFS GYYWSWIRQS PEKGLEWIGE

INHGGYVTYNPSLESRVTIS VDTSKNQFSL KLSSVTAADT AVYYCARDYG

PGNYDWYFDLWGRGTLVTVSS 4-1BB BMS-663513 scFv VL (SEQ ID NO: 55)

EIVLTQSPAT LSLSPGERAT LSCRASQSVS SYLAWYQQKP GQAPRLLIYD

ASNRATGIPARFSGSGSGTD FTLTISSLEP EDFAVYYCQQ RSNWPPALTF

CGGTKVEIKR

-continued

AAC VL-VH (SEQ ID NO: 56)

MALPVTALLLPLALLLHAARPMSYELTQPPSVSVSPGQTASITCSGDNIGDQYA
HWYQQKPGQSPVLVIYQDKNRPSGIPERFSGSNSGNTATLTISGTQAMDEADYYCATYT
GFGSLAVFGGGTKLTVLGSTSGSGKPGSGEGSTKGEVQLVQSGAEVKKPGESLRISCKG
SGYSFSTYWISWVRQMPGKGLEWMGKIYPGDSYTNYSPSFQGQVTISADKSISTAYLQ
WSSLKASDTAMYYCARGYGIFDYWGQGTLVTVSSSGTTTPAPRPPTPAPTIASQPLSLRP
EACRPAAGGAVHTRGLDFACDIYIWAPLAGTCGVLLLSLVITLYCKRGRKKLLYIFKQP
FMRPVQTTQEEDGCSCRFPEEEEGGCELRVKFSRSADAPAYKQGQNQLYNELNLGRRE
EYDVLDKRRGRDPEMGGKPRRKNPQEGLYNELQKDKMAEAYSEIGMKGERRRGKGH
DGLYQGLSTATKDTYDALHMQALPPR*

AAC DNA sequence VL-VH (SEQ ID NO: 57)

ATGGCCCTGCCCGTGACCGCCCTGCTGCTGCCCCTGGCCCTGCTGCTGCACG
CCGCCAGGCCCATGAGCTACGAGCTGACCCAGCCCCCCAGCGTGAGCGTGAGCCCC
GGCCAGACCGCCAGCATCACCTGCAGCGGCGACAACATCGGCGACCAGTACGCCCA
CTGGTACCAGCAGAAGCCCGGCCAGAGCCCCGTGCTGGTGATCTACCAGGACAAGA
ACAGGCCCAGCGGCATCCCCGAGAGGTTCAGCGGCAGCAACAGCGGCAACACCGC
CACCCTGACCATCAGCGGCACCCAGGCCATGGACGAGGCCGACTACTACTGCGCCA
CCTACACCGGCTTCGGCAGCCTGGCCGTGTTCGGCGGCGGCACCAAGCTGACCGTG
CTGGGCAGCACCAGCGGCAGCGGCAAGCCCGGCAGCGGCGAGGGCAGCACCAAGG
GCGAGGTGCAGCTGGTGCAGAGCGGCGCCGAGGTGAAGAAGCCCGGCGAGAGCCT
GAGGATCAGCTGCAAGGGCAGCGGCTACAGCTTCAGCACCTACTGGATCAGCTGGG
TGAGGCAGATGCCCGGCAAGGGCCTGGAGTGGATGGGCAAGATCTACCCCGGCGA
CAGCTACACCAACTACAGCCCCAGCTTCCAGGGCCAGGTGACCATCAGCGCCGACA
AGAGCATCAGCACCGCCTACCTGCAGTGGAGCAGCCTGAAGGCCAGCGACACCGCC
ATGTACTACTGCGCCAGGGGCTACGGCATCTTCGACTACTGGGGCCAGGGCACCCT
GGTGACCGTGAGCAGCAGCGGCACCACCACCCCCGCCCCCAGGCCCCCCACCCCCG
CCCCCACCATCGCCAGCCAGCCCCTGAGCCTGAGGCCCGAGGCCTGCAGGCCCGCC
GCCGGCGGCGCCGTGCACACCAGGGGCCTGGACTTCGCCTGCGACATCTACATCTG
GGCCCCCCTGGCCGGCACCTGCGGCGTGCTGCTGCTGAGCCTGGTGATCACCCTGTA
CTGCAAGAGGGGCAGGAAGAAGCTGCTGTACATCTTCAAGCAGCCCTTCATGAGGC
CCGTGCAGACCACCCAGGAGGAGGACGGCTGCAGCTGCAGGTTCCCCGAGGAGGA
GGAGGGCGGCTGCGAGCTGAGGGTGAAGTTCAGCAGGAGCGCCGACGCCCCCGCC
TACAAGCAGGGCCAGAACCAGCTGTACAACGAGCTGAACCTGGGCAGGAGGGAGG
AGTACGACGTGCTGGACAAGAGGAGGGGCAGGGACCCCGAGATGGGCGGCAAGCC
CAGGAGGAAGAACCCCCAGGAGGGCCTGTACAACGAGCTGCAGAAGGACAAGATG
GCCGAGGCCTACAGCGAGATCGGCATGAAGGGCGAGAGGAGGAGGGGCAAGGGCC
ACGACGGCCTGTACCAGGGCCTGAGCACCGCCACCAAGGACACCTACGACGCCCTG
CACATGCAGGCCCTGCCCCCCAGGTGA

-continued

AAC VH-VL (SEQ ID NO: 58)

ATGGCCCTGCCCGTGACCGCCCTGCTGCTGCCCCTGGCCCTGCTGCTGCACG

CCGCCAGGCCCGAGGTGCAGCTGGTGCAGAGCGGCGCCGAGGTGAAGAAGCCCGG

CGAGAGCCTGAGGATCAGCTGCAAGGGCAGCGGCTACAGCTTCAGCACCTACTGGA

TCAGCTGGGTGAGGCAGATGCCCGGCAAGGGCCTGGAGTGGATGGGCAAGATCTAC

CCCGGCGACAGCTACACCAACTACAGCCCCAGCTTCCAGGGCCAGGTGACCATCAG

CGCCGACAAGAGCATCAGCACCGCCTACCTGCAGTGGAGCAGCCTGAAGGCCAGCG

ACACCGCCATGTACTACTGCGCCAGGGGCTACGGCATCTTCGACTACTGGGGCCAG

GGCACCCTGGTGACCGTGAGCAGCGGCAGCACCAGCGGCAGCGGCAAGCCCGGCA

GCGGCGAGGGCAGCACCAAGGGCATGAGCTACGAGCTGACCCAGCCCCCCAGCGT

GAGCGTGAGCCCCGGCCAGACCGCCAGCATCACCTGCAGCGGCGACAACATCGGCG

ACCAGTACGCCCACTGGTACCAGCAGAAGCCCGGCCAGAGCCCCGTGCTGGTGATC

TACCAGGACAAGAACAGGCCCAGCGGCATCCCCGAGAGGTTCAGCGGCAGCAACA

GCGGCAACACCGCCACCCTGACCATCAGCGGCACCCAGGCCATGGACGAGGCCGAC

TACTACTGCGCCACCTACACCGGCTTCGGCAGCCTGGCCGTGTTCGGCGGCGGCACC

AAGCTGACCGTGCTGAGCGGCACCACCACCCCCGCCCCCAGGCCCCCCACCCCCGC

CCCCACCATCGCCAGCCAGCCCCTGAGCCTGAGGCCCGAGGCCTGCAGGCCCGCCG

CCGGCGGCGCCGTGCACACCAGGGGCCTGGACTTCGCCTGCGACATCTACATCTGG

GCCCCCCTGGCCGGCACCTGCGGCGTGCTGCTGCTGAGCCTGGTGATCACCCTGTAC

TGCAAGAGGGGCAGGAAGAAGCTGCTGTACATCTTCAAGCAGCCCTTCATGAGGCC

CGTGCAGACCACCCAGGAGGAGGACGGCTGCAGCTGCAGGTTCCCCGAGGAGGAG

GAGGGCGGCTGCGAGCTGAGGGTGAAGTTCAGCAGGAGCGCCGACGCCCCCGCCT

ACAAGCAGGGCCAGAACCAGCTGTACAACGAGCTGAACCTGGGCAGGAGGGAGGA

GTACGACGTGCTGGACAAGAGGAGGGGCAGGGACCCCGAGATGGGCGGCAAGCCC

AGGAGGAAGAACCCCCAGGAGGGCCTGTACAACGAGCTGCAGAAGGACAAGATGG

CCGAGGCCTACAGCGAGATCGGCATGAAGGGCGAGAGGAGGAGGGGCAAGGGCCA

CGACGGCCTGTACCAGGGCCTGAGCACCGCCACCAAGGACACCTACGACGCCCTGC

ACATGCAGGCCCTGCCCCCCAGGTGA

FMC63 VH (SEQ ID NO: 59)

EVKLQESGPGLVAPSQSLSVTCTVSGVSLPDYGVSWIRQPPRKGLEWLGVIWGS

ETTYYNSALKSRLTIIKDNSKSQVFLKMNSLQTDDTAIYYCAKHYYYGGSYAMDYWG

QGTSVTVSS

FMC63 VL (SEQ ID NO: 60)

DIQMTQTTSSLSASLGDRVTISCRASQDISKYLNWYQQKPDGTVKLLIYHTSRL

HSGVPSRFSGSGSGTDYSLTISNLEQEDIATYFCQQGNTLPYTFGGGTKLEIT

FMC63 CD19 CAR (SEQ ID NO: 61)

MALPVTALLLPLALLLHAARPDIQMTQTTSSLSASLGDRVTISCRASQDISKYLN

WYQQKPDGTVKLLIYHTSRLHSGVPSRFSGSGSGTDYSLTISNLEQEDIATYFCQQGNTL

PYTFGGGTKLEITGSTSGSGKPGSGEGSTKGEVKLQESGPGLVAPSQSLSVTCTVSGVSL

PDYGVSWIRQPPRKGLEWLGVIWGSETTYYNSALKSRLTIIKDNSKSQVFLKMNSLQTD

-continued

DTAIYYCAKHYYYGGSYAMDYWGQGTSVTVSSSGTTTPAPRPPTPAPTIASQPLSLRPE

ACRPAAGGAVHTRGLDFACDIYIWAPLAGTCGVLLLSLVITLYCKRGRKKLLYIFKQPF

MRPVQTTQEEDGCSCRFPEEEEGGCELRVKFSRSADAPAYKQGQNQLYNELNLGRREE

YDVLDKRRGRDPEMGGKPRRKNPQEGLYNELQKDKMAEAYSEIGMKGERRRGKGHD

GLYQGLSTATKDTYDALHMQALPPR*

Example 8 Study of U-CAR T Cells Expressing E4

Figure 59A:
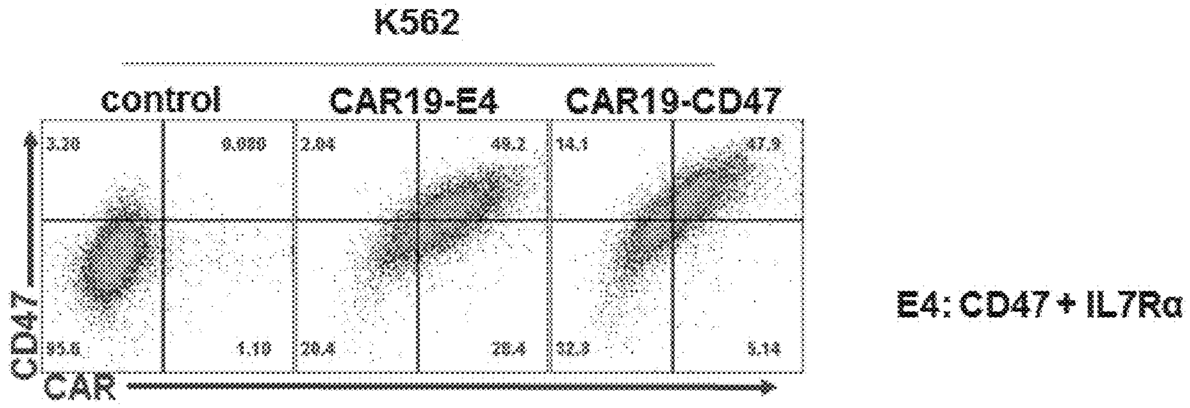
FIGS. 59A and 59B illustrate experimental data of K562-CAR19 profiling and natural killer (NK) cell killing assay.
Figure 59B:
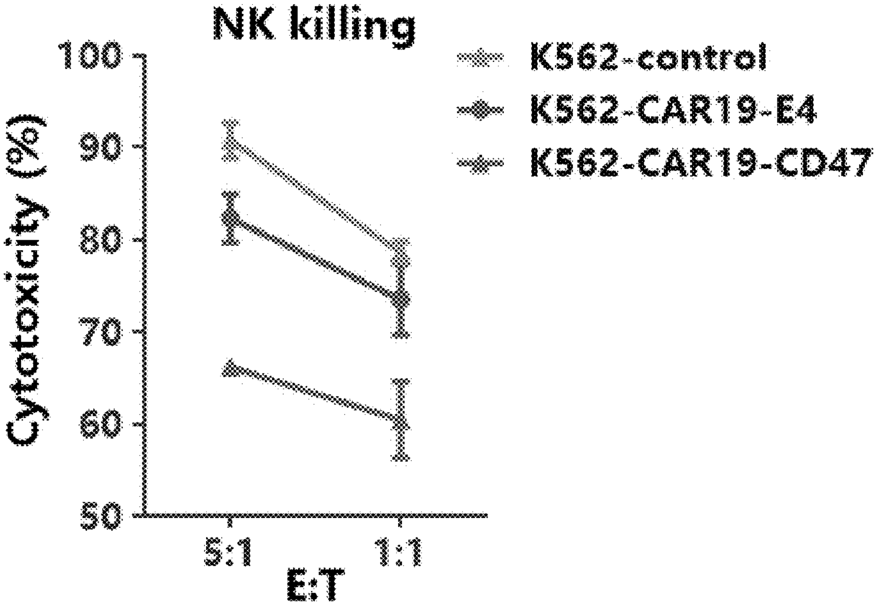

FIG. 59A shows flow cytometry data of fractions of CD19 CAR-T cells expressing enhancer CD47 (CAR19-CD47) or E4 (CAR19-E4). In the E4 design, the ecto domain of C7R is replaced by the ecto domain from an immune cell inhibitor, such as CD47, CD24 or other peptides that inhibit killer or phagocytic immune cell function and protect therapeutic cells. The CAR19-CD47 or CAR19-E4 was expressed in K562 cells, which lacks MHCI/II expression and are very sensitive to NK cell killing due to lack of MHC expression. Expression of CAR19 and CD47 were analyzed by flow cytometry. FIG. 59B shows NK cell killing activity toward CAR19-CD47 and CAR19-E4 cells. Both CD47 and E4 were able to reduce the extent of NK cell killing for K562 cells. The data show that E4 may protect MHCI negative cells from killing by NK cells, which may be used in protection of MHCI KO CAR-T cells.

Figure 60A:
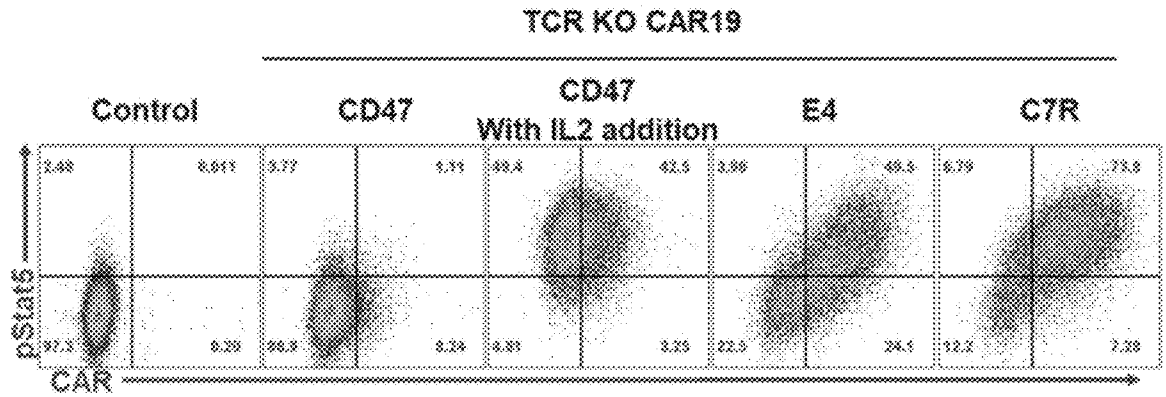
FIGS. 60A and 60B illustrate experimental data showing STAT5 phosphorylation and cell persistence of UCART19 cells (e.g., CAR-T cells having CARs targeting CD19, also referred to as CD19 CAR-T cells or CAR19 cells).
Figure 60B:
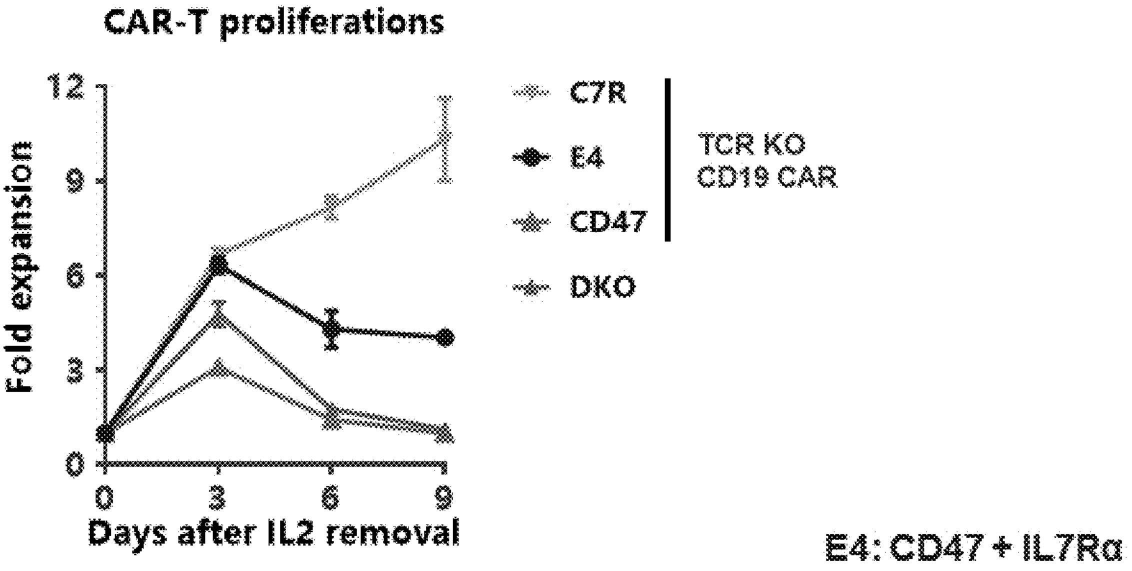

FIG. 60A shows flow cytometry data of fractions of TCR KO CD19 CAR-T cells expressing CD19 and phosphorylated STAT5 (pSTAT5). The CAR19-CD47 or CAR19-E4 was expressed in TCR knockout T cells and accessed for CAR expression and STAT5 phosphorylation. CAR19-E2 and CAR19-CD47 plus IL2 stimulation were used as positive controls. E4 mediates up-regulation of pSTAT5. FIG. 60B shows proliferation of TCR KO CD19 CAR-T cells expressing enhancer CD47 (CAR19-CD47) or E4 (CAR19-E4). The CAR19-CD47, CAR19-E4, CAR19-C7R expressing TCR knockout T cells were compared for cell proliferation and cell survival without IL12 supplement. E4 can mediate stronger cell proliferation as well as maintenance of cell number after removal of IL2 in culture media. The E4 maintains better CAR-T cell stability without IL2 addition. E4 may protect therapeutic cells, such as cells that with HLA-I KO, from NK cell killing or killing by phagocytes and T killer cells.

Sequence of construct design: the etco domain of C7R can replaced by an immune cell inhibitor, such as truncated CD47, CD24, that can inhibit a killer or phagocytic immune cell function and protect the CAR-T/NK cells from being attached by patient's immune system.

CD7CAR-E4 amino acid sequence:

(SEQ ID NO: 103)

MLLLVTSLLLCELPHPAFLLIPQLLFNKTKSVEFTFCNDTVVIPCFVTN

MEAQNTTEVYVKWKFKGRDIYTFDGALNKSTVPTDFSSAKIEVSQLLKG

DASLKMDKSDAVSHTGNYTCEVTELTREGETIIELKYRVVSWFSPNEPI

LLTCPTISILSFFSVALLVILACVLWKKRIKPIVWPSLPDHKKTLEHLC

KKPRKNLNVSFNPESFLDCQIHRVDDIQARDEVEGFLQDTFPQQLEESE

KQRLGGDVQSPNCPSEDVVITPESFGRDSSLTCLAGNVSACDAPILSSS

-continued

RSLDCRESGKNGPHVYQDLLLSLGTTNSTLPPPFSLQSGILTLNPVAQG

QPILTSLGSNQEEAYVTMSSFYQNQ.

Example 9 Clinical Data of CAR7-C7R for Treating T-Acute Lymphoblastic Leukemia (T-ALL) Patients This example provides clinical study designs and clinical data using CAR7-C7R. Patients were enrolled with tumor burden at the enrollment that 38.2% of bone marrow cells were T-ALL cells. Before infusing the CAR7-C7R cells, the patients were treated with pre-conditional regimen. The pre-conditional regimen used chemotherapy drug including fludarabine, cyclophosphamide and etoposide for lymphodepletion. The pre-conditional regimen can provide better CAR-T engraftment and tumor clearance. Two days after completion of lymphodepletion regimen, CAR7-C7R cells were intravenously infused into patients at $1.5\times10^7$/kg. CAR7-C7R rapidly eliminated cancer cells (T-ALL cells) and expanded to the peak around 7-10 days, without affecting innate immune cell subsets such as granulocytes and monocytes. Once cancer cells were completely cleared in both the peripheral blood and in the bone marrow, CAR7-C7R cells very quickly return to minimal level, which allows patients' own immune system to start recovery immediately after cancer cell clearance. T cells and NK cells then gradually recover to normal levels.

FIG. 67 shows the clinical data of CAR7-C7R for treating T-acute lymphoblastic leukemia (T-ALL) patients. The construct of CAR7-C7R used in the clinical studies is shown in FIG. 17. FIG. 67A shows the kinetics of T-ALL elimination in the peripheral blood. T-ALL cells were quickly eliminated within 7-10 days. T-ALL cell concentration were measured in the peripheral blood by flow cytometry. FIGS. 67 B and C shows the CAR7-C7R cell expansion kinetics, where FIG. 67B shows the CAR7-C7R cell concentration in the peripheral blood and FIG. 67C shows CAR7-C7R DNA copy/ug DNA of peripheral blood cells. FIGS. 67 D and E shows the granulocyte and lymphocyte (T and NK cells) recovery in the bone marrow and in peripheral blood.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configu rations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

SEQUENCE LISTING

```
Sequence total quantity: 103
SEQ ID NO: 1           moltype = AA  length = 1138
FEATURE                Location/Qualifiers
REGION                 1..1138
                       note = Description of Artificial Sequence:
                        Syntheticpolypeptide
source                 1..1138
                       mol_type = protein
                       organism = synthetic construct
SEQUENCE: 1
MLLLVTSLLL CELPHPAFLL IPRKVCNGIG IGEFKDSLSI NATNIKHFKN CTSISGDLHI  60
LPVAFRGDSF THTPPLDPQE LDILKTVKEI TGFLLIQAWP ENRTDLHAFE NLEIIRGRTK  120
QHGQFSLAVV SLNITSLGLR SLKEISDGDV IISGNKNLCY ANTINWKKLF GTSGQKTKII  180
SNRGENSCKA TGQVCHALCS PEGCWGPEPR DCVSCRNVSR GRECVDKCNL LEGEPREFVE  240
NSECIQCHPE CLPQAMNITC TGRGPDNCIQ CAHYIDGPHC VKTCPAGVMG ENNTLVWKYA  300
DAGHVCHLCH PNCTYGCTGP GLEGCPTNGP KIPSIATGMV GALLLLLVVA LGIGLFMRAK  360
RGSGATNFSL LKQAGDVEEN PGPMALPVTA LLLPLALLLH AARPQVQLQQ SGAELARPGA  420
SVKMSCKASG YTFTRYTMHW VKQRPGQGLE WIGYINPSRG YTNYNQKFKD KATLTTDKSS  480
STAYMQLSSL TSEDSAVYYC ARYYDDHYCL DYWGQGTTLT VSSGSTSGGG SGGGSGGGGS  540
SQIVLTQSPA IMSASPGEKV TMTCSASSSV SYMNWYQQKS GTSPKRWIYD TSKLASGVPA  600
HFRGSGSGTS YSLTISGMEA EDAATYYCQQ WSSNPFTFGS GTKLEINRGG GGSGGGGSGG  660
GGSDIQMTQT TSSLSASLGD RVTISCRASQ DISKYLNWYQ QKPDGTVKLL IYHTSRLHSG  720
VPSRFSGSGS GTDYSLTISN LEQEDIATYF CQQGNTLPYT FGGGTKLEIT GSTSGSGKPG  780
SGEGSTKGEV KLQESGPGLV APSQSLSVTC TVSGVSLPDY GVSWIRQPPR KGLEWLGVIW  840
GSETTYYNSA LKSRLTIIKD NSKSQVFLKM NSLQTDDTAI YYCAKHYYYG GSYAMDYWGQ  900
GTSVTVSSAA ADYKDDDDKI EVMYPPPYLD NEKSNGTIIH VKGKHLCPSP LFPGPSKPFW  960
VLVVVGGVLA CYSLLVTVAF IIFWVRSKRS RLLHSDYMNM TPRRPGPTRK HYQPYAPPRD  1020
FAAYRSRVKF SRSADAPAYQ QGQNQLYNEL NLGRREEYDV LDKRRGRDPE MGGKPRRKNP  1080
QEGLYNELQK DKMAEAYSEI GMKGERRRGK GHDGLYQGLS TATKDTYDAL HMQALPPR    1138

SEQ ID NO: 2           moltype = DNA  length = 3417
FEATURE                Location/Qualifiers
misc_feature           1..3417
                       note = Description of Artificial Sequence:
                        Syntheticpolynucleotide
source                 1..3417
                       mol_type = other DNA
                       organism = synthetic construct
SEQUENCE: 2
atgttgctcc ttgtgacgag cctcctgctc tgcgagctgc cccatccagc cttcctcctc  60
atcccgcgga aggtgtgcaa tggcataggc attggcgagt ttaaagattc tctgagcata  120
aatgctacga atattaagca tttcaagaat tgtacttcta ttagtggcga cctccatatt  180
cttccggttg ccttcagggg tgactctttc acccacacac ctccattgga tccacaagaa  240
cttgacatcc tgaagacggt taaagagatt acaggcttcc tccttatcca agcgtggccc  300
gagaacagaa cggacttgca cgcctttgag aacctcgaaa taatacgggg tcggacgaag  360
caacacggcc aatttagcct tgcggttgtt agtctgaaca ttacttctct cggccttcgc  420
tctttgaaag aaatcagcga cggagatgtc atcattagtg gaaacaagaa cctgtgctac  480
gcgaacacaa tcaactggaa gaagctcttc ggtacttcag gccaaaagac aaagattatt  540
agtaacagag gagagaatag ctgtaaggct accggacaag tttgtcacgc cttgtgtagt  600
ccagagggtt gctggggacc ggaaccaagg gattgcgtca gttgccggaa cgtgagtcgc  660
ggacgcgagt gtgtggataa gtgcaatctt ctggaagggg aaccgcgaga gtttgtagaa  720
aattccgaat gtatacagtg tcatcccgag tgtcttccac aagcaatgaa tatcacatgt  780
acagggaggg gtcctgataa ctgtatccaa tgtgcacact acatagatgg tcctcactgt  840
gtaaagacgt gccccgccgg agtaatgggt gaaaacaaca ccctcgtgtg gaagtacgcc  900
gatgccgggc atgtctgtca tttgtgtcat cccaactgca catatggctg taccggtcct  960
ggattggagg gctgtccaac aaacgggccg aaaataccga gtatcgcaac aggcatggtg  1020
ggagcacttt tgcttctcct cgttgtcgcc ctgggcatcg gcttgttcat gcgagctaaa  1080
cgaggctcag gcgcgacgaa ctttagtttg ctgaagcaag ctggggatgt agaggaaaat  1140
ccgggtccca tggcccttcc agtgacagcc ttgttgttgc cacttgctct gctgctccac  1200
gctgcgcggc cacaggtcca gttgcagcag tcaggcgccg aattggcgcg accaggggca  1260
agcgtaaaga tgagctgtaa ggcatccggg tacacgttca ctcgctatac catgcattgg  1320
gttaaacaac ggcctgggca gggccttgag tggattgggt atatcaaccc atcccggggc  1380
tacactaact ataatcaaaa gtttaaagat aaagcaaccc ttacgaccga caaatcatct  1440
tctaccgcat acatgcagct cagctccctc accagtgaag attctgccgt ttattattgt  1500
gcacgatact atgacgatca ctattgcctg gactactggg gtcaaggcac cacacttact  1560
gtcagttccg gaagtaccag tgggggaggt tctggcggtg gcagcggggg tgggggtagc  1620
tcacaaatcg tgctgaccca gagtcccgct atcatgagcg cctccccagg ggaaaaggtg  1680
acgatgacat gctcagccag ctccagtgta tcctacatga attggtatca acagaagagt  1740
gggacgtcac ccaaaagatg gatttatgac accagcaaat tggccagcgg agtaccagcg  1800
catttcagag gcagtgggag tggaacatct tattctctca ccattagcgg catggaagca  1860
gaggatgcag caacgtacta ttgtcaacaa tggagctcta atccctttac gttcggcagc  1920
```

-continued

```
ggcactaagc tcgaaattaa taggggtggc ggcggctccg gcggtggcgg gtctggaggt  1980
gggggcagtg acatccagat gacacagact acatcctccc tgtctgcctc tctgggagac  2040
agagtcacca tcagttgcag ggcaagtcag gacattagta aatatttaaa ttggtatcag  2100
cagaaaccag atggaactgt taaactcctg atctaccata catcaagatt acactcagga  2160
gtcccatcaa ggttcagtgg cagtgggtct ggaacagatt attctctcac cattagcaac  2220
ctggagcaag aagatattgc cacttacttt tgccaacagg gtaatacgct tccgtacacg  2280
ttcggagggg ggactaagtt ggaaataaca ggctccacct ctggatccgg caagcccgga  2340
tctggcgagg gatccaccaa gggcgaggtg aaactgcagg agtcaggacc tggcctggtg  2400
gcgccctcac agagcctgtc cgtcacatgc actgtctcag gggtctcatt acccgactat  2460
ggtgtaagct ggattcgcca gcctccacga aagggtctgg agtggctggg agtaatatgg  2520
ggtagtgaaa ccacatacta taattcagct ctcaaatcca gactgaccat catcaaggac  2580
aactccaaga gccaagtttt cttaaaaatg aacagtctgc aaactgatga cacagccatt  2640
tactactgtg ccaaacatta ttactacggt ggtagctatg ctatggacta ctggggtcaa  2700
ggaacctcag tcaccgtctc ctcagcggcc gcagactaca aagacgatga cgacaagatt  2760
gaagttatgt atcctcctcc ttacctagac aatgagaaga gcaatggaac cattatccat  2820
gtgaaaggga aacacctttg tccaagtccc ctatttcccg gaccttctaa gccctttttgg  2880
gtgctggtgg tggttggggg agtcctggct tgctatagct tgctagtaac agtggccttt  2940
attattttct gggtgaggag taagaggagc aggctcctgc acagtgacta catgaacatg  3000
actccccgcc gccccgggcc cacccgcaag cattaccagc cctatgcccc accacgcgac  3060
ttcgcagcct atcgctccag agtgaagttc agcaggagcg cagacgcccc cgcgtaccag  3120
cagggccaga accagctcta taacgagctc aatctaggac gaagagagga gtacgatgtt  3180
ttggacaaga gacgtggccg ggaccctgag atggggggaa agccgagaag gaagaaccct  3240
caggaaggcc tgtacaatga actgcagaaa gataagatgg cggaggccta cagtgagatt  3300
gggatgaaag gcgagcgccg gaggggcaag gggcacgatg gcctttacca gggtctcagt  3360
acagccacca aggacaccta cgacgccctt cacatgcagg ccctgccccc tcgctaa     3417

SEQ ID NO: 3            moltype = AA  length = 1138
FEATURE                 Location/Qualifiers
REGION                  1..1138
                        note = Description of Artificial Sequence:
                         Syntheticpolypeptide
source                  1..1138
                        mol_type = protein
                        organism = synthetic construct
SEQUENCE: 3
MLLLVTSLLL CELPHPAFLL IPRKVCNGIG IGEFKDSLSI NATNIKHFKN CTSISGDLHI  60
LPVAFRGDSF THTPPLDPQE LDILKTVKEI TGFLLIQAWP ENRTDLHAFE NLEIIRGRTK  120
QHGQFSLAVV SLNITSLGLR SLKEISDGDV IISGNKNLCY ANTINWKKLF GTSGQKTKII  180
SNRGENSCKA TGQVCHALCS PEGCWGPEPR DCVSCRNVSR GRECVDKCNL LEGEPREFVE  240
NSECIQCHPE CLPQAMNITC TGRGPDNCIQ CAHYIDGPHC VKTCPAGVMG ENNTLVWKYA  300
DAGHVCHLCH PNCTYGCTGP GLEGCPTNGP KIPSIATGMV GALLLLLVVA LGIGLFMRAK  360
RGSGATNFSL LKQAGDVEEN PGPMALPVTA LLLPLALLLH AARPDIQMTQ SPSSLSASVG  420
DRVTITCRAS QDIRNYLNWY QQKPGKAPKL LIYYTSRLES GVPSRFSGSG SGTDYTLTIS  480
SLQPEDFATY YCQQGNTLPW TFGQGTKVEI KGGGGSGGGG SGGGGSEVQL VESGGGLVQP  540
GGSLRLSCAA SGYSFTGYTM NWVRQAPGKG LEWVALINPY KGVSTYNQKF KDRFTISVDK  600
SKNTAYLQMN SLRAEDTAVY YCARSGYYGD SDWYFDVWGQ GTLVTVSSGG GGSGGGGSGG  660
GGSEVKLQES GPGLVAPSQS LSVTCTVSGV SLPDYGVSWI RQPPRKGLEW LGVIWGSETT  720
YYNSALKSRL TIIKDNSKSQ VFLKMNSLQT DDTAIYYCAK HYYYGGSYAM DYWGQGTSVT  780
VSSGSTSGSG KPGSGEGSTK GDIQMTQTTS SLSASLGDRV TISCRASQDI SKYLNWYQQK  840
PDGTVKLLIY HTSRLHSGVP SRFSGSGSGT DYSLTISNLE QEDIATYFCQ QGNTLPYTFG  900
GGTKLEITAA ADYKDDDDKI EVMYPPPYLD NEKSNGTIIH VKGKHLCPSP LFPGPSKPFW  960
VLVVVGGVLA CYSLLVTVAF IIFWVRSKRS RLLHSDYMNM TPRRPGPTRK HYQPYAPPRD  1020
FAAYRSRVKF SRSADAPAYQ QGQNQLYNEL NLGRREEYDV LDKRRGRDPE MGGKPRRKNP  1080
QEGLYNELQK DKMAEAYSEI GMKGERRRGK GHDGLYQGLS TATKDTYDAL HMQALPPR    1138

SEQ ID NO: 4            moltype = DNA  length = 3417
FEATURE                 Location/Qualifiers
misc_feature            1..3417
                        note = Description of Artificial Sequence:
                         Syntheticpolynucleotide
source                  1..3417
                        mol_type = other DNA
                        organism = synthetic construct
SEQUENCE: 4
atgctgctgc tcgtgacatc cctcttatta tgcgaactcc ctcaccccgc ttttctgctg  60
atccccagaa aggtgtgcaa cggcatcggc attggagagt tcaaggattc tttaagcatc  120
aacgctacca acatcaaaca tttcaagaac tgtacctcca tttccggcga tttacacatc  180
ctccccgttg cctttcgtgg cgatagcttc acacacacac cccctctgga ccctcaagaa  240
ctggacattt taaagaccgt gaaggagatc actggttttt tactgatcca agcttggccc  300
gaaaatagga cagatctcca cgctttcgag aatttagaga tcattcgtgg cagaaccaag  360
cagcacggac agttctcttt agccgtcgtg tctttaaata tcacctcttt aggtttaaga  420
tctttaaaag agatcagcga tggcgacgtc atcatctccg gcaacaagaa cctctgttac  480
gccaacacca ttaattggaa aaagctgttt ggcacctccg gacagaagac caagatcatc  540
agcaacagag gcgagaacag ctgcaaagct accggccaag tttgccacgc tctgtgtagc  600
cccgaaggct gctggggacc cgaacctcgt gactgtgtga gctgtaggaa cgtgtctcgt  660
ggtcgtgagt gtgtggataa gtgcaattta ctcgagggcg agcccagaga gtttgtggaa  720
aatagcgagt gcatccagtg ccaccccgaa tgtctgcccc aagctatgaa cattacttgt  780
actggtcgtg gccccgataa ctgtatccag tgcgctcact acattgacgg cccccactgc  840
gtcaagacat gccccgctgg cgtgatggga gaaaacaaca cactggtgtg gaagtatgcc  900
```

```
gatgccggcc acgtctgtca tctgtgccac cctaactgta cctacggctg taccggaccc  960
ggactggagg gctgtcccac caacggaccc aagatcccta gcatcgccac cggcatggtg  1020
ggagccttac tgctgttact ggtggtggct ctgggcattg gtttattcat gagggccaag  1080
agaggatccg gcgccaccaa cttttcttta ctgaaacaag ctggagacgt cgaggaaaac  1140
cccggaccca tggctctccc cgtgacagct ctgctgctgc ctctcgcttt attactgcac  1200
gccgctaggc ccgatattca gatgacccaa agccctagct ctttatccgc cagcgtcgga  1260
gatagagtca caatcacttg tagagccagc caagatattc gtaattatct caactggtac  1320
cagcagaagc ccggtaaagc ccccaagctg ctcatctatt acacctctcg tctggagagc  1380
ggcgtgcctt ccagattcag cggctccggc agcggcaccg actatacact caccattagc  1440
tctttacagc ccgaagattt cgctacctac tactgccagc aaggtaatac tttaccttgg  1500
accttcggcc aaggtaccaa ggtcgaaatc aagggcggcg gcggatccgg cggcggtgga  1560
tctggtggcg gcggctccga agtccagctg gtcgaatccg gaggcggact ggtccagccc  1620
ggtggatccc tcagactgag ctgcgccgct agcggctatt ccttcaccgg ctacaccatg  1680
aactgggtga gacaagctcc cggcaaagga ctggaatggg tggccctcat caacccctac  1740
aagggcgtgt ccacatataa tcaaaagttt aaggacagat tcaccatcag cgtcgacaag  1800
tccaagaaca ccgcttattt acagatgaac tctttaagag ctgaggatac cgccgtgtac  1860
tattgtgcta ggtccggcta ctacggcgac agcgactggt attttgacgt ctggggacaa  1920
ggtaccctcg tgacagtgag cagcggcggt ggcggttctg gcggcggagg ctccggagga  1980
ggcggcagcg aggtgaagct gcaagaaagc ggacccggtc tcgtggctcc ctcccaatct  2040
ttatccgtga cttgtaccgt gtccggagtc tctttacccg actacggcgt gagctggatt  2100
agacagcccc ccagaaaagg tttagagtgg ctgggcgtga tctggggatc cgagaccaca  2160
tactacaaca gcgctttaaa gtctcgtctg acaatcatca aagacaattc caaaagccaa  2220
gttttcctca agatgaactc tttacagacc gacgacacag ccatttacta ctgcgccaag  2280
cattattact acggcggcag ctacgctatg gactactggg gccaaggtac aagcgtcaca  2340
gtgagctccg gcagcacatc cggaagcgga aagcccggca gcggagaggg cagcacaaag  2400
ggagacatcc agatgaccca gaccacctcc tctttaagcg cctctttagg agatagggtg  2460
accattagct gcagagcctc ccaagacatc agcaagtatc tcaattggta ccagcaaaag  2520
cccgatggca ccgtcaagct gctgatctac cacacctctc gtctccattc cggcgtgccc  2580
agcagattta gcggaagcgg atccggaaca gactattctt taacaatcag caatttagag  2640
caagaagaca tcgccacata tttctgccaa caaggtaaca ctttacccta caccttcgga  2700
ggcggcacca aactggagat tacagcggcc gcagactaca aagacgatga cgacaagatt  2760
gaagttatgt atcctcctcc ttacctagac aatgagaaga gcaatggaac cattatccat  2820
gtgaaaggga aacacctttg tccaagtccc ctatttcccg gaccttctaa gcccttttgg  2880
gtgctggtgg tggttggggg agtcctggct tgctatagct tgctagtaac agtggccttt  2940
attattttct gggtgaggag taagaggagc aggctcctgc acagtgacta catgaacatg  3000
actccccgcc gccccgggcc cacccgcaag cattaccagc cctatgcccc accacgcgac  3060
ttcgcagcct atcgctccag agtgaagttc agcaggagcg cagacgcccc cgcgtaccag  3120
cagggccaga accagctcta taacgagctc aatctaggac gaagagagga gtacgatgtt  3180
ttggacaaga gacgtggccg ggaccctgag atggggggaa agccgagaag gaagaaccct  3240
caggaaggcc tgtacaatga actgcagaaa gataagatgg cggaggccta cagtgagatt  3300
gggatgaaag gcgagcgccg gaggggcaag gggcacgatg gcctttacca gggtctcagt  3360
acagccacca aggacaccta cgacgccctt cacatgcagg ccctgccccc tcgctaa     3417

SEQ ID NO: 5           moltype = DNA  length = 20
FEATURE                Location/Qualifiers
misc_feature           1..20
                       note = Description of Artificial Sequence:
                        Syntheticoligonucleotide
source                 1..20
                       mol_type = other DNA
                       organism = synthetic construct
SEQUENCE: 5
tgtgctagac atgaggtcta                                              20

SEQ ID NO: 6           moltype =   length =
SEQUENCE: 6
000

SEQ ID NO: 7           moltype = AA  length = 157
FEATURE                Location/Qualifiers
REGION                 1..157
                       note = Description of Artificial Sequence:
                        Syntheticpolypeptide
source                 1..157
                       mol_type = protein
                       organism = synthetic construct
SEQUENCE: 7
MGTSLLCWMA LCLLGADHAD ACPYSNPSLC SGGGGSELPT QGTFSNVSTN VSPAKPTTTA  60
CPYSNPSLCS GGGGSPAPRP PTPAPTIASQ PLSLRPEACR PAAGGAVHTR GLDFACDIYI  120
WAPLAGTCGV LLLSLVITLY CNHRNRRRVC KCPRPVV                           157

SEQ ID NO: 8           moltype = DNA  length = 534
FEATURE                Location/Qualifiers
misc_feature           1..534
                       note = Description of Artificial Sequence:
                        Syntheticpolynucleotide
source                 1..534
                       mol_type = other DNA
                       organism = synthetic construct
```

-continued

```
SEQUENCE: 8
atgggcacct ctctgctgtg ctggatggct ctgtgtctgc tgggcgctga ccatgctgat  60
gcttgcccct attccaaccc ctctctgtgc tccggaggag gaggatccga actgcctacc  120
caaggcacct tcagcaacgt gtccaccaac gtgagccccg ctaagcctac caccaccgct  180
tgcccttact ccaatcccag cctctgctcc ggaggcggag gatcccccgc ccccagacct  240
cctacacccg ctcccacaat cgccagccag cctctgtctc tgagacccga agcttgcaga  300
cccgctgccg gaggagctgt gcatacaaga ggactggatt tcgcttgcga catctacatc  360
tgggcccctc tggctggcac atgtggcgtg ctgctgctgt ctctggtcat tacactgtac  420
tgcaaccata gaaatagaag aagggtgtgc aagtgtccca gacccgtggt gggcagcgga  480
gaaggaagag gctctctgct gacatgcgga gacgtggaag agaaccccgg cccc        534

SEQ ID NO: 9           moltype = AA  length = 497
FEATURE                Location/Qualifiers
REGION                 1..497
                       note = Description of Artificial Sequence:
                        Syntheticpolypeptide
source                 1..497
                       mol_type = protein
                       organism = synthetic construct
SEQUENCE: 9
MLLLVTSLLL CELPHPAFLL IPDIQMTQTT SSLSASLGDR VTISCRASQD ISKYLNWYQQ  60
KPDGTVKLLI YHTSRLHSGV PSRFSGSGSG TDYSLTISNL EQEDIATYFC QQGNTLPYTF  120
GGGTKLEITG STSGSGKPGS GEGSTKGEVK LQESGPGLVA PSQSLSVTCT VSGVSLPDYG  180
VSWIRQPPRK GLEWLGVIWG SETTYYNSAL KSRLTIIKDN SKSQVFLKMN SLQTDDTAIY  240
YCAKHYYYGG SYAMDYWGQG TSVTVSSAAA DYKDDDDKIE VMYPPPYLDN EKSNGTIIHV  300
KGKHLCPSPL FPGPSKPFWV LVVVGGVLAC YSLLVTVAFI IFWVRSKRSR LLHSDYMNMT  360
PRRPGPTRKH YQPYAPPRDF AAYRSRVKFS RSADAPAYQQ GQNQLYNELN LGRREEYDVL  420
DKRRGRDPEM GGKPRRKNPQ EGLYNELQKD KMAEAYSEIG MKGERRRGKG HDGLYQGLST  480
ATKDTYDALH MQALPPR                                                 497

SEQ ID NO: 10          moltype = DNA  length = 1491
FEATURE                Location/Qualifiers
misc_feature           1..1491
                       note = Description of Artificial Sequence:
                        Syntheticpolynucleotide
source                 1..1491
                       mol_type = other DNA
                       organism = synthetic construct
SEQUENCE: 10
atgcttctcc tggtgacaag ccttctgctc tgtgagttac cacacccagc attcctcctg  60
atcccagaca tccagatgac acagactaca tcctccctgt ctgcctctct gggagacaga  120
gtcaccatca gttgcagggc aagtcaggac attagtaaat atttaaattg gtatcagcag  180
aaaccagatg gaactgttaa actcctgatc taccatacat caagattaca ctcaggagtc  240
ccatcaaggt tcagtggcag tgggtctgga acagattatt ctctcaccat tagcaacctg  300
gagcaagaag atattgccac ttacttttgc caacagggta atacgcttcc gtacacgttc  360
ggaggggga ctaagttgga aataacaggc tccacctctg gatccggcaa gcccggatct  420
ggcgagggat ccaccaaggg cgaggtgaaa ctgcaggagt caggacctgg cctggtggcg  480
ccctcacaga gcctgtccgt cacatgcact gtctcagggg tctcattacc cgactatggt  540
gtaagctgga ttcgccagcc tccacgaaag ggtctggagt ggctgggagt aatatggggt  600
agtgaaacca catactataa ttcagctctc aaatccagac tgaccatcat caaggacaac  660
tccaagagcc aagttttctt aaaaatgaac agtctgcaaa ctgatgacac agccatttac  720
tactgtgcca aacattatta ctacggtggt agctatgcta tggactactg gggtcaagga  780
acctcagtca ccgtctcctc agcggccgca gactacaaag acgatgacga caagattgaa  840
gttatgtatc ctcctcctta cctagacaat gagaagagca atggaaccat tatccatgtg  900
aaagggaaac acctttgtcc aagtccccta tttcccggac cttctaagcc cttttgggtg  960
ctggtggtgg ttgggggagt cctggcttgc tatagcttgc tagtaacagt ggcctttatt  1020
attttctggg tgaggagtaa gaggagcagg ctcctgcaca gtgactacat gaacatgact  1080
ccccgccgcc ccgggcccac ccgcaagcat taccagccct atgccccacc acgcgacttc  1140
gcagcctatc gctccagagt gaagttcagc aggagcgcag acgcccccgc gtaccagcag  1200
ggccagaacc agctctataa cgagctcaat ctaggacgaa gagaggagta cgatgttttg  1260
gacaagagac gtggccggga ccctgagatg gggggaaagc cgagaaggaa gaaccctcag  1320
gaaggcctgt acaatgaact gcagaaagat aagatggcgg aggcctacag tgagattggg  1380
atgaaaggcg agcgccggag gggcaagggg cacgatggcc tttaccaggg tctcagtaca  1440
gccaccaagg acacctacga cgcccttcac atgcaggccc tgccccctcg c           1491

SEQ ID NO: 11          moltype = AA  length = 395
FEATURE                Location/Qualifiers
REGION                 1..395
                       note = Description of Artificial Sequence:
                        Syntheticpolypeptide
source                 1..395
                       mol_type = protein
                       organism = synthetic construct
SEQUENCE: 11
MDWTWILFLV AAATRVHSNW VNVISDLKKI EDLIQSMHID ATLYTESDVH PSCKVTAMKC  60
FLLELQVISL ESGDASIHDT VENLIILANN SLSSNGNVTE SGCKECEELE EKNIKEFLQS  120
FVHIVQMFIN TSSGGGSGGG GSGGGGSGGG GSGGGSLQIT CPPPMSVEHA DIWVKSYSLY  180
SRERYICNSG FKRKAGTSSL TECVLNKATN VAHWTTPSLK CIRDPALVHQ RPAPPSTVTT  240
AGVTPQPESL SPSGKEPAAS SPSSNNTAAT TAAIVPGSQL MPSKSPSTGT TEISSHESSH  300
```

```
GTPSQTTAKN WELTASASHQ PPGVYPQGHS DTTVAISTST VLLCGLSAVS LLACYLKSRQ  360
TPPLASVEME AMEALPVTWG TSSRDEDLEN CSHHL                             395

SEQ ID NO: 12          moltype = DNA  length = 1188
FEATURE                Location/Qualifiers
misc_feature           1..1188
                       note = Description of Artificial Sequence:
                        Syntheticpolynucleotide
source                 1..1188
                       mol_type = other DNA
                       organism = synthetic construct
SEQUENCE: 12
atggattgga cttggatttt gttcctcgtt gccgcagcga ctcgcgtcca tagtaattgg  60
gtgaacgtaa ttagtgactt gaaaaaaatt gaggacctta tacaaagtat gcatatcgat  120
gcaacactgt acacggagtc cgacgtgcac ccaagctgca aggtcaccgc aatgaaatgc  180
tttttgctcg aattgcaagt tatctcactt gagtcagggg acgcttcaat ccatgatact  240
gtggagaatt tgataatcct ggcgaacaat agccttagtt caaatggcaa cgtcactgag  300
tcaggctgca aggaatgtga ggaattggaa gaaaaaaata tcaaggaatt tttgcaatct  360
tttgttcaca tagttcagat gttcattaac actagttccg ggggcggcag tggaggtggc  420
ggtagcggcg gggggtggctc tggtggaggc ggctctgggg gcggaagtct gcagataaca  480
tgcccccccac ctatgagtgt tgaacatgct gatatctggg ttaaatctta ctccctttac  540
agtcgagaaa ggtacatttg caactccggc tttaaacgca aagccgggac tagttcactg  600
actgaatgtg tattgaataa agcgacaaat gtcgcacact ggactacccc ttccctcaaa  660
tgcattcgcg atcctgcctt ggtgcatcag cgaccagcac cgccgtccac ggtaactacc  720
gcaggagtaa caccgcagcc cgagagcctt tccccctcag gcaaagagcc ggccgcatcc  780
tccccatctt ccaataatac cgcagctacc accgcagcaa tcgtacccgg gtcccagctg  840
atgcccagca aaagtccgag tactggaacg actgaaatct ccagtcacga gtcttctcat  900
ggaactccga gtcaaactac agcaaagaat tgggagctga ctgcttccgc ttcacaccag  960
ccgccaggcg tttatcctca gggacactca gataccacgg tggcgattag cacaagcacc  1020
gtcctcctgt gtgggctgag tgcagtgtca cttctcgcct gctaccttaa gtccagacag  1080
acaccccctt tggcaagcgt tgaaatggaa gccatggaag ccttgcctgt cacatggggg  1140
acttcatccc gcgatgaaga cttggagaac tgctcacacc atctttga             1188

SEQ ID NO: 13          moltype = AA  length = 177
FEATURE                Location/Qualifiers
REGION                 1..177
                       note = Description of Artificial Sequence:
                        Syntheticpolypeptide
source                 1..177
                       mol_type = protein
                       organism = synthetic construct
SEQUENCE: 13
MFHVSFRYIF GLPPLILVLL PVASSDCDIE GKDGKQYESV LMVSIDQLLD SMKEIGSNCL  60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEH     177

SEQ ID NO: 14          moltype = DNA  length = 614
FEATURE                Location/Qualifiers
misc_feature           1..614
                       note = Description of Artificial Sequence:
                        Syntheticpolynucleotide
source                 1..614
                       mol_type = other DNA
                       organism = synthetic construct
SEQUENCE: 14
gaattcggca gcggcgtcaa gcagacactg aacttcgatc tgctgaagct ggccggagac  60
gtcgagagca accccggccc tatgttccac gtgagcttta gatacatctt cggactgccc  120
cctctgattc tggtgctgct gcccgtggcc agcagcgact gcgatatcga gggcaaggac  180
ggcaagcagt atgagtccgt gctgatggtc tccatcgatc agctgctgga cagcatgaag  240
gagatcggct ccaactgcct caacaacgag ttcaactttt tcaagaggca catctgcgac  300
gccaacaagg agggcatgtt tctgtttaga gccgctagaa agctgaggca gtttctgaag  360
atgaacagca ccggcgactt tgatctgcat ctgctgaaag tgagcgaggg caccaccatt  420
ctgctgaact gcaccggcca agtgaaagga agaaagcccg ccgctctggg cgaggctcag  480
cctaccaagt ctctggaaga gaacaagtct ctgaaggagc agaagaagct caacgatctg  540
tgcttcctca agaggctgct gcaagagatc aagacatgct ggaacaagat cctcatgggc  600
accaaggaac actg                                                    614

SEQ ID NO: 15          moltype = AA  length = 513
FEATURE                Location/Qualifiers
REGION                 1..513
                       note = Description of Artificial Sequence:
                        Syntheticpolypeptide
source                 1..513
                       mol_type = protein
                       organism = synthetic construct
SEQUENCE: 15
MLVRRGARAG PRMPRGWTAL CLLSLLPSGF MSLDNNGTAT PELPTQGTFS NVSTNVSYQE  60
TTTPSTLGST SLHPVSQHGN EATTNITETT VKFTSTSVIT SVYGNTNSSV QSQTSVISTV  120
FTTPANVSTP ETTLKPSLSP GNVSDLSTTS TSLATSPTKP YTSSSPILSD IKAEIKCSGI  180
```

-continued

```
REVKLTQGIC LEQNKTSSCA EFKKDRGEGL ARVLCGEEQA DADAGAQVCS LLLAQSEVRP  240
QCLLLVLANR TEISSKLQLM KKHQSDLKKL GILDFTEQDV ASHQSYSQKT PILLTCPTIS  300
ILSFFSVALL VILACVLWKK RIKPIVWPSL PDHKKTLEHL CKKPRKNLNV SFNPESFLDC  360
QIHRVDDIQA RDEVEGFLQD TFPQQLEESE KQRLGGDVQS PNCPSEDVVI TPESFGRDSS  420
LTCLAGNVSA CDAPILSSSR SLDCRESGKN GPHVYQDLLL SLGTTNSTLP PPFSLQSGIL  480
TLNPVAQGQP ILTSLGSNQE EAYVTMSSFY QNQ                              513

SEQ ID NO: 16          moltype = DNA  length = 1608
FEATURE                Location/Qualifiers
misc_feature           1..1608
                       note = Description of Artificial Sequence:
                        Syntheticpolynucleotide
source                 1..1608
                       mol_type = other DNA
                       organism = synthetic construct
SEQUENCE: 16
ggaagcggcg ccacaaactt ttctctgctg aagcaagccg gcgacgtcga agagaacccc  60
ggccctatgc tggtgaggag aggcgctagg gctggaccca gaatgcccag aggctggacc  120
gctctgtgtc tgctgtctct gctgcccagc ggcttcatga gcctcgataa taacggcacc  180
gctacccccg agctgcccac acaaggcacc ttctccaatg tgagcaccaa cgtgtcctac  240
caagagacca ccaccccttc cacactggga agcacatctc tgcatcccgt ctcccagcac  300
ggcaatgaag ccaccacaaa catcaccgag accaccgtga agttcaccag cacctccgtc  360
attaccagcg tgtacggcaa caccaatagc tccgtgcaaa gccagacatc cgtgatttcc  420
accgtgttta ccacccccgc caatgtcagc acacccgaga caacactgaa accttctctg  480
tcccccggaa acgtgagcga tctgagcaca accagcacca gcctcgccac cagccccaca  540
aagccttaca caagcagcag ccccattctg agcgacatca aggccgaaat caagtgctcc  600
ggaattagag aggtcaagct gacccaagga atctgtctgg agcagaataa gaccagcagc  660
tgcgccgagt tcaagaaaga cagaggcgaa ggactggcca gagtgctctg cggcgaggaa  720
caagccgatg ccgatgccgg agctcaagtg tgcagcctcc tcctcgctca gagcgaggtc  780
agaccccaat gtctgctgct cgtgctggcc aataggaccg agatctcctc caaactgcag  840
ctgatgaaga agcaccagag cgacctcaag aagctcggca tcctcgactt taccgagcaa  900
gacgtggcct cccatcaatc ctatagccag aagaccccca ttctgctgac atgtcccaca  960
atcagcatcc tcagcttctt cagcgtcgct ctgctcgtca ttctggcttg tgtgctgtgg  1020
aagaagagga tcaagcctat tgtgtggccc tctctgcccg accacaagaa gaccctcgaa  1080
cacctctgca agaaacctag aaagaacctc aacgtgagct tcaaccccga gtcctttctg  1140
gactgtcaaa tccatagggt ggatgacatc caagctagag acgaggtcga gggctttctg  1200
caagacacct tccctcagca gctggaagaa agcgagaagc aaagactggg cggagatgtg  1260
cagtccccta attgcccctc cgaggacgtg gtgattaccc ccgagagctt cggaagagac  1320
agctctctga catgtctggc cggaaatgtg tccgcttgcg atgcccctat tctgagcagc  1380
tccagatctc tggactgcag agagtccggc aagaacggcc ctcatgtgta ccaagatctg  1440
ctgctgtctc tgggaaccac aaactccaca ctgcctcccc cctttagcct ccagtccggc  1500
attctgacac tgaaccccgt ggctcaaggc caacctatcc tcacatccct cggctccaat  1560
caagaggaag cctacgtgac catgagctcc ttctatcaga accagtga              1608

SEQ ID NO: 17          moltype = AA  length = 635
FEATURE                Location/Qualifiers
REGION                 1..635
                       note = Description of Artificial Sequence:
                        Syntheticpolypeptide
source                 1..635
                       mol_type = protein
                       organism = synthetic construct
SEQUENCE: 17
MALPVTALLL PLALLLHAAR PDCDIEGKDG KQYESVLMVS IDQLLDSMKE IGSNCLNNEF  60
NFFKRHICDA NKEGMFLFRA ARKLRQFLKM NSTGDFDLHL LKVSEGTTIL LNCTGQVKGR  120
KPAALGEAQP TKSLEENKSL KEQKKLNDLC FLKRLLQEIK TCWNKILMGT KEHGGGSGGG  180
GSGGGGSGGG GSGGGSESGY AQNGDLEDAE LDDYSFSCYS QLEVNGSQHS LTCAFEDPDV  240
NITNLEFEIC GALVEVKCLN FRKLQEIYFI ETKKFLLIGK SNICVKVGEK SLTCKKIDLT  300
TIVKPEAPFD LSVVYREGAN DFVVTFNTSH LQKKYVKVLM HDVAYRQEKD ENKWTHVNLS  360
STKLTLLQRK LQPAAMYEIK VRSIPDHYFK GFWSEWSPSY YFRTPEINNS SGEMDPILLT  420
ISILSFFSVA LLVILACVLW KKRIKPIVWP SLPDHKKTLE HLCKKPRKNL NVSFNPESFL  480
DCQIHRVDDI QARDEVEGFL QDTFPQQLEE SEKQRLGGDV QSPNCPSEDV VITPESFGRD  540
SSLTCLAGNV SACDAPILSS SRSLDCRESG KNGPHVYQDL LLSLGTTNST LPPPFSLQSG  600
ILTLNPVAQG QPILTSLGSN QEEAYVTMSS FYQNQ                            635

SEQ ID NO: 18          moltype = DNA  length = 1905
FEATURE                Location/Qualifiers
misc_feature           1..1905
                       note = Description of Artificial Sequence:
                        Syntheticpolynucleotide
source                 1..1905
                       mol_type = other DNA
                       organism = synthetic construct
SEQUENCE: 18
atggctctgc ctgttacagc tctgctgctg cctctggctc tgcttctgca tgccgccaga  60
cctgactgtg acatcgaggg caaagacggc aagcagtacg agagcgtgct gatggtgtcc  120
atcgaccagc tgctggacag catgaaggaa atcggcagca actgcctgaa caacgagttc  180
aacttcttca agcggcacat ctgcgacgcc aacaaagaag gcatgttcct gttcagagcc  240
gccagaaagc tgcggcagtt cctgaagatg aacagcaccg gcgacttcga cctgcatctg  300
```

-continued

```
ctgaaagtgt ctgagggcac caccatcctg ctgaattgca ccggccaagt gaagggcaga  360
aagcctgctg ctctgggaga agcccagcct accaagagcc tggaagagaa caagtccctg  420
aaagagcaga agaagctgaa cgacctctgc ttcctgaagc ggctgctgca agagatcaag  480
acctgctgga acaagatcct gatgggcacc aaagagcacg gcggaggatc tggcggaggt  540
ggaagcggcg gaggcggtag cggtggcgga ggaagtggtg gcggatctga atctggctac  600
gcccagaacg gcgacctgga agatgccgag ctggacgact acagcttcag ctgctacagc  660
cagctggaag tgaacggcag ccagcactct ctgacctgcg cctttgaaga tcccgacgtg  720
aacatcacca accttgagtt cgagatttgt ggcgccctgg tggaagtcaa gtgcctgaat  780
ttccggaagc tgcaagaaat ctactttatc gagacaaaga agttcctgct gatcggcaag  840
agcaacatct gtgtgaaagt gggcgagaaa agcctgacct gcaagaagat cgacctgacc  900
accatcgtga agcccgaggc tcctttcgat ctgagcgtgg tgtatagaga gggcgccaac  960
gacttcgtgg tcaccttcaa caccagccac ctccaaaaga aatacgtgaa ggtgctgatg  1020
cacgacgtgg cctaccggca agagaaggac gagaacaaat ggacccacgt gaacctgagc  1080
agcaccaagc tgaccctgct gcagagaaaa ctgcagcctg ccgctatgta cgagatcaaa  1140
gtgcggagca tccccgacca ctactttaaa ggcttttgga gcgagtggtc ccctagctac  1200
tacttcagaa cccctgagat caacaactcc agcggcgaga tggaccccat tctgctgaca  1260
atcagcatcc tgagcttttt cagcgtggcc ctgctggtca tcctggcctg tgtgctgtgg  1320
aagaagcgga tcaagcccat cgtgtggccc agcctgcctg accacaagaa aaccctggaa  1380
cacctgtgca agaagccccg gaaaaacctg aacgtgtcct tcaatcccga gagcttcctg  1440
gactgccaga tccacagagt ggacgacatc caggccaggg acgaagtgga aggatttctg  1500
caggacacat tccctcagca gctcgaagag agcgagaagc aaagactcgg aggcgacgtg  1560
cagagcccta attgcccttc tgaggacgtg gtcatcaccc cagagagctt cggcagagat  1620
agcagcctga catgtctggc cggcaatgtg tccgcctgtg atgcccctat cctgtcctct  1680
agcagaagcc tggattgcag agagagcggc aagaacggcc ctcacgtgta ccaggatctg  1740
ctcctgtctc tgggcaccac aaacagcaca ctgcctccac cattcagcct gcagagcggc  1800
atcctgacac tgaaccctgt tgctcagggc cagcctatcc tgacaagcct gggcagcaat  1860
caagaagagg cctacgtcac catgagcagc ttctaccaga accag                  1905

SEQ ID NO: 19          moltype =   length =
SEQUENCE: 19
000

SEQ ID NO: 20          moltype = DNA  length = 20
FEATURE                Location/Qualifiers
misc_feature           1..20
                       note = Description of Artificial Sequence:
                        Syntheticoligonucleotide
source                 1..20
                       mol_type = other DNA
                       organism = synthetic construct
SEQUENCE: 20
ttcggaaccc aatcactgac                                              20

SEQ ID NO: 21          moltype = DNA  length = 20
FEATURE                Location/Qualifiers
misc_feature           1..20
                       note = Description of Artificial Sequence:
                        Syntheticoligonucleotide
source                 1..20
                       mol_type = other DNA
                       organism = synthetic construct
SEQUENCE: 21
tcagggttct ggatatctgt                                              20

SEQ ID NO: 22          moltype = DNA  length = 20
FEATURE                Location/Qualifiers
misc_feature           1..20
                       note = Description of Artificial Sequence:
                        Syntheticoligonucleotide
source                 1..20
                       mol_type = other DNA
                       organism = synthetic construct
SEQUENCE: 22
aagttcctgt gatgtcaagc                                              20

SEQ ID NO: 23          moltype =   length =
SEQUENCE: 23
000

SEQ ID NO: 24          moltype =   length =
SEQUENCE: 24
000

SEQ ID NO: 25          moltype = DNA  length = 20
FEATURE                Location/Qualifiers
misc_feature           1..20
                       note = Description of Artificial Sequence:
                        Syntheticoligonucleotide
source                 1..20
```

```
                         mol_type = other DNA
                         organism = synthetic construct
SEQUENCE: 25
gaggtcaatg tctacggctc                                                20

SEQ ID NO: 26            moltype = DNA  length = 20
FEATURE                  Location/Qualifiers
misc_feature             1..20
                         note = Description of Artificial Sequence:
                          Syntheticoligonucleotide
source                   1..20
                         mol_type = other DNA
                         organism = synthetic construct
SEQUENCE: 26
atcacggagg tcaatgtcta                                                20

SEQ ID NO: 27            moltype = DNA  length = 20
FEATURE                  Location/Qualifiers
misc_feature             1..20
                         note = Description of Artificial Sequence:
                          Syntheticoligonucleotide
source                   1..20
                         mol_type = other DNA
                         organism = synthetic construct
SEQUENCE: 27
gtagacattg acctccgtga                                                20

SEQ ID NO: 28            moltype = DNA  length = 20
FEATURE                  Location/Qualifiers
misc_feature             1..20
                         note = Description of Artificial Sequence:
                          Syntheticoligonucleotide
source                   1..20
                         mol_type = other DNA
                         organism = synthetic construct
SEQUENCE: 28
ggagcaggtg atgttgacgg                                                20

SEQ ID NO: 29            moltype = DNA  length = 20
FEATURE                  Location/Qualifiers
misc_feature             1..20
                         note = Description of Artificial Sequence:
                          Syntheticoligonucleotide
source                   1..20
                         mol_type = other DNA
                         organism = synthetic construct
SEQUENCE: 29
caaagagatt acgaatgcct                                                20

SEQ ID NO: 30            moltype = DNA  length = 20
FEATURE                  Location/Qualifiers
misc_feature             1..20
                         note = Description of Artificial Sequence:
                          Syntheticoligonucleotide
source                   1..20
                         mol_type = other DNA
                         organism = synthetic construct
SEQUENCE: 30
gtgccacaaa gaccatcaag                                                20

SEQ ID NO: 31            moltype = DNA  length = 20
FEATURE                  Location/Qualifiers
misc_feature             1..20
                         note = Description of Artificial Sequence:
                          Syntheticoligonucleotide
source                   1..20
                         mol_type = other DNA
                         organism = synthetic construct
SEQUENCE: 31
agagggtcat cacacacaag                                                20

SEQ ID NO: 32            moltype = DNA  length = 20
FEATURE                  Location/Qualifiers
misc_feature             1..20
                         note = Description of Artificial Sequence:
                          Syntheticoligonucleotide
source                   1..20
                         mol_type = other DNA
                         organism = synthetic construct
```

```
SEQUENCE: 32
cttgtagata tcctgatcat                                           20

SEQ ID NO: 33          moltype =   length =
SEQUENCE: 33
000

SEQ ID NO: 34          moltype = DNA  length = 20
FEATURE                Location/Qualifiers
misc_feature           1..20
                       note = Description of Artificial Sequence:
                        Syntheticoligonucleotide
source                 1..20
                       mol_type = other DNA
                       organism = synthetic construct
SEQUENCE: 34
gaggtcaatg tctacggctc                                           20

SEQ ID NO: 35          moltype = DNA  length = 1461
FEATURE                Location/Qualifiers
misc_feature           1..1461
                       note = Description of Artificial Sequence:
                        Syntheticpolynucleotide
source                 1..1461
                       mol_type = other DNA
                       organism = synthetic construct
SEQUENCE: 35
atggcactcc ctgtaactgc acttcttttg ccacttgcct tgctcctgca cgcagcgcgg  60
ccggacatcg agctgaccca gagccccgcc atcatgagcg ccagcctggg cgaggagatc  120
accctgacct gcagcgccag cagcagcgtg agctacatgc actggtacca gcagaagagc  180
ggcaccagcc ccaagctgct gatctacagc accagcaacc tggccagcgg cgtgcccagc  240
aggttcagcg gcagcggcag cggcaccttc tacagcctga ccatcagcag cgtggaggcc  300
gaggacgccg ccgactacta ctgccaccag tggagcagct acaccttcgg cggcggcacc  360
aagctggaga tcaagagggg cggcggcggc agcggcggcg gcggcagcgg cggcggcggc  420
agccaggtga agctgcagga gagcggcggc ggcctggtga agcccggcgg cagcctgaag  480
ctgagctgcg ccgccagcgg cttcaccttc agcagctacg ccatgagctg ggtgaggcag  540
acccccgaga agaggctgga gtgggtggcc accatcagca gcggcggcag ctacacctac  600
taccccgaca gcgtgaaggg caggttcacc atcagcaggg acaacgccaa gaacaccctg  660
tacctgcaga tgagcagcct gaggagcgag gacaccgcca tgtactactg cgccaggcag  720
gacggctact accccggctg gttcgccaac tggggccagg gcaccaccgt gaccgtgagc  780
agctccggaa caacgacacc agcaccacgg ccacccactc ctgctccgac aattgcgtct  840
cagccccttt cccttcgacc cgaagcttgt cgccctgctg cgggaggagc ggtccacacg  900
cgcgggcttg acttcgcttg cgacatctac atttgggcac ccttggccgg gacatgcggc  960
gtcttgctcc tgagtctggt tataacgctg tattgtaagc gaggtcggaa gaagcttttg  1020
tatatcttta aacagccctt tatgaggccc gtacaaacca cacaagagga ggatgggtgc  1080
tcatgcagat ttcctgaaga ggaagagggc ggttgcgaac ttagagtcaa attcagccgc  1140
tccgcagatg cacctgctta taaacagggt cagaatcaat tgtataatga acttaatctc  1200
gggaggcgcg aggagtatga tgtgctggac aagcgacggg gtcgagaccc agagatgggc  1260
ggtaaacccc gccgaaagaa cccccaggag ggactgtata atgagctgca aaaggacaaa  1320
atggcagaag cctattccga aatagggatg aagggagagc ggcggcgagg taagggacat  1380
gacggtcttt atcaaggtct tagtactgca actaaggaca cctatgacgc gctgcatatg  1440
caggctctcc cacctagata a                                         1461

SEQ ID NO: 36          moltype = AA  length = 486
FEATURE                Location/Qualifiers
REGION                 1..486
                       note = Description of Artificial Sequence:
                        Syntheticpolypeptide
source                 1..486
                       mol_type = protein
                       organism = synthetic construct
SEQUENCE: 36
MALPVTALLL PLALLLHAAR PDIELTQSPA IMSASLGEEI TLTCSASSSV SYMHWYQQKS  60
GTSPKLLIYS TSNLASGVPS RFSGSGSGTF YSLTISSVEA EDAADYYCHQ WSSYTFGGGT  120
KLEIKRGGGG SGGGGSGGGG SQVKLQESGG GLVKPGGSLK LSCAASGFTF SSYAMSWVRQ  180
TPEKRLEWVA TISSGGSYTY YPDSVKGRFT ISRDNAKNTL YLQMSSLRSE DTAMYYCARQ  240
DGYYPGWFAN WGQGTTVTVS SSGTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                          486

SEQ ID NO: 37          moltype = DNA  length = 2721
FEATURE                Location/Qualifiers
misc_feature           1..2721
                       note = Description of Artificial Sequence:
                        Syntheticpolynucleotide
source                 1..2721
                       mol_type = other DNA
```

```
                        organism = synthetic construct
SEQUENCE: 37
atggcactcc ctgtaactgc acttcttttg ccacttgcct tgctcctgca cgcagcgcgg  60
ccggacatcg agctgaccca gagccccgcc atcatgagcg ccagcctggg cgaggagatc  120
accctgacct gcagcgccag cagcagcgtg agctacatgc actggtacca gcagaagagc  180
ggcaccagcc ccaagctgct gatctacagc accagcaacc tggccagcgg cgtgcccagc  240
aggttcagcg gcagcggcag cggcaccttc tacagcctga ccatcagcag cgtggaggcc  300
gaggacgccg ccgactacta ctgccaccag tggagcagct acaccttcgg cggcggcacc  360
aagctggaga tcaagagggg cggcggcggc agcggcggcg gcggcagcgg cggcggcggc  420
agccaggtga agctgcagga gagcggcggc ggcctggtga agcccggcgg cagcctgaag  480
ctgagctgcg ccgccagcgg cttcaccttc agcagctacg ccatgagctg ggtgaggcag  540
accccccgaga agaggctgga gtgggtggcc accatcagca gcggcggcag ctacacctac  600
taccccgaca gcgtgaaggg caggttcacc atcagcaggg acaacgccaa gaacaccctg  660
tacctgcaga tgagcagcct gaggagcgag gacaccgcca tgtactactg cgccaggcag  720
gacggctact accccggctg gttcgccaac tggggccagg gcaccaccgt gaccgtgagc  780
agctccggaa caacgacacc agcaccacgg ccacccactc ctgctccgac aattgcgtct  840
cagcccccttt cccttcgacc cgaagcttgt cgccctgctg cgggaggagc ggtccacacg  900
cgcgggcttg acttcgcttg cgacatctac atttgggcac ccttggccgg gacatgcggc  960
gtcttgctcc tgagtctggt tataacgctg tattgtaagc gaggtcggaa gaagcttttg  1020
tatatcttta aacagccctt tatgaggccc gtacaaacca cacaagagga ggatgggtgc  1080
tcatgcagat ttcctgaaga ggaagagggc ggttgcgaac ttagagtcaa attcagccgc  1140
tccgcagatg cacctgctta taaacagggt cagaatcaat tgtataatga acttaatctc  1200
gggaggcgcg aggagtatga tgtgctggac aagcgacggg gtcgagaccc agagatgggc  1260
ggtaaacccc gccgaaagaa cccccaggag ggactgtata atgagctgca aaaggacaaa  1320
atggcagaag cctattccga aatagggatg aagggagagc ggcggcgagg taagggacat  1380
gacggtcttt atcaaggtct tagtactgca actaaggaca cctatgacgc gctgcatatg  1440
caggctctcc cacctagacg agctaaacga ggctcaggcg cgacgaactt tagtttgctg  1500
aagcaagctg gggatgtaga ggaaaatccg ggtcccatgg attggacttg gatttgttc  1560
ctcgttgccg cagcgactcg cgtccatagt aattgggtga acgtaattag tgacttgaaa  1620
aaaattgagg accttataca aagtatgcat atcgatgcaa cactgtacac ggagtccgac  1680
gtgcacccaa gctgcaaggt caccgcaatg aaatgctttt tgctcgaatt gcaagttatc  1740
tcacttgagt caggggacgc ttcaatccat gatactgtgg agaatttgat aatcctggcg  1800
aacaatagcc ttagttcaaa tggcaacgtc actgagtcag gctgcaagga atgtgaggaa  1860
ttggaagaaa aaaatatcaa ggaattttg caatcttttg ttcacatagt tcagatgttc  1920
attaacacta gttccggggg cggcagtgga ggtggcggta gcggcggggg tggctctggt  1980
ggaggcggct ctgggggcgg aagtctgcag ataacatgcc ccccacctat gagtgttgaa  2040
catgctgata tctgggttaa atcttactcc ctttacagtc gagaaaggta catttgcaac  2100
tccggcttta aacgcaaagc cggactagt tcactgactg aatgtgtatt gaataaagcg  2160
acaaatgtcg cacactggac taccccttcc ctcaaatgca ttcgcgatcc tgccttggtg  2220
catcagcgac cagcaccgcc gtccacggta actaccgcag gagtaacacc gcagcccgag  2280
agcctttccc cctcaggcaa agagccggcc gcatcctccc catcttccaa taataccgca  2340
gctaccaccg cagcaatcgt acccggatcc cagctgatgc ccagcaaaag tccgagtact  2400
ggaacgactg aaatctccag tcacgagtct tctcatggaa ctccgagtca aactacagca  2460
aagaattggg agctgactgc ttccgcttca caccagccgc caggcgttta tcctcaggga  2520
cactcagata ccacggtggc gattagcaca agcaccgtcc tcctgtgtgg gctgagtgca  2580
gtgtcacttc tcgcctgcta ccttaagtcc agacagacac ccccttggc aagcgttgaa  2640
atggaagcca tggaagcctt gcctgtcaca tgggggactt catcccgcga tgaagacttg  2700
gagaactgct cacaccatct t                                            2721

SEQ ID NO: 38           moltype = AA  length = 907
FEATURE                 Location/Qualifiers
REGION                  1..907
                        note = Description of Artificial Sequence:
                         Syntheticpolypeptide
source                  1..907
                        mol_type = protein
                        organism = synthetic construct
SEQUENCE: 38
MALPVTALLL PLALLLHAAR PDIELTQSPA IMSASLGEEI TLTCSASSSV SYMHWYQQKS  60
GTSPKLLIYS TSNLASGVPS RFSGSGSGTF YSLTISSVEA EDAADYYCHQ WSSYTFGGGT  120
KLEIKRGGGG SGGGGSGGGG SQVKLQESGG GLVKPGGSLK LSCAASGFTF SSYAMSWVRQ  180
TPEKRLEWVA TISSGGSYTY YPDSVKGRFT ISRDNAKNTL YLQMSSLRSE DTAMYYCARQ  240
DGYYPGWFAN WGQGTTVTVS SSGTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPRRAKR GSGATNFSLL KQAGDVEENP GPMDWTWILF LVAAATRVHS NWVNVISDLK  540
KIEDLIQSMH IDATLYTESD VHPSCKVTAM KCFLLELQVI SLESGDASIH DTVENLIILA  600
NNSLSSNGNV TESGCKECEE LEEKNIKEFL QSFVHIVQMF INTSSGGGSG GGGSGGGGSG  660
GGGSGGGSLQ ITCPPPMSVE HADIWVKSYS LYSRERYICN SGFKRKAGTS SLTECVLNKA  720
TNVAHWTTPS LKCIRDPALV HQRPAPPSTV TTAGVTPQPE SLSPSGKEPA ASSPSSNNTA  780
ATTAAIVPGS QLMPSKSPST GTTEISSHES SHGTPSQTTA KNWELTASAS HQPPGVYPQG  840
HSDTTVAIST STVLLCGLSA VSLLACYLKS RQTPPLASVE MEAMEALPVT WGTSSRDEDL  900
ENCSHHL                                                            907

SEQ ID NO: 39           moltype = DNA  length = 3063
FEATURE                 Location/Qualifiers
misc_feature            1..3063
                        note = Description of Artificial Sequence:
```

```
                       Syntheticpolynucleotide
source                 1..3063
                       mol_type = other DNA
                       organism = synthetic construct
SEQUENCE: 39
atggcactcc ctgtaactgc acttcttttg ccacttgcct tgctcctgca cgcagcgcgg  60
ccggacatcg agctgaccca gagccccgcc atcatgagcg ccagcctggg cgaggagatc  120
accctgacct gcagcgccag cagcagcgtg agctacatgc actggtacca gcagaagagc  180
ggcaccagcc ccaagctgct gatctacagc accagcaacc tggccagcgg cgtgcccagc  240
aggttcagcg gcagcggcag cggcaccttc tacagcctga ccatcagcag cgtggaggcc  300
gaggacgccg ccgactacta ctgccaccag tggagcagct acaccttcgg cggcggcacc  360
aagctggaga tcaagagggg cggcggcggc agcggcggcg gcggcagcgg cggcggcggc  420
agccaggtga agctgcagga gagcggcggc ggcctggtga agcccggcgg cagcctgaag  480
ctgagctgcg ccgccagcgg cttcaccttc agcagctacg ccatgagctg ggtgaggcag  540
acccccgaga agaggctgga gtgggtggcc accatcagca gcggcggcag ctacacctac  600
taccccgaca gcgtgaaggg caggttcacc atcagcaggg acaacgccaa gaacaccctg  660
tacctgcaga tgagcagcct gaggagcgag gacaccgcca tgtactactg cgccaggcag  720
gacggctact accccggctg gttcgccaac tggggccagg gcaccaccgt gaccgtgagc  780
agctccggaa caacgacacc agcaccacgg ccacccactc ctgctccgac aattgcgtct  840
cagcccottt cccttcgacc cgaagcttgt cgccctgctg cgggaggagc ggtccacacg  900
cgcgggcttg acttcgcttg cgacatctac atttgggcac ccttggccgg gacatgcggc  960
gtcttgctcc tgagtctggt tataacgctg tattgtaagc gaggtcggaa gaagcttttg  1020
tatatcttta aacagccctt tatgaggccc gtacaaacca cacaagagga ggatgggtgc  1080
tcatgcagat ttcctgaaga ggaagagggc ggttgcgaac ttagagtcaa attcagccgc  1140
tccgcagatg cacctgctta taaacagggt cagaatcaat tgtataatga acttaatctc  1200
gggaggcgcg aggagtatga tgtgctggac aagcgacggg gtcgagaccc agagatgggc  1260
ggtaaacccc gccgaaagaa cccccaggag ggactgtata atgagctgca aaaggacaaa  1320
atggcagaag cctattccga aatagggatg aagggagagc ggcggcgagg taagggacat  1380
gacggtcttt atcaaggtct tagtactgca actaaggaca cctatgacgc gctgcatatg  1440
caggctctcc cacctagagg ctcaggcgcg acgaacttta gtttgctgaa gcaagctggg  1500
gatgtagagg aaaatccggg tcccatgttg gtgcgccgag gcgcacgagc aggacctcgg  1560
atgccgcgag gctggacagc cctctgtctc ctctctttgc ttccatccgg gttcatgagt  1620
ctcgacaata atggtacggc aaccccggaa ctcccgaccc aaggaacctt tagtaacgtt  1680
tcaaccaatg tgtcctatca ggagacaaca accccttcta cactgggcag taccagcttg  1740
catcccgtca gccaacacgg caacgaggca acaactaaca tcacagagac tacggtcaag  1800
tttactagta cttccgtaat cacgtctgtg tacgggaata caaattcatc agttcagagt  1860
caaacgtcag ttatatctac agtcttcact actcccgcga atgtatccac cccagaaacc  1920
accctcaaac cttctcttag tccaggaaat gttagcgatt tgtcaacgac gagcacgagt  1980
ttggcgacta gtccaacgaa accgtacact tccagcagtc ccatactgtc cgacattaag  2040
gcagaaataa aatgttctgg gatcagggag gtcaagctta cgcagggaat atgtcttgag  2100
caaaataaga cgtcctcatg cgcagaattc aagaaagatc gcggcgaagg tctggccaga  2160
gtcctctgtg gagaggagca ggcggatgct gacgcaggag cgcaggtttg tagtctcctg  2220
ctcgcgcaaa gtgaagttag gccccaatgt ctcttgttgg tactggctaa ccgaactgaa  2280
attagcagca agcttcaact catgaaaaaa caccagagtg atttgaaaaa acttgggata  2340
cttgacttca cggagcaaga cgttgcgtct caccaatcct actcacagaa aaccccgata  2400
ctgttgacat gccccaccat atcaatcttg tctttcttca gtgtggctct tctggtgatc  2460
ttggcgtgcg tgctgtggaa aaaaaggatt aaaccgatcg tttggcctag tctgccggat  2520
cacaaaaaga cactggagca cctctgcaag aagccacgaa aaaacctgaa tgtgagcttt  2580
aaccccgagt ctttttgga ctgtcagata caccgagtcg acgatataca ggcaagagat  2640
gaggttgagg gtttcctgca agacacattc ccgcaacaac tcgaagaatc cgagaaacag  2700
cgccttggtg gagatgtcca gtctccgaac tgtccgagcg aggacgtagt aattacccca  2760
gaaagcttcg gtcgagatag tagccttacg tgtctcgccg ggaacgtgtc agcgtgtgac  2820
gcgcctattc tttcaagttc acgcagtttg gactgtcgag aatcagggaa aaacggacct  2880
cacgtgtatc aggatctcct tctcagcctg ggcacgacaa acagtacctt gcctcctccg  2940
ttttccctgc agtcaggtat tctgacgctc aatccagtcg cacaagggca acctatcctg  3000
acctccttgg gttctaacca ggaagaggca tacgtcacta tgtccagctt ctatcagaat  3060
cag                                                                3063

SEQ ID NO: 40          moltype = AA  length = 1021
FEATURE                Location/Qualifiers
REGION                 1..1021
                       note = Description of Artificial Sequence:
                       Syntheticpolypeptide
source                 1..1021
                       mol_type = protein
                       organism = synthetic construct
SEQUENCE: 40
MALPVTALLL PLALLLHAAR PDIELTQSPA IMSASLGEEI TLTCSASSSV SYMHWYQQKS  60
GTSPKLLIYS TSNLASGVPS RFSGSGSGTF YSLTISSVEA EDAADYYCHQ WSSYTFGGGT  120
KLEIKRGGGG SGGGGSGGGG SQVKLQESGG GLVKPGGSLK LSCAASGFTF SSYAMSWVRQ  180
TPEKRLEWVA TISSGGSYTY YPDSVKGRFT ISRDNAKNTL YLQMSSLRSE DTAMYYCARQ  240
DGYYPGWFAN WGQGTTVTVS SSGTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPRGSGA TNFSLLKQAG DVEENPGPML VRRGARAGPR MPRGWTALCL LSLLPSGFMS  540
LDNNGTATPE LPTQGTFSNV STNVSYQETT TPSTLGSTSL HPVSQHGNEA TTNITETTVK  600
FTSTSVITSV YGNTNSSVQS QTSVISTVFT TPANVSTPET TLKPSLSPGN VSDLSTTSTS  660
LATSPTKPYT SSSPILSDIK AEIKCSGIRE VKLTQGICLE QNKTSSCAEF KKDRGEGLAR  720
```

```
VLCGEEQADA DAGAQVCSLL LAQSEVRPQC LLLVLANRTE ISSKLQLMKK HQSDLKKLGI  780
LDFTEQDVAS HQSYSQKTPI LLTCPTISIL SFFSVALLVI LACVLWKKRI KPIVWPSLPD  840
HKKTLEHLCK KPRKNLNVSF NPESFLDCQI HRVDDIQARD EVEGFLQDTF PQQLEESEKQ  900
RLGGDVQSPN CPSEDVVITP ESFGRDSSLT CLAGNVSACD APILSSSRSL DCRESGKNGP  960
HVYQDLLLSL GTTNSTLPPP FSLQSGILTL NPVAQGQPIL TSLGSNQEEA YVTMSSFYQN  1020
Q                                                                 1021

SEQ ID NO: 41          moltype = DNA  length = 2181
FEATURE                Location/Qualifiers
misc_feature           1..2181
                       note = Description of Artificial Sequence:
                        Syntheticpolynucleotide
source                 1..2181
                       mol_type = other DNA
                       organism = synthetic construct
SEQUENCE: 41
atggcactcc ctgtaactgc acttcttttg ccacttgcct tgctcctgca cgcagcgcgg  60
ccggatattc aaatgacaca aactaccagc tccctttcag catctttggg cgatagagta  120
actataagtt gccgcgcgtc ccaagacatc tctaagtacc ttaactggta tcaacaaaaa  180
ccggacggga cggtcaaact gttgatctat cacacatcca gattgcactc aggcgtgccg  240
agcaggttca gtgggagtgg gtcaggaacg gattacagct tgacgattag taacctggag  300
caagaagaca ttgccaccta cttctgccag caaggtaaca ctctcccata tacgttcggg  360
ggtggcacca agctggaaat cactggcggc ggaggatccg aggtgcagct ggtgcagagc  420
ggcgccgagg tgaagaagcc cggcgagagc ctgaggatca gctgcaaggg cagcggctac  480
agcttcagca cctactggat cagctgggtg aggcagatgc ccggcaaggg cctggagtgg  540
atgggcaaga tctaccccgg cgacagctac accaactaca gccccagctt ccagggccag  600
gtgaccatca gcgccgacaa gagcatcagc accgcctacc tgcagtggag cagcctgaag  660
gccagcgaca ccgccatgta ctactgcgcc aggggctacg gcatcttcga ctactggggc  720
cagggcaccc tggtgaccgt gagcagcggc agcacaagcg gctctggcaa gcctggatct  780
ggcgagggct ctaccaaggg catgagctac gagctgaccc agccccccag cgtgagcgtg  840
agccccggcc agaccgccag catcacctgc agcggcgaca acatcggcga ccagtacgcc  900
cactggtacc agcagaagcc cggccagagc cccgtgctgg tgatctacca ggacaagaac  960
aggcccagcg gcatccccga gaggttcagc ggcagcaaca gcggcaacac cgccaccctg  1020
accatcagcg gcacccaggc catggacgag gccgactact actgcgccac ctacaccggc  1080
ttcggcagcc tggccgtgtt cggcggcggc accaagctga ccgtgctggg gggaggcggc  1140
agcgaggtga aactgcagga gtccgggccc ggtctcgtgg caccttccca gtcactgtcc  1200
gtgacctgca ccgtatctgg ggtaagtctg ccggattatg ggtttcatg gatccggcaa  1260
cctccgagga aagggttgga atggctggga gtcatctggg gaagcgagac aacttattat  1320
aattctgctt tgaagagccg cttgacgata atcaaggaca acagtaagag tcaggttttc  1380
ttgaagatga attctcttca gacagatgac accgctattt attattgtgc aaaacattat  1440
tattacggag gatcctacgc gatggactat tggggacagg gtacctctgt tacggtgtcc  1500
tcatccggaa caacgacacc agcaccacgg ccacccactc ctgctccgac aattgcgtct  1560
cagcccctt cccttcgacc cgaagcttgt cgccctgctg cgggaggagc ggtccacacg  1620
cgcgggcttg acttcgcttg cgacatctac atttgggcac ccttggccgg gacatgcggc  1680
gtcttgctcc tgagtctggt tataacgctg tattgtaagc gaggtcggaa gaagcttttg  1740
tatatcttta aacagccctt tatgaggccc gtacaaacca cacaagagga ggatgggtgc  1800
tcatgcagat ttcctgaaga ggaagagggc ggttgcgaac ttagagtcaa attcagccgc  1860
tccgcagatg cacctgctta taaacagggt cagaatcaat tgtataatga acttaatctc  1920
gggaggcgcg aggagtatga tgtgctggac aagcgacggg gtcgagaccc agagatgggc  1980
ggtaaacccc gccgaaagaa cccccaggag ggactgtata atgagctgca aaaggacaaa  2040
atggcagaag cctattccga aatagggatg aagggagagc ggcggcgagg taagggacat  2100
gacggtcttt atcaaggtct tagtactgca actaaggaca cctatgacgc gctgcatatg  2160
caggctctcc cacctagata a                                           2181

SEQ ID NO: 42          moltype =   length =
SEQUENCE: 42
000

SEQ ID NO: 43          moltype =   length =
SEQUENCE: 43
000

SEQ ID NO: 44          moltype =   length =
SEQUENCE: 44
000

SEQ ID NO: 45          moltype = DNA  length = 20
FEATURE                Location/Qualifiers
misc_feature           1..20
                       note = Description of Artificial Sequence:
                        Syntheticoligonucleotide
source                 1..20
                       mol_type = other DNA
                       organism = synthetic construct
SEQUENCE: 45
aacgtggcat ctgtcgaccc                                             20

SEQ ID NO: 46          moltype = DNA  length = 20
FEATURE                Location/Qualifiers
```

```
misc_feature          1..20
                      note = Description of Artificial Sequence:
                       Syntheticoligonucleotide
source                1..20
                      mol_type = other DNA
                      organism = synthetic construct
SEQUENCE: 46
gcgctggaga aactatttgg                                              20

SEQ ID NO: 47         moltype = DNA  length = 20
FEATURE               Location/Qualifiers
misc_feature          1..20
                      note = Description of Artificial Sequence:
                       Syntheticoligonucleotide
source                1..20
                      mol_type = other DNA
                      organism = synthetic construct
SEQUENCE: 47
acatttaacg atcagaaacg                                              20

SEQ ID NO: 48         moltype = DNA  length = 20
FEATURE               Location/Qualifiers
misc_feature          1..20
                      note = Description of Artificial Sequence:
                       Syntheticoligonucleotide
source                1..20
                      mol_type = other DNA
                      organism = synthetic construct
SEQUENCE: 48
ggtcctttgt ccacctgcgc                                              20

SEQ ID NO: 49         moltype = DNA  length = 20
FEATURE               Location/Qualifiers
misc_feature          1..20
                      note = Description of Artificial Sequence:
                       Syntheticoligonucleotide
source                1..20
                      mol_type = other DNA
                      organism = synthetic construct
SEQUENCE: 49
gagaaactat ttggaggaca                                              20

SEQ ID NO: 50         moltype = DNA  length = 20
FEATURE               Location/Qualifiers
misc_feature          1..20
                      note = Description of Artificial Sequence:
                       Syntheticoligonucleotide
source                1..20
                      mol_type = other DNA
                      organism = synthetic construct
SEQUENCE: 50
ggagaaacta tttggaggac                                              20

SEQ ID NO: 51         moltype = AA  length = 254
FEATURE               Location/Qualifiers
REGION                1..254
                      note = Description of Artificial Sequence:
                       Syntheticpolypeptide
source                1..254
                      mol_type = protein
                      organism = synthetic construct
SEQUENCE: 51
MEYASDASLD PEAPWPPAPR ARACRVLPWA LVAGLLLLLL LAAACAVFLA CPWAVSGARA  60
SPGSAASPRL REGPELSPDD PAGLLDLRQG MFAQLVAQNV LLIDGPLSWY SDPGLAGVSL  120
TGGLSYKEDT KELVVAKAGV YYVFFQLELR RVVAGEGSGS VSLALHLQPL RSAAGAAALA  180
LTVDLPPASS EARNSAFGFQ GRLLHLSAGQ RLGVHLHTEA RARHAWQLTQ GATVLGLFRV  240
TPEIPAGLPS PRSE                                                    254

SEQ ID NO: 52         moltype = AA  length = 116
FEATURE               Location/Qualifiers
REGION                1..116
                      note = Description of Artificial Sequence:
                       Syntheticpolypeptide
source                1..116
                      mol_type = protein
                      organism = synthetic construct
SEQUENCE: 52
EVQLVQSGAE VKKPGESLRI SCKGSGYSFS TYWISWVRQM PGKGLEWMGK IYPGDSYTNY  60
SPSFQGQVTI SADKSISTAY LQWSSLKASD TAMYYCARGY GIFDYWGQGT LVTVSS      116
```

```
SEQ ID NO: 53           moltype = AA  length = 109
FEATURE                 Location/Qualifiers
REGION                  1..109
                        note = Description of Artificial Sequence:
                         Syntheticpolypeptide
source                  1..109
                        mol_type = protein
                        organism = synthetic construct
SEQUENCE: 53
MSYELTQPPS VSVSPGQTAS ITCSGDNIGD QYAHWYQQKP GQSPVLVIYQ DKNRPSGIPE  60
RFSGSNSGNT ATLTISGTQA MDEADYYCAT YTGFGSLAVF GGGTKLTVL              109

SEQ ID NO: 54           moltype = AA  length = 121
FEATURE                 Location/Qualifiers
REGION                  1..121
                        note = Description of Artificial Sequence:
                         Syntheticpolypeptide
source                  1..121
                        mol_type = protein
                        organism = synthetic construct
SEQUENCE: 54
QVQLQQWGAG LLKPSETLSL TCAVYGGSFS GYYWSWIRQS PEKGLEWIGE INHGGYVTYN  60
PSLESRVTIS VDTSKNQFSL KLSSVTAADT AVYYCARDYG PGNYDWYFDL WGRGTLVTVS  120
S                                                                  121

SEQ ID NO: 55           moltype = AA  length = 110
FEATURE                 Location/Qualifiers
REGION                  1..110
                        note = Description of Artificial Sequence:
                         Syntheticpolypeptide
source                  1..110
                        mol_type = protein
                        organism = synthetic construct
SEQUENCE: 55
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPALTF CGGTKVEIKR             110

SEQ ID NO: 56           moltype = AA  length = 489
FEATURE                 Location/Qualifiers
REGION                  1..489
                        note = Description of Artificial Sequence:
                         Syntheticpolypeptide
source                  1..489
                        mol_type = protein
                        organism = synthetic construct
SEQUENCE: 56
MALPVTALLL PLALLLHAAR PMSYELTQPP SVSVSPGQTA SITCSGDNIG DQYAHWYQQK  60
PGQSPVLVIY QDKNRPSGIP ERFSGSNSGN TATLTISGTQ AMDEADYYCA TYTGFGSLAV  120
FGGGTKLTVL GSTSGSGKPG SGEGSTKGEV QLVQSGAEVK KPGESLRISC KGSGYSFSTY  180
WISWVRQMPG KGLEWMGKIY PGDSYTNYSP SFQGQVTISA DKSISTAYLQ WSSLKASDTA  240
MYYCARGYGI FDYWGQGTLV TVSSSGTTTP APRPPTPAPT IASQPLSLRP EACRPAAGGA  300
VHTRGLDFAC DIYIWAPLAG TCGVLLLSLV ITLYCKRGRK KLLYIFKQPF MRPVQTTQEE  360
DGCSCRFPEE EEGGCELRVK FSRSADAPAY KQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                          489

SEQ ID NO: 57           moltype = DNA  length = 1470
FEATURE                 Location/Qualifiers
misc_feature            1..1470
                        note = Description of Artificial Sequence:
                         Syntheticpolynucleotide
source                  1..1470
                        mol_type = other DNA
                        organism = synthetic construct
SEQUENCE: 57
atggccctgc ccgtgaccgc cctgctgctg cccctggccc tgctgctgca cgccgccagg  60
cccatgagct acgagctgac ccagcccccc agcgtgagcg tgagccccgg ccagaccgcc  120
agcatcacct gcagcggcga caacatcggc gaccagtacg cccactggta ccagcagaag  180
cccggccaga gccccgtgct ggtgatctac caggacaaga acaggcccag cggcatcccc  240
gagaggttca gcggcagcaa cagcggcaac accgccaccc tgaccatcag cggcacccag  300
gccatggacg aggccgacta ctactgcgcc acctacaccg gcttcggcag cctggccgtg  360
ttcggcggcg gcaccaagct gaccgtgctg ggcagcacca gcggcagcgg caagcccggc  420
agcggcgagg gcagcaccaa gggcgaggtg cagctggtgc agagcggcgc cgaggtgaag  480
aagcccggcg agagcctgag gatcagctgc aagggcagcg gctacagctt cagcacctac  540
tggatcagct gggtgaggca gatgcccggc aagggcctgg agtggatggg caagatctac  600
cccggcgaca gctacaccaa ctacagcccc agcttccagg gccaggtgac catcagcgcc  660
gacaagagca tcagcaccgc ctacctgcag tggagcagcc tgaaggccag cgacaccgcc  720
atgtactact gcgccagggg ctacggcatc ttcgactact ggggccaggg caccctggtg  780
```

```
accgtgagca gcagcggcac caccaccccc gcccccaggc cccccacccc cgcccccacc  840
atcgccagcc agcccctgag cctgaggccc gaggcctgca ggcccgccgc cggcggcgcc  900
gtgcacacca ggggcctgga cttcgcctgc gacatctaca tctgggcccc cctggccggc  960
acctgcggcg tgctgctgct gagcctggtg atcaccctgt actgcaagag gggcaggaag  1020
aagctgctgt acatcttcaa gcagcccttc atgaggcccg tgcagaccac ccaggaggag  1080
gacggctgca gctgcaggtt ccccgaggag gaggagggcg gctgcgagct gagggtgaag  1140
ttcagcagga gcgccgacgc ccccgcctac aagcagggcc agaaccagct gtacaacgag  1200
ctgaacctgg gcaggaggga ggagtacgac gtgctggaca agaggagggg cagggacccc  1260
gagatgggcg gcaagcccag gaggaagaac ccccaggagg gcctgtacaa cgagctgcag  1320
aaggacaaga tggccgaggc ctacagcgag atcggcatga agggcgagag gaggaggggc  1380
aagggccacg acggcctgta ccagggcctg agcaccgcca ccaaggacac ctacgacgcc  1440
ctgcacatgc aggccctgcc ccccaggtga                                  1470

SEQ ID NO: 58          moltype = DNA  length = 1470
FEATURE                Location/Qualifiers
misc_feature           1..1470
                       note = Description of Artificial Sequence:
                        Syntheticpolynucleotide
source                 1..1470
                       mol_type = other DNA
                       organism = synthetic construct
SEQUENCE: 58
atggccctgc ccgtgaccgc cctgctgctg cccctggccc tgctgctgca cgccgccagg  60
cccgaggtgc agctggtgca gagcggcgcc gaggtgaaga agcccggcga gagcctgagg  120
atcagctgca agggcagcgg ctacagcttc agcacctact ggatcagctg ggtgaggcag  180
atgcccggca agggcctgga gtggatgggc aagatctacc ccggcgacag ctacaccaac  240
tacagcccca gcttccaggg ccaggtgacc atcagcgccg acaagagcat cagcaccgcc  300
tacctgcagt ggagcagcct gaaggccagc gacaccgcca tgtactactg cgccaggggc  360
tacggcatct tcgactactg gggccagggc accctggtga ccgtgagcag cggcagcacc  420
agcggcagcg gcaagcccgg cagcggcgag ggcagcacca agggcatgag ctacgagctg  480
acccagcccc ccagcgtgag cgtgagcccc ggccagaccg ccagcatcac ctgcagcggc  540
gacaacatcg gcgaccagta cgcccactgg taccagcaga agcccggcca gagccccgtg  600
ctggtgatct accaggacaa gaacaggccc agcggcatcc ccgagaggtt cagcggcagc  660
aacagcggca acaccgccac cctgaccatc agcggcaccc aggccatgga cgaggccgac  720
tactactgcg ccacctacac cggcttcggc agcctggccg tgttcggcgg cggcaccaag  780
ctgaccgtgc tgagcggcac caccaccccc gcccccaggc cccccacccc cgcccccacc  840
atcgccagcc agcccctgag cctgaggccc gaggcctgca ggcccgccgc cggcggcgcc  900
gtgcacacca ggggcctgga cttcgcctgc gacatctaca tctgggcccc cctggccggc  960
acctgcggcg tgctgctgct gagcctggtg atcaccctgt actgcaagag gggcaggaag  1020
aagctgctgt acatcttcaa gcagcccttc atgaggcccg tgcagaccac ccaggaggag  1080
gacggctgca gctgcaggtt ccccgaggag gaggagggcg gctgcgagct gagggtgaag  1140
ttcagcagga gcgccgacgc ccccgcctac aagcagggcc agaaccagct gtacaacgag  1200
ctgaacctgg gcaggaggga ggagtacgac gtgctggaca agaggagggg cagggacccc  1260
gagatgggcg gcaagcccag gaggaagaac ccccaggagg gcctgtacaa cgagctgcag  1320
aaggacaaga tggccgaggc ctacagcgag atcggcatga agggcgagag gaggaggggc  1380
aagggccacg acggcctgta ccagggcctg agcaccgcca ccaaggacac ctacgacgcc  1440
ctgcacatgc aggccctgcc ccccaggtga                                  1470

SEQ ID NO: 59          moltype = AA  length = 120
FEATURE                Location/Qualifiers
REGION                 1..120
                       note = Description of Artificial Sequence:
                        Syntheticpolypeptide
source                 1..120
                       mol_type = protein
                       organism = synthetic construct
SEQUENCE: 59
EVKLQESGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY YGGSYAMDYW GQGTSVTVSS  120

SEQ ID NO: 60          moltype = AA  length = 107
FEATURE                Location/Qualifiers
REGION                 1..107
                       note = Description of Artificial Sequence:
                        Syntheticpolypeptide
source                 1..107
                       mol_type = protein
                       organism = synthetic construct
SEQUENCE: 60
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEIT               107

SEQ ID NO: 61          moltype = AA  length = 491
FEATURE                Location/Qualifiers
REGION                 1..491
                       note = Description of Artificial Sequence:
                        Syntheticpolypeptide
source                 1..491
                       mol_type = protein
```

-continued

```
                         organism = synthetic construct
SEQUENCE: 61
MALPVTALLL PLALLLHAAR PDIQMTQTTS SLSASLGDRV TISCRASQDI SKYLNWYQQK  60
PDGTVKLLIY HTSRLHSGVP SRFSGSGSGT DYSLTISNLE QEDIATYFCQ QGNTLPYTFG  120
GGTKLEITGS TSGSGKPGSG EGSTKGEVKL QESGPGLVAP SQSLSVTCTV SGVSLPDYGV  180
SWIRQPPRKG LEWLGVIWGS ETTYYNSALK SRLTIIKDNS KSQVFLKMNS LQTDDTAIYY  240
CAKHYYYGGS YAMDYWGQGT SVTVSSSGTT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYKQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                      491

SEQ ID NO: 62            moltype =   length =
SEQUENCE: 62
000

SEQ ID NO: 63            moltype =   length =
SEQUENCE: 63
000

SEQ ID NO: 64            moltype =   length =
SEQUENCE: 64
000

SEQ ID NO: 65            moltype =   length =
SEQUENCE: 65
000

SEQ ID NO: 66            moltype =   length =
SEQUENCE: 66
000

SEQ ID NO: 67            moltype =   length =
SEQUENCE: 67
000

SEQ ID NO: 68            moltype =   length =
SEQUENCE: 68
000

SEQ ID NO: 69            moltype =   length =
SEQUENCE: 69
000

SEQ ID NO: 70            moltype =   length =
SEQUENCE: 70
000

SEQ ID NO: 71            moltype =   length =
SEQUENCE: 71
000

SEQ ID NO: 72            moltype =   length =
SEQUENCE: 72
000

SEQ ID NO: 73            moltype =   length =
SEQUENCE: 73
000

SEQ ID NO: 74            moltype =   length =
SEQUENCE: 74
000

SEQ ID NO: 75            moltype = AA  length = 486
FEATURE                  Location/Qualifiers
REGION                   1..486
                         note = Description of Artificial Sequence:
                          Syntheticpolypeptide
source                   1..486
                         mol_type = protein
                         organism = synthetic construct
SEQUENCE: 75
MALPVTALLL PLALLLHAAR PDIELTQSPA IMSASLGEEI TLTCSASSSV SYMHWYQQKS  60
GTSPKLLIYS TSNLASGVPS RFSGSGSGTF YSLTISSVEA EDAADYYCHQ WSSYTFGGGT  120
KLEIKRGGGG SGGGGSGGGG SQVKLQESGG GLVKPGGSLK LSCAASGFTF SSYAMSWVRQ  180
TPEKRLEWVA TISSGGSYTY YPDSVKGRFT ISRDNAKNTL YLQMSSLRSE DTAMYYCARQ  240
DGYYPGWFAN WGQGTTVTVS SSGTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
```

-continued

```
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                             486

SEQ ID NO: 76          moltype = AA  length = 490
FEATURE                Location/Qualifiers
REGION                 1..490
                       note = Description of Artificial Sequence:
                        Syntheticpolypeptide
source                 1..490
                       mol_type = protein
                       organism = synthetic construct
SEQUENCE: 76
MALPVTALLL PLALLLHAAR PAAYKDIQMT QTTSSLSASL GDRVTISCSA SQGISNYLNW  60
YQQKPDGTVK LLIYYTSSLH SGVPSRFSGS GSGTDYSLTI SNLEPEDIAT YYCQQYSKLP  120
YTFGGGTKLE IKRGGGGSGG GGSGGGGSEV QLVESGGGLV KPGGSLKLSC AASGLTFSSY  180
AMSWVRQTPE KRLEWVASIS SGGFTYYPDS VKGRFTISRD NARNILYLQM SSLRSEDTAM  240
YYCARDEVRG YLDVWGAGTT VTVSSSGTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YKQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                         490

SEQ ID NO: 77          moltype = AA  length = 492
FEATURE                Location/Qualifiers
REGION                 1..492
                       note = Description of Artificial Sequence:
                        Syntheticpolypeptide
source                 1..492
                       mol_type = protein
                       organism = synthetic construct
SEQUENCE: 77
MALPVTALLL PLALLLHAAR PDIQMTQSPA SLSASVGETV TITCRASGNI HNYLAWYQQK  60
QGKSPQLLVY NAKTLADGVP SRFSGSGSGT QYSLKINSLQ PEDFGSYYCQ HFWTTPPWTF  120
GGGTKLEIKG GGGSGGGGSG GGGSQIQLVQ SGPELKKPGE TVKISCKASG YTFTNYGMNW  180
VKQAPGKGLK WMGWINTYNG EPTYADDFKG RFDFSLETSA STAYLQINNL KNEDTATYFC  240
ARRGYYYGSR YGAMDYWGQG TSVTVSSSGT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYKQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                      492

SEQ ID NO: 78          moltype = AA  length = 492
FEATURE                Location/Qualifiers
REGION                 1..492
                       note = Description of Artificial Sequence:
                        Syntheticpolypeptide
source                 1..492
                       mol_type = protein
                       organism = synthetic construct
SEQUENCE: 78
MALPVTALLL PLALLLHAAR PQIQLVQSGP ELKKPGETVK ISCKASGYTF TNYGMNWVKQ  60
APGKGLKWMG WINTYNGEPT YADDFKGRFD FSLETSASTA YLQINNLKNE DTATYFCARR  120
GYYYGSRYGA MDYWGQGTSV TVSSGGGGSG GGGSGGGGSD IQMTQSPASL SASVGETVTI  180
TCRASGNIHN YLAWYQQKQG KSPQLLVYNA KTLADGVPSR FSGSGSGTQY SLKINSLQPE  240
DFGSYYCQHF WTTPPWTFGG GTKLEIKSGT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYKQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                      492

SEQ ID NO: 79          moltype = AA  length = 726
FEATURE                Location/Qualifiers
REGION                 1..726
                       note = Description of Artificial Sequence:
                        Syntheticpolypeptide
source                 1..726
                       mol_type = protein
                       organism = synthetic construct
SEQUENCE: 79
MALPVTALLL PLALLLHAAR PDIQMTQTTS SLSASLGDRV TISCRASQDI SKYLNWYQQK  60
PDGTVKLLIY HTSRLHSGVP SRFSGSGSGT DYSLTISNLE QEDIATYFCQ QGNTLPYTFG  120
GGTKLEITGG GGSQVKLQES GGGLVKPGGS LKLSCAASGF TFSSYAMSWV RQTPEKRLEW  180
VATISSGGSY TYYPDSVKGR FTISRDNAKN TLYLQMSSLR SEDTAMYYCA RQDGYYPGWF  240
ANWGQGTTVT VSSGSTSGSG KPGSGEGSTK GDIELTQSPA IMSASLGEEI TLTCSASSSV  300
SYMHWYQQKS GTSPKLLIYS TSNLASGVPS RFSGSGSGTF YSLTISSVEA EDAADYYCHQ  360
WSSYTFGGGT KLEIKRGGGG SEVKLQESGP GLVAPSQSLS VTCTVSGVSL PDYGVSWIRQ  420
PPRKGLEWLG VIWGSETTYY NSALKSRLTI IKDNSKSQVF LKMNSLQTDD TAIYYCAKHY  480
YYGGSYAMDY WGQGTSVTVS SSGTTTPAPR PPTPAPTIAS QPLSLRPEAC RPAAGGAVHT  540
```

-continued

```
RGLDFACDIY IWAPLAGTCG VLLLSLVITL YCKRGRKKLL YIFKQPFMRP VQTTQEEDGC  600
SCRFPEEEEG GCELRVKFSR SADAPAYKQG QNQLYNELNL GRREEYDVLD KRRGRDPEMG  660
GKPRRKNPQE GLYNELQKDK MAEAYSEIGM KGERRRGKGH DGLYQGLSTA TKDTYDALHM  720
QALPPR                                                             726

SEQ ID NO: 80          moltype = AA  length = 726
FEATURE                Location/Qualifiers
REGION                 1..726
                       note = Description of Artificial Sequence:
                        Syntheticpolypeptide
source                 1..726
                       mol_type = protein
                       organism = synthetic construct
SEQUENCE: 80
MALPVTALLL PLALLLHAAR PEVKLQESGP GLVAPSQSLS VTCTVSGVSL PDYGVSWIRQ  60
PPRKGLEWLG VIWGSETTYY NSALKSRLTI IKDNSKSQVF LKMNSLQTDD TAIYYCAKHY  120
YYGGSYAMDY WGQGTSVTVS SGGGGSDIEL TQSPAIMSAS LGEEITLTCS ASSSVSYMHW  180
YQQKSGTSPK LLIYSTSNLA SGVPSRFSGS GSGTFYSLTI SSVEAEDAAD YYCHQWSSYT  240
FGGGTKLEIK RGSTSGSGKP GSGEGSTKGQ VKLQESGGGL VKPGGSLKLS CAASGFTFSS  300
YAMSWVRQTP EKRLEWVATI SSGGSYTYYP DSVKGRFTIS RDNAKNTLYL QMSSLRSEDT  360
AMYYCARQDG YYPGWFANWG QGTTVTVSSG GGGSDIQMTQ TTSSLSASLG DRVTISCRAS  420
QDISKYLNWY QQKPDGTVKL LIYHTSRLHS GVPSRFSGSG SGTDYSLTIS NLEQEDIATY  480
FCQQGNTLPY TFGGGTKLEI TSGTTTPAPR PPTPAPTIAS QPLSLRPEAC RPAAGGAVHT  540
RGLDFACDIY IWAPLAGTCG VLLLSLVITL YCKRGRKKLL YIFKQPFMRP VQTTQEEDGC  600
SCRFPEEEEG GCELRVKFSR SADAPAYKQG QNQLYNELNL GRREEYDVLD KRRGRDPEMG  660
GKPRRKNPQE GLYNELQKDK MAEAYSEIGM KGERRRGKGH DGLYQGLSTA TKDTYDALHM  720
QALPPR                                                             726

SEQ ID NO: 81          moltype = AA  length = 746
FEATURE                Location/Qualifiers
REGION                 1..746
                       note = Description of Artificial Sequence:
                        Syntheticpolypeptide
source                 1..746
                       mol_type = protein
                       organism = synthetic construct
SEQUENCE: 81
MALPVTALLL PLALLLHAAR PDIQMTQTTS SLSASLGDRV TISCRASQDI SKYLNWYQQK  60
PDGTVKLLIY HTSRLHSGVP SRFSGSGSGT DYSLTISNLE QEDIATYFCQ QGNTLPYTFG  120
GGTKLEITGG GGSGGGGSGG GGSEVKLQES GPGLVAPSQS LSVTCTVSGV SLPDYGVSWI  180
RQPPRKGLEW LGVIWGSETT YYNSALKSRL TIIKDNSKSQ VFLKMNSLQT DDTAIYYCAK  240
HYYYGGSYAM DYWGQGTSVT VSSGSTSGSG KPGSGEGSTK GDIELTQSPA IMSASLGEEI  300
TLTCSASSSV SYMHWYQQKS GTSPKLLIYS TSNLASGVPS RFSGSGSGTF YSLTISSVEA  360
EDAADYYCHQ WSSYTFGGGT KLEIKRGGGG SGGGGSGGGG SQVKLQESGG GLVKPGGSLK  420
LSCAASGFTF SSYAMSWVRQ TPEKRLEWVA TISSGGSYTY YPDSVKGRFT ISRDNAKNTL  480
YLQMSSLRSE DTAMYYCARQ DGYYPGWFAN WGQGTTVTVS SSGTTTPAPR PPTPAPTIAS  540
QPLSLRPEAC RPAAGGAVHT RGLDFACDIY IWAPLAGTCG VLLLSLVITL YCKRGRKKLL  600
YIFKQPFMRP VQTTQEEDGC SCRFPEEEEG GCELRVKFSR SADAPAYKQG QNQLYNELNL  660
GRREEYDVLD KRRGRDPEMG GKPRRKNPQE GLYNELQKDK MAEAYSEIGM KGERRRGKGH  720
DGLYQGLSTA TKDTYDALHM QALPPR                                       746

SEQ ID NO: 82          moltype = AA  length = 743
FEATURE                Location/Qualifiers
REGION                 1..743
                       note = Description of Artificial Sequence:
                        Syntheticpolypeptide
source                 1..743
                       mol_type = protein
                       organism = synthetic construct
SEQUENCE: 82
MALPVTALLL PLALLLHAAR PDIQMTQTTS SLSASLGDRV TISCRASQDI SKYLNWYQQK  60
PDGTVKLLIY HTSRLHSGVP SRFSGSGSGT DYSLTISNLE QEDIATYFCQ QGNTLPYTFG  120
GGTKLEITGG GGSGGGGSGG GGSEVKLQES GPGLVAPSQS LSVTCTVSGV SLPDYGVSWI  180
RQPPRKGLEW LGVIWGSETT YYNSALKSRL TIIKDNSKSQ VFLKMNSLQT DDTAIYYCAK  240
HYYYGGSYAM DYWGQGTSVT VSSEAAAKEA AAKEAAAKDI ELTQSPAIMS ASLGEEITLT  300
CSASSSVSYM HWYQQKSGTS PKLLIYSTSN LASGVPSRFS GSGSGTFYSL TISSVEAEDA  360
ADYYCHQWSS YTFGGGTKLE IKRGGGGSGG GGSGGGGSQV KLQESGGGLV KPGGSLKLSC  420
AASGFTFSSY AMSWVRQTPE KRLEWVATIS SGGSYTYYPD SVKGRFTISR DNAKNTLYLQ  480
MSSLRSEDTA MYYCARQDGY YPGWFANWGQ GTTVTVSSSG TTTPAPRPPT PAPTIASQPL  540
SLRPEACRPA AGGAVHTRGL DFACDIYIWA PLAGTCGVLL LSLVITLYCK RGRKKLLYIF  600
KQPFMRPVQT TQEEDGCSCR FPEEEEGGCE LRVKFSRSAD APAYKQGQNQ LYNELNLGRR  660
EEYDVLDKRR GRDPEMGGKP RRKNPQEGLY NELQKDKMAE AYSEIGMKGE RRRGKGHDGL  720
YQGLSTATKD TYDALHMQAL PPR                                          743

SEQ ID NO: 83          moltype = AA  length = 746
FEATURE                Location/Qualifiers
REGION                 1..746
                       note = Description of Artificial Sequence:
                        Syntheticpolypeptide
```

```
source                1..746
                      mol_type = protein
                      organism = synthetic construct
SEQUENCE: 83
MALPVTALLL PLALLLHAAR PDIELTQSPA IMSASLGEEI TLTCSASSSV SYMHWYQQKS  60
GTSPKLLIYS TSNLASGVPS RFSGSGSGTF YSLTISSVEA EDAADYYCHQ WSSYTFGGGT  120
KLEIKRGGGG SGGGGSGGGG SQVKLQESGG GLVKPGGSLK LSCAASGFTF SSYAMSWVRQ  180
TPEKRLEWVA TISSGGSYTY YPDSVKGRFT ISRDNAKNTL YLQMSSLRSE DTAMYYCARQ  240
DGYYPGWFAN WGQGTTVTVS SGSTSGSGKP GSGEGSTKGD IQMTQTTSSL SASLGDRVTI  300
SCRASQDISK YLNWYQQKPD GTVKLLIYHT SRLHSGVPSR FSGSGSGTDY SLTISNLEQE  360
DIATYFCQQG NTLPYTFGGG TKLEITGGGG SGGGGSGGGG SEVKLQESGP GLVAPSQSLS  420
VTCTVSGVSL PDYGVSWIRQ PPRKGLEWLG VIWGSETTYY NSALKSRLTI IKDNSKSQVF  480
LKMNSLQTDD TAIYYCAKHY YYGGSYAMDY WGQGTSVTVS SSGTTTPAPR PPTPAPTIAS  540
QPLSLRPEAC RPAAGGAVHT RGLDFACDIY IWAPLAGTCG VLLLSLVITL YCKRGRKKLL  600
YIFKQPFMRP VQTTQEEDGC SCRFPEEEEG GCELRVKFSR SADAPAYKQG QNQLYNELNL  660
GRREEYDVLD KRRGRDPEMG GKPRRKNPQE GLYNELQKDK MAEAYSEIGM KGERRRGKGH  720
DGLYQGLSTA TKDTYDALHM QALPPR                                      746

SEQ ID NO: 84         moltype = AA  length = 746
FEATURE               Location/Qualifiers
REGION                1..746
                      note = Description of Artificial Sequence:
                       Syntheticpolypeptide
source                1..746
                      mol_type = protein
                      organism = synthetic construct
SEQUENCE: 84
MALPVTALLL PLALLLHAAR PDIELTQSPA IMSASLGEEI TLTCSASSSV SYMHWYQQKS  60
GTSPKLLIYS TSNLASGVPS RFSGSGSGTF YSLTISSVEA EDAADYYCHQ WSSYTFGGGT  120
KLEIKRGGGG SGGGGSGGGG SQVKLQESGG GLVKPGGSLK LSCAASGFTF SSYAMSWVRQ  180
TPEKRLEWVA TISSGGSYTY YPDSVKGRFT ISRDNAKNTL YLQMSSLRSE DTAMYYCARQ  240
DGYYPGWFAN WGQGTTVTVS SGSTSGSGKP GSGEGSTKGE VKLQESGPGL VAPSQSLSVT  300
CTVSGVSLPD YGVSWIRQPP RKGLEWLGVI WGSETTYYNS ALKSRLTIIK DNSKSQVFLK  360
MNSLQTDDTA IYYCAKHYYY GGSYAMDYWG QGTSVTVSSG GGGSGGGGSG GGGSDIQMTQ  420
TTSSLSASLG DRVTISCRAS QDISKYLNWY QQKPDGTVKL LIYHTSRLHS GVPSRFSGSG  480
SGTDYSLTIS NLEQEDIATY FCQQGNTLPY TFGGGTKLEI TSGTTTPAPR PPTPAPTIAS  540
QPLSLRPEAC RPAAGGAVHT RGLDFACDIY IWAPLAGTCG VLLLSLVITL YCKRGRKKLL  600
YIFKQPFMRP VQTTQEEDGC SCRFPEEEEG GCELRVKFSR SADAPAYKQG QNQLYNELNL  660
GRREEYDVLD KRRGRDPEMG GKPRRKNPQE GLYNELQKDK MAEAYSEIGM KGERRRGKGH  720
DGLYQGLSTA TKDTYDALHM QALPPR                                      746

SEQ ID NO: 85         moltype = AA  length = 1261
FEATURE               Location/Qualifiers
REGION                1..1261
                      note = Description of Artificial Sequence:
                       Syntheticpolypeptide
source                1..1261
                      mol_type = protein
                      organism = synthetic construct
SEQUENCE: 85
MALPVTALLL PLALLLHAAR PDIQMTQTTS SLSASLGDRV TISCRASQDI SKYLNWYQQK  60
PDGTVKLLIY HTSRLHSGVP SRFSGSGSGT DYSLTISNLE QEDIATYFCQ QGNTLPYTFG  120
GGTKLEITGG GGSQVKLQES GGGLVKPGGS LKLSCAASGF TFSSYAMSWV RQTPEKRLEW  180
VATISSGGSY TYYPDSVKGR FTISRDNAKN TLYLQMSSLR SEDTAMYYCA RQDGYYPGWF  240
ANWGQGTTVT VSSGSTSGSG KPGSGEGSTK GDIELTQSPA IMSASLGEEI TLTCSASSSV  300
SYMHWYQQKS GTSPKLLIYS TSNLASGVPS RFSGSGSGTF YSLTISSVEA EDAADYYCHQ  360
WSSYTFGGGT KLEIKRGGGG SEVKLQESGP GLVAPSQSLS VTCTVSGVSL PDYGVSWIRQ  420
PPRKGLEWLG VIWGSETTYY NSALKSRLTI IKDNSKSQVF LKMNSLQTDD TAIYYCAKHY  480
YYGGSYAMDY WGQGTSVTVS SSGTTTPAPR PPTPAPTIAS QPLSLRPEAC RPAAGGAVHT  540
RGLDFACDIY IWAPLAGTCG VLLLSLVITL YCKRGRKKLL YIFKQPFMRP VQTTQEEDGC  600
SCRFPEEEEG GCELRVKFSR SADAPAYKQG QNQLYNELNL GRREEYDVLD KRRGRDPEMG  660
GKPRRKNPQE GLYNELQKDK MAEAYSEIGM KGERRRGKGH DGLYQGLSTA TKDTYDALHM  720
QALPPRGSGA TNFSLLKQAG DVEENPGPML VRRGARAGPR MPRGWTALCL LSLLPSGFMS  780
LDNNGTATPE LPTQGTFSNV STNVSYQETT TPSTLGSTSL HPVSQHGNEA TTNITETTVK  840
FTSTSVITSV YGNTNSSVQS QTSVISTVFT TPANVSTPET TLKPSLSPGN VSDLSTTSTS  900
LATSPTKPYT SSSPILSDIK AEIKCSGIRE VKLTQGICLE QNKTSSCAEF KKDRGEGLAR  960
VLCGEEQADA DAGAQVCSLL LAQSEVRPQC LLLVLANRTE ISSKLQLMKK HQSDLKKLGI  1020
LDFTEQDVAS HQSYSQKTPI LLTCPTISIL SFFSVALLVI LACVLWKKRI KPIVWPSLPD  1080
HKKTLEHLCK KPRKNLNVSF NPESFLDCQI HRVDDIQARD EVEGFLQDTF PQQLEESEKQ  1140
RLGGDVQSPN CPSEDVVITP ESFGRDSSLT CLAGNVSACD APILSSSRSL DCRESGKNGP  1200
HVYQDLLLSL GTTNSTLPPP FSLQSGILTL NPVAQGQPIL TSLGSNQEEA YVTMSSFYQN  1260
Q                                                                 1261

SEQ ID NO: 86         moltype = AA  length = 1263
FEATURE               Location/Qualifiers
REGION                1..1263
                      note = Description of Artificial Sequence:
                       Syntheticpolypeptide
source                1..1263
```

```
                      mol_type = protein
                      organism = synthetic construct
SEQUENCE: 86
MASRILWHEM WHEGLEEASR LYFGERNVKG MFEVLEPLHA MMERGPQTLK ETSFNQAYGR  60
DLMEAQEWCR KYMKSGNVKD LLQAWDLYYH VFRRISKLEY SGGGSLEGVQ VETISPGDGR  120
TFPKRGQTCV VHYTGMLEDG KKFDSSRDRN KPFKFMLGKQ EVIRGWEEGV AQMSVGQRAK  180
LTISPDYAYG ATGHPGIIPP HATLVFDVEL LKLESGGGGS GGGGSGGGGS GVDGFGDVGA  240
LESLRGNADL AYILSMEPCG HCLIINNVNF CRESGLRTRT GSNIDCEKLR RRFSSLHFMV  300
EVKGDLTAKK MVLALLELAQ QDHGALDCCV VVILSHGCQA SHLQFPGAVY GTDGCPVSVE  360
KIVNIFNGTS CPSLGGKPKL FFIQACGGEQ KDHGFEVAST SPEDESPGSN PEPDATPFQE  420
GLRTFDQLDA ISSLPTPSDI FVSYSTFPGF VSWRDPKSGS WYVETLDDIF EQWAHSEDLQ  480
SLLLRVANAV SVKGIYKQMP GCFNFLRKKL FFKTSGSGAT NFSLLKQAGD VEENPGPMAL  540
PVTALLLPLA LLLHAARPDI QMTQTTSSLS ASLGDRVTIS CRASQDISKY LNWYQQKPDG  600
TVKLLIYHTS RLHSGVPSRF SGSGSGTDYS LTISNLEQED IATYFCQQGN TLPYTFGGGT  660
KLEITGGGGS QVKLQESGGG LVKPGGSLKL SCAASGFTFS SYAMSWVRQT PEKRLEWVAT  720
ISSGGSYTYY PDSVKGRFTI SRDNAKNTLY LQMSSLRSED TAMYYCARQD GYYPGWFANW  780
GQGTTVTVSS GSTSGSGKPG SGEGSTKGDI ELTQSPAIMS ASLGEEITLT CSASSSVSYM  840
HWYQQKSGTS PKLLIYSTSN LASGVPSRFS GSGSGTFYSL TISSVEAEDA ADYYCHQWSS  900
YTFGGGTKLE IKRGGGGSEV KLQESGPGLV APSQSLSVTC TVSGVSLPDY GVSWIRQPPR  960
KGLEWLGVIW GSETTYYNSA LKSRLTIIKD NSKSQVFLKM NSLQTDDTAI YYCAKHYYYG  1020
GSYAMDYWGQ GTSVTVSSGR TTTPAPRPPT PAPTIASQPL SLRPEACRPA AGGAVHTRGL  1080
DFACDIYIWA PLAGTCGVLL LSLVITLYCK RGRKKLLYIF KQPFMRPVQT TQEEDGCSCR  1140
FPEEEEGGCE LRVKFSRSAD APAYKQGQNQ LYNELNLGRR EEYDVLDKRR GRDPEMGGKP  1200
RRKNPQEGLY NELQKDKMAE AYSEIGMKGE RRRGKGHDGL YQGLSTATKD TYDALHMQAL  1260
PPR                                                                1263

SEQ ID NO: 87         moltype = AA  length = 107
FEATURE               Location/Qualifiers
REGION                1..107
                      note = Description of Artificial Sequence:
                       Syntheticpolypeptide
source                1..107
                      mol_type = protein
                      organism = synthetic construct
SEQUENCE: 87
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEIT                107

SEQ ID NO: 88         moltype = AA  length = 120
FEATURE               Location/Qualifiers
REGION                1..120
                      note = Description of Artificial Sequence:
                       Syntheticpolypeptide
source                1..120
                      mol_type = protein
                      organism = synthetic construct
SEQUENCE: 88
EVKLQESGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY YGGSYAMDYW GQGTSVTVSS  120

SEQ ID NO: 89         moltype = AA  length = 491
FEATURE               Location/Qualifiers
REGION                1..491
                      note = Description of Artificial Sequence:
                       Syntheticpolypeptide
source                1..491
                      mol_type = protein
                      organism = synthetic construct
SEQUENCE: 89
MALPVTALLL PLALLLHAAR PDIQMTQTTS SLSASLGDRV TISCRASQDI SKYLNWYQQK  60
PDGTVKLLIY HTSRLHSGVP SRFSGSGSGT DYSLTISNLE QEDIATYFCQ QGNTLPYTFG  120
GGTKLEITGS TSGSGKPGSG EGSTKGEVKL QESGPGLVAP SQSLSVTCTV SGVSLPDYGV  180
SWIRQPPRKG LEWLGVIWGS ETTYYNSALK SRLTIIKDNS KSQVFLKMNS LQTDDTAIYY  240
CAKHYYYGGS YAMDYWGQGT SVTVSSSGTT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYKQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                       491

SEQ ID NO: 90         moltype = AA  length = 105
FEATURE               Location/Qualifiers
REGION                1..105
                      note = Description of Artificial Sequence:
                       Syntheticpolypeptide
source                1..105
                      mol_type = protein
                      organism = synthetic construct
SEQUENCE: 90
DIELTQSPAI MSASLGEEIT LTCSASSSVS YMHWYQQKSG TSPKLLIYST SNLASGVPSR  60
```

-continued

```
FSGSGSGTFY SLTISSVEAE DAADYYCHQW SSYTFGGGTK LEIKR                105

SEQ ID NO: 91          moltype = AA  length = 120
FEATURE                Location/Qualifiers
REGION                 1..120
                       note = Description of Artificial Sequence:
                        Syntheticpolypeptide
source                 1..120
                       mol_type = protein
                       organism = synthetic construct
SEQUENCE: 91
QVKLQESGGG LVKPGGSLKL SCAASGFTFS SYAMSWVRQT PEKRLEWVAT ISSGGSYTYY  60
PDSVKGRFTI SRDNAKNTLY LQMSSLRSED TAMYYCARQD GYYPGWFANW GQGTTVTVSS  120

SEQ ID NO: 92          moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 92
EAAAK                                                            5

SEQ ID NO: 93          moltype = AA  length = 30
FEATURE                Location/Qualifiers
REGION                 1..30
                       note = Description of Artificial Sequence:
                        Syntheticpolypeptide
SITE                   1..30
                       note = This sequence may encompass 2-6 "Gly Gly Gly Gly
                        Ser"repeating units
source                 1..30
                       mol_type = protein
                       organism = synthetic construct
SEQUENCE: 93
GGGGSGGGGS GGGGSGGGGS GGGGSGGGGS                                 30

SEQ ID NO: 94          moltype = AA  length = 4
FEATURE                Location/Qualifiers
REGION                 1..4
                       note = Description of Artificial Sequence: Syntheticpeptide
source                 1..4
                       mol_type = protein
                       organism = synthetic construct
SEQUENCE: 94
RGDS                                                             4

SEQ ID NO: 95          moltype = AA  length = 116
FEATURE                Location/Qualifiers
REGION                 1..116
                       note = Description of Artificial Sequence:
                        Syntheticpolypeptide
source                 1..116
                       mol_type = protein
                       organism = synthetic construct
SEQUENCE: 95
QLQQPGAELV RPGSSVKLSC KASGYTFTRY WIHWVKQRPI QGLEWIGNID PSDSETHYNQ  60
KFKDKATLTV DKSSGTAYMQ LSSLTSEDSA VYYCATEDLY YAMEYWGQGT SVTVSS      116

SEQ ID NO: 96          moltype = AA  length = 113
FEATURE                Location/Qualifiers
REGION                 1..113
                       note = Description of Artificial Sequence:
                        Syntheticpolypeptide
source                 1..113
                       mol_type = protein
                       organism = synthetic construct
SEQUENCE: 96
DIMMTQSPSS LAVSAGEKVT MTCKSSQSVL YSSNQKNYLA WYQQKPGQSP KLLIYWASTR  60
ESGVPDRFTG SGSGTDFTLT ISSVQPEDLA VYYCHQYLSS HTFGGGTKLE IKR        113

SEQ ID NO: 97          moltype = AA  length = 120
FEATURE                Location/Qualifiers
REGION                 1..120
                       note = Description of Artificial Sequence:
                        Syntheticpolypeptide
source                 1..120
                       mol_type = protein
```

```
                         organism = synthetic construct
SEQUENCE: 97
QVQLQQPGTE LVRPGSSVKL SCKASGYTFT SYWVNWVKQR PDQGLEWIGR IDPYDSETHY  60
NQKFTDKAIS TIDTSSNTAY MQLSTLTSDA SAVYYCSRSP RDSSTNLADW GQGTLVTVSS  120

SEQ ID NO: 98            moltype = AA  length = 108
FEATURE                  Location/Qualifiers
REGION                   1..108
                         note = Description of Artificial Sequence:
                          Syntheticpolypeptide
source                   1..108
                         mol_type = protein
                         organism = synthetic construct
SEQUENCE: 98
DIVMTQSPAT LSVTPGDRVS LSCRASQSIS DYLHWYQQKS HESPRLLIKY ASQSISGIPS  60
RFSGSGSGSD FTLSINSVEP EDVGVYYCQN GHSFPLTFGA GTKLELRR               108

SEQ ID NO: 99            moltype = AA  length = 903
FEATURE                  Location/Qualifiers
REGION                   1..903
                         note = Description of Artificial Sequence:
                          Syntheticpolypeptide
source                   1..903
                         mol_type = protein
                         organism = synthetic construct
SEQUENCE: 99
MALPVTALLL PLALLLHAAR PDIELTQSPA IMSASLGEEI TLTCSASSSV SYMHWYQQKS  60
GTSPKLLIYS TSNLASGVPS RFSGSGSGTF YSLTISSVEA EDAADYYCHQ WSSYTFGGGT  120
KLEIKRGGGG SGGGGSGGGG SQVKLQESGG GLVKPGGSLK LSCAASGFTF SSYAMSWVRQ  180
TPEKRLEWVA TISSGGSYTY YPDSVKGRFT ISRDNAKNTL YLQMSSLRSE DTAMYYCARQ  240
DGYYPGWFAN WGQGTTVTVS SSGTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPRGSGA TNFSLLKQAG DVEENPGPMD WTWILFLVAA ATRVHSNWVN VISDLKKIED  540
LIQSMHIDAT LYTESDVHPS CKVTAMKCFL LELQVISLES GDASIHDTVE NLIILANNSL  600
SSNGNVTESG CKECEELEEK NIKEFLQSFV HIVQMFINTS SGGGSGGGGS GGGGSGGGGS  660
GGGSLQITCP PPMSVEHADI WVKSYSLYSR ERYICNSGFK RKAGTSSLTE CVLNKATNVA  720
HWTTPSLKCI RDPALVHQRP APPSTVTTAG VTPQPESLSP SGKEPAASSP SSNNTAATTA  780
AIVPGSQLMP SKSPSTGTTE ISSHESSHGT PSQTTAKNWE LTASASHQPP GVYPQGHSDT  840
TVAISTSTVL LCGLSAVSLL ACYLKSRQTP PLASVEMEAM EALPVTWGTS SRDEDLENCS  900
HHL                                                                903

SEQ ID NO: 100           moltype = AA  length = 1065
FEATURE                  Location/Qualifiers
REGION                   1..1065
                         note = Description of Artificial Sequence:
                          Syntheticpolypeptide
source                   1..1065
                         mol_type = protein
                         organism = synthetic construct
SEQUENCE: 100
MALPVTALLL PLALLLHAAR PDIELTQSPA IMSASLGEEI TLTCSASSSV SYMHWYQQKS  60
GTSPKLLIYS TSNLASGVPS RFSGSGSGTF YSLTISSVEA EDAADYYCHQ WSSYTFGGGT  120
KLEIKRGGGG SGGGGSGGGG SQVKLQESGG GLVKPGGSLK LSCAASGFTF SSYAMSWVRQ  180
TPEKRLEWVA TISSGGSYTY YPDSVKGRFT ISRDNAKNTL YLQMSSLRSE DTAMYYCARQ  240
DGYYPGWFAN WGQGTTVTVS SSGTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPRGSGA TNFSLLKQAG DVEENPGPML LLVTSLLLCE LPHPAFLLIP RKVCNGIGIG  540
EFKDSLSINA TNIKHFKNCT SISGDLHILP VAFRGDSFTH TPPLDPQELD ILKTVKEITG  600
FLLIQAWPEN RTDLHAFENL EIIRGRTKQH GQFSLAVVSL NITSLGLRSL KEISDGDVII  660
SGNKNLCYAN TINWKKLFGT SGQKTKIISN RGENSCKATG QVCHALCSPE GCWGPEPRDC  720
VSCRNVSRGR ECVDKCNLLE GEPREFVENS ECIQCHPECL PQAMNITCTG RGPDNCIQCA  780
HYIDGPHCVK TCPAGVMGEN NTLVWKYADA GHVCHLCHPN CTYGCTGPGL EGCPTNGPKI  840
PSPILLTCPT ISILSFFSVA LLVILACVLW KKRIKPIVWP SLPDHKKTLE HLCKKPRKNL  900
NVSFNPESFL DCQIHRVDDI QARDEVEGFL QDTFPQQLEE SEKQRLGGDV QSPNCPSEDV  960
VITPESFGRD SSLTCLAGNV SACDAPILSS SRSLDCRESG KNGPHVYQDL LLSLGTTNST  1020
LPPPFSLQSG ILTLNPVAQG QPILTSLGSN QEEAYVTMSS FYQNQ                  1065

SEQ ID NO: 101           moltype = AA  length = 851
FEATURE                  Location/Qualifiers
REGION                   1..851
                         note = Description of Artificial Sequence:
                          Syntheticpolypeptide
source                   1..851
                         mol_type = protein
                         organism = synthetic construct
```

-continued

```
SEQUENCE: 101
MALPVTALLL PLALLLHAAR PDIELTQSPA IMSASLGEEI TLTCSASSSV SYMHWYQQKS  60
GTSPKLLIYS TSNLASGVPS RFSGSGSGTF YSLTISSVEA EDAADYYCHQ WSSYTFGGGT  120
KLEIKRGGGG SGGGGSGGGG SQVKLQESGG GLVKPGGSLK LSCAASGFTF SSYAMSWVRQ  180
TPEKRLEWVA TISSGGSYTY YPDSVKGRFT ISRDNAKNTL YLQMSSLRSE DTAMYYCARQ  240
DGYYPGWFAN WGQGTTVTVS SSGTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPRGSGA TNFSLLKQAG DVEENPGPML LLVTSLLLCE LPHPAFLLIP CHPECQPQNG  540
SVTCFGPEAD QCVACAHYKD PPFCVARCPS GVKPDLSYMP IWKFPDEEGA CQPCPINCTH  600
SCVDLDDKGC PAEQRASPLT GGGSGGGSPI LLTCPTISIL SFFSVALLVI LACVLWKKRI  660
KPIVWPSLPD HKKTLEHLCK KPRKNLNVSF NPESFLDCQI HRVDDIQARD EVEGFLQDTF  720
PQQLEESEKQ RLGGDVQSPN CPSEDVVITP ESFGRDSSLT CLAGNVSACD APILSSSRSL  780
DCRESGKNGP HVYQDLLLSL GTTNSTLPPP FSLQSGILTL NPVAQGQPIL TSLGSNQEEA  840
YVTMSSFYQN Q                                                      851

SEQ ID NO: 102          moltype = AA  length = 15
FEATURE                 Location/Qualifiers
REGION                  1..15
                        note = Description of Artificial Sequence: Syntheticpeptide
source                  1..15
                        mol_type = protein
                        organism = synthetic construct
SEQUENCE: 102
EAAAKEAAAK EAAAK                                                  15

SEQ ID NO: 103          moltype = AA  length = 368
FEATURE                 Location/Qualifiers
REGION                  1..368
                        note = Description of Artificial Sequence:
                         Syntheticpolypeptide
source                  1..368
                        mol_type = protein
                        organism = synthetic construct
SEQUENCE: 103
MLLLVTSLLL CELPHPAFLL IPQLLFNKTK SVEFTFCNDT VVIPCFVTNM EAQNTTEVYV  60
KWKFKGRDIY TFDGALNKST VPTDFSSAKI EVSQLLKGDA SLKMDKSDAV SHTGNYTCEV  120
TELTREGETI IELKYRVVSW FSPNEPILLT CPTISILSFF SVALLVILAC VLWKKRIKPI  180
VWPSLPDHKK TLEHLCKKPR KNLNVSFNPE SFLDCQIHRV DDIQARDEVE GFLQDTFPQQ  240
LEESEKQRLG GDVQSPNCPS EDVVITPESF GRDSSLTCLA GNVSACDAPI LSSSRSLDCR  300
ESGKNGPHVY QDLLLSLGTT NSTLPPPFSL QSGILTLNPV AQGQPILTSL GSNQEEAYVT  360
MSSFYQNQ                                                          368
```

What is claimed is:

1. A method for treating cancer in a human subject while reducing host-versus-graft (HvG) rejection by an innate T cell or NK cell in the human subject, the method comprising:

administering an engineered cytotoxic T cell to the human subject, wherein the engineered cytotoxic T cell comprises one or more chimeric antigen receptors (CARs) comprising:

a first antigen binding moiety exhibiting specific binding to CD7, wherein the first antigen binding moiety comprises a first scFv comprising a heavy chain variable domain (VH1) comprising the polypeptide sequence of SEQ ID NO: 91 and a light chain variable domain (VL1) comprising the polypeptide sequence of SEQ ID NO: 90; and a second antigen binding moiety exhibiting specific binding to CD19, wherein the second antigen binding domain comprises a second scFv comprising a heavy chain variable domain (VH2) comprising the polypeptide sequence of SEQ ID NO: 88 and a light chain variable domain (VL2) comprising the polypeptide sequence of SEQ ID NO: 87, wherein each CAR of the one or more CARs further comprises:

a hinge polypeptide, which is C-terminal to the first antigen binding moiety and the second antigen-binding moiety;

a transmembrane polypeptide, which is C-terminal to the hinge polypeptide; and an intracellular signaling polypeptide comprising a signaling domain of CD3-zeta, which is C-terminal to the transmembrane polypeptide.

2. The method of claim 1, wherein the first antigen binding moiety and the second antigen binding moiety are arranged, from the amino terminus to the carboxyl terminus, according to one of the following formulas (I-a)-(I-f):

the VL2- the VL1- the VH1- the VH2 (I-a);
the VH2- the VH1- the VL1- the VL2 (I-b);
the VL1- the VL2- the VH2- the VH1 (I-c);
the VH1- the VH2- the VL2- the VL1 (I-d);
the VL2- the VH2- the VH1- the VH1 (I-e); and
the VL1- the VH1- the VH2- the VL2 (I-f).

3. The method of claim 1, wherein the first antigen binding moiety and the second antigen binding moiety are arranged, from the amino terminus to the carboxyl terminus, according to one of the following formulas (II-a)-(II-j):

the VL2- the VH1- the VL1- the VH2 (II-a);
the VH2- the VL1- the VH1- the VL2 (II-b);
the VL1- the VH2- the VL2- the VH1 (II-c);
the VH1- the VL2- the VH2- the VL1 (II-d);
the VL2- the VH2- the VL1- the VH1 (II-e);
the VL1- the VH1- the VL2- the VH2 (II-f);
the VH2- the VL2- the VL1- the VH1 (II-g);
the VH2- the VL2- the VH1- the VL1 (II-h);

the VH1- the VL1- the VL2- the VH2 (II-i); and the VH1- the VL1- the VH2- the VL2 (II-j).

4. The method of claim 1, wherein, in the engineered cytotoxic T cell, an endogenous gene encoding CD7 is knocked out or silenced, to induce fratricide resistance.

5. The method of claim 1, wherein a subunit of an endogenous T cell receptor (TCR) of the engineered cytotoxic T cell is knocked out or silenced, to reduce graft-versus-host disease (GVHD) effect of the engineered cytotoxic T cell in the human subject.

6. The method of claim 5, wherein the subunit is TCR alpha.

7. The method of claim 1, wherein the engineered cytotoxic T cell further comprises a heterologous polypeptide comprising the polypeptide sequence of SEQ ID NO: 11.

8. The method of claim 1, wherein the engineered cytotoxic T cell further comprises a heterologous polypeptide comprising the polypeptide sequence of SEQ ID NO: 15.

9. The method of claim 1, wherein the engineered cytotoxic T cell further comprises a heterologous polypeptide comprising the polypeptide sequence of SEQ ID NO: 17.

10. The method of claim 1, wherein the first scFV comprises the polypeptide sequence of SEQ ID NO: 75.

11. The method of claim 1, wherein the intracellular signaling polypeptide further comprises a costimulatory signaling domain, wherein the costimulatory signaling domain comprises a signaling domain of 4-1BB, a signaling domain of CD28, or the signaling domains of both 4-1BB and CD28.

* * * * *